United States Patent [19]
Silver et al.

[11] Patent Number: 6,063,610
[45] Date of Patent: May 16, 2000

[54] CARBOXYLESTERASE NUCLEIC ACID MOLECULES, PROTEINS AND USES THEREOF

[75] Inventors: Gary M. Silver; Nancy Wisnewski, both of Fort Collins, Colo.

[73] Assignee: Heska Corporation, Fort Collins, Colo.

[21] Appl. No.: 08/747,221

[22] Filed: Nov. 12, 1996

[51] Int. Cl.⁷ .............................. C07K 16/40; C12N 9/18
[52] U.S. Cl. ...................... 435/197; 435/196; 530/387.9; 530/399
[58] Field of Search ................................. 530/399, 387.9, 530/388.26; 435/196, 197; 536/24.31

[56] References Cited

U.S. PATENT DOCUMENTS 5,001,909   2/1991   Borovsky et al. ...................... 530/328

OTHER PUBLICATIONS

Argentine, et al., "Characterization of a Salivary Gland–specific Esterase in the Vector Mosquito, *Aedes aegypti*," 1995, pp. 621–630, *Insect Biochem. Molec. Biol. 25:5*.

Bonning, et al., "Futher Development of a Recombinant Baculovirus Insecticide Expressing the Enzyme Juvenile Hormone Esterase From *Heliothis virescens*," 1992, pp. 453–458, *Insect Biochem. Molec. Biol. 22:5*.

Bonning, et al., "Insect Control by Use of Recombinant Baculoviruses Expressing Juvenile Hormone Esterase," 1994, pp. 368–383, *Natural and Engineered Pest Management Agents*, by Paul A. Hedin, et al., American Chemical Society, Washington, DC.

Borovsky, D., "Oostatic Hormone Inhibits Biosynthesis of Midgut Proteolytic Enzymes and Egg Development in Mosquitoes," 1988, pp. 187–210, *Archives of Insect Biochemistry and Physiology 7*.

Cao, et al., "A Comparative Study of Esterase Isoenzymes from Three Species of Fleas," 1991, pp. 209–212, *Chinese Journal of Parasitology and Parasitic Diseases 9 (3)*.

Chen et al., "Purification and Characterization of Carboxylesterases of a Rice Brown Planthopper, *Nilaparvata lugens* Stal*,*" 1994, pp. 347–355, *Insect Biochem. Molec. Biol. 24:4*.

Cooke, et al., "Amino acid polymorphisms for esterase–6 in *Drosophila melanogaster*," 1989, pp. 1426–1430, *Proc. Natl. Acad. Sci. USA 86*.

Eldridge, et al., "Insecticidal Properties of Genetically Engineered Baculoviruses Expressing an Insect Juvenile Hormone Esterase Gene," 1992, pp. 1583–1591, *Applied and Environmental Microbiology 58:5*.

Hanzlik, et al., "Isolation and Sequencing of cDNA Clones Coding for Juvenile Hormone Esterase from *Heliothis virescens*," 1989, pp. 12419–12425, *The Journal of Biological Chemistry 264:21*.

Harshman, et al., "Cloning, Characterization, and Genetics of the Juvenile Hormone Esterase Gene from *Heliothis virescens*," 1994, pp. 671–676, *Insect Biochem. Molec. Biol. 24:7*.

Jones, et al., "Structure, expression and gene sequence of a juvenile hormone esterase–related protein from metamorphosing larvae of *Trichoplusia ni*," 1994, pp. 827–835, *Biochem. J. 302*.

McCutchen, et al., "Characterization of a Spectrophotometric Assay for Juvenile Hormone Esterase," 1995, pp. 119–126, *Insect Biochem. Molec. Biol. 25:1*.

Mouches, et al., "Characterization of amplicication core and esterase B1 gene responsible for insecticide resistance in Culex," 1990, pp. 2574–2578, *Proc. Natl. Acad. Sci. USA 87*.

Valaitis, A.P., "Use of Concanavalin A in the Purification of Juvenile Hormone Esterase from the Hemolymph and the Fat Body of *Lymantria dispar*," 1992, pp. 639–648, *Insect Biochem. Molec. Biol. 22:7*.

Vaughan, et al., "Mosquito Carboxylesterase Estα2 ($A_2$)— Cloning and Sequence of the Full–length cDNA for a Major Insecticide Resistance Gene Worldwide in the Mosquito *Culex quinquefasciatus*," 1995, pp. 17044–17049, *The Journal of Biological Chemistry 270:28*.

Venkataraman, et al., "Regulation of Juvenile Hormone Esterase Gene Transcription by Juvenile Hormone," 1994, pp. 391–400, *Developmental Genetics 15*.

Venkatash, et al., "Characterization of Affinity–purified Juvenile Hormone Esterase from the Plasma of the Tabacco Hornworm, *Manduca sexta*," 1990, pp. 21727–21732, *The Journal of Biological Chemistry 265:35*.

Ward, et al., "Analysis of the Catalytic Mechanism of Juvenile Hormone Esterase by Site–Directed Mutagenesis," 1992, pp. 1933–1941, *Int. J. Biochem. 24:12*.

Whyard, et al., "Insecticide Resistance and Malathion Carboxylesterase in the Sheeep Blowfly, *Lucilia cuprina*," 1994, pp. 9–24, *Biochemical Genetics 32:1/2*.

*Primary Examiner*—Scott W. Houtteman
*Attorney, Agent, or Firm*—Heska Corporation

[57] ABSTRACT

The present invention relates to arthropod esterase proteins; to arthropod esterase nucleic acid molecules, including those that encode such esterase proteins; to antibodies raised against such esterase proteins; and to other compounds that inhibit arthropod esterase activity. The present invention also includes methods to obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to protect animals from hematophagous arthropod infestation.

7 Claims, 5 Drawing Sheets

CARBOXYLESTERASE NUCLEIC ACID MOLECULES, PROTEINS AND USES THEREOF

FIELD OF THE INVENTION

The present invention relates to arthropod esterase nucleic acid molecules, proteins encoded by such nucleic acid molecules, antibodies raised against such proteins, and inhibitors of such proteins. The present invention also includes therapeutic compositions comprising such nucleic acid molecules, proteins, antibodies, and/or other inhibitors, as well as their use to protect an animal from hematophagous arthropod infestation.

BACKGROUND OF THE INVENTION

Hematophagous arthropod infestation of animals is a health and economic concern because hematophagous arthropods are known to cause and/or transmit a variety of diseases. Hematophagous arthropods directly cause a variety of diseases, including allergies, and also carry a variety of infectious agents including, but not limited to, endoparasites (e.g., nematodes, cestodes, trematodes and protozoa), bacteria and viruses. In particular, the bites of hematophagous arthropods are a problem for animals maintained as pets because the infestation becomes a source of annoyance not only for the pet but also for the pet owner who may find his or her home generally contaminated with insects. As such, hematophagous arthropods are a problem not only when they are on an animal but also when they are in the general environment of the animal.

Bites from hematophagous arthropods are a particular problem because they not only can lead to disease transmission but also can cause a hypersensitive response in animals which is manifested as disease. For example, bites from fleas can cause an allergic disease called flea allergic (or allergy) dermatitis (FAD). A hypersensitive response in animals typically results in localized tissue inflammation and damage, causing substantial discomfort to the animal.

The medical importance of arthropod infestation has prompted the development of reagents capable of controlling arthropod infestation. Commonly encountered methods to control arthropod infestation are generally focused on use of insecticides. While some of these products are efficacious, most, at best, offer protection of a very limited duration. Furthermore, many of the methods are often not successful in reducing arthropod populations. In particular, insecticides have been used to prevent hematophagous arthropod infestation of animals by adding such insecticides to shampoos, powders, collars, sprays, foggers and liquid bath treatments (i.e., dips). Reduction of hematophagous arthropod infestation on the pet has been unsuccessful for one or more of the following reasons: (1) failure of owner compliance (frequent administration is required); (2) behavioral or physiological intolerance of the pet to the pesticide product or means of administration; and (3) the emergence of hematophagous arthropod populations resistant to the prescribed dose of pesticide. However, hematophagous arthropod populations have been found to become resistant to insecticides.

Prior investigators have described insect carboxylesterase (CE) protein biochemistry, for example, Chen et al., *Insect Biochem. Molec. Biol.*, 24:347–355, 1994; Whyard et al., *Biochemical Genetics*, 32:924, 1994 and Argentine et al., *Insect Biochem. Molec Biol*, 25:621–630, 1995. Other investigators have disclosed certain insect CE amino acid sequences, for example, Mouches et al., *Proc Natl Acad Sci USA*, 87:2574–2578, 1990 and Cooke et al., *Proc Natl Acad Sci USA*, 86:1426–1430, 1989, and nucleic acid sequence (Vaughn et al., *J. Biol. Chem.*, 270:17044–17049, 1995).

Prior investigators have described certain insect juvenile hormone esterase (JHE) nucleic acid and amino acid sequences: for example, sequence for *Heliothis virescens* is disclosed by Hanzlik et al., *J. Biol. Chem.*, 264:12419–12425, 1989; Eldridge et al., *App Environ Microbiol*, 58:1583–1591, 1992; Bonning et al., *Insect Biochem. Molec. Biol.*, 22:453–458, 1992; Bonning et al., *Natural and Engineered Pest Management Agents*, pp. 368–383, 1994 and Harshman et al., *Insect Biochem. Molec. Biol*, 24:671–676, 1994; sequence for *Manduca sexta* is disclosed by Vankatesh et al., *J Biol Chem*, 265:21727–21732, 1990; sequence for *Trichoplusia ni* is disclosed by Venkataraman et al., *Dev. Genet.*, 15:391–400, 1994 and Jones et al., *Biochem. J.*, 302:827–835, 1994; and sequence for *Lymantria dispar* is disclosed by Valaitis, *Insect Biochem. Molec. Biol.*, 22:639–648, 1992.

Identification of an esterase of the present invention is unexpected, however, because even the most similar nucleic acid sequence identified by previous investigators could not be used to identify an esterase of the present invention. In addition, identification of an esterase protein of the present invention is unexpected because a protein fraction from flea prepupal larvae that was obtained by monitoring for serine protease activity surprisingly also contained esterase proteins of the present invention.

In summary, there remains a need to develop a reagent and a method to protect animals or plants from hematophagous arthropod infestation.

SUMMARY OF THE INVENTION

The present invention relates to a novel product and process for protection of animals or plants from arthropod infestation. According to the present invention there are provided arthropod esterase proteins and mimetopes thereof; arthropod nucleic acid molecules, including those that encode such proteins; antibodies raised against such esterase proteins (i.e., anti-arthropod esterase antibodies); and compounds that inhibit arthropod esterase activity (i.e, inhibitory compounds or inhibitors).

The present invention also includes methods to obtain such proteins, mimetopes, nucleic acid molecules, antibodies and inhibitory compounds. Also included in the present invention are therapeutic compositions comprising such proteins, mimetopes, nucleic acid molecules, antibodies, and/or inhibitory compounds, as well as use of such therapeutic compositions to protect animals from arthropod infestation.

Identification of an esterase of the present invention is unexpected, however, because the most similar nucleic acid sequence identified by previous investigators could not be used to identify an esterase of the present invention. In addition, identification of an esterase protein of the present invention is unexpected because a protein fraction from flea prepupal larvae that was obtained by monitoring for serine protease activity surprisingly also contained esterase proteins of the present invention.

One embodiment of the present invention is an isolated nucleic acid molecule that hybridizes under stringent hybridization conditions with a gene comprising a nucleic acid sequence including SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:17, SEQ ID NO:18, SEQ ID NO:20, SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:32, SEQ I) NO:33, SEQ ID NO:34, SEQ ID NO:35, SEQ ID NO:36, SEQ ID NO:38, SEQ ID NO:51, SEQ ID NO:52, SEQ ID NO:57, SEQ ID NO:59, SEQ ID NO:60 and/or SEQ ID NO:61.

The present invention also includes a nucleic acid molecule that hybridizes under stringent hybridization conditions with a nucleic acid molecule encoding a protein comprising at least one of the following amino acid sequences: SEQ ID NO:2, SEQ ID NO:5, SEQ ID NO:8, SEQ ID NO:11, SEQ ID NO:14, SEQ ID NO:19, SEQ ID NO:25, SEQ ID NO:31, SEQ ID NO:37, SEQ ID NO:39, SEQ ID NO:40, SEQ ID NO:41, SEQ ID NO:42, SEQ ID NO:43, SEQ ID NO:44, SEQ ID NO:53, SEQ ID NO:54, SEQ ID NO:55 and/or SEQ ID NO:58; and particularly a nucleic acid molecule that hybridizes with a nucleic acid sequence that is a complement of a nucleic acid sequence encoding any of the amino acid sequences. A preferred nucleic acid molecule of the present invention includes a nucleic acid molecule comprising a nucleic acid sequence including SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:17, SEQ ID NO:18, SEQ ID NO:20, SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:38, SEQ ID NO:51, SEQ ID NO:52, SEQ ID NO:57, SEQ ID NO:59, SEQ ID NO:60 and/or SEQ ID NO:61, and allelic variants thereof.

The present invention also includes an isolated carboxylesterase nucleic acid molecule comprising a nucleic acid sequence encoding a protein comprising an amino acid sequence including SEQ ID NO:5, SEQ ID NO:19, SEQ ID NO:39, SEQ ID NO:40, SEQ ID NO:41, SEQ ID NO:42, SEQ ID NO:43, SEQ ID NO:44 and/or SEQ ID NO:53. SEQ ID NO:39, SEQ ID NO:40, SEQ ID NO:41, SEQ ID NO:42, SEQ ID NO:43 and SEQ ID NO:44 represent N-terminal amino acid sequences of carboxylesterases isolated from prepupal flea larvae, the production of which are described in the Examples of the present application.

The present invention also relates to recombinant molecules, recombinant viruses and recombinant cells that include a nucleic acid molecule of the present invention. Also included are methods to produce such nucleic acid molecules, recombinant molecules, recombinant viruses and recombinant cells.

Another embodiment of the present invention includes an isolated esterase protein that is encoded by a nucleic acid molecule that hybridizes under stringent hybridization conditions to (a) a nucleic acid molecule that includes at least one of the following nucleic acid sequences: SEQ ID NO:3, SEQ ID NO:6, SEQ ID NO:9, SEQ ID NO:12, SEQ ID NO:15, SEQ ID NO:17, SEQ ID NO:20, SEQ ID NO:22, SEQ ID NO:26, SEQ ID NO:29, SEQ ID NO:32, SEQ ID NO:35, SEQ ID NO:38, SEQ ID NO:52, SEQ ID NO:59 and SEQ ID NO:61; and/or (b) a nucleic acid molecule encoding a protein including at least one of the following amino acid sequences: SEQ ID NO:39, SEQ ID NO:40, SEQ ID NO:41, SEQ ID NO:42, SEQ ID NO:43, SEQ ID NO:44, SEQ ID NO:53, SEQ ID NO:54 and SEQ ID NO:55. One embodiment is a carboxylesterase protein encoded by a nucleic acid molecule that hybridizes under stringent hybridization conditions to a nucleic acid molecule that encodes a protein comprising at least one of the following amino acid sequences: SEQ ID NO:5, SEQ ID NO:19, SEQ ID NO:39, SEQ ID NO:40, SEQ ID NO:41, SEQ ID NO:42, SEQ ID NO:43, SEQ ID NO:44 and/or SEQ ID NO:53. Preferred proteins of the present invention are isolated flea proteins including at least one of the following amino acid sequences: SEQ ID NO:2, SEQ ID NO:5, SEQ ID NO:8, SEQ ID NO:11, SEQ ID NO:14, SEQ ID NO:19, SEQ ID NO:25, SEQ ID NO:31, SEQ ID NO:37, SEQ ID NO:39, SEQ ID NO:40, SEQ ID NO:41, SEQ ID NO:42, SEQ ID NO:43, SEQ ID NO:44, SEQ ID NO:53, SEQ ID NO:54, SEQ ID NO:55 and SEQ ID NO:58; also included are proteins encoded by allelic variants of nucleic acid molecules encoding proteins comprising any of the above-listed amino acid sequences.

The present invention also relates to mimetopes of arthropod esterase proteins as well as to isolated antibodies that selectively bind to arthropod esterase proteins or mimetopes thereof. Also included are methods, including recombinant methods, to produce proteins, mimetopes and antibodies of the present invention.

The present invention also includes a formulation of flea carboxylesterase proteins, in which the proteins, when submitted to 14% Tris-glycine SDS-PAGE, comprise a fractionation profile as depicted in FIG. 3, in which the proteins have carboxylesterase activity.

Also included in the present invention is a formulation of flea carboxylesterase proteins, in which the proteins, when submitted to IEF-PAGE, comprise a fractionation profile as depicted in FIG. 4, lane 3, lane 4, lane 5, lane 6 and/or lane 7, wherein the proteins have carboxylesterase activity.

Another embodiment of the present invention is an isolated flea protein or a formulation of flea proteins that hydrolyzes α-naphtyl acetate to produce α-napthol, when the protein is incubated in the presence of α-napthyl acetate contained in 20 mM Tris at pH 8.0 for about 15 minutes at about 37° C.

Yet another embodiment of the present invention is an isolated flea protein or a formulation of flea proteins that hydrolyzes the methyl ester group of juvenile hormone to produce a juvenile hormone acid.

Another embodiment of the present invention is a method to identify a compound capable of inhibiting flea carboxylesterase activity, the method comprising: (a) contacting an isolated flea carboxylesterase with a putative inhibitory compound under conditions in which, in the absence of the compound, the protein has carboxylesterase activity; and (b) determining if the putative inhibitory compound inhibits the activity. Also included in the present invention is a test kit to identify a compound capable of inhibiting flea carboxylesterase activity, the test kit comprising an isolated flea carboxylesterase protein having esterase activity and a means for determining the extent of inhibition of the activity in the presence of a putative inhibitory compound.

Yet another embodiment of the present invention is a therapeutic composition that is capable of reducing hematophagous ectoparasite infestation. Such a therapeutic composition includes at least one of the following protective compounds: an isolated hematophagous ectoparasite carboxylesterase protein or a mimetope thereof, an isolated carboxylesterase nucleic acid molecule that hybridizes under stringent hybridization conditions with a *Ctenocephalides felis* carboxylesterase gene, an isolated antibody that selectively binds to a hematophagous ectoparasite carboxylesterase protein, and an inhibitor of carboxylesterase activity identified by its ability to inhibit the activity of a flea carboxylesterase. A therapeutic composition of the present invention can also include an excipient, an adjuvant and/or a carrier. Preferred esterase nucleic acid molecule compounds of the present invention include naked nucleic acid vaccines, recombinant virus vaccines and recombinant cell vaccines. Also included in the present invention is a method to protect an animal from hematophagous ectoparasite infestation, comprising the step of administering to the animal a therapeutic composition of the present invention.

DETAILED DESCRIPTION OF THE INVENTION

The present invention provides for isolated arthropod esterase proteins, isolated arthropod esterase nucleic acid molecules, antibodies directed against arthropod esterase proteins and other inhibitors of arthropod esterase activity. As used herein, the terms isolated arthropod esterase proteins and isolated arthropod esterase nucleic acid molecules refers to esterase proteins and esterase nucleic acid molecules derived from arthropods and, as such, can be obtained from their natural source or can be produced using, for example, recombinant nucleic acid technology or chemical synthesis. Also included in the present invention is the use of these proteins, nucleic acid molecules, antibodies and inhibitors as therapeutic compositions to protect animals from hematophagous ectoparasite infestation as well as in other applications, such as those disclosed below.

Arthropod esterase proteins and nucleic acid molecules of the present invention have utility because they represent novel targets for anti-arthropod vaccines and drugs. The products and processes of the present invention are advantageous because they enable the inhibition of arthropod development, metamorphosis, feeding, digestion and reproduction processes that involve esterases. While not being bound by theory, it is believed that expression of arthropod esterase proteins are developmentally regulated, thereby suggesting that esterase proteins are involved in arthropod development and/or reproduction. The present invention is particularly advantageous because the proteins of the present invention were identified in larval fleas, thereby suggesting the importance of the proteins as developmental proteins.

Figure 1:
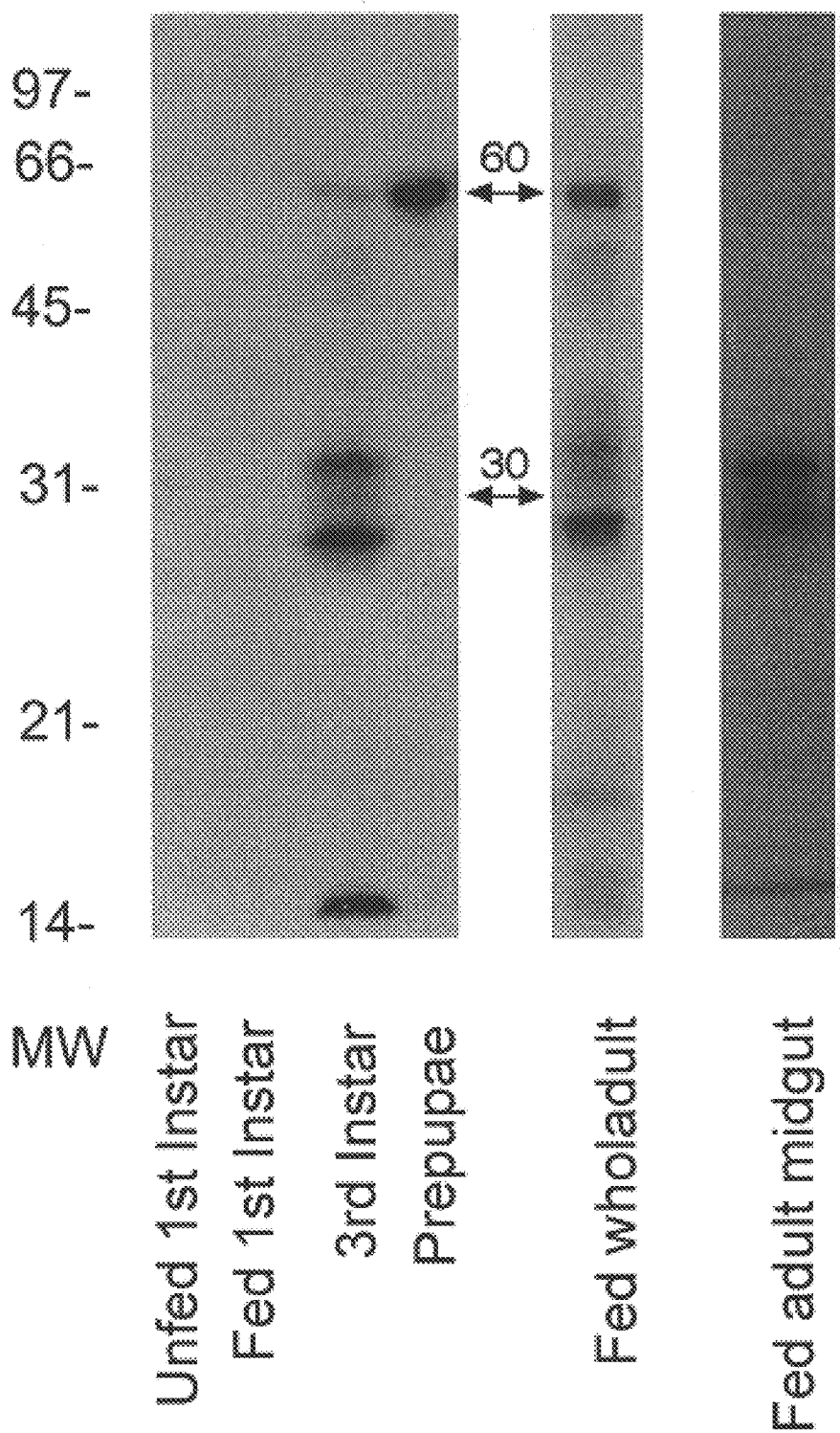
FIG. 1 depicts SDS-PAGE analysis of DFP-labeled esterase proteins.

One embodiment of the present invention is an esterase formulation that includes one or more esterase proteins capable of binding to diisopropylfluorophosphate (DFP). A preferred embodiment of an esterase formulation of the present invention comprises one or more arthropod esterase proteins that range in molecular weight from about 20 kilodaltons (kD) to about 200 kD, more preferably from about 40 kD to about 100 kD, and even more preferably from about 60 kD to about 75 kD, as determined by SDS-PAGE (sodium dodecyl sulfate polyacrylamide gel electrophoresis). An even more preferred formulation includes one or more flea esterase proteins having elution (or migration) patterns as shown in FIG. 1.

Another embodiment of the present invention is a formulation comprising one or more hematophagous ectoparasite carboxylesterase (CE) proteins. The present invention includes the discovery that such a formulation has general CE activity. General CE activity can be identified using methods known to those of skill in the art and described in the Examples section herein. A suitable formulation of the present invention comprises one or more flea proteins capable of hydrolyzing α-napthyl acetate to produce α-napthol when the proteins are incubated in the presence of α-napthyl acetate contained in 20 mm Tris at pH 8.0 for about 15 minutes at about 37° C. General CE activity can be identified following such incubation by detecting the production of from about 0.3 to about 2.5 absorbance units in the presence of Fast Blue when measured at 590 nm.

A preferred CE formulation of the present invention includes one or more flea CE proteins having acidic to neutral isoelectric points, or pI values. An isoelectric pH, or pI, value refers to the pH value at which a molecule has no net electric charge and fails to move in an electric field. A preferred formulation of the present invention includes one or more proteins having a pI value ranging from about pI 2 to about 10, more preferably from about pI 3 to about 8, and even more preferably from about pI 4.7 to about 5.2, as determined by IEF-PAGE.

An esterase formulation, including a CE formulation, of the present invention can be prepared by a method that includes the steps of: (a) preparing an extract by isolating flea tissue, homogenizing the tissue by sonication and clarifying the extract by centrifugation at a low speed spin, e.g., about 18,000 rpm for about 30 minutes; (b) recovering soluble proteins from said centrifuged extract and applying the proteins to a p-aminobenzamidine agarose bead column; (c) recovering unbound protein from the column and clarifying by filtration; (d) applying the clarified protein to a gel filtration column and eluting and collecting fractions with esterase activity; (e) dilayzing the eluate against 20 mM MES buffer, pH 6.0, containing 10 mM NaCl; (f) applying the dialysate to a cation exchange chromatography column, eluting protein bound to the column with a linear gradient of from about 10 mM NaCl to about 1 M NaCl in 20 mM MES buffer, pH 6, and collecting fractions having esterase activity; (g) adjusting the pH of the resulting fractions to pH 7 and applying the fractions to an anion exchange chromatography column; (h) eluting protein bound to the column with a linear gradient of from about 0 to about 1 M NaCl in 25 mM Tris buffer, pH 6.8 and collecting fractions having esterase activity, such activity elutes from the column at about 170 mM NaCl.

Tissue can be obtained from unfed fleas or from fleas that recently consumed a blood meal (i.e., blood-fed fleas). Such flea tissues are referred to herein as, respectively, unfed flea and fed flea tissue. Preferred flea tissue from which to obtain an esterase formulation of the present invention includes pre-pupal larval tissue, 3rd instar tissue, fed adult tissue and unfed adult tissue.

In a preferred embodiment, a CE formulation of the present invention comprises a flea protein comprising amino acid sequence SEQ ID NO:5, SEQ ID NO:19, SEQ ID NO:39, SEQ ID NO:40, SEQ ID NO:41, SEQ ID NO:42, SEQ ID NO:43, SEQ ID NO:44 and/or SEQ ID NO:53.

Another embodiment of the present invention is a juvenile hormone esterase (JHE) formulation comprising one or more arthropod JHE proteins, the arthropod being of the order Hemiptera, Anoplura, Mallophaga, Diptera, Siphonaptera, Parasitiformes, Acariformes and Acarina. The present invention includes the discovery that such a formulation has JHE activity. JHE activity can be identified using methods known to those of skill in the art and described in the Examples section herein. A suitable formulation of the present invention comprises one or more arthropod proteins capable of hydrolyzing a methyl ester group of juvenile hormone to produce a juvenile hormone acid. Preferably, such a protein is capable of releasing of at least about 120 counts per minute when such a protein is incubated in the presence of $^3$H-juvenile hormone to create a reaction mixture, the reaction mixture is combined with isooctane, the aqueous phase is recovered and the amount of $^3$H-juvenile hormone present in that phase is determined. Such a protein is also preferably capable of causing release of methane thiol when such protein is incubated in the presence of methyl 1-heptylthioacetothioate (HEPTAT) using the method generally disclosed in McCutchen et al., *Insect Biochem. Molec. Biol.*, Vol. 25, No. 1, pg 119–126, 1995, which is incorporated in its entirety by this reference.

According to the present invention, an arthropod that is not of the order lepidoptera includes an arthropod of the order Hemiptera, Anoplura, Mallophaga, Diptera, Siphonaptera, Parasitiformes, Acariformes and Acarina. Preferred arthropods include *Hemiptera cimicidae, Hemiptera reduviidae, Anoplura pediculidae, Anoplura pthiridae, Diptera culicidae, Diptera simuliidae, Diptera psychodidae, Diptera ceratopogonidae, Diptera chaoboridae, Diptera tabanidae, Diptera rhagionidae, athericidae, Diptera chloropidae, Diptera muscidae, Diptera hippoboscidae, Diptera calliphoridae, Diptera sarcophagidae, Diptera oestridae, Diptera gastrophilidae, Diptera cuterebridae, Siphonaptera ceratophyllidae, Siphonaptera leptopsyllidae, Siphonaptera pulicidae, Siphonaptera tungidae, Parasitiformes dermanyssidae, Acariformes tetranychidae, Acariformes cheyletide, Acariformes demodicidae, Acariformes erythraeidae, Acariformes trombiculidae, Acariformes psoroptidae, Acariformes sarcoptidae, Acarina argasidae* and *Acarina ixodidae*. Preferred Diptera muscidae include Musca, Hydrotaea, Stomoxys Haematobia. Preferred Siphonaptera include *Ceratophyllidae nosopsyllus, Ceratophyllidae diamanus, Ceratophyllidae ceratophyllus, Leptopsyllidae leptopsylla, Pulicidae pulex, Pulicidae ctenocephalides, Pulicidae xenopsylla, Pulicidae echidnophaga* and *Tungidae tunga*. Preferred Parasitiformes dermanyssidae include Omithonyssus and Liponyssoides. Preferred Acarina include *Argasidae argas, Argasidae ornithodoros, Argasidae otobius, Ixodidae ixodes, Ixodidae hyalomma, Ixodidae nosomma, Ixodidae rhipicephalus, Ixodidae boophilus, Ixodidae dermacentor, Ixodidae haemaphysalus, Ixodidae amblyomma* and *Ixodidae anocentor*.

One embodiment of a JHE formulation of the present invention is one or more arthropod JHE proteins that range in molecular weight from about 20 kD to about 200 kD, more preferably from about 40 kD to about 100 kD, and even more preferably from about 60 kD to about 75 kD, as determined by SDS-PAGE (sodium dodecyl sulfate polyacrylamide gel electrophoresis).

A JHE formulation of the present invention can be prepared by a method that includes the steps of: (a) preparing soluble proteins from arthropod extracts as described above for CE purification and purifying such soluble proteins by gel filtration; (b) collecting fractions having JHE activity from the gel filtration step, loading the fractions onto a cation exchange column, eluting the cation exchange column with a linear gradient of from about 10 mM NaCl to about 1 M NaCl in 20 mM MES buffer, pH 6 and collecting fractions having JHE activity; (c) adjusting the pH of the collected fractions to about pH 7 are dialyzed against about 10 mM phosphate buffer (pH 7.2) containing about 10 mM NaCl; (d) applying the dialysate to a hydroxyapatite column, eluting protein bound to the column with a linear gradient of from about 10 mM phosphate buffer (pH 7.2) containing 10 mM NaCl to about 0.5 M phosphate buffer (pH 6.5) containing 10 mM NaCl and collecting fractions having JHE activity; (e) dialyzing the fractions against 20 mM Tris buffer (pH 8.0) containing 10 mM NaCl; (f) applying the dialysate an anion exchange chromatography column and eluting protein bound to the column with a linear gradient of from about 10 mM to about 1 M NaCl in 20 mM Tris buffer, pH 8 and collecting fractions containing JHE activity.

A JHE formulation of the present invention can be prepared by a method that includes the steps of: (a) preparing flea extracts as described herein in the Examples section and applying the extract to p-aminobenzamidine linked agarose beads and collecting protein not bound to the beads; (b) applying the unbound protein to a Superdex 200 HR gel filtration column and collecting fractions having JHE activity; (c) applying the fractions to an anion exchange chromatography column, eluting the anion exchange column with a linear gradient of 0 to 1 M NaCl in 25 mM Tris buffer, pH 6.8 and collecting fractions having JHE activity; (d) dialyzing the fractions overnight against about 1 L of 20 mM Tris buffer, pH 8.0, containing 10 mM NaCl; (e) applying the dialysate to a Poros 10 HQ anion exchange column, eluting the column with buffer containing about 120 mM NaCl and collecting fractions having JHE activity.

Suitable arthropods from which to isolate a JHE formulation of the present invention include, but are not limited to agricultural pests, stored product pests, forest pests, structural pests or animal health pests. Suitable agricultural pests of the present invention include, but are not limited to Colorado potato beetles, corn earworms, fleahoppers, weevils, pink boll worms, cotton aphids, beet armyworms, lygus bugs, hessian flies, sod webworms, whites grubs, diamond back moths, white flies, planthoppers, leafhoppers, mealy bugs, mormon crickets and mole crickets. Suitable stored product pests of the present invention include, but are not limited to dermestids, anobeids, saw toothed grain beetles, indian mealmoths, flour beetles, long-horn wood boring beetles and metallic wood boring beetles. Suitable forest pests of the present invention include, but are not limited to southern pine bark bettles, gypsy moths, elm beetles, ambrosia bettles, bag worms, tent worms and tussock moths. Suitable structural pests of the present invention include, but are not limited to, bess beetles, termites, fire ants, carpenter ants, wasps, hornets, cockroaches, silverfish, *Musca domestica* and *Musca autumnalis*. Suitable animal health pests of the present invention include, but are not limited to fleas, ticks, mosquitoes, black flies, lice, true bugs, sand flies, Psychodidae, tsetse flies, sheep blow flies, cattle grub, mites, horn flies, heel flies, deer flies, Culicoides and warble flies. Preferred arthropods from which to isolate a JHE formulation of the present invention include fleas, midges, mosquitos, sand flies, black flies, horse flies, snipe flies, louse flies, horn flies, deer flies, tsetse flies, buffalo flies, blow flies, stable flies, myiasis-causing flies, biting gnats, lice, mites, bee, wasps, ants, true bugs and ticks, preferably fleas, ticks and blow flies, and more preferably fleas. Preferred fleas from which to isolate JHE proteins include Ctenocephalides, Ceratophyllus, Diamanus, Echidnophaga, Nosopsyllus, Pulex, Tunga, Oropsylla, Orchopeus and Xenopsylla. More preferred fleas include *Ctenocephalides felis, Ctenocephalides canis, Ceratophyl-*

*lus pulicidae, Pulex irritans, Oropsylla* (*Thrassis*) *bacchi, Oropsylla* (*Diamanus*) *montana, Orchopeus howardi, Xenopsylla cheopis* and *Pulex simulans*, with *C. felis* being even more preferred.

Suitable tissue from which to isolate a JHE formulation of the present invention includes unfed fleas or fleas that recently consumed a blood meal (i.e., blood-fed fleas). Such flea tissues are referred to herein as, respectively, unfed flea and fed flea tissue. Preferred flea tissue from which to obtain a JHE formulation of the present invention includes pre-pupal larval tissue, 3rd instar tissue, fed or unfed adult tissue, with unfed adult gut tissue being more preferred than fed or unfed whole adult tissue. It is of note that a JHE formulation of the present invention obtained from pre-pupal larval tissue does not hydrolyze α-napthyl acetate.

Another embodiment of the present invention is an esterase formulation comprising a combination of one or more arthropod CE and JHE proteins of the present invention. Suitable arthropods from which to isolate a combined CE and JHE formulation include those arthropods described herein for the isolation of a JHE formulation of the present invention. Preferred arthropods from which to isolate a combined CE and JHE formulation include fleas, midges, mosquitos, sand flies, black flies, horse flies, horn flies, deer flies, tsetse flies, buffalo flies, blow flies, stable flies, myiasis-causing flies, biting gnats, lice, bee, wasps, ants, true bugs and ticks, preferably fleas, ticks and blow flies, and more preferably fleas. Suitable flea tissue from which to isolate a combined CE and JHE formulation of the present invention includes 3rd instar tissue, fed or unfed adult tissue and unfed adult tissue, with unfed adult gut tissue being more preferred than fed or unfed whole adult tissue.

Another embodiment of the present invention is an isolated protein comprising an arthropod esterase protein. It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology or can be produced by chemical synthesis.

As used herein, an isolated arthropod esterase protein can be a full-length protein or any homolog of such a protein. An isolated protein of the present invention, including a homolog, can be identified in a straight-forward manner by the protein's ability to elicit an immune response against arthropod esterase proteins, to hydrolyze α-napthyl acetate, to hydrolyze the methyl ester group of juvenile hormone or bind to DFP. Esterase proteins of the present invention include CE and JHE proteins. As such, an esterase protein of the present invention can comprise a protein capable of hydrolyzing α-napthyl acetate, hydrolyzing the methyl ester group of juvenile hormone and/or binding to DFP. Examples of esterase homologs include esterase proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog includes at least one epitope capable of eliciting an immune response against an arthropod esterase protein. That is, when the homolog is administered to an animal as an immunogen, using techniques known to those skilled in the art, the animal will produce an immune response against at least one epitope of a natural arthropod esterase protein. The ability of a protein to effect an immune response, can be measured using techniques known to those skilled in the art. Esterase protein homologs of the present invention also include esterase proteins that hydrolyze α-napthyl acetate and/or that hydrolyze the methyl ester group of juvenile hormone.

Arthropod esterase protein homologs can be the result of natural allelic variation or natural mutation. Esterase protein homologs of the present invention can also be produced using techniques known in the art including, but not limited to, direct modifications to the protein or modifications to the gene encoding the protein using, for example, classic or recombinant nucleic acid techniques to effect random or targeted mutagenesis.

Isolated esterase proteins of the present invention have the further characteristic of being encoded by nucleic acid molecules that hybridize under stringent hybridization conditions to a gene encoding a *Ctenocephalides felis* protein (i.e., a *C. felis* esterase gene). As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual*, Cold Spring Harbor Labs Press, 1989; Sambrook et al., ibid., is incorporated by reference herein in its entirety. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., 1984, *Anal. Biochem.* 138, 267–284; Meinkoth et al., ibid., is incorporated by reference herein in its entirety.

As used herein, a *C. felis* esterase gene includes all nucleic acid sequences related to a natural *C. felis* esterase gene such as regulatory regions that control production of the *C. felis* esterase protein encoded by that gene (such as, but not limited to, transcription, translation or post-translation control regions) as well as the coding region itself. In one embodiment, a *C. felis* esterase gene of the present invention includes the nucleic acid sequence SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:17, SEQ ID NO:18, SEQ ID NO:20, SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:38, SEQ ID NO:51, SEQ ID NO:52, SEQ ID NO:57, SEQ ID NO:59, SEQ ID NO:60 and/or SEQ ID NO:61. Nucleic acid sequence SEQ ID NO:1 represents the deduced sequence of the coding strand of a PCR amplified nucleic acid molecule denoted herein as nfE1$_{401}$, the production of which is disclosed in the Examples. The complement of SEQ ID NO:1 (represented herein by SEQ ID NO:3) refers to the nucleic acid sequence of the strand complementary to the strand having SEQ ID NO:1, which can easily be determined by those skilled in the art. Likewise, a nucleic acid sequence complement of any nucleic acid sequence of the present invention refers to the nucleic acid sequence of the nucleic acid strand that is complementary to (i.e., can form a complete double helix with) the strand for which the sequence is cited.

Nucleic acid sequence SEQ ID NO:4 represents the deduced sequence of the coding strand of a PCR amplified nucleic acid molecule denoted herein as nfE2$_{364}$, the production of which is disclosed in the Examples. The complement of SEQ ID NO:4 is represented herein by SEQ ID NO:6.

Nucleic acid sequence SEQ ID NO:7 represents the deduced sequence of the coding strand of a PCR amplified nucleic acid molecule denoted herein as nfE3$_{421}$, the production of which is disclosed in the Examples. The complement of SEQ ID NO:7 is represented herein by SEQ ID NO:9.

Nucleic acid sequence SEQ ID NO:10 represents the deduced sequence of the coding strand of a PCR amplified nucleic acid molecule denoted herein as nfE4$_{524}$, the production of which is disclosed in the Examples. The complement of SEQ ID NO:10 is represented herein by SEQ ID NO:12.

Nucleic acid sequence SEQ ID NO:13 represents the deduced sequence of the coding strand of an apparent coding region of a complementary DNA (cDNA) nucleic acid molecule denoted herein as nfE5$_{1982}$, the production of which is disclosed in the Examples. The complement of SEQ ID NO:13 is represented herein by SEQ ID NO:15.

Nucleic acid sequence SEQ ID NO:18 represents the deduced sequence of the coding strand of an apparent coding region of a cDNA nucleic acid molecule denoted herein as nfE6$_{1792}$, the production of which is disclosed in the Examples. The complement of SEQ ID NO:18 is represented herein by SEQ ID NO:20.

Nucleic acid sequence SEQ ID NO:24 represents the deduced sequence of the coding strand of an apparent coding region of a cDNA nucleic acid molecule denoted herein as nfE7$_{2836}$, the production of which is disclosed in the Examples. The complement of SEQ ID NO:24 is represented herein by SEQ ID NO:26.

Nucleic acid sequence SEQ ID NO:30 represents the deduced sequence of the coding strand of an apparent coding region of a cDNA nucleic acid molecule denoted herein as nfE8$_{2801}$, the production of which is disclosed in the Examples. The complement of SEQ ID NO:30 is represented herein by SEQ ID NO:32.

Nucleic acid sequence SEQ ID NO:36 represents the deduced sequence of the coding strand of an apparent coding region of a cDNA nucleic acid molecule denoted herein as nfE9$_{2007}$, the production of which is disclosed in the Examples. The complement of SEQ ID NO:36 is represented herein by SEQ ID NO:38.

Nucleic acid sequence SEQ ID NO:57 represents the deduced sequence of the coding strand of an apparent coding region of a cDNA nucleic acid molecule denoted herein as nfE5$_{2144}$, the production of which is disclosed in the Examples. The complement of SEQ ID NO:57 is represented herein by SEQ ID NO:59.

It should be noted that since nucleic acid sequencing technology is not entirely error-free, the nucleic acid sequences and amino acid sequences presented herein represent, respectively, apparent nucleic acid sequences of nucleic acid molecules of the present invention and apparent amino acid sequences of esterase proteins of the present invention..

In another embodiment, a *C. felis* esterase gene can be an allelic variant that includes a similar but not identical sequence to SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:17, SEQ ID NO:18, SEQ ID NO:20, SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:38, SEQ ID NO:51, SEQ ID NO:52, SEQ ID NO:57, SEQ ID NO:59, SEQ ID NO:60 and/or SEQ ID NO:61. An allelic variant of a *C. felis* esterase gene is a gene that occurs at essentially the same locus (or loci) in the genome as the gene including SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:17, SEQ ID NO:18, SEQ ID NO:20, SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:38, SEQ ID NO:51, SEQ ID NO:52, SEQ ID NO:57, SEQ ID NO:59, SEQ ID NO:60 and/or SEQ ID NO:61, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given arthropod since the genome is diploid and/or among a group of two or more arthropods.

The minimal size of an esterase protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As such, the size of the nucleic acid molecule encoding such a protein homolog is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode an esterase protein homolog of the present invention is from about 12 to about 18 nucleotides in length. Thus, the minimal size of an esterase protein homolog of the present invention is from about 4 to about 6 amino acids in length. There is no limit, other than a practical limit, on the maximal size of such a nucleic acid molecule in that the nucleic acid molecule can include a portion of a gene, an entire gene, multiple genes, or portions thereof. The preferred size of a protein encoded by a nucleic acid molecule of the present invention depends on whether a full-length, fusion, multivalent, or functional portion of such a protein is desired.

One embodiment of the present invention includes an arthropod esterase protein having CE enzyme activity. Such a CE protein preferably includes: a catalytic triad of serine-histidine-glutamic acid as well as the essential amino acids arginine and aspartic acid at positions similar to those described for juvenile hormone esterase, for example by Ward et al., 1992, *Int J Biochem* 24: 1933–1941; this reference is incorporated by reference herein in its entirety. Analysis of the apparent full-length protein sequences disclosed herein indicates that each of these amino acid sequences includes these amino acid motifs, as well as surrounding consensus sequences.

Suitable arthropods from which to isolate esterase proteins having general CE activity of the present invention (including isolation of the natural protein or production of the protein by recombinant or synthetic techniques) preferably include insects and acarines but not Culicidae, Drosophilidae, Calliphoridae, Sphingidae, Lymantriidae, Noctuidae, Fulgoroidae and Aphididae. Preferred arthropods from which to isolate CE proteins having general CE activity include fleas, ticks, black flies, lice, true bugs, sand flies, Psychodidae, tsetse flies, cattle grub, mites, horn flies, heel flies, deer flies, Culicoides and warble flies. Preferred arthropods from which to isolate an esterase proteins having general CE activity include fleas, midges,, sand flies, black flies, horse flies, snipe flies, louse flies, horn flies, deer flies, tsetse flies, buffalo flies, blow flies, stable flies, myiasis-causing flies, biting gnats, lice, mites, bee, wasps, ants, true bugs and ticks, preferably fleas, ticks and blow flies, and more preferably fleas. Preferred fleas from which to isolate esterase proteins having general CE activity include Ctenocephalides, Ceratophyllus, Diamanus, Echidnophaga, Nosopsyllus, Pulex, Tunga, Oropsylla, Orchopeus and Xenopsylla. More preferred fleas include *Ctenocephalides felis, Ctenocephalides canis, Ceratophyllus pulicidae, Pulex irritans, Oropsylla* (*Thrassis*) *bacchi, Oropsylla* (*Diamanus*) *montana, Orchopeus howardi, Xenopsylla cheopis* and *Pulex simulans*, with *C. felis* being even more preferred.

A preferred arthropod esterase protein of the present invention is a compound that when administered to an animal in an effective manner, is capable of protecting that animal from hematophagous ectoparasite infestation. In accordance with the present invention, the ability of an esterase protein of the present invention to protect an animal from hematophagous ectoparasite infestation refers to the ability of that protein to, for example, treat, ameliorate and/or prevent infestation caused by hematophagous arthropods. In particular, the phrase "to protect an animal from hematophagous ectoparasite infestation" refers to reducing the potential for hematophagous ectoparasite population expansion on and around the animal (i.e., reducing the hematophagous ectoparasite burden). Preferably, the hematophagous ectoparasite population size is decreased, optimally to an extent that the animal is no longer bothered by hematophagous ectoparasites. A host animal, as used herein, is an animal from which hematophagous ectoparasites can feed by attaching to and feeding through the skin of the animal. Hematophagous ectoparasites, and other ectoparasites, can live on a host animal for an extended period of time or can attach temporarily to an animal in order to feed. At any given time, a certain percentage of a hematophagous ectoparasite population can be on a host animal whereas the remainder can be in the environment of the animal. Such an environment can include not only adult hematophagous ectoparasites, but also hematophagous ectoparasite eggs and/or hematophagous ectoparasite larvae. The environment can be of any size such that hematophagous ectoparasites in the environment are able to jump onto and off of a host animal. For example, the environment of an animal can include plants, such as crops, from which hematophagous ectoparasites infest an animal. As such, it is desirable not only to reduce the hematophagous ectoparasite burden on an animal per se, but also to reduce the hematophagous ectoparasite burden in the environment of the animal. In one embodiment, an esterase protein of the present invention can elicit an immune response (including a humoral and/or cellular immune response) against a hematophagous ectoparasite.

Suitable hematophagous ectoparasites to target include any hematophagous ectoparasite that is essentially incapable of infesting an animal administered an esterase protein of the present invention. As such, a hematophagous ectoparasite to target includes any hematophagous ectoparasite that produces a protein having one or more epitopes that can be targeted by a humoral and/or cellular immune response against an esterase protein of the present invention and/or that can be targeted by a compound that otherwise inhibits esterase activity (e.g., a compound that inhibits hydrolysis of α-napthyl acetate, hydrolysis of the methyl ester group of juvenile hormone, and/or binds to DFP), thereby resulting in the decreased ability of the hematophagous ectoparasite to infest an animal. Preferred hematophagous ectoparasite to target include ectoparasites disclosed herein as being useful in the production of esterase proteins of the present invention.

The present invention also includes mimetopes of esterase proteins of the present invention. As used herein, a mimetope of an esterase protein of the present invention refers to any compound that is able to mimic the activity of such a protein (e.g., ability to elicit an immune response against an arthropod esterase protein of the present invention and/or ability to inhibit esterase activity), often because the mimetope has a structure that mimics the esterase protein. It is to be noted, however, that the mimetope need not have a structure similar to an esterase protein as long as the mimetope functionally mimics the protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); synthetic or natural organic or inorganic molecules, including nucleic acids; and/or any other peptidomimetic compounds. Mimetopes of the present invention can be designed using computer-generated structures of esterase proteins of the present invention. Mimetopes can also be obtained by generating random samples of molecules, such as oligonucleotides, peptides or other organic molecules, and screening such samples by affinity chromatography techniques using the corresponding binding partner, (e.g., an esterase substrate, an esterase substrate analog, or an anti-esterase antibody). A preferred mimetope is a peptidomimetic compound that is structurally and/or functionally similar to an esterase protein of the present invention, particularly to the active site of the esterase protein.

The present invention also includes mimetopes of esterase proteins of the present invention. As used herein, a mimetope of an esterase protein of the present invention refers to any compound that is able to mimic the activity of such an esterase protein, often because the mimetope has a structure that mimics the esterase protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of an arthropod esterase protein of the present invention is a fusion protein that includes an arthropod esterase protein-containing domain attached to one or more fusion segments. Suitable fusion segments for use with the present invention include, but are not limited to, segments that can: enhance a protein's stability; act as an immunopotentiator to enhance an immune response against an esterase protein; and/or assist purification of an esterase protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the esterase-containing domain of the protein and can be susceptible to cleavage in order to enable straight-forward recovery of an esterase protein. Fusion proteins are preferably produced by culturing a recombinant cell transformed with a fusion nucleic acid molecule that encodes a protein including the fusion segment attached to either the carboxyl and/or amino terminal end of an esterase-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide. Examples of particularly preferred fusion proteins of the present invention include PHIS-PfE7$_{570}$ and PHIS-PfE8$_{570}$, production of which are disclosed herein.

In another embodiment, an arthropod esterase protein of the present invention also includes at least one additional protein segment that is capable of protecting an animal from hematophagous ectoparasite infestations. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from hematophagous ectoparasite infestation by, for example, targeting two different arthropod proteins.

Examples of multivalent protective compounds include, but are not limited to, an esterase protein of the present invention attached to one or more compounds protective against one or more arthropod compounds. Preferred second compounds are proteinaceous compounds that effect active immunization (e.g., antigen vaccines), passive immunization (e.g., antibodies), or that otherwise inhibit a arthropod activity that when inhibited can reduce hematophagous ectoparasite burden on and around an animal. Examples of second compounds include a compound that inhibits binding between an arthropod protein and its ligand (e.g., a compound that inhibits flea ATPase activity or a compound that inhibits binding of a peptide or steroid hormone to its receptor), a compound that inhibits hormone (including peptide or steroid hormone) synthesis, a compound that inhibits vitellogenesis (including production of vitellin and/or transport and maturation thereof into a major egg yolk protein), a compound that inhibits fat body function, a compound that inhibits muscle action, a compound that inhibits the nervous system, a compound that inhibits the immune system and/or a compound that inhibits hematophagous ectoparasite feeding. Examples of second compounds also include proteins obtained from different stages of hematophagous ectoparasite development. Particular examples of second compounds include, but are not limited to, serine proteases, cysteine proteases, aminopeptidases, serine protease inhibitor proteins, calreticulins, larval serum proteins and echdysone receptors, as well as antibodies to and inhibitors of such proteins. In one embodiment, an arthropod esterase protein of the present invention is attached to one or more additional compounds protective against hematophagous ectoparasite infestation. In another embodiment, one or more protective compounds, such as those listed above, can be included in a multivalent vaccine comprising an arthropod esterase protein of the present invention and one or more other protective molecules as separate compounds.

A preferred isolated protein of the present invention is a protein encoded by a nucleic acid molecule that hybridizes under stringent hybridization conditions with nucleic acid molecules nfE1$_{401}$, nfE2$_{364}$, nfE3$_{421}$, nfE4$_{524}$, nfE5$_{1982}$, nfE5$_{1515}$, nfE5$_{2144}$, nfE5$_{1650}$, nfE6$_{1792}$, nfE6$_{1650}$, nfE7$_{2836}$, nfE7$_{1788}$, nfE7$_{1710}$, nfE8$_{2801}$, nfE8$_{1785}$, nfE8$_{1710}$, nfE9$_{2007}$ and/or nfE9$_{1584}$. A further preferred isolated protein is encoded by a nucleic acid molecule that hybridizes under stringent hybridization conditions with a nucleic acid molecule having nucleic acid sequence SEQ ID NO:3, SEQ ID NO:6, SEQ ID NO:9, SEQ ID NO:12, SEQ ID NO:15, SEQ ID NO:17, SEQ ID NO:20, SEQ ID NO:22, SEQ ID NO:26, SEQ ID NO:29, SEQ ID NO:32, SEQ ID NO:35, SEQ ID NO:38, SEQ ID NO:52, SEQ ID NO:59 and/or SEQ ID NO:61.

Translation of SEQ ID NO:1 suggests that nucleic acid molecule nfE1$_{401}$ encodes a non-full-length arthropod esterase protein of about 103 amino acids, referred to herein as PfE1$_{103}$, represented by SEQ ID NO:2, assuming the first codon spans from about nucleotide 92 through about nucleotide 94 of SEQ ID NO:1.

Comparison of amino acid sequence SEQ ID NO:2 (i.e., the amino acid sequence of PfE1$_{103}$) with amino acid sequences reported in GenBank indicates that SEQ ID NO:2, showed the most homology, i.e., about 33% identity, between SEQ ID NO:2 and alpha esterase protein from *Drosophila melanogaster.*

Translation of SEQ ID NO:4 suggests that nucleic acid molecule nfE2$_{364}$ encodes a non-full-length arthropod esterase protein of about 121 amino acids, referred to herein as PfE2$_{121}$, represented by SEQ ID NO:5, assuming the first codon spans from about nucleotide 2 through about nucleotide 4 of SEQ ID NO:4.

Comparison of amino acid sequence SEQ ID NO:5 (i.e., the amino acid sequence of PfE2$_{121}$) with amino acid sequences reported in GenBank indicates that SEQ ID NO:5, showed the most homology, i.e., about 38% identity, between SEQ ID NO:5 and alpha esterase protein from *Drosophila melanogaster*.

Translation of SEQ ID NO:7 suggests that nucleic acid molecule $nfE3_{421}$ encodes a non-full-length arthropod esterase protein of about 103 amino acids, referred to herein as $PfE3_{103}$, represented by SEQ ID NO:8, assuming the first codon spans from about nucleotide 113 through about nucleotide 115 of SEQ ID NO:7.

Comparison of amino acid sequence SEQ ID NO:8 (i.e., the amino acid sequence of $PfE3_{103}$) with amino acid sequences reported in GenBank indicates that SEQ ID NO:8, showed the most homology, i.e., about 39% identity, between SEQ ID NO:8 and alpha esterase protein from *Drosophila melanogaster*.

Translation of SEQ ID NO:10 suggests that nucleic acid molecule $nfE4_{524}$ encodes a non-full-length arthropod esterase protein of about 137 amino acids, referred to herein as $PfE4_{137}$, represented by SEQ ID NO:11, assuming the first codon spans from about nucleotide 113 through about nucleotide 115 of SEQ ID NO:10.

Comparison of amino acid sequence SEQ ID NO:11 (i.e., the amino acid sequence of $PfE4_{137}$) with amino acid sequences reported in GenBank indicates that SEQ ID NO:11, showed the most homology, i.e., about 30% identity, between SEQ ID NO:11 and *Leptinotarsa decemlineata* acetylcholinesterase.

Translation of SEQ ID NO:57 suggests that nucleic acid molecule $nfE5_{2144}$ encodes a full-length arthropod esterase protein of about 550 amino acids, referred to herein as $PfE5_{550}$, represented by SEQ ID NO:58, assuming an open reading frame in which the initiation codon spans from about nucleotide 30 through about nucleotide 32 of SEQ ID NO:57 and the termination (stop) codon spans from about nucleotide 1680 through about nucleotide 1682 of SEQ ID NO:57. The complement of SEQ ID NO:57 is represented herein by SEQ ID NO:59. The coding region encoding $PfE5_{550}$ is represented by the nucleic acid molecule $nfE5_{1650}$, having a coding strand with the nucleic acid sequence represented by SEQ ID NO:60 and a complementary strand with nucleic acid sequence SEQ ID NO:61. The deduced amino acid sequence of $PfE5_{550}$ (i.e., SEQ ID NO:58) predicts that $PfE5_{550}$ has an estimated molecular weight of about 61.8 kD and an estimated pI of about 5.5.

Comparison of amino acid sequence SEQ ID NO:58 (i.e., the amino acid sequence of $PfE5_{550}$) with amino acid sequences reported in GenBank indicates that SEQ ID NO:58 showed the most homology, i.e., about 36% identity between SEQ ID NO:58 and *Drosophila melanogaster* alpha esterase protein.

Translation of SEQ ID NO:18 suggests that nucleic acid molecule $nfE6_{1792}$ encodes a full-length arthropod esterase protein of about 550 amino acids, referred to herein as $PfE6_{550}$, represented by SEQ ID NO:19, assuming an open reading frame having an initiation codon spanning from about nucleotide 49 through about nucleotide 51 of SEQ ID NO:18 and a stop codon spanning from about nucleotide 1699 through about nucleotide 1701 of SEQ ID NO:18. The coding region encoding $PfE6_{550}$, is represented by nucleic acid molecule $nfE6_{1650}$, having a coding strand with the nucleic acid sequence represented by SEQ ID NO:21 and a complementary strand with nucleic acid sequence SEQ ID NO:22. The proposed mature protein, denoted herein as $PfE6_{530}$, contains about 530 amino acids which is represented herein as SEQ ID NO:53. The nucleic acid molecule encoding $PfE6_{530}$ is denoted herein as $nfE6_{1590}$ and has a coding strand having the nucleic acid sequence SEQ ID NO:23. The deduced amino acid sequence SEQ ID NO:19 suggests a protein having a molecular weight of about 61.8 kD and an estimated pI of about 5.5.

Comparison of amino acid sequence SEQ ID NO:19 (i.e., the amino acid sequence of $PfE6_{550}$) with amino acid sequences reported in GenBank indicates that SEQ ID NO:19 showed the most homology, i.e., about 28% identity between SEQ ID NO:19 and *Drosophila melanogaster* alpha esterase protein.

Translation of SEQ ID NO:24 suggests that nucleic acid molecule $nfE7_{2836}$ encodes a full-length arthropod esterase protein of about 596 amino acids, referred to herein as $PfE7_{596}$, represented by SEQ ID NO:25, assuming an open reading frame having an initiation codon spanning from about nucleotide 99 through about nucleotide 101 of SEQ ID NO:24 and a stop codon spanning from about nucleotide 1887 through about nucleotide 1889 of SEQ ID NO:24. The coding region encoding $PfE7_{596}$, is represented by nucleic acid molecule $nfE7_{1788}$, having a coding strand with the nucleic acid sequence represented by SEQ ID NO:28 and a complementary strand with nucleic acid sequence SEQ ID NO:29. The proposed mature protein, denoted herein as $PfE7_{570}$, contains about 570 amino acids which is represented herein as SEQ ID NO:54. The nucleic acid molecule encoding $PfE7_{570}$ is denoted herein as $nfE7_{1710}$ and has a coding strand having the nucleic acid sequence SEQ ID NO:27. The deduced amino acid sequence SEQ ID NO:25 suggests a protein having a molecular weight of about 68.7 kD and an estimated pI of about 6.1.

Comparison of amino acid sequence SEQ ID NO:25 (i.e., the amino acid sequence of $PfE7_{596}$) with amino acid sequences reported in GenBank indicates that SEQ ID NO:25 showed the most homology, i.e., about 27% identity between SEQ ID NO:25 and *Drosophila melanogaster* alpha esterase protein.

Translation of SEQ ID NO:30 suggests that nucleic acid molecule $nfE8_{2801}$ encodes a full-length arthropod esterase protein of about 595 amino acids, referred to herein as $PfE8_{595}$, represented by SEQ ID NO:31, assuming an open reading frame having an initiation codon spanning from about nucleotide 99 through about nucleotide 101 of SEQ ID NO:30 and a stop codon spanning from about nucleotide 1884 through about nucleotide 1886 of SEQ ID NO:30. The coding region encoding $PfE8_{595}$, is represented by nucleic acid molecule $nfE8_{1785}$, having a coding strand with the nucleic acid sequence represented by SEQ ID NO:34 and a complementary strand with nucleic acid sequence SEQ ID NO:35. The proposed mature protein, denoted herein as $PfE8_{570}$, contains about 570 amino acids which is represented herein as SEQ ID NO:55. The nucleic acid molecule encoding $PfE8_{570}$ is denoted herein as $nfE8_{1710}$ and has a coding strand having the nucleic acid sequence SEQ ID NO:33. The deduced amino acid sequence SEQ ID NO:31 suggests a protein having a molecular weight of about 68.6 kD and an estimated pI of about 6.1.

Comparison of amino acid sequence SEQ ID NO:31 (i.e., the amino acid sequence of $PfE8_{595}$) with amino acid sequences reported in GenBank indicates that SEQ ID NO:31 showed the most homology, i.e., about 28% identity between SEQ ID NO:31 and estalpha-2 esterase of *Culex pipiens quinquefasciatus*.

Translation of SEQ ID NO:36 suggests that nucleic acid molecule $nfE9_{2007}$ encodes a full-length arthropod esterase protein of about 528 amino acids, referred to herein as PfE9$_{528}$, represented by SEQ ID NO:37, assuming an open reading frame having an initiation codon spanning from about nucleotide 11 through about nucleotide 13 of SEQ ID NO:36 and a stop codon spanning from about nucleotide 1595 through about nucleotide 1597 of SEQ ID NO:36. The coding region encoding PfE9$_{528}$, is represented by nucleic acid molecule nfE9$_{1584}$, having a coding strand with the nucleic acid sequence represented by SEQ ID NO:51 and a complementary strand with nucleic acid sequence SEQ ID NO:52. The deduced amino acid sequence SEQ ID NO:37 suggests a protein having a molecular weight of about 60 kD and an estimated pI of about 5.43.

Comparison of amino acid sequence SEQ ID NO:37 (i.e., the amino acid sequence of PfE9$_{528}$) with amino acid sequences reported in GenBank indicates that SEQ ID NO:37 showed the most homology, i.e., about 37% identity between SEQ ID NO:37 and alpha esterase protein from *Drosophila melanogaster.*

More preferred arthropod esterase proteins of the present invention include proteins comprising amino acid sequences that are at least about 40%, preferably at least about 45%, more preferably at least about 50%, even more preferably at least about 55%, even more preferably at least about 60%, even more preferably at least about 70%, even more preferably at least about 80%, even more preferably at least about 90%, and even more preferably at least about 95%, identical to amino acid sequence SEQ ID NO:2, SEQ ID NO:5, SEQ ID NO:8, SEQ ID NO:11, SEQ ID NO:14, SEQ ID NO:19, SEQ ID NO:25, SEQ ID NO:31, SEQ ID NO:37, SEQ ID NO:39, SEQ ID NO:40, SEQ ID NO:41, SEQ ID NO:42, SEQ ID NO:43, SEQ ID NO:44, SEQ ID NO:53, SEQ ID NO:54, SEQ ID NO:55 and/or SEQ ID NO:58.

More preferred arthropod esterase proteins of the present invention include proteins encoded by a nucleic acid molecule comprising at least a portion of nfE1$_{401}$, nfE2$_{364}$, nfE3$_{421}$, nfE4$_{524}$, nfE5$_{1982}$, nfE5$_{1515}$, nfE5$_{2144}$, nfE5$_{1650}$, nfE6$_{1792}$, nfE6$_{1650}$, nfE7$_{2836}$, nfE7$_{1788}$, nfE7$_{1710}$, nfE8$_{2801}$, nfE8$_{1785}$, nfE8$_{1710}$, nfE9$_{2007}$ and/or nfE9$_{1584}$, or of allelic variants of such nucleic acid molecules. More preferred is an esterase protein encoded by nfE1$_{401}$, nfE2$_{364}$, nfE3$_{421}$, nfE4$_{524}$, nfE5$_{1982}$, nfE5$_{1515}$, nfE5$_{2144}$, nfE5$_{1650}$, nfE6$_{1792}$, nfE6$_{1650}$, nfE7$_{2836}$, nfE7$_{1788}$, nfE7$_{1710}$, nfE8$_{2801}$, nfE5$_{1785}$, nfE8$_{1710}$, nfE9$_{2007}$ and/or nfE9$_{1584}$, or by an allelic variant of such nucleic acid molecules. Particularly preferred arthropod esterase proteins are PfE1$_{103}$, PfE2$_{121}$, PfE3$_{103}$, PfE4$_{137}$, PfE5$_{505}$, PfE5$_{550}$, PfE6$_{550}$, PfE6$_{530}$, PfE7$_{596}$, PfE7$_{570}$, PfE8$_{595}$, PfE8$_{570}$, and PfE9$_{528}$.

In one embodiment, a preferred esterase protein of the present invention is encoded by at least a portion of SEQ ID NO:1, SEQ ID NO:4, SEQ ID NO:7, SEQ ID NO:10, SEQ ID NO:13, SEQ ID NO:16, SEQ ID NO:18, SEQ ID NO:21, SEQ ID NO:23, SEQ ID NO:24, SEQ ID NO:27, SEQ ID NO:28, SEQ ID NO:30, SEQ ID NO:33, SEQ ID NO:34, SEQ ID NO:36, SEQ ID NO:51, SEQ ID NO:57 and/or SEQ ID NO:60, and, as such, has an amino acid sequence that includes at least a portion of SEQ ID NO:2, SEQ ID NO:5, SEQ ID NO:8, SEQ ID NO:11, SEQ ID NO:14, SEQ ID NO:19, SEQ ID NO:25, SEQ ID NO:31, SEQ ID NO:37, SEQ ID NO:53, SEQ ID NO:54, SEQ ID NO:55 and/or SEQ ID NO:58. Also preferred is a protein encoded by an allelic variant of a nucleic acid molecule comprising at least a portion of the above-listed nucleic acid sequences.

Particularly preferred esterase proteins of the present invention include SEQ ID NO:2, SEQ ID NO:5, SEQ ID NO:8, SEQ ID NO:11, SEQ ID NO:14, SEQ ID NO:19, SEQ ID NO:25, SEQ ID NO:31, SEQ ID NO:37, SEQ ID NO:39, SEQ ID NO:40, SEQ ID NO:41, SEQ ID NO:42, SEQ ID NO:43, SEQ ID NO:44, SEQ ID NO:53, SEQ ID NO:54, SEQ ID NO:55 and/or SEQ ID NO:58 (including, but not limited to, the proteins consisting of such sequences, fusion proteins and multivalent proteins) and proteins encoded by allelic variants of SEQ ID NO:1, SEQ ID NO:4, SEQ ID NO:7, SEQ ID NO:10, SEQ ID NO:13, SEQ ID NO:16, SEQ ID NO:18, SEQ ID NO:21, SEQ ID NO:23, SEQ ID NO:24, SEQ ID NO:27, SEQ ID NO:28, SEQ ID NO:30, SEQ ID NO:33, SEQ ID NO:34, SEQ ID NO:36, SEQ ID NO:51, SEQ ID NO:57 and/or SEQ ID NO:60.

Another embodiment of the present invention is an isolated nucleic acid molecule that hybridizes under stringent hybridization conditions with a *C. felis* esterase gene. The identifying characteristics of such a gene are heretofore described. A nucleic acid molecule of the present invention can include an isolated natural arthropod esterase gene or a homolog thereof, the latter of which is described in more detail below. A nucleic acid molecule of the present invention can include one or more regulatory regions, full-length or partial coding regions, or combinations thereof. The minimal size of a nucleic acid molecule of the present invention is the minimal size that can form a stable hybrid with a *C. felis* esterase gene under stringent hybridization conditions.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated arthropod esterase nucleic acid molecule of the present invention can be isolated from its natural source or can be produced using recombinant DNA technology (e.g., polymerase chain reaction (PCR) amplification, cloning) or chemical synthesis. Isolated esterase nucleic acid molecules can include, for example, natural allelic variants and nucleic acid molecules modified by nucleotide insertions, deletions, substitutions, and/or inversions in a manner such that the modifications do not substantially interfere with the nucleic acid molecule's ability to encode an esterase protein of the present invention or to form stable hybrids under stringent conditions with natural gene isolates.

An arthropod esterase nucleic acid molecule homolog can be produced using a number of methods known to those skilled in the art (see, for example, Sambrook et al., ibid.). For example, nucleic acid molecules can be modified using a variety of techniques including, but not limited to, classic mutagenesis and recombinant DNA techniques (e.g., site-directed mutagenesis, chemical treatment, restriction enzyme cleavage, ligation of nucleic acid fragments and/or PCR amplification), synthesis of oligonucleotide mixtures and ligation of mixture groups to "build" a mixture of nucleic acid molecules and combinations thereof. Nucleic acid molecule homologs can be selected by hybridization with a *C. felis* esterase gene or by screening for the function of a protein encoded by the nucleic acid molecule (e.g., ability to elicit an immune response against at least one epitope of an arthropod esterase protein, hydrolyze α-napthyl acetate, hydrolyze the methyl ester group of juvenile hormone and/or bind to DFP).

An isolated nucleic acid molecule of the present invention can include a nucleic acid sequence that encodes at least one arthropod esterase protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding an arthropod esterase protein.

A preferred nucleic acid molecule of the present invention, when administered to an animal, is capable of protecting that animal from infestation by a hematophagous ectoparasite. As will be disclosed in more detail below, such a nucleic acid molecule can be, or can encode, an antisense RNA, a molecule capable of triple helix formation, a ribozyme, or other nucleic acid-based drug compound. In additional embodiments, a nucleic acid molecule of the present invention can encode a protective esterase protein (e.g., an esterase protein of the present invention), the nucleic acid molecule being delivered to the animal, for example, by direct injection (i.e, as a naked nucleic acid) or in a vehicle such as a recombinant virus vaccine or a recombinant cell vaccine.

One embodiment of the present invention is an esterase nucleic acid molecule that hybridizes under stringent hybridization conditions with nucleic acid molecule $nfE1_{401}$ and preferably with a nucleic acid molecule having nucleic acid sequence SEQ ID NO:1 and/or SEQ ID NO:3.

Another embodiment of the present invention is an esterase nucleic acid molecule that hybridizes under stringent hybridization conditions with nucleic acid molecule $nfE2_{364}$ and preferably with a nucleic acid molecule having nucleic acid sequence SEQ ID NO:4 and/or SEQ ID NO:6.

Another embodiment of the present invention is an esterase nucleic acid molecule that hybridizes under stringent hybridization conditions with nucleic acid molecule $nfE3_{421}$ and preferably with a nucleic acid molecule having nucleic acid sequence SEQ ID NO:7 and/or SEQ ID NO:9.

Another embodiment of the present invention is an esterase nucleic acid molecule that hybridizes under stringent hybridization conditions with nucleic acid molecule $nfE4_{524}$ and preferably with a nucleic acid molecule having nucleic acid sequence SEQ ID NO:10 and/or SEQ ID NO:12.

Another embodiment of the present invention is an esterase nucleic acid molecule that hybridizes under stringent hybridization conditions with nucleic acid molecule $nfE5_{2144}$ and preferably with a nucleic acid molecule having nucleic acid sequence SEQ ID NO:57 and/or SEQ ID NO:59.

Another embodiment of the present invention is an esterase nucleic acid molecule that hybridizes under stringent hybridization conditions with nucleic acid molecule $nfE6_{1792}$ and preferably with a nucleic acid molecule having nucleic acid sequence SEQ ID NO:18 and/or SEQ ID NO:20.

Another embodiment of the present invention is an esterase nucleic acid molecule that hybridizes under stringent hybridization conditions with nucleic acid molecule $nfE7_{2836}$ and preferably with a nucleic acid molecule having nucleic acid sequence SEQ ID NO:24 and/or SEQ ID NO:26.

Another embodiment of the present invention is an esterase nucleic acid molecule that hybridizes under stringent hybridization conditions with nucleic acid molecule $nfE8_{2801}$ and preferably with a nucleic acid molecule having nucleic acid sequence SEQ ID NO:30 and/or SEQ ID NO:32.

Another embodiment of the present invention is an esterase nucleic acid molecule that hybridizes under stringent hybridization conditions with nucleic acid molecule $nfE9_{2007}$ and preferably with a nucleic acid molecule having nucleic acid sequence SEQ ID NO:36 and/or SEQ ID NO:38.

Comparison of nucleic acid sequence SEQ ID NO:1 (i.e., the nucleic acid sequence of $nfE1_{401}$) with nucleic acid sequences reported in GenBank indicates that SEQ ID NO:1 showed no identifiable identity with any sequence reported in GenBank.

Comparison of nucleic acid sequence SEQ ID NO:4 (i.e., the coding strand of nucleic acid sequence of $nfE2_{364}$) with nucleic acid sequences reported in GenBank indicates that SEQ ID NO:4 showed the most homolog, i.e., about 43% identity, between SEQ ID NO:4 and a *H. virescens* juvenile hormone esterase gene.

Comparison of nucleic acid sequence SEQ ID NO:7 (i.e., the coding strand of nucleic acid sequence of $nfE3_{421}$) with nucleic acid sequences reported in GenBank indicates that SEQ ID NO:7 showed the most homolog, i.e., about 53% identity, between SEQ ID NO:7 and a *Torpedo marmorata* acetylcholinesterase gene.

Comparison of nucleic acid sequence SEQ ID NO:10 (i.e., the coding strand of nucleic acid sequence of $nfE4_{524}$) with nucleic acid sequences reported in GenBank indicates that SEQ ID NO:10 showed the most homolog, i.e., about 47% identity, between SEQ ID NO:10 and an *Anas platyrhyncos* thioesterase B gene.

Comparison of nucleic acid sequence SEQ ID NO:57 (i.e., the coding strand of nucleic acid sequence of $nfE5_{2144}$) with nucleic acid sequences reported in GenBank indicates that SEQ ID NO:57 showed the most homolog, i.e., about 41% identity, between SEQ ID NO:57 and a esterase mRNA from *Myzus persicae*.

Comparison of nucleic acid sequence SEQ ID NO:18 (i.e., the coding strand of nucleic acid sequence of $nfE6_{1792}$) with nucleic acid sequences reported in GenBank indicates that SEQ ID NO:18 showed the most homolog, i.e., about 41% identity, between SEQ ID NO:18 and a esterase gene from *Myzus persicae*.

Comparison of nucleic acid sequence SEQ ID NO:24 (i.e., the coding strand of nucleic acid sequence of $nfE7_{2836}$) with nucleic acid sequences reported in GenBank indicates that SEQ ID NO:24 showed the most homolog, i.e., about 48% identity, between SEQ ID NO:24 and an *Anas platychyncos* thioesterase B gene.

Comparison of nucleic acid sequence SEQ ID NO:30 (i.e., the coding strand of nucleic acid sequence of $nfE8_{2801}$) with nucleic acid sequences reported in GenBank indicates that SEQ ID NO:30 showed the most homolog, i.e., about 46% identity, between SEQ ID NO:30 and a *Mus musculus* carboxyl ester lipase gene.

Comparison of nucleic acid sequence SEQ ID NO:36 (i.e., the coding strand of nucleic acid sequence of $nfE9_{2007}$) with nucleic acid sequences reported in GenBank indicates that SEQ ID NO:36 showed the most homolog, i.e., about 47% identity, between SEQ ID NO:36 and a hamster mRNA for CE precursor gene.

Preferred arthropod esterase nucleic acid molecules include nucleic acid molecules having a nucleic acid sequence that is at least about 55%, preferably at least about 60%, more preferably at least about 65%, more preferably at least about 70%, more preferably at least about 75%, more preferably at least about 80%, more preferably at least about 90%, and even more preferably at least about 95% identical to nucleic acid sequence SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:17, SEQ ID NO:18, SEQ ID NO:20, SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:38, SEQ ID NO:51, SEQ ID NO:52, SEQ ID NO:57, SEQ ID NO:59, SEQ ID NO:60 and/or SEQ ID NO:61.

Another preferred nucleic acid molecule of the present invention includes at least a portion of nucleic acid sequence SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:17, SEQ ID NO:18, SEQ ID NO:20, SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:38, SEQ ID NO:51, SEQ ID NO:52, SEQ ID NO:57, SEQ ID NO:59, SEQ ID NO:60 and/or SEQ ID NO:61, that is capable of hybridizing to a *C. felis* esterase gene of the present invention, as well as allelic variants thereof. A more preferred nucleic acid molecule includes the nucleic acid sequence SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:17, SEQ ID NO:18, SEQ ID NO:20, SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:38, SEQ ID NO:51, SEQ ID NO:52, SEQ ID NO:57, SEQ ID NO:59, SEQ ID NO:60 and/or SEQ ID NO:61, as well as allelic variants thereof. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound. Particularly preferred nucleic acid molecules include $nfE1_{401}$, $nfE2_{364}$, $nfE3_{421}$, $nfE4_{524}$, $nfE5_{1982}$, $nfE5_{1515}$, $nfE5_{2144}$, $nfE5_{1650}$, $nfE6_{1792}$, $nfE6_{1650}$, $nfE7_{2836}$, $nfE7_{1788}$, $nfE7_{1710}$, $nfE8_{2801}$, $nfE8_{1785}$, $nfE8_{1710}$, $nfE9_{2007}$ and $nfE9_{1584}$.

The present invention also includes a nucleic acid molecule encoding a protein having at least a portion of SEQ ID NO:2, SEQ ID NO:5, SEQ ID NO:8, SEQ ID NO:11, SEQ ID NO:14, SEQ ID NO:19, SEQ ID NO:25, SEQ ID NO:31, SEQ ID NO:37, SEQ ID NO:39, SEQ ID NO:40, SEQ ID NO:41, SEQ ID NO:42, SEQ ID NO:43, SEQ ID NO:44, SEQ ID NO:53, SEQ ID NO:54, SEQ ID NO:55 and/or SEQ ID NO:58, including nucleic acid molecules that have been modified to accommodate codon usage properties of the cells in which such nucleic acid molecules are to be expressed.

Knowing the nucleic acid sequences of certain arthropod esterase nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain esterase nucleic acid molecules from other arthropods. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify nucleic acid molecule include flea pre-pupal, 3rd instar or adult cDNA libraries as well as genomic DNA libraries. Similarly, preferred DNA sources to screen or from which to amplify nucleic acid molecules include flea pre-pupal, 3rd instar or adult cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising arthropod esterase genes or other arthropod esterase nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. Minimal size characteristics are disclosed herein. The present invention includes oligonucleotides that can be used as, for example, probes to identify nucleic acid molecules, primers to produce nucleic acid molecules or therapeutic reagents to inhibit esterase protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulation of arthropod esterase nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, insect, other animal, and plant cells. Preferred expression vectors of the present invention can direct gene expression in bacterial, yeast, insect and mammalian cells and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with arthropods, such as, *C. felis.*

Suitable and preferred nucleic acid molecules to include in recombinant vectors of the present invention are as disclosed herein. Preferred nucleic acid molecules to include in recombinant vectors, and particularly in recombinant molecules, include $nfE1_{401}$, $nfE2_{364}$, $nfE3_{421}$, $nfE4_{524}$, $nfE5_{1982}$, $nfE5_{1515}$, $nfE5_{2144}$, $nfE5_{1650}$, $nfE6_{1792}$, $nfE6_{1650}$, $nfE7_{2836}$, $nfE7_{1788}$, $nfE7_{1710}$, $nfE8_{2801}$, $nfE8_{1785}$, $nfE8_{1710}$, $nfE9_{2007}$ and/or $nfE9_{1584}$. Particularly preferred recombinant molecules of the present invention include pTrc-$nfE7_{1710}$, pTrc-$nfE8_{1710}$, pTrc-$nfE5_{1650}$, pTrc-$nE9_{1584}$, pVL-$nfE7_{1802}$ and pVL-$nfE8_{1792}$, the production of which are described in the Examples section.

Recombinant molecules of the present invention may also (a) contain secretory signals (i.e., signal segment nucleic acid sequences) to enable an expressed arthropod protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments, as well as natural signal sequences. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include arthropod esterase nucleic acid molecules disclosed herein. Particularly preferred nucleic acid molecules with which to transform a cell include $nfE1_{401}$, $nfE2_{364}$, $nfE3_{421}$, $nfE4_{524}$, $nfE5_{1982}$, $nfE5_{1515}$, $nfE5_{2144}$, $nfE5_{1650}$, $nfE6_{1792}$, $nfE6_{1650}$, $nfE7_{2836}$, $nfE7_{1788}$, $nfE7_{1710}$, $nfE8_{2801}$, $nfE8_{1785}$, $nfE8_{1710}$, $nfE9_{2007}$ and/or $nfE9_{1584}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing arthropod esterase proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite, other insect, other animal and plant cells. Preferred host cells include bacterial, mycobacterial, yeast, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi; Salmonella typhimurium*, including attenuated strains such as UK-$1_x$3987 and SR-$11_x$4072; *Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein. Particularly preferred recombinant molecules include pTrc-nfE7$_{1710}$, pTrc-nfE8$_{1710}$, pTrc-nfE5$_{1650}$, pTrc-nPfE9$_{1584}$, pVL-nfE7$_{1802}$ and pVL-nfE8$_{1792}$.

A recombinant cell of the present invention includes any cell transformed with at least one of any nucleic acid molecule of the present invention. Suitable and preferred nucleic acid molecules as well as suitable and preferred recombinant molecules with which to transform cells are disclosed herein. Particularly preferred recombinant cells include $E.$ $coli$:pTrc-nfE7$_{1710}$, $E.$ $coli$:pTrc-nfE8$_{1710}$, $E.$ $coli$:pTrc-nfE5$_{1650}$, $E.$ $coli$:pTrc-nfE9$_{1584}$, $S.$ $frugiperda$:pVL-nfE7$_{1802}$ and $S.$ $frugiperda$:pVL-nfE8$_{1792}$. Details regarding the production of these recombinant cells are disclosed herein.

Recombinant cells of the present invention can also be co-transformed with one or more recombinant molecules including arthropod esterase nucleic acid molecules encoding one or more proteins of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated esterase proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce an arthropod esterase protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in $E.$ $coli$; or be retained on the outer surface of a cell or viral membrane. The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to an arthropod esterase protein of the present invention or a mimetope thereof (i.e., anti-arthropod esterase antibodies). As used herein, the term "selectively binds to" an esterase protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid. An anti-arthropod esterase antibody preferably selectively binds to an arthropod esterase protein in such a way as to reduce the activity of that protein.

Isolated antibodies of the present invention can include antibodies in a bodily fluid (such as, but not limited to, serum), or antibodies that have been purified to varying degrees. Antibodies of the present invention can be polyclonal or monoclonal, functional equivalents such as antibody fragments and genetically-engineered antibodies, including single chain antibodies or chimeric antibodies that can bind to more than one epitope.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce arthropod esterase proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from arthropods susceptible to treatment by such antibodies and/or (b) as tools to screen expression libraries and/or to recover desired proteins of the present invention from a mixture of proteins and other contaminants. Furthermore, antibodies of the present invention can be used to target cytotoxic agents to hematophagous ectoparasites such as those discloses herein, in order to directly kill such hematophagous ectoparasites. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from infestation by hematophagous ectoparasite. Therapeutic compositions of the present invention include at least one of the following protective compounds: an isolated hematophagous arthropod esterase protein (including a peptide); a mimetope of such a protein; an isolated nucleic acid molecule that hybridizes under stringent hybridization conditions with a *Ctenocephalides felis* esterase gene; an isolated antibody that selectively binds to an hematophagous arthropod esterase protein; and inhibitors of hematophagous arthropod esterase activity (including esterase substrate analogs). As used herein, a protective compound refers to a compound that, when administered to an animal in an effective manner, is able to treat, ameliorate, and/or prevent disease caused by an arthropod of the present invention. Preferred arthropods to target are heretofore disclosed. Examples of proteins, nucleic acid molecules, antibodies and inhibitors of the present invention are disclosed herein.

A preferred therapeutic composition of the present invention includes at least one of the following protective compounds: an isolated hematophagous ectoparasite carboxylesterase protein (including a peptide); a mimetope of such a protein; an isolated hematophagous ectoparasite carboxylesterase nucleic acid molecule that hybridizes under stringent hybridization conditions with a *Ctenocephalides felis* carboxylesterase gene; an isolated antibody that selectively binds to a hematophagous ectoparasite carboxylesterase protein; and an inhibitor of carboxylesterase activity identified by its ability to inhibit the activity of a flea carboxylesterase (including a substrate analog).

Suitable inhibitors of esterase activity are compounds that interact directly with an esterase protein's active site, thereby inhibiting that esterase's activity, usually by binding to or otherwise interacting with or otherwise modifying the esterase's active site. Esterase inhibitors can also interact with other regions of the esterase protein to inhibit esterase activity, for example, by allosteric interaction. Inhibitors of esterases are usually relatively small compounds and as such differ from anti-esterase antibodies. Preferably, an esterase inhibitor of the present invention is identified by its ability to bind to, or otherwise interact with, a flea esterase protein, thereby inhibiting the activity of the flea esterase.

Esterase inhibitors can be used directly as compounds in compositions of the present invention to treat animals as long as such compounds are not harmful to host animals being treated. Esterase inhibitors can also be used to identify preferred types of arthropod esterases to target using compositions of the present invention, for example by affinity chromatography. Preferred esterase inhibitors of the present invention include, but are not limited to, flea esterase substrate analogs, and other molecules that bind to a flea esterase (e.g., to an allosteric site) in such a manner that esterase activity of the flea esterase is inhibited; examples include, but are not limited to, juvenile hormone analogs and cholinesterase inhibitors as well as other neural transmission inhibitors. An esterase substrate analog refers to a compound that interacts with (e.g., binds to, associates with, modifies) the active site of an esterase protein. A preferred esterase substrate analog inhibits esterase activity. Esterase substrate analogs can be of any inorganic or organic composition, and, as such, can be, but are not limited to, peptides, nucleic acids, and peptidomimetic compounds. Esterase substrate analogs can be, but need not be, structurally similar to an esterase's natural substrate as long as they can interact with the active site of that esterase protein. Esterase substrate analogs can be designed using computer-generated structures of esterase proteins of the present invention or computer structures of esterases's natural substrates. Substrate analogs can also be obtained by generating random samples of molecules, such as oligonucleotides, peptides, peptidomimetic compounds, or other inorganic or organic molecules, and screening such samples by affinity chromatography techniques using the corresponding binding partner, (e.g., a flea esterase). A preferred esterase substrate analog is a peptidomimetic compound (i.e., a compound that is structurally and/or functionally similar to a natural substrate of an esterase of the present invention, particularly to the region of the substrate that interacts with the esterase active site, but that inhibits esterase activity upon interacting with the esterase active site).

Esterase peptides, mimetopes and substrate analogs, as well as other protective compounds, can be used directly as compounds in compositions of the present invention to treat animals as long as such compounds are not harmful to the animals being treated.

The present invention also includes a therapeutic composition comprising at least one arthropod esterase-based compound of the present invention in combination with at least one additional compound protective against hematophagous ectoparasite infestation. Examples of such compounds are disclosed herein.

In one embodiment, a therapeutic composition of the present invention can be used to protect an animal from hematophagous ectoparasite infestation by administering such composition to a hematophagous ectoparasite, such as to a flea, in order to prevent infestation. Such administration could be oral, or by application to the environment (e.g., spraying). Examples of such compositions include, but are not limited to, transgenic vectors capable of producing at least one therapeutic composition of the present invention. In another embodiment, a hematophagous ectoparasite, such as a flea, can ingest therapeutic compositions, or products thereof, present in the blood of a host animal that has been administered a therapeutic composition of the present invention.

Compositions of the present invention can be administered to any animal susceptible to hematophagous ectoparasite infestation (i.e., a host animal), including warm-blooded animals. Preferred animals to treat include mammals and birds, with cats, dogs, humans, cattle, chinchillas, ferrets, goats, mice, minks, rabbits, raccoons, rats, sheep, squirrels, swine, chickens, ostriches, quail and turkeys as well as other furry animals, pets, zoo animals, work animals and/or food animals, being more preferred. Particularly preferred animals to protect are cats and dogs.

In accordance with the present invention, a host animal (i.e., an animal that is or is capable of being infested with a hematophagous ectoparasite) is treated by administering to the animal a therapeutic composition of the present invention in such a manner that the composition itself (e.g., an esterase inhibitor, an esterase synthesis suppressor (i.e., a compound that decreases the production of esterase in the hematophagous ectoparasite), an esterase mimetope, or an anti-esterase antibody) or a product generated by the animal in response to administration of the composition (e.g., antibodies produced in response to administration of an arthropod esterase protein or nucleic acid molecule, or conversion of an inactive inhibitor "prodrug" to an active esterase inhibitor) ultimately enters the hematophagous ectoparasite. A host animal is preferably treated in such a way that the compound or product thereof enters the blood stream of the animal. Hematophagous ectoparasites are then exposed to the composition or product when they feed from the animal. For example, flea esterase inhibitors administered to an animal are administered in such a way that the inhibitors enter the blood stream of the animal, where they can be taken up by feeding fleas. In another embodiment, when a host animal is administered an arthropod esterase protein or nucleic acid molecule, the treated animal mounts an immune response resulting in the production of antibodies against the esterase (i.e., anti-esterase antibodies) which circulate in the animal's blood stream and are taken up by hematophagous ectoparasites upon feeding. Blood taken up by hematophagous ectoparasites enters the hematophagous ectoparasites where compounds of the present invention, or products thereof, such as anti-esterase antibodies, esterase inhibitors, esterase mimetopes and/or esterase synthesis suppressors, interact with, and reduce esterase activity in the hematophagous ectoparasite.

The present invention also includes the ability to reduce larval hematophagous ectoparasite infestation in that when hematophagous ectoparasites feed from a host animal that has been administered a therapeutic composition of the present invention, at least a portion of compounds of the present invention, or products thereof, in the blood taken up by the hematophagous ectoparasite are excreted by the hematophagous ectoparasite in feces, which is subsequently ingested by hematophagous ectoparasite larvae. In particular, it is of note that flea larvae obtain most, if not all, of their nutrition from flea feces.

In accordance with the present invention, reducing esterase activity in a hematophagous ectoparasite can lead to a number of outcomes that reduce hematophagous ectoparasite burden on treated animals and their surrounding environments. Such outcomes include, but are not limited to, (a) reducing the viability of hematophagous ectoparasites that feed from the treated animal, (b) reducing the fecundity of female hematophagous ectoparasites that feed from the treated animal, (c) reducing the reproductive capacity of male hematophagous ectoparasites that feed from the treated animal, (d) reducing the viability of eggs laid by female hematophagous ectoparasites that feed from the treated animal, (e) altering the blood feeding behavior of hematophagous ectoparasites that feed from the treated animal (e.g., hematophagous ectoparasites take up less volume per feeding or feed less frequently), (f) reducing the viability of hematophagous ectoparasite larvae, for example due to the feeding of larvae from feces of hematophagous ectoparasites that feed from the treated animal and/or (g) altering the development of hematophagous ectoparasite larvae (e.g., by decreasing feeding behavior, inhibiting growth, inhibiting (e.g., slowing or blocking) molting, and/or otherwise inhibiting maturation to adults).

Therapeutic compositions of the present invention also include excipients in which protective compounds are formulated. An excipient can be any material that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, dog serum albumin, cat serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), and Leishmania elongation initiating factor (LEIF); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of an animal at a constant rate sufficient to attain therapeutic dose levels of the composition to protect an animal from hematophagous ectoparasite infestation. The therapeutic composition is preferably released over a period of time ranging from about 1 to about 12 months. A preferred controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Acceptable protocols to administer therapeutic compositions of the present invention in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram ($\mu$g) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal, intraocular and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid vaccine (e.g., as naked DNA or RNA molecules, such as is taught, for example in Wolff et al., 1990, Science 247, 1465–1468) or (b) administering a nucleic acid molecule packaged as a recombinant virus vaccine or as a recombinant cell vaccine (i.e., the nucleic acid molecule is delivered by a viral or cellular vehicle).

A naked nucleic acid vaccine of the present invention includes a nucleic acid molecule of the present invention and preferably includes a recombinant molecule of the present invention that preferably is replication, or otherwise amplification, competent. A naked nucleic acid vaccine of the present invention can comprise one or more nucleic acid molecules of the present invention in the form of, for example, a bicistronic recombinant molecule having, for example one or more internal ribosome entry sites. Preferred naked nucleic acid vaccines include at least a portion of a viral genome (i.e., a viral vector). Preferred viral vectors include those based on alphaviruses, poxviruses, adenoviruses, herpesviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences are also preferred.

Naked nucleic acid vaccines of the present invention can be administered in a variety of ways, with intramuscular, subcutaneous, intradermal, transdermal, intranasal and oral routes of administration being preferred. A preferred single dose of a naked nucleic acid vaccines ranges from about 1 nanogram (ng) to about 100 $\mu$g, depending on the route of administration and/or method of delivery, as can be determined by those skilled in the art. Suitable delivery methods include, for example, by injection, as drops, aerosolized and/or topically. Naked DNA of the present invention can be contained in an aqueous excipient (e.g., phosphate buffered saline) alone or a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging-deficient and/or encodes an attenuated virus. A number of recombinant viruses can be used, including, but not limited to, those based on alphaviruses, poxviruses, adenoviruses, herpesviruses, and retroviruses. Preferred recombinant virus vaccines are those based on alphaviruses (such as Sindbis virus), raccoon poxviruses, species-specific herpesviruses and species-specific poxviruses. An example of methods to produce and use alphavirus recombinant virus vaccines is disclosed in PCT Publication No. WO 94/17813, by Xiong et al., published Aug. 18, 1994, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from hematophagous ectoparasite infestation. For example, a recombinant virus vaccine comprising an arthropod CE nucleic acid molecule of the present invention is administered according to a protocol that results in the animal producing a sufficient immune response to protect itself from hematophagous ectoparasite infestation. A preferred single dose of a recombinant virus vaccine of the present invention is from about $1 \times 10^4$ to about $1 \times 10^7$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include Salmonella, *E. coli*, Listeria, Mycobacterium, *S. frugiperda*, yeast, (including *Saccharomyces cerevisiae*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to protect an animal from hematophagous ectoparasite infestation can be tested in a variety of ways including, but not limited to, detection of anti-arthropod esterase antibodies (using, for example, proteins or mimetopes of the present invention), detection of cellular immunity within the treated animal, or challenge of the treated animal with hematophagous ectoparasites to determine whether, for example, the feeding, fecundity or viability of hematophagous ectoparasites feeding from the treated animal is disrupted. Challenge studies can include attachment of chambers containing hematophagous ectoparasites onto the skin of the treated animal. In one embodiment, therapeutic compositions can be tested in animal models such as mice. Such techniques are known to those skilled in the art.

One preferred embodiment of the present invention is the use of arthropod protective compounds, such as proteins, mimetopes, nucleic acid molecules, antibodies and inhibitory compounds of the present invention, to protect an animal from hematophagous ectoparasite, and particularly flea, infestation. Preferred protective compounds of the present invention include, but are not limited to, *C. felis* esterase nucleic acid molecules, *C. felis* esterase proteins and mimetopes thereof, anti-*C. felis* esterase antibodies, and inhibitors of *C. felis* esterase activity. More preferred protective compounds of the present invention include, but are not limited to, CE or JHE formulations of the present invention, *C. felis* CE nucleic acid molecules, *C. felis* CE proteins and mimetopes thereof, anti-flea CE antibodies, anti-flea JHE antibodies, inhibitors of *C. felis* CE activity and inhibitors of flea JHE activity. Additional protection may be obtained by administering additional protective compounds, including other proteins, mimetopes, nucleic acid molecules, antibodies and inhibitory compounds, as disclosed herein.

One therapeutic composition of the present invention includes an inhibitor of arthropod esterase activity, i.e., a compound capable of substantially interfering with the function of an arthropod esterase susceptible to inhibition by an inhibitor of arthropod esterase activity. An inhibitor of esterase activity can be identified using arthropod esterase proteins of the present invention. One embodiment of the present invention is a method to identify a compound capable of inhibiting esterase activity of an arthropod. Such a method includes the steps of (a) contacting (e.g., combining, mixing) an isolated flea esterase protein, preferably a *C. felis* esterase protein of the present invention, with a putative inhibitory compound under conditions in which, in the absence of the compound, the protein has esterase activity, and (b) determining if the putative inhibitory compound inhibits the esterase activity. Putative inhibitory compounds to screen include small organic molecules, antibodies (including mimetopes thereof) and substrate analogs. Methods to determine esterase activity are known to those skilled in the art; see, for example, the Examples section of the present application.

The present invention also includes a test kit to identify a compound capable of inhibiting esterase activity of an arthropod. Such a test kit includes an isolated flea esterase protein, preferably a *C. felis* esterase protein, having esterase activity and a means for determining the extent of inhibition of esterase activity in the presence of (i.e., effected by) a putative inhibitory compound. Such compounds are also screened to identify those that are substantially not toxic in host animals.

Esterase inhibitors isolated by such a method, and/or test kit, can be used to inhibit any esterase that is susceptible to such an inhibitor. Preferred esterase proteins to inhibit are those produced by arthropods. A particularly preferred esterase inhibitor of the present invention is capable of protecting an animal from hematophagous ectoparasite infestation. Effective amounts and dosing regimens can be determined using techniques known to those skilled in the art.

The following examples are provided for the purposes of illustration and are not intended to limit the scope of the present invention.

EXAMPLES

It is to be noted that the Examples include a number of molecular biology, microbiology, immunology and biochemistry techniques considered to be known to those skilled in the art. Disclosure of such techniques can be found, for example, in Sambrook et al., ibid., Borovsky, *Arch Insect Biochem. and Phys.*, 7:187–210, 1988, and related references.

Example 1

This example describes labeling of proteases and esterases with radiolabeled diisopropylfluorophosphate.

Tissue samples were isolated from unfed or bovine blood-fed 1st instar *Ctenocephalides felis* flea larvae; bovine blood-fed or cat blood-fed 3rd instar *Ctenocephalides felis* flea larvae; bovine blood-fed or cat blood-fed *Ctenocephalides felis* prepupal flea larvae; bovine blood-fed or cat blood-fed adult *Ctenocephalides felis* flea midgut tissue, and whole unfed, bovine blood-fed or cat blood-fed adult *Ctenocephalides felis* fleas. The 1st instar, 3rd instar, prepupal and adult midgut tissues were then homogenized by freeze-fracture and sonicated in a Tris buffer comprising 50 mM Tris, pH 8.0 and 100 mM $CaCl_2$. The whole adult flea sample was then homogenized by freeze-fracture and ground with a microtube mortar and pestle. The extracts were centrifuged at about 14,000×g for 20 minutes (min.) and the soluble material recovered. The soluble material was then diluted to a final concentration of about 1 to about 1.2 tissue equivalents per microliter ($\mu$l) of Tris buffer. Each sample was labeled with [1,3-³H]-diisopropylfluorophosphate (³H-DFP) (available from DuPont-NEN, Wilmington, Del.) using the method generally described in Borovsky, ibid. About 20 tissue equivalents of each tissue sample were mixed with about 1 μCi of ³H-DFP and incubated for about 18 hours at 4° C. Proteins contained in each sample were then resolved using a 14% Tris-glycine sodium dodecyl sulfate polyacrylamide gel electrophoresis (SDS-PAGE) (available from Novex, San Diego, Calif.) under reducing conditions. The gel was soaked in Entensify (available from DuPont-NEN) according to manufacturers instructions, and exposed to X-ray film (available from Kodak X-0mat AR, Rochester, N.Y.) for about 3 days at −70° C.

Analysis of the resulting autoradiogram (shown in FIG. 1) indicated that tissue samples from 3rd instar, prepupal larvae and whole adult flea contained proteins that labeled with DFP, having a molecular weight (MW) of about 60 kilodalton (kD). No proteins of this MW were labeled in tissue samples from unfed or fed 1st instar larvae and adult midgut. The results indicated preferred tissue distribution and stage-specific expression of DFP-labeled serine esterases in fleas.

Example 2

This example describes the identification of general CE activity in flea tissue extracts.

Tissue samples and soluble extracts were prepared as described above in Example 1, except not labelled, from unfed (UF) and bovine blood-fed 1st instar flea larvae, bovine blood-fed 3rd instar flea larvae, bovine blood-fed prepupal flea larvae, unfed whole adult fleas, cat blood-fed adult (ACF) whole fleas, cat blood-fed adult fleas that have had their heads and midguts removed (referred to herein as fed adult partial fleas), unfed adult flea midguts and cat blood-fed adult flea midguts. About 5 tissue equivalents of each tissue were assayed for general CE activity using the following method. Tissue samples of about 5 μl were added to separate wells of flat-bottomed microtiter plate (available from Becton Dickinson, Lincoln Park, N.J.). A control well was prepared by adding about 5 μl of Tris buffer to an empty well of the plate. About 95 μl of 25 mM Tris-HCl (pH 8.0) was then added to each sample to increase the volume in each well to about 100 μl. About 100 μl of 0.25 mM α-napthyl acetate (available from Sigma, St. Louis, Mo.) dissolved in 25 mM Tris-HCl (pH 8.0) was then added to each well. The plate was then incubated for about 15 min. at 37° C. Following the incubation, about 40 μl of 0.3% Fast Blue salt BN (tetrazotized o-dianisidine; available from Sigma) dissolved in 3.3% SDS in water was added to each well.

The microtiter plate was then analyzed using a Cambridge Technology, Inc. (Watertown, Pa.) model 7500 Microplate Reader set to 590 nm. The absorbance value for the control sample was subtracted from absorbance values of experimental samples, such that the background value was zero.

Figure 2:
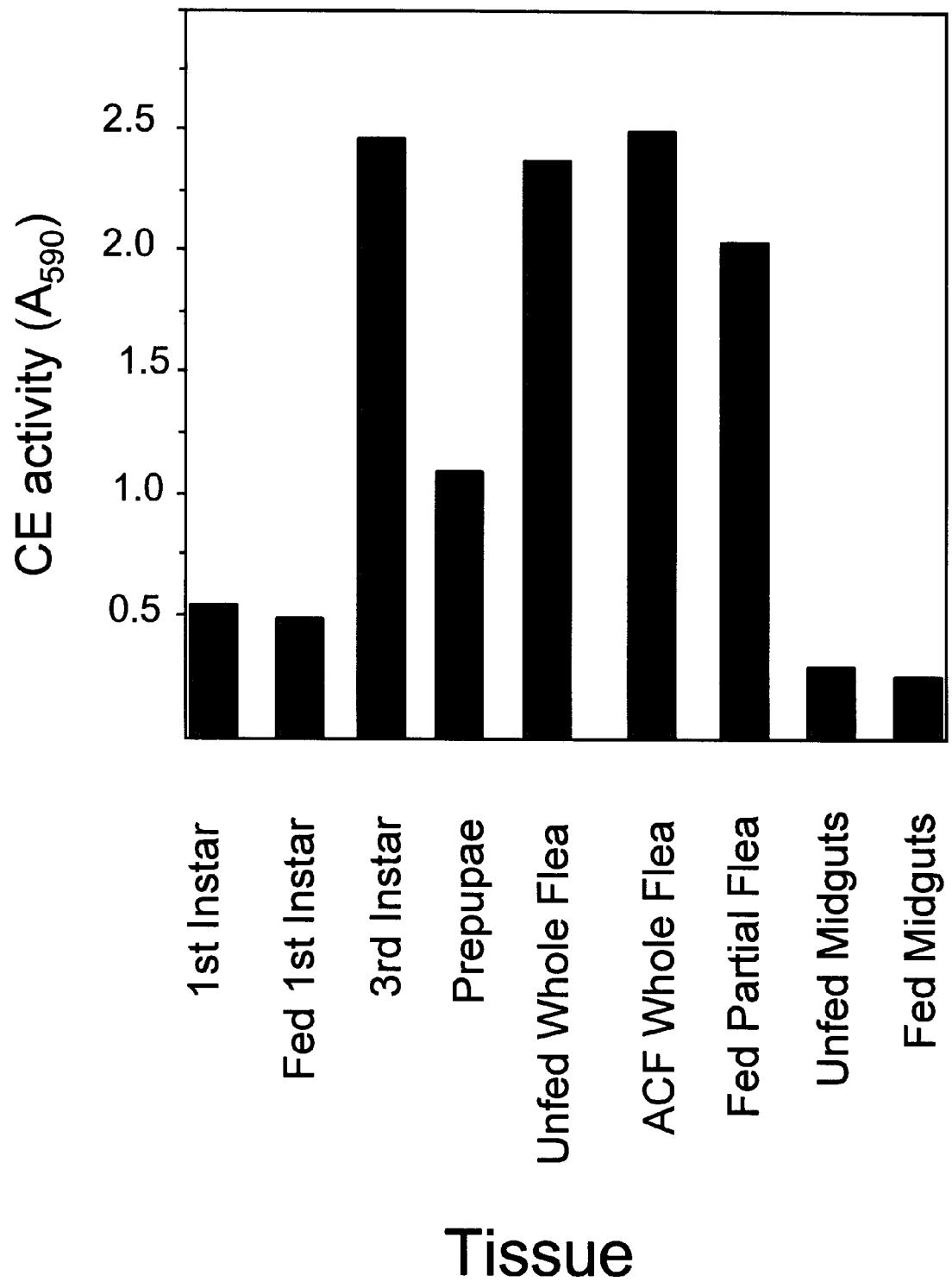
FIG. 2 depicts carboxylesterase activity of certain esterase proteins of the present invention.

The results shown in FIG. 2 indicated that general CE activity was detected in all tissue samples. The level of activity varied, with unfed and fed 1st instar larvae, unfed adult flea midguts, and fed adult flea midguts having relatively lower activity than in the other tissues. Thus, the results indicated preferred tissue distribution and stage-specific expression of general CE activity in fleas.

Example 3

This example describes the determination of general CE activity using isoelectric focusing (IEF)-PAGE and non-reducing SDS-PAGE.

A. Non-reducing SDS-PAGE.

Soluble extracts from unfed and bovine blood-fed 1st instar flea larvae, bovine blood-fed 3rd instar flea larvae, bovine blood-fed prepupal flea larvae, bovine blood-fed adult (ABF) whole fleas and cat blood-fed adult whole fleas were prepared using the method described in Example 1. Each soluble extract sample was combined with SDS sample buffer (available from Novex) and proteins in the samples were resolved by gel electrophoresis using 14% Tris-glycine SDS electrophoresis gels (available from Novex). The gels were run at room temperature for about 1 hour at 200 volts. After electrophoresis, the gels were soaked for about for 30 minutes in 50 mM Tris, pH 8.0, containing 2.5% Triton X-100 to renature the proteins. The gels were then soaked in 50 mM Tris, pH 8.0, for about 5 minutes and then stained for about 5 min. in 50 milliliters (ml) of 25 mM Tris, pH 8.0, containing 50 mg Fast blue salt BN and 10 mg α-napthyl acetate (dissolved in 1 ml acetone). Once protein was detected on the stained gels, the gels were rinsed with water and photographed.

B. IEF-PAGE.

Soluble extracts from unfed and bovine blood-fed 1st instar flea larvae, bovine blood-fed 3rd instar flea larvae, bovine blood-fed prepupal flea larvae, unfed and cat blood-fed whole fleas, cat blood-fed adult partial fleas and cat blood-fed adult midguts were prepared as described above in Section A. The extracts were each combined with IEF sample buffer pH 3–7 (available from Novex) and loaded onto pH 3–7 IEF electrophoresis gels (available from Novex). The gels were electrophoresed at room temperature first for about 1 hour at about 100 volts, then for about 1 hour at about 200 volts, and then for about 30 min. at about 500 volts. Following electrophoresis, the gels were soaked in 25 mM Tris buffer, pH 8.0, for about 5 min. and then stained for about 1–5 min. in 50 ml of 25 mM Tris buffer, pH 8.0, containing 50 mg Fast blue salt BN and 10 mg α-napthyl acetate (dissolved in 1 ml acetone). Once protein was detected on the stained gels, the gels were rinsed with water and photographed.

C. Results.

Figure 3:
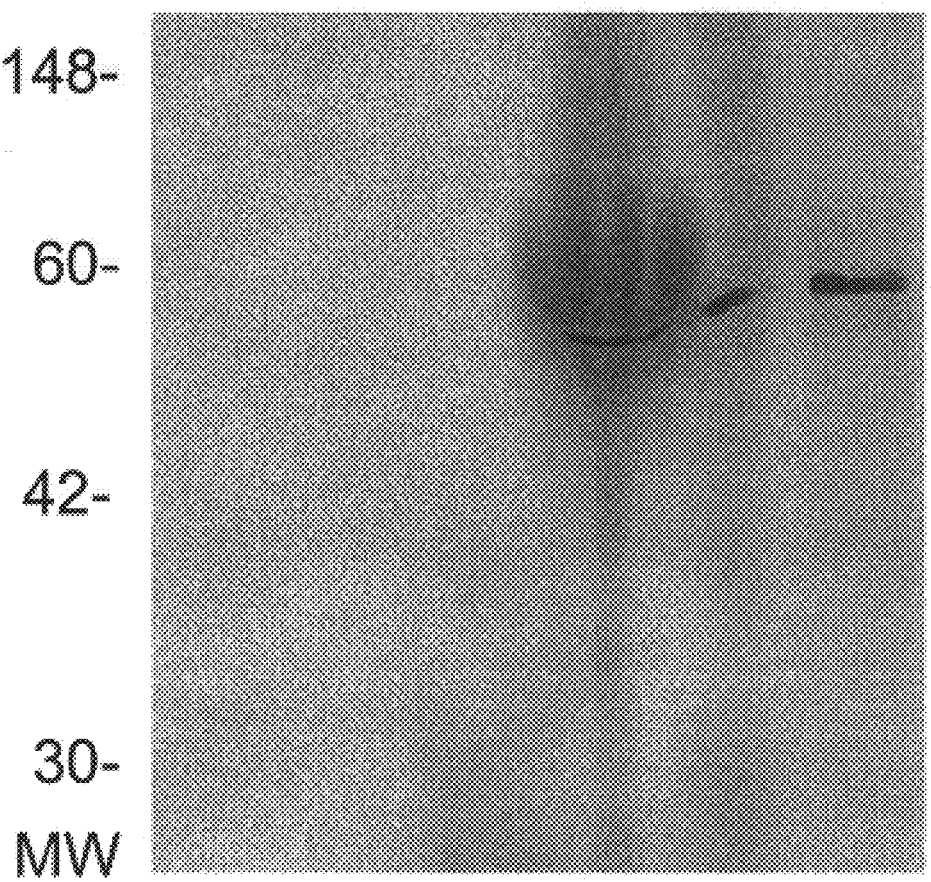
FIG. 3 depicts SDS-PAGE analysis of carboxylesterase activity of certain esterase proteins of the present invention.
Figure 4:
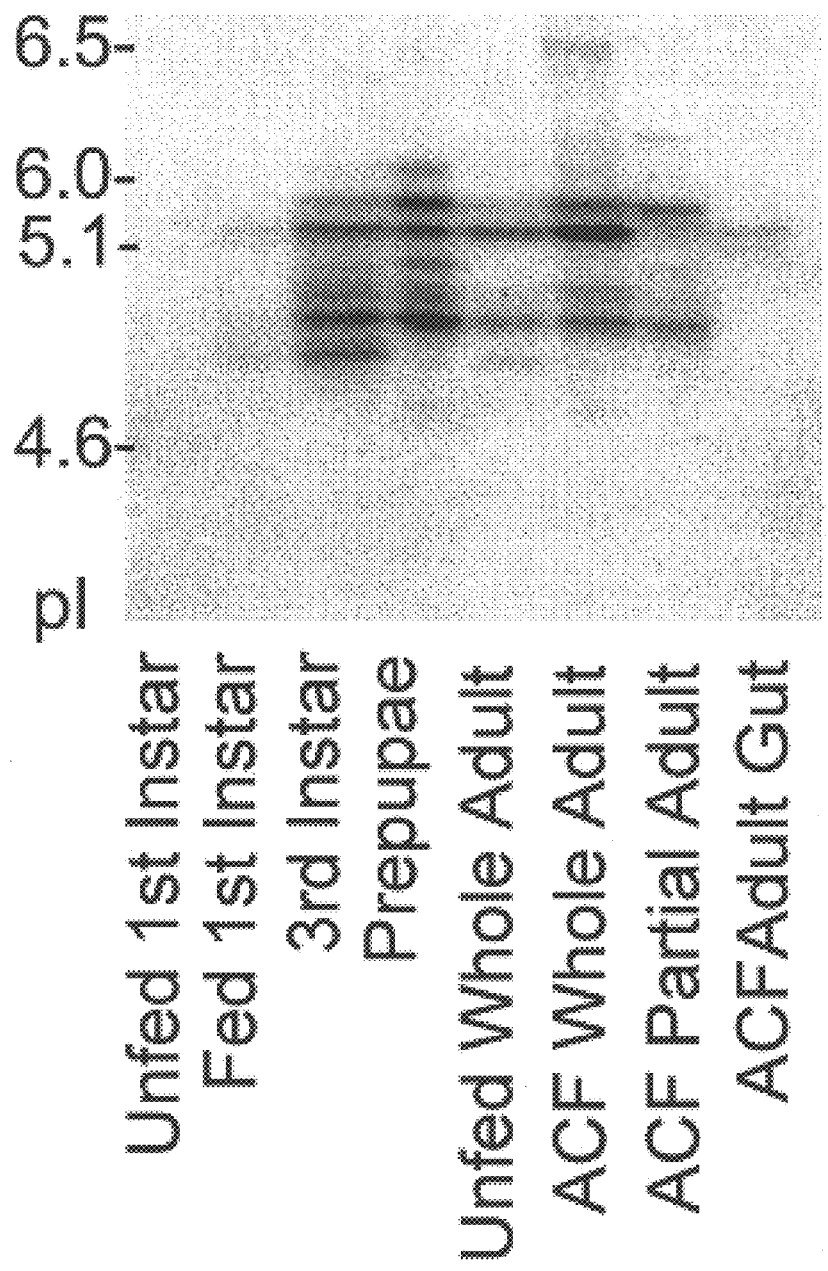
FIG. 4 depicts IEF analysis of certain esterase proteins of the present invention.

The results from gel electrophoresis experiments described above in Sections A and B are shown in FIGS. 3 and 4. The results indicated that certain flea tissues contain proteins having MW's of from about 60 to about 70 kD and native pI values of from about 4.7 to about 5.2 that have CE activity. In particular, CE activity was identified in prepupal larvae and fed adult flea extracts resolved by non-reduced SDS-PAGE. No CE activity was identified in unfed and fed 1st instar larvae or fed 3rd instar larvae extracts (see FIG. 3). When extracts were resolved by native IEF-PAGE, CE activity was identified in fed 3rd instar larvae, prepupal larvae, unfed and fed whole adult flea, and fed adult partial flea extracts (see FIG. 4, lanes 3–7)). No CE activity was identified in unfed or fed 1st instar larvae, or in fed adult flea midgut extracts (see FIG. 4, lanes 1, 2, and 8).

Example 4

This example describes the purification of CE protein from prepupal flea larvae.

About 15,000 bovine blood-fed prepupal flea larvae were collected and the larvae were homogenized in TBS by sonication in 50 ml Oak Ridge centrifuge tubes (available from Nalgene Co., Rochester, N.Y.) by sonicating 4 times 20 seconds each at a setting of 5 of a model W-380 Sonicator (available from Heat Systems-Ultrasonics, Inc.). The sonicates were clarified by centrifugation at 18,000 RPM for 30 minutes to produce an extract. Soluble protein in the extract was removed by aspiration and diluted to a volume of about 20 ml in TBS (equivalent to about 1 larva per μl TBS). The extract was then added to a column containing about 5 ml of p-aminobenzamidine linked to agarose beads (available from Sigma, St. Louis, Mo.) and incubated overnight at 4° C. The column was then washed with about 30 ml TBS to remove unbound protein. The collected unbound protein was then concentrated to a volume of about 20 ml using a Macrosep 10 centrifugal protein concentrator (Filtron Technology Corp., Northborough, Mass.) and filtered sequentially through a 1 μm syringe filter and then through a 0.2 μm syringe filter to clarify the sample for chromatography.

Aliquots of about 0.5 ml were loaded onto a 20 ml Superdex 200 HR gel filtration column (available from Pharmacia, Piscataway, N.J.) equilibrated in TBS, operated on a BioLogic liquid chromatography system (available from BioRad, Burlingame, Calif.). About 1 ml fractions were then collected. Repetitive runs were performed until about 30 ml of each fraction was collected. The fractions were analyzed for CE activity using the assay described above in Example 2. In preparation for cation exchange chromatography, fractions having CE activity ($V_e$=16–18 ml) were combined and dialyzed against about 2 liters of 20 mM MES buffer (2-(N-morpholino)ethanesulfonic acid), pH 6.0, containing 10 mM NaCl, for about 1.5 hours, and then against about 1 liter of the same buffer overnight at 4° C. Prior to loading onto the cation exchange chromatography column, the sample was again filtered through a 0.2 μm syringe filter to remove precipitated proteins. The sample was then applied to a Bio-Scale S2 cation exchange column (available from BioRad) at a rate of about 0.5 ml/min. The column was washed with MES buffer until all unbound protein was removed. Protein bound to the column was then eluted with a linear gradient from 10 mM to 1 M NaCl in 20 mM MES buffer, pH 6. Fractions were assayed for CE activity using the assay described above in Example 2. The results indicated that CE activity was not retained on the cation exchange column using the above conditions, and all of the activity was found in the flow-through fractions.

Fractions containing CE activity were pooled and adjusted to pH 7 using 0.5 M Tris, pH 8.0, in preparation for anion exchange chromatography. The pooled fractions were then loaded onto a 4.5 mm×50 mm Poros 10 HQ anion exchange chromatography column (available from PerSeptive Biosystems, Cambridge, Mass.) equilibrated in 25 mM Tris buffer, pH 6.8. The column was washed with the loading buffer, and bound proteins were eluted with a linear gradient of 0 to 1 M NaCl in 25 mM Tris buffer, pH 6.8. Fractions were tested for CE activity using the assay described above in Example 2. The results indicated that CE activity was eluted at about 170 mM NaCl. Fractions containing CE activity were pooled and diafiltered into TBS.

Example 5

This example describes the determination of N-terminal amino acid sequences of carboxylesterases isolated from prepupal flea larvae.

A. Anion exchange chromatography fractions.

Anion exchange chromatography fractions described above in Example 4 that contained proteins having CE activity were pooled, diafiltered into TBS buffer and concentrated 3-fold in a Speed-Vac Concentrator (available from Savant Instruments, Holbrook, N.Y.). Proteins in the concentrated samples were then resolved on a reducing, 10% SDS-PAGE Tris-glycine gel (available from Novex) for 1 hour at about 200 V. The proteins on the gel were then blotted onto a polyvinylidene difluoride (PVDF) membrane (available from Novex) for about 70 min in 10 mM CAPS buffer (3-[cyclohexylamino]-1-propanesulfonic acid; available from Sigma), pH 11, with 0.5 mM dithiothreitol (DTT). The membrane was then stained for 1 minute in 0.1% Coomassie Blue R-250 dissolved in 40% methanol and 1% acetic acid. The membrane was destained in 50% methanol for about 10 minutes, rinsed with MilliQ water and air dried. Three stained protein bands were identified having apparent molecular weights of about 64 kD, 65 kD, and 66 kD, respectively. The portion of the membrane containing each band was excised separately. Protein contained in each membrane segment was subjected to N-terminal amino acid sequencing using a 473A Protein Sequencer (available from Applied Biosystems, Foster City, Calif.) and using standard techniques.

The results indicated that the N-terminal amino acid sequence of the putative 64 kD protein was DPPTVTLPQ-GEL (denoted SEQ ID NO:39); the N-terminal amino acid sequence of the putative 65 kD protein was DPPTVTLPQGELVGKATNEnxk (denoted SEQ ID NO:40); and the N-terminal amino acid sequence of the putative 66 kD protein was DppTVTLPQGEL (denoted SEQ ID NO:41), in which the lower case letters designate uncertainties and "x" designates an undetermined residue.

B. Proteins Resolved by Native IEF-PAGE.

Proteins isolated by anion exchange chromatography as described above in Section A were further resolved by native IEF-PAGE. Proteins were loaded onto a pH 3–10 IEF gel (available from Novex) and separated in Novex's IEF buffers according to Novex's standard procedure (60 min at 100 V; then 60 min at 200 V; and then 30 min at 500 V). Following electrophoresis, part of the gel was stained for CE activity using the method described above in Example 2. The remaining portion of the gel was blotted onto PVDF membrane by reversing the orientation of the gel and membrane so that positively charged proteins migrated to the membrane, electrophoresing the protein for 60 min at 10 V, using 0.7% acetic acid as the transfer buffer. The membrane was stained as described above in Section A. After the membrane was dried, stained protein bands on the membrane were compared to bands on the gel tested for CE activity to identify corresponding bands. Protein bands on the membrane corresponding to proteins having CE activity were excised and submitted to N-terminal sequencing as described in Section A.

N-terminal amino acid sequence was obtained for protein contained in two bands having pI values of about pI 4.8 and about pI 4.9. N-terminal amino acid sequence of the pI 4.8 band was DPPTVTLPQGELVGKALSNen (denoted SEQ ID NO:42) and N-terminal amino acid sequence of the pI 4.9 band was DPPTVTLP (denoted SEQ ID NO:43). A comparison of the N-terminal amino acid sequences identified here and described in Section A indicates closely related proteins having a consensus sequence of DPPTVTLPQGELVGKALTNEnGk (denoted SEQ ID NO:44).

The amino acid sequences of SEQ ID NO:39, SEQ ID NO:40, SEQ ID NO:41, SEQ ID NO:42, SEQ ID NO:43 and SEQ ID NO:44 are substantially contained within SEQ ID NO:5, SEQ ID NO:19 and SEQ ID NO:53, which are described below in Example 11.

Example 6

This example describes partial purification of CE from 3rd instar flea larvae.

Using the extract preparation methods described in Example 1 without labelling, extracts were prepared from about 50,000 bovine blood-fed 3rd instar flea larvae. The extract was then further purified over a p-aminobenzamidine linked agarose bead column using the method also described in Example 1. Collected unbound protein was concentrated to about 70 ml using a 200 ml stirred cell fitted with a YM-10 membrane (available from Amicon, Beverly, Mass.). Seven ml (about 5,000 3rd instar flea larval equivalents) of the concentrated extract was used for the remainder of the purification scheme described in Example 4. Resulting fractions from the anion exchange chromatography column were tested for CE activity using the assay described above in Example 2.

The results indicated that CE activity was eluted in two overlapping peaks at about 120 mM and about 210 mM NaCl.

Example 7

This example describes the identification of JHE activity in different flea tissues.

Tissue samples were prepared as described above in Example 1 from unfed and bovine blood-fed 1st instar flea larvae, bovine blood-fed 3rd instar flea larvae, bovine blood-fed prepupal flea larvae, unfed and cat blood-fed whole adult fleas, cat blood-fed adult partial fleas and cat blood-fed adult flea midguts. About 5 tissue equivalents of each tissue was assayed for JHE activity as follows.

Unlabeled juvenile hormone (JH; available from ICN Biomedicals, Inc., Aurora, Ohio) was diluted in hexane to concentration of about 0.025 M. Labeled 10-$^3$H-juvenile hormone ($^3$H-JH; available from Dupont-NEN) was diluted in hexane to concentration of about 80,000 cpm/$\mu$l. A JH substrate mixture was prepared by mixing about 20 $\mu$l of unlabeled JH with about 80 $\mu$l of $^3$H-JH (about 5 $\mu$Ci) in a 4 ml screw cap vial. The substrate mixture was then covered with nitrogen (i.e., "blanketed") and the solvent contained in the mixture was evaporated by heating the mixture at 35° C. When just dry, about 1 ml of absolute anhydrous ethanol (final concentration $5 \times 10^{-4}$ M, or 6400 cpm/$\mu$l) was added to the vial. The substrate mixture was then stored at −20° C.

About 5 equivalents of each tissue (about 5 $\mu$l of protein) was added into the bottom of a small glass autosampler vial. About 95 $\mu$l of Tris-buffered saline (TBS) was added to each vial to bring the final volume in each vial to about 100 $\mu$l. Two control samples were also prepared by adding 100 $\mu$l TBS to two separate vials. About 1 $\mu$l of the substrate mixture described above was added to all of the vials including the control samples. The final JH concentration in each vial was about $5 \times 10^{-6}$ M. The vials were then capped and spun in a microfuge to bring all of the liquid to the bottom of each vial. The vials were then transferred to a heat block and incubated at 35° C. for about 30 minutes. Following the incubation, enzyme activity was stopped by adding about 50 $\mu$l of methanol buffer (methanol:water:concentrated ammonium hydroxide at a 10:9:1 ratio, respectively) to each vial and removing the vials from the heat block.

To measure labeled juvenile hormone acid, about 250 $\mu$l isooctane was added to each vial. Each vial was vortexed for about 15 seconds or until an emulsion formed. Each vial was then centrifuged in a microfuge for about 1 minute to separate aqueous and organic phases. About 75 $\mu$l of the aqueous layer was removed from each vial and added to about 2 ml Eco-lume scintillation fluid (available from ICN). The amount of $^3$H-juvenile hormone acid contained in each vial was determined using a Beckman LS-1801 liquid scintillation counter (available from Beckman, Fullerton, Calif.).

Figure 5:
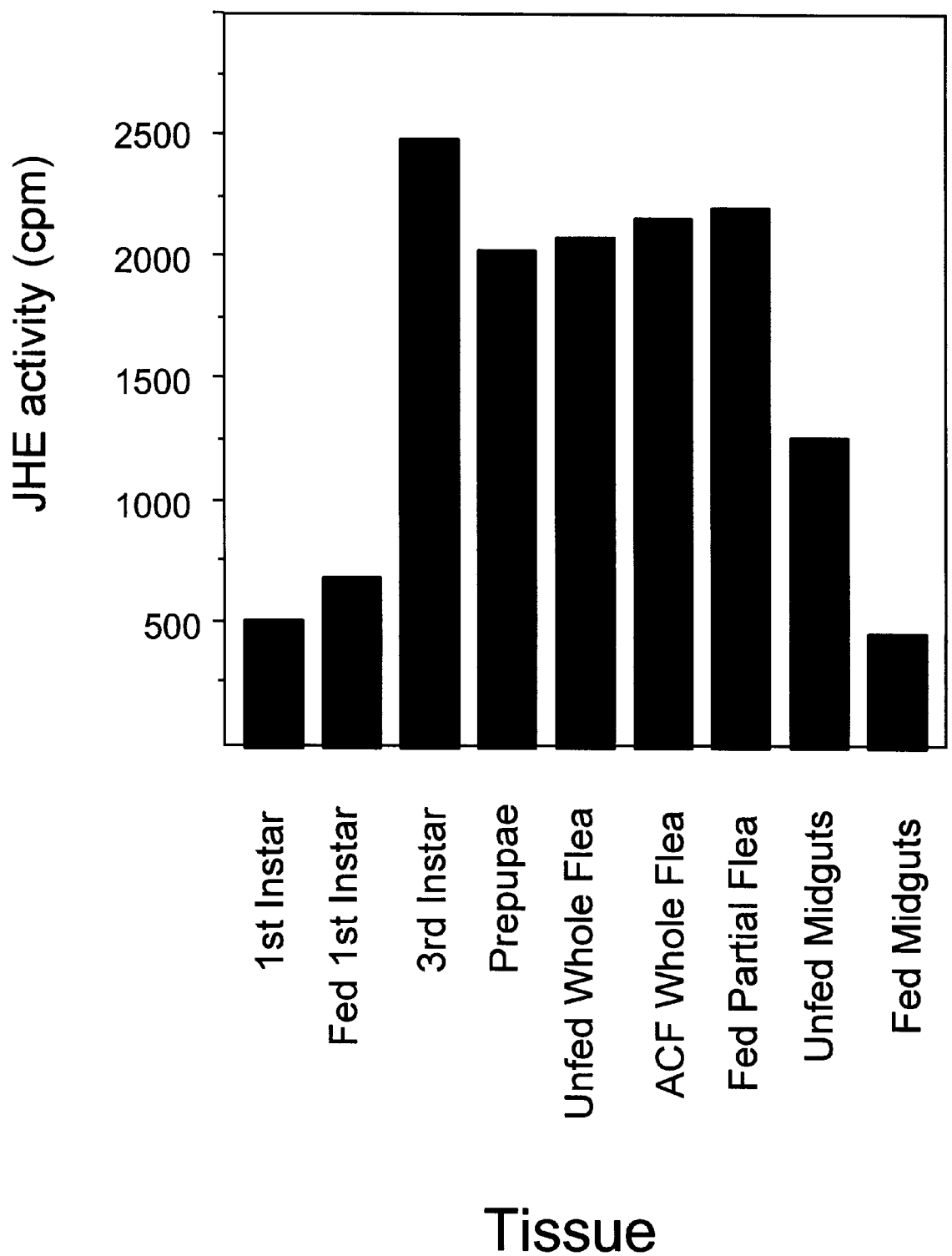
FIG. 5 depicts juvenile hormone esterase activity of certain esterase proteins of the present invention.

The results shown in FIG. 5 indicated that all flea tissues tested contain active JHE. Referring to Example 2, the level of CE activity differed from JHE activity in various tissue samples. The combined JHE and CE data indicated the differential expression of these two enzymatic activities during the development of a flea.

Example 8

This example describes the purification of JHE protein from cat blood-fed adult midguts.

About 23,000 cat blood-fed adult midguts were collected and prepared using the method described in Example 1. The extract was then added in 4 aliquots to columns containing about 3 to about 5 ml of p-aminobenzamidine linked agarose beads (available from Sigma), equilibrated in 50 mM Tris (pH 8.0), 100 mM CaCl$_2$, 400 mM NaCl, and incubated overnight at 4° C. The columns were then washed with about 15 to about 125 ml of the equilibration Tris buffer to remove unbound protein. The collected unbound protein was pooled and then concentrated to a volume of about 5 ml using an Ultrafree-20 10 kD centrifugal concentrator (available from Millipore, Bedford, Mass.) and filtered sequentially through a 0.2 $\mu$m centrifugal ultrafiltration membrane (available from Lida, Kenosha, Wis.) to clarify the sample for chromatography.

Aliquots of about 0.5 ml were loaded onto a Superdex 200 HR gel filtration column using the method described in Example 4. Repeated runs were performed until about 10 ml of each fraction was collected. The fractions were analyzed for JHE activity using the assay described in Example 7. In preparation for anion exchange chromatography, fractions having JHE activity ($V_e$=17–18 ml) were combined and dialyzed overnight against about 1 L of 20 mM Tris buffer, pH 8.0, containing 10 mM NaCl. The sample was then loaded onto a Poros 10 HQ anion exchange column using the method described in Example 4. Resulting fractions were tested for JHE activity as described in Example 7.

The results indicated that midgut JHE activity was eluted from the anion exchange column in a single peak at about 120 mM NaCl.

Example 9

This example describes partial purification of JHE from prepupal flea larvae and 3rd instar larvae.

A. JHE Purification from Prepupal Tissue

Using the extract preparation methods described in Example 1, gel filtration fractions were obtained using a Superdex 200 HR gel filtration column (available from Pharmacia) using the method described in Example 4, from about 15,000 bovine blood-fed prepupal flea larvae. The fractions were analyzed for JHE activity using the assay described above in Example 7. Those fractions containing protein having JHE activity ($V_e$=16–18 ml) were combined and dialyzed using the method described in Example 8.

The fractions were then further purified by passing the fractions over a Bio-Scale S2 cation exchange column (available from BioRad) at a rate of about 0.5 ml/min. The column was washed with MES until all unbound protein was eluted. Bound protein was then eluted with a linear gradient of 20 mM MES buffer, pH 6.0, containing 10 mM NaCl to 1 M NaCl. Resulting fractions were assayed for JHE activity using the method described in Example 7. The results indicated that proteins having JHE activity using prepupal tissue eluted from the column in about 200 to 300 mM NaCl.

The fractions containing JHE activity were combined and the pH adjusted to pH 7 using 0.5 M Tris buffer (pH 8.0). The fractions were then dialyzed twice against about 1 liter of 10 mM phosphate buffer (pH 7.2) containing 10 mM NaCl at 4° C. The resulting dialyzed fractions were then loaded onto a Bio-Scale CHT2-I Hydroxyapatite Column (available from BioRad) at a rate of about 0.5 ml/min. Unbound protein was washed from the column using the dialysis buffer. Bound protein was then eluted with a linear gradient of from 10 mM phosphate buffer, pH 7.2, containing 10 mM NaCl to 0.5 M phosphate buffer pH 6.5 containing 10 mM NaCl. One ml fractions were collected and each tested for JHE activity by the method described in Example 7.

The results indicated that JHE eluted in 2 overlapping peaks at about 100 mM and 150 mM phosphate. These two JHE activities were designated PP JHE I and PP JHE II, and were kept separate for the remainder of the purification. Both JHE samples were dialyzed overnight against 20 mM Tris buffer (pH 8.0) containing 10 mM NaCl. The two samples were then loaded, separately, onto a 4.5 mm×50 mm Poros 10 HQ anion exchange chromatography column (available from PerSeptive Biosystems) equilibrated with 20 mM Tris buffer, pH 8.0, containing 10 mM NaCl. Unbound proteins were washed from the column using the same buffer. Bound proteins were eluted with a linear gradient of from 10 mM to 1 M NaCl in 20 mM Tris buffer, pH 8.0. Resulting fractions were tested for JHE activity using the method described in Example 7.

The results indicated that in both samples, JHE activity was eluted from the column in a single peak at about 100 mM NaCl.

B. JHE Purification from $3^{rd}$ Instar Tissue

Using the procedure described above in Section A, proteins having JHE activity were obtained using about 5,000 bovine blood-fed $3^{rd}$ instar flea larvae. Following purification by cation exchange, proteins having JHE activity using $3^{rd}$ instar tissue were found to elute in 2 peaks. The first peak having JHE activity was not retained on the column and also exhibited CE activity (referred to herein as CE/JHE fractions). The second peak having JHE activity eluted from the column in about 100–200 mM NaCl and did not contain CE activity.

The CE/JHE fractions were pooled and adjusted to about pH 7 using 0.5 M Tris, pH 8.0. The fractions were then loaded onto a 4.5 mm×50 mm Poros 10 HQ anion exchange chromatography column (available from PerSeptive Biosystems) and the column was equilibrated in 25 mM Tris buffer, pH 6.8. The column was washed with the same buffer and bound proteins were eluted with a linear gradient of 0 to 1 M NaCl in 25 mM Tris buffer, pH 6.8. Fractions were then tested for JHE activity using the method described in Example 7. JHE activity was eluted in two overlapping peaks at about 120 mM and 210 mM NaCl. The fraction containing JHE activity also contained CE activity when tested using the method described in Example 2.

Fractions from the cation exchange column containing only JHE activity were combined, diluted in 20 mM Tris buffer, pH 8.0 containing 10 mM NaCl, and concentrated to about 5 ml. The fractions were purified on a Poros 10 HQ anion exchange chromatography column as described immediately above. Fractions were then tested for JHE activity using the method described in Example 7. The JHE activity was eluted in a single peak at about 120 mM. The peak contained no detectable CE activity.

Example 10

This example describes the purification of JHE protein from unfed adult midguts.

About 16,000 unfed adult midguts were collected in 20 mM Tris buffer (pH 7.7), containing 130 mM NaCl, 1 mM sodium EDTA, 1 mM Pefabloc® (available from Boehringer Mannheim, Indianapolis, Ind.), 1 microgram/ml (µg/ml) leupeptin and 1 µg/ml pepstatin. The midguts were homogenized by freeze-fracture and sonication, and then centrifuged at about 14,000×g for 20 min. The soluble material from the centrifugation step was recovered. The soluble material was then concentrated to about 1 ml using an Ultrafree-20 10 kD centrifugal concentrator (available from Millipore) and filtered sequentially through a 0.2 µm centrifugal ultrafiltration membrane to clarify the sample for chromatography. Aliquots of about 0.5 ml were loaded onto a Superdex 200 HR gel filtration column using the method described in Example 4. Repeated column runs were performed until about 2 ml of each fraction was collected. The fractions were analyzed for JHE activity using the assay described in Example 7. In preparation for cation exchange chromatography, fractions having JHE activity ($V_e$=15–17 ml) were combined and dialyzed overnight against about 1 L of 20 mM MES buffer, pH 6.0, containing 10 mM NaCl. The sample was then applied to a Bio-Scale S2 cation exchange column using the method described in Example 4. Fractions of eluate were assayed for JHE activity using the method described in Example 7.

The results indicate that JHE is present in unfed midguts in two forms, one that is not retained on the cation exchange column and one that is bound to the column under low salt conditions at about 100 mM NaCl. The form that was not retained under low salt conditions was shown to have general CE activity using the methods described in Example 2.

Example 11

This example describes the identification of certain esterase nucleic acid molecules of the present invention.

Several flea esterase nucleic acid molecules, representing one or more partial flea esterase genes, were PCR amplified from a flea mixed instar cDNA library or a flea prepupal cDNA library. The flea mixed instar cDNA library was produced using unfed 1st instar, bovine blood-fed 1st instar, bovine blood-fed $2^{nd}$ instar and bovine blood-fed $3^{rd}$ instar flea larvae (this combination of tissues is referred to herein as mixed instar larval tissues for purposes of this example). The flea prepupal cDNA library was produced using prepupal flea larvae. For each library, total RNA was extracted from mixed instar or prepupal tissue, respectfully, using an acid-guanidinium-phenol-chloroform method similar to that described by Chomczynski et al., 1987, Anal. Biochem. 162, p. 156–159. Approximately 5,164 mixed instar larvae or 3,653 prepupal larvae were used in each RNA preparation. Poly A+ selected RNA was separated from each total RNA preparation by oligo-dT cellulose chromatography using Poly(A)Quick® mRNA isolation kits (available from Stratagene Cloning Systems, La Jolla, Calif.), according to the method recommended by the manufacturer.

A mixed instar cDNA expression library and a prepupal cDNA expression library were constructed in lambda (λ)

Uni-ZAP™XR vector (available from Stratagene Cloning Systems) using Stratagene's ZAP-cDNA Synthesis Kit® protocol. About 6.34 μg of mixed instar poly A+ RNA were used to produce the mixed instar library and about 6.72 μg of prepupal poly A+ RNA were used to produce the prepupal library. The resultant mixed instar library was amplified to a titer of about $2.17 \times 10^{10}$ pfu/ml with about 97% recombinants. The resultant prepupal library was amplified to a titer of about $3.5 \times 10^{10}$ pfu/ml with about 97% recombinants.

A pair of primers was used to amplify DNA from the cDNA libraries. A sense vector primer T-3X (corresponding to the vector in which nucleic acid molecules of the present invention had been ligated), having the nucleic acid sequence AATTAACCCT CACTAAAGGG (available from Gibco BRL, Gaithersburg, Md.; denoted SEQ ID NO:45), was used in combination with a degenerate primer, the design of which was based on a highly conserved esterase amino acid sequence (disclosed in Hanzlik et al., J. Biol. Chem. 264:12419–12423, 1989; I Y/H G G G F/L) located in a region downstream from the mature amino terminus in a number of known esterases. The degenerate primer, referred to herein as FCEF, is an anti-sense primer having the nucleic acid sequence ARDCCDCCDC CRTRDAT (R indicating an A or G; and D indicating an A, G or T; denoted SEQ ID NO:46). The resultant PCR products from the mixed instar cDNA library, obtained using standard PCR conditions (e.g., Sambrook et al., ibid.), were about 550 nucleotides. The resultant PCR products from the prepupal cDNA library were from about 500 nucleotides to about 860 nucleotides.

A. PCR Products.

PCR products were gel purified and cloned into the TA VECTOR™ (available from InVitrogen Corp., San Diego, Calif.). Approximately 8 clones were identified from the prepupal library and 6 clones were identified from the mixed instar library. These nucleic acid molecules were subjected to nucleic acid sequencing using the Sanger dideoxy chain termination method, as described in Sambrook et al., ibid.

1. Flea esterase clone 1 isolated from the mixed instar cDNA library was determined to comprise nucleic acid molecule $nfE1_{401}$, the nucleic acid sequence of the coding strand which is denoted herein as SEQ ID NO:1. Translation of SEQ ID NO:1 suggests that nucleic acid molecule $nfE1_{401}$ encodes a non-full-length flea esterase protein of about 103 amino acids, referred to herein as $PfE1_{103}$, having amino acid sequence SEQ ID NO:2, assuming an initiation codon spanning from about nucleotide 92 through about nucleotide 94 of SEQ ID NO:1. The complement of SEQ ID NO:1 is represented herein by SEQ ID NO:3. Comparison of amino acid sequence SEQ ID NO:2 (i.e., the amino acid sequence of $PfE1_{103}$) with amino acid sequences reported in GenBank indicates that SEQ ID NO:2, showed the most homology, i.e., about 33% identity, between SEQ ID NO:2 and alpha esterase protein from Drosophila melanogaster.

2. Flea esterase clone 2 isolated from the mixed instar cDNA library was determined to comprise nucleic acid molecule $nfE2_{364}$, the nucleic acid sequence of the coding strand which is denoted herein as SEQ ID NO:4. Translation of SEQ ID NO:4 suggests that nucleic acid molecule $nfE2_{364}$ encodes a non-full-length flea esterase protein of about 121 amino acids, referred to herein as $PfE2_{121}$, having amino acid sequence SEQ ID NO:5, assuming the first codon spans from about nucleotide 2 through about nucleotide 4 of SEQ ID NO:4. The complement of SEQ ID NO:4 is represented herein by SEQ ID NO:6. Comparison of nucleic acid sequence SEQ ID NO:4 with nucleic acid sequences reported in GenBank indicates that SEQ ID NO:4 showed the most homology, i.e., about 43% identity, between SEQ ID NO:4 and a H. virescens JHE gene. Comparison of amino acid sequence SEQ ID NO:5 (i.e., the amino acid sequence of $PfE2_{121}$) with amino acid sequences reported in GenBank indicates that SEQ ID NO:5, showed the most homology, i.e., about 38% identity, between SEQ ID NO:5 and alpha esterase protein from Drosophila melanogaster.

3. Flea esterase clone 3 isolated from the prepupal cDNA library was determined to comprise nucleic acid molecule $nfE3_{421}$, the nucleic acid sequence of the coding strand which is denoted herein as SEQ ID NO:7. Translation of SEQ ID NO:7 suggests that nucleic acid molecule $nfE3_{421}$ encodes a non-full-length flea esterase protein of about 103 amino acids, referred to herein as $PfE3_{103}$, having amino acid sequence SEQ ID NO:8, assuming an initiation codon spanning from about nucleotide 113 through about nucleotide 115 of SEQ ID NO:7. The complement of SEQ ID NO:7 is represented herein by SEQ ID NO:9. Comparison of nucleic acid sequence SEQ ID NO:7 with nucleic acid sequences reported in GenBank indicates that SEQ ID NO:7 showed the most homology, i.e., about 53% identity, between SEQ ID NO:7 and a Torpedo marmorata acetylcholinesterase gene. Comparison of amino acid sequence SEQ ID NO:8 (i.e., the amino acid sequence of $PfE3_{103}$) with amino acid sequences reported in GenBank indicates that SEQ ID NO:8, showed the most homology, i.e., about 39% identity, between SEQ ID NO:5 and alpha esterase protein from Drosophila melanogaster.

4. Flea esterase clone 4 isolated from the prepupal cDNA library was determined to comprise nucleic acid molecule $nfE4_{524}$, the nucleic acid sequence of the coding strand which is denoted herein as SEQ ID NO:10. Translation of SEQ ID NO:10 suggests that nucleic acid molecule $nfE4_{524}$ encodes a non-full-length flea esterase protein of about 137 amino acids, referred to herein as $PfE4_{137}$, having amino acid sequence SEQ ID NO:11, assuming an initiation codon spanning from about nucleotide 113 through about nucleotide 115 of SEQ ID NO:10. The complement of SEQ ID NO:10 is represented herein by SEQ ID NO:12. Comparison of nucleic acid sequence SEQ ID NO:10 with nucleic acid sequences reported in GenBank indicates that SEQ ID NO:10 showed the most homology, i.e., about 47% identity, between SEQ ID NO:10 and an Anas platyrhyncos thioesterase B gene. Comparison of amino acid sequence SEQ ID NO:11 (i.e., the amino acid sequence of $PfE4_{137}$) with amino acid sequences reported in GenBank indicates that SEQ ID NO:11, showed the most homology, i.e., about 30% identity, between SEQ ID NO:11 and Leptinotarsa decemlineata acetylcholinesterase.

B. cDNA Clones.

Certain amplified PCR fragments were used as probes to identify full-length flea esterase genes in the prepupal cDNA library.

1. Nucleic acid molecule $nfE2_{364}$ was labeled with $^{32}P$ and used as a probe to screen the mixed instar cDNA library described in Section A, using standard hybridization techniques. Two clones were isolated. A first clone included about a 2300-nucleotide insert, referred to herein as $nfE5_{2300}$. Nucleic acid sequence was obtained using standard techniques from $nfE5_{2300}$, to yield a flea esterase nucleic acid molecule named $nfE5_{1982}$ having a nucleic acid sequence of the coding strand which is denoted herein as SEQ ID NO:13. Translation of SEQ ID NO:13 suggests that nucleic acid molecule $nfE5_{1982}$ encodes a non-full-length flea esterase protein of about 505 amino acids, referred to herein as PfE5$_{505}$, having amino acid sequence SEQ ID NO:14, assuming the first codon spans from about nucleotide 1 through about nucleotide 3 of SEQ ID NO:13 and the stop codon spans from about nucleotide 1518 through about nucleotide 1520 of SEQ ID NO:13. The complement of SEQ ID NO:13 is represented herein by SEQ ID NO:15. The amino acid sequence of PfE5$_{505}$ (i.e., SEQ ID NO:14) predicts that PfE5$_{505}$ has an estimated molecular weight of about 56.8 kD and an estimated pI of about 5.5. The nucleic acid molecule representing the coding region for PfE5$_{505}$ is referred to herein as nfE5$_{1515}$; the nucleic acid sequences of the coding strand and the complementary strand are represented by SEQ ID NO:16 and SEQ ID NO:17, respectively.

The nucleic acid sequence of nfE5$_{1982}$ was used to design primers to use in combination with a vector primer to PCR amplify the 5' terminal fragment of the remainder of the flea esterase coding region from the flea mixed instar cDNA library. A pair of primers was used to amplify DNA from the cDNA library. A sense vector primer T3-X (corresponding to the vector in which nucleic acid molecules of the present invention had been ligated), having the nucleic acid sequence 5' AATTAACCCT CACTAAAGGG 3' (denoted SEQ ID NO:45), was used in combination with an anti-sense primer M6/M265', having the nucleic acid sequence 5' GTGCGTACAC GTTTACTACC 3' (denoted SEQ ID NO:56). The resultant PCR product from the mixed instar cDNA library, obtained using standard PCR conditions (e.g., Sambrook et al., ibid.), were about 354 nucleotides.

The PCR product was subjected to DNA sequencing analysis, and a composite sequence representing a full-length flea esterase coding region was deduced. The nucleic acid sequence of the composite nucleic acid molecule, referred to herein as nfE5$_{2144}$ is denoted herein as SEQ ID NO:57. Translation of SEQ ID NO:57 suggests that nucleic acid molecule nfE5$_{2144}$ encodes a full-length flea esterase protein of about 550 amino acids, referred to herein as PfE5$_{550}$, having amino acid sequence SEQ ID NO:58, assuming an open reading frame in which the initiation codon spans from about nucleotide 30 through about nucleotide 32 of SEQ ID NO:57 and the stop codon spans from about nucleotide 1680 through about nucleotide 1682 of SEQ ID NO:57. The complement of SEQ ID NO:57 is represented herein by SEQ ID NO:59. The coding region encoding PfE5$_{550}$ is represented by the nucleic acid molecule nfE5$_{1650}$, having a coding strand with the nucleic acid sequence represented by SEQ ID NO:60 and a complementary strand with nucleic acid sequence SEQ ID NO:61. The amino acid sequence of PfE5$_{550}$ (i.e., SEQ ID NO:58) predicts that PfE5$_{550}$ has an estimated molecular weight of about 61.8 kD and an estimated pI of about 5.5.

Comparison of nucleic acid sequence SEQ ID NO:57 with nucleic acid sequences reported in GenBank indicates that SEQ ID NO:57 showed the most homology, i.e., about 41% identity, between SEQ ID NO:57 and a *M. persicae* esterase FE4 mRNA sequence. Comparison of amino acid sequence SEQ ID NO:58 (i.e., the amino acid sequence of PfE5$_{550}$) with amino acid sequences reported in GenBank indicates that SEQ ID NO:58 showed the most homology, i.e., about 36% identity between SEQ ID NO:58 and *Drosophila melanogster* alpha esterase protein.

A second clone included about a 1900 nucleotide insert, referred to herein as nfE6$_{1900}$. Nucleic acid sequence was obtained using standard techniques from nfE6$_{1900}$, to yield a flea esterase nucleic acid molecule named nfE6$_{1792}$ having a nucleic acid sequence of the coding strand which is denoted herein as SEQ ID NO:18. Translation of SEQ ID NO:18 suggests that nucleic acid molecule nfE6$_{1792}$ encodes a full-length flea esterase protein of about 550 amino acids, referred to herein as PfE6$_{550}$, having amino acid sequence SEQ ID NO:19, assuming an open reading frame in which the initiation codon spans from about nucleotide 49 through about nucleotide 51 of SEQ ID NO:18 and a stop codon spanning from about nucleotide 1699 through about nucleotide 1701 of SEQ ID NO:18. The complement of SEQ ID NO:18 is represented herein by SEQ ID NO:20. The coding region encoding PfE6$_{550}$, is represented by nucleic acid molecule nfE6$_{1650}$, having a coding strand with the nucleic acid sequence represented by SEQ ID NO:21 and a complementary strand with nucleic acid sequence SEQ ID NO:22. The proposed mature protein, denoted herein as PfE6$_{530}$, contains about 530 amino acids which is represented herein as SEQ ID NO:53. The nucleic acid molecule encoding PfE6$_{530}$ is denoted herein as nfE6$_{1590}$ and has a coding strand having the nucleic acid sequence SEQ ID NO:23. The amino acid sequence of PfE6$_{550}$ (i.e., SEQ ID NO:19) predicts that PfE6$_{550}$ has an estimated molecular weight of about 61.8 kD and an estimated pI of about 5.5.

Comparison of nucleic acid sequence SEQ ID NO:18 with nucleic acid sequences reported in GenBank indicates that SEQ ID NO:18 showed the most homology, i.e., about 41% identity, between SEQ ID NO:18 and a *Myzus pericae* esterase gene. Comparison of amino acid sequence SEQ ID NO:19 (i.e., the amino acid sequence of PfE6$_{550}$) with amino acid sequences reported in GenBank indicates that SEQ ID NO:19 showed the most homology, i.e., about 28% identity between SEQ ID NO:19 and *Drosophila melanogaster* alpha esterase protein.

2. Nucleic acid molecule nfE4$_{524}$ was labeled with $^{32}$P and used as a probe to screen the prepupal cDNA library described in Example 11, using standard hybridization techniques (e.g., Sambrook et al., ibid.). Two clones were isolated. A first clone included about a 3000 nucleotide insert, referred to herein as nfE7$_{3000}$. Nucleic acid sequence was obtained using standard techniques from nfE7$_{3000}$, to yield a flea esterase nucleic acid molecule named nfE7$_{2836}$ having a nucleic acid sequence of the coding strand which is denoted herein as SEQ ID NO:24. Translation of SEQ ID NO:24 suggests that nucleic acid molecule nfE7$_{2836}$ encodes a full-length flea esterase protein of about 596 amino acids, referred to herein as PfE7$_{596}$, having amino acid sequence SEQ ID NO:25, assuming an open reading frame in which the initiation codon spans from about nucleotide 99 through about nucleotide 101 of SEQ ID NO:24 and a stop codon spanning from about nucleotide 1887 through about nucleotide 1889 of SEQ ID NO:25. The complement of SEQ ID NO:24 is represented herein by SEQ ID NO:26. The coding region encoding PfE7$_{596}$, is represented by nucleic acid molecule nfE7$_{1788}$, having a coding strand with the nucleic acid sequence represented by SEQ ID NO:28 and a complementary strand with nucleic acid sequence SEQ ID NO:29. The proposed mature protein, denoted herein as PfE7$_{570}$, contains about 570 amino acids which is represented herein as SEQ ID NO:54. The nucleic acid molecule encoding PfE7$_{570}$ is denoted herein as nfE7$_{1710}$ and has a coding strand having the nucleic acid sequence SEQ ID NO:27. The amino acid sequence of PfE7$_{596}$ (i.e., SEQ ID NO:25) predicts that PfE7$_{596}$ has an estimated molecular weight of about 68.7 kD and an estimated pI of about 6.1.

Comparison of nucleic acid sequence SEQ ID NO:24 with nucleic acid sequences reported in GenBank indicates that SEQ ID NO:24 showed the most homology, i.e., about 48% identity, between SEQ ID NO:24 and an *Anas platychyncos* thioesterase B gene. Comparison of amino acid sequence SEQ ID NO:25 (i.e., the amino acid sequence of PfE7$_{596}$) with amino acid sequences reported in GenBank indicates that SEQ ID NO:25 showed the most homology, i.e., about 27% identity between SEQ ID NO:25 and *Drosophila melanogaster* alpha esterase protein.

A second clone included about a 3000 nucleotide insert, referred to herein as nfE8$_{3000}$. Nucleic acid sequence was obtained using standard techniques from nfE8$_{3000}$, to yield a flea esterase nucleic acid molecule named nfE8$_{2801}$ having a nucleic acid sequence of the coding strand which is denoted herein as SEQ ID NO:30. Translation of SEQ ID NO:30 suggests that nucleic acid molecule nfE8$_{2801}$ encodes a full-length flea esterase protein of about 595 amino acids, referred to herein as PfE8$_{595}$, having amino acid sequence SEQ ID NO:31, assuming an open reading frame in which the initiation codon spans from about nucleotide 99 through about nucleotide 101 of SEQ ID NO:30 and a stop codon spanning from about nucleotide 1884 through about nucleotide 1886 of SEQ ID NO:30. The complement of SEQ ID NO:30 is represented herein by SEQ ID NO:32. The coding region encoding PfE8$_{595}$, is represented by nucleic acid molecule nfE8$_{1785}$, having a coding strand with the nucleic acid sequence represented by SEQ ID NO:34 and a complementary strand with nucleic acid sequence SEQ ID NO:35. The proposed mature protein, denoted herein as PfE8$_{570}$, contains about 570 amino acids which is represented herein as SEQ ID NO:55. The nucleic acid molecule encoding PfE8$_{570}$ is denoted herein as nfE8$_{1710}$ and has a coding strand having the nucleic acid sequence SEQ ID NO:33. The amino acid sequence of PfE8$_{595}$ (i.e., SEQ ID NO:31) predicts that PfE8$_{595}$ has an estimated molecular weight of about 68.6 kD and an estimated pI of about 6.1.

Comparison of nucleic acid sequence SEQ ID NO:30 with nucleic acid sequences reported in GenBank indicates that SEQ ID NO:30 showed the most homology, i.e., about 46% identity, between SEQ ID NO:30 and a *Mus musculus* carboxyl ester lipase gene. Comparison of amino acid sequence SEQ ID NO:31 (i.e., the amino acid sequence of PfE8$_{595}$) with amino acid sequences reported in GenBank indicates that SEQ ID NO:31 showed the most homology, i.e., about 28% identity between SEQ ID NO:31 and estalpha-2 esterase of *Culex pipiens quinque fasciatus*.

3. Nucleic acid molecule nfE3$_{421}$ was labeled with $^{32}$P and used as a probe to screen the prepupal cDNA library using standard hybridization techniques (e.g., Sambrook et al., ibid.). Two clones were isolated. One clone included about a 1900 nucleotide insert, referred to herein as nfE9$_{1900}$. Nucleic acid sequence was obtained using standard techniques from nfE9$_{1900}$, to yield a flea esterase nucleic acid molecule named nfE9$_{2007}$ having nucleic acid sequence of the coding strand which is denoted herein as SEQ ID NO:36. Translation of SEQ ID NO:36 suggests that nucleic acid molecule nfE9$_{2007}$ encodes a full-length flea esterase protein of about 528 amino acids, referred to herein as PfE9$_{528}$, having amino acid sequence SEQ ID NO:37, assuming an open reading frame in which the initiation codon spans from about nucleotide 11 through about nucleotide 13 of SEQ ID NO:36 and a stop codon spanning from about nucleotide 1595 through about nucleotide 1597 of SEQ ID NO:36. The complement of SEQ ID NO:36 is represented herein by SEQ ID NO:38. The coding region encoding PfE9$_{528}$, is represented by nucleic acid molecule nfE9$_{1584}$, having a coding strand with the nucleic acid sequence represented by SEQ ID NO:51 and a complementary strand with nucleic acid sequence SEQ ID NO:52. The amino acid sequence of PfE9$_{528}$ (i.e., SEQ ID NO:37) predicts that PfE9$_{528}$ has an estimated molecular weight of about 60 kD and an estimated pI of about 5.43.

Comparison of nucleic acid sequence SEQ ID NO:36 with nucleic acid sequences reported in GenBank indicates that SEQ ID NO:36 showed the most homology, i.e., about 47% identity, between SEQ ID NO:36 and a hamster mRNA for carboxylesterase precursor gene. Comparison of amino acid sequence SEQ ID NO:37 (i.e., the amino acid sequence of PfE9$_{528}$) with amino acid sequences reported in GenBank indicates that SEQ ID NO:37 showed the most homology, i.e., about 37% identity between SEQ ID NO:37 and alpha esterase protein from *Drosophila melanogaster*.

As is the case for any of the nucleic acid molecules described in this example, variations between sequences may be due to a number of factors, such as but not limited to, sequencing errors or allelic variation.

Example 12

This Example demonstrates the production of esterase proteins of the present invention in *E. coli* cells.

A. Flea esterase protein PHIS-PfE7$_{570}$ and flea esterase protein PHIS-PfE8$_{570}$ were produced in the following manner. A pair of primers was used to amplify DNA from flea esterase nucleic acid molecule nfE7$_{2836}$ or nfE8$_{2801}$ produced as described in Example 11. A sense primer containing an XhoI site (shown in bold) having the nucleic acid sequence 5' TGTGCTCGAG ATGGGATAAC CTAGAT-CAGC ATTTGTGC 3' (denoted SEQ ID NO:47), was used in combination with an anti-sense primer containing a KpnI site (shown in bold) having the nucleic acid sequence 5' TTAAGGTACC TCATCTAATA CTTCCTTCAT TACAG 3' (denoted SEQ ID NO:48). A PCR product was derived from nfE7$_{2836}$, and is referred to herein as nfE7$_{1710}$, having nucleic acid sequence SEQ ID NO:27. The PCR product was digested with XhoI and KpnI restriction endonucleases, gel purified and subcloned into expression vector pTrcHisB (available from InVitrogen). The resultant recombinant molecule, referred to herein as pTrc-nfE7$_{1710}$, was transformed into *E. coli* HB 101 competent cells (available from Gibco BRL) to form recombinant cell *E. coli*:pTrc-nfE7$_{1710}$.

The PCR product derived from nfE8$_{2801}$ using the primers is referred to herein as nfE8$_{1710}$, having nucleic acid sequence SEQ ID NO:33. PCR product nfE8$_{1710}$ was digested with XhoI and KpnI restriction endonucleases, gel purified and subcloned into expression vector pTrcHisB. The resultant recombinant molecule, referred to herein as pTrc-nfE8$_{1710}$, was transformed into *E. coli* HB101 competent cells to form recombinant cell *E. coli*:pTrc-nfE8$_{1710}$.

The recombinant cells were cultured in enriched bacterial growth medium containing 0.1 mg/ml ampicillin and 0.1% glucose at about 32° C. When the cells reached an OD$_{600}$ of about 0.4–0.5, expression of recombinant protein was induced by the addition of 0.5 mM isopropyl-B-D-thiogalactoside (IPTG), and the cells were cultured for about 2 hours at about 32° C. Inmunoblot analysis of recombinant cell *E. coli*:pTrc-nfE7$_{1710}$ and *E. coli*:pTrc-nfE8$_{1710}$ lysates using a T7 tag monoclonal antibody (available from Novagen, Inc., Madison, Wis.) directed against the fusion portion of the recombinant PHIS-PfE7$_{570}$ and PHIS-PfE8$_{570}$ fusion proteins identified proteins of appropriate size, namely an about 65 kD protein for each fusion protein.

B. Flea esterase protein PHIS-PfE5$_{550}$ was produced in the following manner. A pair of primers was used to amplify DNA from flea esterase nucleic acid molecule nfE5$_{2144}$ produced as described in Example 11. A sense primer containing an XhoI site having the nucleic acid sequence 5' AAACTCGAGT CCCCCGACTG TAACTTTGC 3' (denoted SEQ ID NO:62; XhoI site shown in bold), was used in combination with an anti-sense primer containing a PstI site having the nucleic acid sequence 5' TCATCTGCAG TTATTGACTG TGCAAAGTTT TTGTGG 3' (denoted SEQ ID NO:63; PstI site shown in bold). A PCR product was derived from nfE5$_{2144}$, and is referred to herein as nfE5$_{1650}$, having nucleic acid sequence SEQ ID NO:60. The PCR product was digested with XhoI and PstI restriction endonucleases, gel purified and subcloned into expression vector pTrcHisB (available from In Vitrogen). The resultant recombinant molecule, referred to herein as pTrc-nfE5$_{1650}$, was transformed into E. coli HB101 competent cells (available from Gibco BRL) to form recombinant cell E. coli:pTrc-nfE5$_{1650}$.

The recombinant cells were cultured using the method described in Section A of this example. Inmunoblot analysis of recombinant cell E. coli:pTrc-nfE5$_{1650}$ lysate using a T7 tag monoclonal antibody (available from Novagen, Inc., Madison, Wis.) directed against the fusion portion of the recombinant PHIS-PfE5$_{550}$ fusion proteins identified proteins of appropriate size, namely an about 60 kD protein for each fusion protein.

C. Flea esterase protein PHIS-PfE9$_{528}$ was produced in the following manner. A pair of primers was used to amplify DNA from flea esterase nucleic acid molecule nfE9$_{2007}$ produced as described in Example 11. A sense primer containing an BamHI site having the nucleic acid sequence 5' TTCCGGATCC GGCTGATCTA CAAGTGACTT TG 3' (denoted SEQ ID NO:64; BamHI site shown in bold), was used in combination with an anti-sense primer containing a XhoI site having the nucleic acid sequence 5' TGG-TACTCGA GTCATAAAAA TTTATTCCAA AATC 3' (denoted SEQ ID NO:65; XhoI site shown in bold). A PCR product was derived from nfE9$_{2007}$, and is referred to herein as nfE9$_{1584}$, having nucleic acid sequence SEQ ID NO:51. The PCR product was digested with BamI and XhoI restriction endonucleases, gel purified and subcloned into expression vector pTrcHisB (available from In Vitrogen). The resultant recombinant molecule, referred to herein as pTrc-nfE9$_{1584}$, was transformed into E. coli HB101 competent cells (available from Gibco BRL) to form recombinant cell E. coli:pTrc-nfE9$_{1584}$.

The recombinant cells were cultured using the method described in Section A of this example.

EXAMPLE 13

This Example demonstrates the production of esterase proteins of the present invention in eukaryotic cells.

Recombinant molecule pBv-nfE7$_{1788}$, containing a flea esterase nucleic acid molecule spanning nucleotides from about 99 through about 1886 of SEQ ID NO:24, and pBv-nfE8$_{1785}$, containing a flea esterase nucleic acid molecule spanning nucleotides from about 99 through about 1883 of SEQ ID NO:30 each, operatively linked to baculovirus polyhedron transcription control sequences were produced in the following manner. In order to subclone a flea esterase nucleic acid molecule into baculovirus expression vectors, flea esterase nucleic acid molecule-containing fragments were separately PCR amplified from nfE7$_{2836}$ or nfE8$_{2801}$ DNA. A PCR fragment of 1858 nucleotides, named nfE7$_{1858}$, was amplified from nfE7$_{2836}$ using a sense primer E1113 FWD having the nucleic acid sequence 5'-AAAACTGCAG TATAAATATG TTACCTCACA GTAGTG-3' (SEQ ID NO:49; PstI site shown in bold) and an antisense primer E 1113/2212 REV having the nucleic acid sequence 5'-TGCTCTAGAT TATCTAATAC TTCCT-TCATT ACAG (SEQ ID NO:50; XbaI site shown in bold). A PCR fragment of 1858 nucleotides, named nfE8$_{1858}$, was amplified from nfE8$_{2801}$ using a sense primer E2212 FWD having the nucleic acid sequence 5'-AAAACTGCAG TATAAATATG TTACCTCACA GTGCATTAG-3' (SEQ ID NO:66; PstI site shown in bold), and the antisense primer E 1113/2212 REV. The N-terminal primer was designed from the pol h sequence of baculovirus with modifications to enhance expression in the baculovirus system.

In order to produce a baculovirus recombinant molecule capable of directing the production of PfE7$_{596}$, the about 1,802 base pair PCR product (referred to as Bv-nfE7$_{1802}$) was digested with PstI and XbaI and subcloned into unique PstI and XbaI sites of pVL1392 baculovirus shuttle plasmid (available from Pharmingen, San Diego, Calif.) to produce the recombinant molecule referred to herein as pVL-nfE7$_{1802}$.

In order to produce a baculovirus recombinant molecule capable of directing the production of PfE8$_{595}$, the about 1,792 base pair PCR product (referred to as Bv-nfE8$_{1792}$) was digested with PstI and XbaI and subcloned into PstI and XbaI digested to produce the recombinant molecule referred to herein as pVL-nfE8$_{1792}$.

The resultant recombinant molecules, pVL-nf7$_{1802}$ and pVL-nfE8$_{1792}$, were verified for proper insert orientation by restriction mapping. Such a recombinant molecule can be co-transfected with a linear Baculogold baculovirus DNA (available from Pharmingen) into S. frugiperda Sf9 cells (available from In Vitrogen) to form the recombinant cells denoted S. frugiperda:pVL-nfE7$_{1802}$ and S. frugiperda:pVL-fE8$_{1792}$. S. frugiperda:pVL-nfE7$_{1802}$ can be cultured in order to produce a flea esterase protein PfE7$_{596}$. S. frugiperda:pVL-nfE8$_{1792}$ can be cultured in order to produce a flea esterase protein PfE8$_{595}$.

SEQUENCE LISTING (1) GENERAL INFORMATION:

(iii) NUMBER OF SEQUENCES: 66

(2) INFORMATION FOR SEQ ID NO:1:

(i) SEQUENCE CHARACTERISTICS:
      (A) LENGTH: 401 nucleotides
      (B) TYPE: nucleic acid
      (C) STRANDEDNESS: single
      (D) TOPOLOGY: linear (ii) MOLECULE TYPE: cDNA (iii) FEATURE:
             (A) NAME/KEY: CDS
             (B) LOCATION: 92..400

(iv) FEATURE:
             (A) NAME/KEY: Xaa = Ile, Thr Lys or Arg
             (B) LOCATION: 218

(v) FEATURE:
             (A) NAME/KEY: Xaa = Lys, Glu or Gln
             (B) LOCATION: 275, 329

(vi) FEATURE:
             (A) NAME/KEY: Xaa = Asn, Tyr or Asp
             (B) LOCATION: 332

(vii) SEQUENCE DESCRIPTION: SEQ ID NO:1:

```
TTTACATCAT TAATAAACAT AAATCTAATA AATCTTGTGG ATCAAGATCA                      50

AGTTTATTAG TGAGAGTGTT GGATTTGTGA AATATTTCAA A ATG AAT                       97
                                               Met Asn
                                                 1

TCT TTA ATT GTA AAA ATT TCT CAA GGA GCT ATT GAG GGG AAG                    139
Ser Leu Ile Val Lys Ile Ser Gln Gly Ala Ile Glu Gly Lys
          5                  10                  15

GAA ATG ATT AAT GAT AAT GGA AAG TCG TTT AGA GGA TTT TTG                    181
Glu Met Ile Asn Asp Asn Gly Lys Ser Phe Arg Gly Phe Leu
              20                  25                  30

GGT ATA CCT TAT GCT AAA CCG CCT ATA GGA AAT CTT ANA TTT                    223
Gly Ile Pro Tyr Ala Lys Pro Pro Ile Gly Asn Leu Xaa Phe
                  35                  40

AAG CCT CCT CAA AAG CCT GAT GAT TGG AAT GAT GTT CGA CCA                    265
Lys Pro Pro Gln Lys Pro Asp Asp Trp Asn Asp Val Arg Pro
45                  50                  55

GCT ACT GAA NAA GCA AAT GGT TGT AGA TCG AAA CAT ATG CTG                    307
Ala Thr Glu Xaa Ala Asn Gly Cys Arg Ser Lys His Met Leu
         60                  65                  70

CAG CAT CAT ATT ATT GGA GAC NAA NAT TGT CTA TAC CTA AAC                    349
Gln His His Ile Ile Gly Asp Xaa Xaa Cys Leu Tyr Leu Asn
             75                  80                  85

GTN TAT GTT CCA TTG ACT TCC AAA TTG GAG AAA CTA CCA GTA                    391
Val Tyr Val Pro Leu Thr Ser Lys Leu Glu Lys Leu Pro Val
                 90                  95                 100

ATG TTC TGG G                                                              401
Met Phe Trp
```

(2) INFORMATION FOR SEQ ID NO:2:

(i) SEQUENCE CHARACTERISTICS:
         (A) LENGTH: 103 amino acids
         (B) TYPE: amino acid
         (D) TOPOLOGY: linear (ii) MOLECULE TYPE: protein (iii) FEATURE:
         (A) NAME/KEY: Xaa = Ile, Thr, Lys or Arg
         (B) LOCATION: 43

(iv) FEATURE:
         (A) NAME/KEY: Xaa = Lys, Glu or Gln
         (B) LOCATION: 62, 80

(v) FEATURE:
         (A) NAME/KEY: Xaa = Asn, Tyr or Asp
         (B) LOCATION: 81

(vi) SEQUENCE DESCRIPTION: SEQ ID NO:2:

Met Asn Ser Leu Ile Val Lys Ile Ser Gln Gly Ala Ile Glu
 1               5                  10

Gly Lys Glu Met Ile Asn Asp Asn Gly Lys Ser Phe Arg Gly
 15                  20                  25

Phe Leu Gly Ile Pro Tyr Ala Lys Pro Pro Ile Gly Asn Leu
         30                  35                  40

Xaa Phe Lys Pro Pro Gln Lys Pro Asp Asp Trp Asn Asp Val
             45                  50                  55

Arg Pro Ala Thr Glu Xaa Ala Asn Gly Cys Arg Ser Lys His
                 60                  65                  70

Met Leu Gln His His Ile Ile Gly Asp Xaa Xaa Cys Leu Tyr
                     75                  80

Leu Asn Val Tyr Val Pro Leu Thr Ser Lys Leu Glu Lys Leu
 85                  90                  95

Pro Val Met Phe Trp
    100

(2) INFORMATION FOR SEQ ID NO:3:

(i) SEQUENCE CHARACTERISTICS:
        (A) LENGTH: 401 nucleotides
        (B) TYPE: nucleic acid
        (C) STRANDEDNESS: single
        (D) TOPOLOGY: linear (ii) MOLECULE TYPE: cDNA (iii) SEQUENCE DESCRIPTION: SEQ ID NO:3:

```
CCCAGAACAT TACTGGTAGT TTCTCCAATT TGGAAGTCAA TGGAACATAN           50

ACGTTTAGGT ATAGACAATN TTNGTCTCCA ATAATATGAT GCTGCAGCAT          100

ATGTTTCGAT CTACAACCAT TTGCTTNTTC AGTAGCTGGT CGAACATCAT          150

TCCAATCATC AGGCTTTTGA GGAGGCTTAA ATNTAAGATT TCCTATAGGC          200

GGTTTAGCAT AAGGTATACC CAAAAATCCT CTAAACGACT TTCCATTATC          250

ATTAATCATT TCCTTCCCCT CAATAGCTCC TTGAGAAATT TTTACAATTA          300

AAGAATTCAT TTTGAAATAT TTCACAAATC CAACACTCTC ACTAATAAAC          350

TTGATCTTGA TCCACAAGAT TTATTAGATT TATGTTTATT AATGATGTAA          400

A                                                              401
```

(2) INFORMATION FOR SEQ ID NO:4:

(i) SEQUENCE CHARACTERISTICS:
        (A) LENGTH: 364 nucleotides
        (B) TYPE: nucleic acid
        (C) STRANDEDNESS: single
        (D) TOPOLOGY: linear (ii) MOLECULE TYPE: cDNA (iii) FEATURE:
        (A) NAME/KEY: CDS
        (B) LOCATION: 2..364

(xi) SEQUENCE DESCRIPTION: SEQ ID NO:4:

G TCT CGT GTT ATT TTT TTA AGT TGT ATT TTT TTG TTT AGT           40
  Ser Arg Val Ile Phe Leu Ser Cys Ile Phe Leu Phe Ser
   1               5                  10

```
TTT AAT TTT ATA AAC TGT GAT TCC CCG ACT GTA ACT TTG CCC          82
Phe Asn Phe Ile Asn Cys Asp Ser Pro Thr Val Thr Leu Pro
 15                  20                  25

CAA GGC GAA TTG GTT GGA AAA GCT TTG ACG AAC GAA AAT GGA         124
Gln Gly Glu Leu Val Gly Lys Ala Leu Thr Asn Glu Asn Gly
         30                  35                  40

AAA GAG TAT TTT AGC TAC ACA GGT GTA CCT TAT GCT AAA CCT         166
Lys Glu Tyr Phe Ser Tyr Thr Gly Val Pro Tyr Ala Lys Pro
                 45                  50                  55

CCT GTT GGA GAA CTT AGA TTT AAG CCT CCA CAG AAA GCT GAG         208
Pro Val Gly Glu Leu Arg Phe Lys Pro Pro Gln Lys Ala Glu
                         60                  65

CCA TGG CAA GGT GTT TTC AAC GCC ACA TTA TAC GGA AAT GTG         250
Pro Trp Gln Gly Val Phe Asn Ala Thr Leu Tyr Gly Asn Val
 70                  75                  80

TGT AAA TCT TTA AAT TTC TTC TTG AAG AAA ATT GAA GGA GAC         292
Cys Lys Ser Leu Asn Phe Phe Leu Lys Lys Ile Glu Gly Asp
         85                  90                  95

GAA GAC TGC TTG GTA GTA AAC GTG TAC GCA CCA AAA ACA ACT         334
Glu Asp Cys Leu Val Val Asn Val Tyr Ala Pro Lys Thr Thr
                100                 105                 110

TCT GAT AAA AAA CTT CCA GTA TTT TTC TGG                         364
Ser Asp Lys Lys Leu Pro Val Phe Phe Trp
                115                 120
```

(2) INFORMATION FOR SEQ ID NO:5:

(i) SEQUENCE CHARACTERISTICS:
        (A) LENGTH: 121 amino acids
        (B) TYPE: amino acid
        (D) TOPOLOGY: linear (ii) MOLECULE TYPE: protein (iii) SEQUENCE DESCRIPTION: SEQ ID NO:5:

```
Ser Arg Val Ile Phe Leu Ser Cys Ile Phe Leu Phe Ser Phe
 1                   5                  10

Asn Phe Ile Asn Cys Asp Ser Pro Thr Val Thr Leu Pro Gln
15                  20                  25

Gly Glu Leu Val Gly Lys Ala Leu Thr Asn Glu Asn Gly Lys
         30                  35                  40

Glu Tyr Phe Ser Tyr Thr Gly Val Pro Tyr Ala Lys Pro Pro
                 45                  50                  55

Val Gly Glu Leu Arg Phe Lys Pro Pro Gln Lys Ala Glu Pro
                         60                  65                  70

Trp Gln Gly Val Phe Asn Ala Thr Leu Tyr Gly Asn Val Cys
                         75                  80

Lys Ser Leu Asn Phe Phe Leu Lys Lys Ile Glu Gly Asp Glu
85                  90                  95

Asp Cys Leu Val Val Asn Val Tyr Ala Pro Lys Thr Thr Ser
        100                 105                 110

Asp Lys Lys Leu Pro Val Phe Phe Trp
                115                 120
```

(2) INFORMATION FOR SEQ ID NO:6:

(i) SEQUENCE CHARACTERISTICS:
        (A) LENGTH: 364 nucleotides
        (B) TYPE: nucleic acid
        (C) STRANDEDNESS: single
        (D) TOPOLOGY: linear (ii) MOLECULE TYPE: cDNA (iii) SEQUENCE DESCRIPTION: SEQ ID NO:6:

| | |
|---|---:|
| CCAGAAAAAT ACTGGAAGTT TTTTATCAGA AGTTGTTTTT GGTGCGTACA | 50 |
| CGTTTACTAC CAAGCAGTCT TCGTCTCCTT CAATTTTCTT CAAGAAGAAA | 100 |
| TTTAAAGATT TACACACATT TCCGTATAAT GTGGCGTTGA AAACACCTTG | 150 |
| CCATGGCTCA GCTTTCTGTG GAGGCTTAAA TCTAAGTTCT CCAACAGGAG | 200 |
| GTTTAGCATA AGGTACACCT GTGTAGCTAA ATACTCTTT TCCATTTTCG | 250 |
| TTCGTCAAAG CTTTTCCAAC CAATTCGCCT TGGGGCAAAG TTACAGTCGG | 300 |
| GGAATCACAG TTTATAAAAT TAAAACTAAA CAAAAAAATA CAACTTAAAA | 350 |
| AAATAACACG AGAC | 364 |

(2) INFORMATION FOR SEQ ID NO:7:

(i) SEQUENCE CHARACTERISTICS:
        (A) LENGTH: 421 nucleotides
        (B) TYPE: nucleic acid
        (C) STRANDEDNESS: single
        (D) TOPOLOGY: linear (ii) MOLECULE TYPE: cDNA (iii) FEATURE:
        (A) NAME/KEY: CDS
        (B) LOCATION: 113..421

(iv) SEQUENCE DESCRIPTION: SEQ ID NO:7:

```
TTTACATTAC ATCAAATCAT ATTTTTATTA GTATATTTTT TAGAAGAACC              50

TAGCCAAAAA ATATGGACTT TAGACTGTGA TTAATTTATT TTACCTGAGA             100

TTTTCCTTTA CA ATG GGT GAT CTT CAA GTG ACT TTA CAA                  142
              Met Gly Asp Leu Gln Val Thr Leu Gln
                1               5

GGT TCT TTG AGA GGA AAA GAG CAA ATT AAT GAA AAG GGA AAT            184
Gly Ser Leu Arg Gly Lys Glu Gln Ile Asn Glu Lys Gly Asn
         15                  20

GTG TTT TAT AGT TAT TCT GGA ATT CCA TAT GCC AAA CCT CCA            226
Val Phe Tyr Ser Tyr Ser Gly Ile Pro Tyr Ala Lys Pro Pro
 25              30                  35

GTT GGT GAT CTA AGA TTC AAG CCA CCT CAA CCT GCA GAA CCT            268
Val Gly Asp Leu Arg Phe Lys Pro Pro Gln Pro Ala Glu Pro
     40                  45                  50

TGG TCA GGT GTC CTT GAT GCT ACT AAA GAA GGG AAT AGT TGT            310
Trp Ser Gly Val Leu Asp Ala Thr Lys Glu Gly Asn Ser Cys
         55                  60                  65

AGA TCT GTA CAT TTT ATT AAA AAG ATT AAA GTA GGG GCT GAA            352
Arg Ser Val His Phe Ile Lys Lys Ile Lys Val Gly Ala Glu
             70                  75                  80

GAT TGT CTA TAC CTC AAT GTC TAT GTA CCA AAA ACA TCA GAG            394
Asp Cys Leu Tyr Leu Asn Val Tyr Val Pro Lys Thr Ser Glu
                 85                  90

AAA TCC CTT CTT CCA GTA ATG GTA TGG                                421
Lys Ser Leu Leu Pro Val Met Val Trp
 95                 100
```

(2) INFORMATION FOR SEQ ID NO:8:

(i) SEQUENCE CHARACTERISTICS:
        (A) LENGTH: 103 amino acids (B) TYPE:  amino acid
        (D) TOPOLOGY:  linear (ii) MOLECULE TYPE:  protein (iii) SEQUENCE DESCRIPTION:  SEQ ID NO:8:

Met Gly Asp Leu Gln Val Thr Leu Leu Gln Gly Ser Leu Arg
1               5                   10

Gly Lys Glu Gln Ile Asn Glu Lys Gly Asn Val Phe Tyr Ser
15                  20                  25

Tyr Ser Gly Ile Pro Tyr Ala Lys Pro Pro Val Gly Asp Leu
            30                  35                  40

Arg Phe Lys Pro Pro Gln Pro Ala Glu Pro Trp Ser Gly Val
            45                  50                  55

Leu Asp Ala Thr Lys Glu Gly Asn Ser Cys Arg Ser Val His
                60                  65                  70

Phe Ile Lys Lys Ile Lys Val Gly Ala Glu Asp Cys Leu Tyr
                75                  80

Leu Asn Val Tyr Val Pro Lys Thr Ser Glu Lys Ser Leu Leu
85                  90                  95

Pro Val Met Val Trp
    100

(2) INFORMATION FOR SEQ ID NO:9:

(i) SEQUENCE CHARACTERISTICS:
        (A) LENGTH:  421 nucleotides
        (B) TYPE:  nucleic acid
        (C) STRANDEDNESS:  single
        (D) TOPOLOGY:  linear (ii) MOLECULE TYPE:  cDNA (iii) SEQUENCE DESCRIPTION:  SEQ ID NO:9:

CCATACCATT ACTGGAAGAA GGGATTTCTC TGATGTTTTT GGTACATAGA              50

CATTGAGGTA TAGACAATCT TCAGCCCCTA CTTTAATCTT TTTAATAAAA             100

TGTACAGATC TACAACTATT CCCTTCTTTA GTAGCATCAA GGACACCTGA             150

CCAAGGTTCT GCAGGTTGAG GTGGCTTGAA TCTTAGATCA CCAACTGGAG             200

GTTTGGCATA TGGAATTCCA GAATAACTAT AAAACACATT TCCCTTTTCA             250

TTAATTTGCT CTTTTCCTCT CAAAGAACCT TGTAACAAAG TCACTTGAAG             300

ATCACCCATT GTAAAGGAAA ATCTCAGGTA AAATAAATTA ATCACAGTCT             350

AAAGTCCATA TTTTTTGGCT AGGTTCTTCT AAAAAATATA CTAATAAAAA             400

TATGATTTGA TGTAATGTAA A                                            421

(2) INFORMATION FOR SEQ ID NO:10:

(i) SEQUENCE CHARACTERISTICS:
        (A) LENGTH:  524 nucleotides
        (B) TYPE:  nucleic acid
        (C) STRANDEDNESS:  single
        (D) TOPOLOGY:  linear (ii) MOLECULE TYPE:  cDNA (iii) FEATURE:
        (A) NAME/KEY:  CDS
        (B) LOCATION:  113..523

(iv) SEQUENCE DESCRIPTION:  SEQ ID NO:10:

```
GAACGTTGAT ACGATAGACA TGTCGTCTTC AAAACGTCTA TTTTATCATA              50

AACAAAACGA GATAAATAAT AACAATTAAG CAACCAAAAT GCATTAAAAA             100

ACACAATAAA AA ATG TTA CCT CAC AGT AGT GCA TTA GTT TTA              142
              Met Leu Pro His Ser Ser Ala Leu Val Leu
               1               5                  10

TTT TTA TTT TTT TTA TTT TTC TTA TTT ACA CCT ATC TTG TGC            184
Phe Leu Phe Phe Leu Phe Phe Leu Phe Thr Pro Ile Leu Cys
             15                  20

ATA CTA TGG GAT AAC CTA GAT CAG CAT TTG TGC AGA GTT CAA            226
Ile Leu Trp Asp Asn Leu Asp Gln His Leu Cys Arg Val Gln
 25              30                  35

TTT AAC AGG ATC ACG GAA GGA AAA CCG TTC CGA TAT AAA GAT            268
Phe Asn Arg Ile Thr Glu Gly Lys Pro Phe Arg Tyr Lys Asp
     40              45                  50

CAT AGG AAT GAT GTA TAT TGT TCT TAT TTG GGA ATT CCT TAT            310
His Arg Asn Asp Val Tyr Cys Ser Tyr Leu Gly Ile Pro Tyr
             55                  60                  65

GCC GAA CCG CCT ATT GGA CCA TTA CGA TTT CAG TCT CCA AAA            352
Ala Glu Pro Pro Ile Gly Pro Leu Arg Phe Gln Ser Pro Lys
                 70                  75                  80

CCA ATA TCA AAT CCA AAA ACA GGA TTC GTA CAG GCT CGA ACT            394
Pro Ile Ser Asn Pro Lys Thr Gly Phe Val Gln Ala Arg Thr
                     85                  90

TTG GGA GAC AAA TGT TTC CAG GAA AGT CTA ATA TAT TCT TAT            436
Leu Gly Asp Lys Cys Phe Gln Glu Ser Leu Ile Tyr Ser Tyr
 95                 100                 105

GCA GGA AGC GAA GAT TGC TTA TAT CTG AAT ATA TTC ACG CCA            478
Ala Gly Ser Glu Asp Cys Leu Tyr Leu Asn Ile Phe Thr Pro
         110                 115                 120

GAG ACT GTT AAT TCT GCG AAC AAT ACA AAA TAT CCT GTA ATG            520
Glu Thr Val Asn Ser Ala Asn Asn Thr Lys Tyr Pro Val Met
             125                 130                 135

TTC T                                                              524
Phe (2) INFORMATION FOR SEQ ID NO:11:

(i) SEQUENCE CHARACTERISTICS:
        (A) LENGTH:  137 amino acids
        (B) TYPE:  amino acid
        (D) TOPOLOGY:  linear (ii) MOLECULE TYPE:  protein (iii) SEQUENCE DESCRIPTION:  SEQ ID NO:11:

Met Leu Pro His Ser Ser Ala Leu Val Leu Phe Leu Phe
 1               5                  10

Leu Phe Phe Leu Phe Thr Pro Ile Leu Cys Ile Leu Trp Asp
15                  20                  25

Asn Leu Asp Gln His Leu Cys Arg Val Gln Phe Asn Arg Ile
        30                  35                  40

Thr Glu Gly Lys Pro Phe Arg Tyr Lys Asp His Arg Asn Asp
                45                  50                  55

Val Tyr Cys Ser Tyr Leu Gly Ile Pro Tyr Ala Glu Pro Pro
            60                  65                  70

Ile Gly Pro Leu Arg Phe Gln Ser Pro Lys Pro Ile Ser Asn
                75                  80

Pro Lys Thr Gly Phe Val Gln Ala Arg Thr Leu Gly Asp Lys
85                  90                  95
```

```
Cys Phe Gln Glu Ser Leu Ile Tyr Ser Tyr Ala Gly Ser Glu
    100                 105                 110

Asp Cys Leu Tyr Leu Asn Ile Phe Thr Pro Glu Thr Val Asn
        115                 120                 125

Ser Ala Asn Asn Thr Lys Tyr Pro Val Met Phe
            130                 135

(2) INFORMATION FOR SEQ ID NO:12:

(i) SEQUENCE CHARACTERISTICS:
        (A) LENGTH: 524 nucleotides
        (B) TYPE: nucleic acid
        (C) STRANDEDNESS: single
        (D) TOPOLOGY: linear (ii) MOLECULE TYPE: cDNA (iii) SEQUENCE DESCRIPTION: SEQ ID NO:12:

AGAACATTAC AGGATATTTT GTATTGTTCG CAGAATTAAC AGTCTCTGGC         50

GTGAATATAT TCAGATATAA GCAATCTTCG CTTCCTGCAT AAGAATATAT        100

TAGACTTTCC TGGAAACATT TGTCTCCCAA AGTTCGAGCC TGTACGAATC        150

CTGTTTTTGG ATTTGATATT GGTTTTGGAG ACTGAAATCG TAATGGTCCA        200

ATAGGCGGTT CGGCATAAGG AATTCCCAAA TAAGAACAAT ATACATCATT        250

CCTATGATCT TTATATCGGA ACGGTTTTCC TTCCGTGATC CTGTTAAATT        300

GAACTCTGCA CAAATGCTGA TCTAGGTTAT CCCATAGTAT GCACAAGATA        350

GGTGTAAATA AGAAAAATAA AAAAAATAAA AATAAAACTA ATGCACTACT        400

GTGAGGTAAC ATTTTTTATT GTGTTTTTTA ATGCATTTTG GTTGCTTAAT        450

TGTTATTATT TATCTCGTTT TGTTTATGAT AAAATAGACG TTTTGAAGAC        500

GACATGTCTA TCGTATCAAC GTTC                                   524

(2) INFORMATION FOR SEQ ID NO:13:

(i) SEQUENCE CHARACTERISTICS:
        (A) LENGTH: 1982 nucleotides
        (B) TYPE: nucleic acid
        (C) STRANDEDNESS: single
        (D) TOPOLOGY: linear (ii) MOLECULE TYPE: cDNA (iii) FEATURE:
         (A) NAME/KEY: CDS
         (B) LOCATION: 31..1517

(iv) FEATURE:
         (A) NAME/KEY: Asx = Asn or Asp
         (B) LOCATION: 300

(v) SEQUENCE DESCRIPTION: SEQ ID NO:13:

AT TTT AGC TAC ACA GGT GTA CCT TAT GCT AAA CCT CCT GTT          41
   Phe Ser Tyr Thr Gly Val Pro Tyr Ala Lys Pro Pro Val
    1               5                   10

GGA GAA CTT AGA TTT AAG CCT CCA CAG AAA GCT GAG CCA TGG         83
Gly Glu Leu Arg Phe Lys Pro Pro Gln Lys Ala Glu Pro Trp
 15                  20                  25

CAA GGT GTT TTC AAC GCC ACA TTA TAC GGA AAT GTG TGT AAA        125
Gln Gly Val Phe Asn Ala Thr Leu Tyr Gly Asn Val Cys Lys
     30                  35                  40

TCT TTA AAT TTC TTC TTG AAG AAA ATT GAA GGA GAC GAA GAC        167
```

-continued

```
    Ser Leu Asn Phe Phe Leu Lys Lys Ile Glu Gly Asp Glu Asp
                 45                  50                  55

TGC TTG GTA GTA AAC GTG TAC GCA CCA AAA ACA ACT TCT GAT        209
Cys Leu Val Val Asn Val Tyr Ala Pro Lys Thr Thr Ser Asp
                 60                  65

AAA AAA CTT CCA GTA TTT TTC TGG GTT CAT GGT GGT GGT TTT        251
Lys Lys Leu Pro Val Phe Phe Trp Val His Gly Gly Gly Phe
70                   75                  80

GTG ACT GGA TCC GGA AAT TTA GAA TTC CAA AGC CCA GAT TAT        293
Val Thr Gly Ser Gly Asn Leu Glu Phe Gln Ser Pro Asp Tyr
        85                  90                  95

TTA GTA RAT TTT GAT GTT ATT TTC GTA ACT TTC AAT TAC CGA        335
Leu Val Asx Phe Asp Val Ile Phe Val Thr Phe Asn Tyr Arg
                100                 105                 110

TTG GGA CCT CTC GGA TTT CTG AAT TTG GAG TTG GAG GGT GCT        377
Leu Gly Pro Leu Gly Phe Leu Asn Leu Glu Leu Glu Gly Ala
                115                 120                 125

CCA GGA AAT GTA GGA TTA TTG GAT CAG GTG GCA GCT CTG AAA        419
Pro Gly Asn Val Gly Leu Leu Asp Gln Val Ala Ala Leu Lys
                130                 135

TGG ACC AAA GAA AAC ATT GAG AAA TTT GGT GGA GAT CCA GAA        461
Trp Thr Lys Glu Asn Ile Glu Lys Phe Gly Gly Asp Pro Glu
140                 145                 150

AAT ATT ACA ATT GGT GGT GTT TCT GCT GGT GGA GCA AGT GTT        503
Asn Ile Thr Ile Gly Gly Val Ser Ala Gly Gly Ala Ser Val
        155                 160                 165

CAT TAT CTT TTG TTA TCT CAT ACA ACC ACT GGA CTT TAC AAA        545
His Tyr Leu Leu Leu Ser His Thr Thr Thr Gly Leu Tyr Lys
                170                 175                 180

AGG GCA ATT GCT CAA AGT GGA AGT GCT TTT AAT CCA TGG GCC        587
Arg Ala Ile Ala Gln Ser Gly Ser Ala Phe Asn Pro Trp Ala
                185                 190                 195

TTC CAA AGA CAT CCA GTA AAG CGT AGT CTT CAA CTT GCT GAG        629
Phe Gln Arg His Pro Val Lys Arg Ser Leu Gln Leu Ala Glu
                200                 205

ATA TTG GGT CAT CCC ACA AAC AAT ACT CAA GAT GCT TTA GAA        671
Ile Leu Gly His Pro Thr Asn Asn Thr Gln Asp Ala Leu Glu
210                 215                 220

TTC TTA CAA AAA GCC CCC GTA GAC AGT CTC CTG AAG AAA ATG        713
Phe Leu Gln Lys Ala Pro Val Asp Ser Leu Leu Lys Lys Met
        225                 230                 235

CCA GCT GAA ACA GAA GGT GAA ATA ATA GAA GAG TTT GTC TTC        755
Pro Ala Glu Thr Glu Gly Glu Ile Ile Glu Glu Phe Val Phe
                240                 245                 250

GTA CCA TCA ATT GAA AAA GTT TTC CCA TCC CAC CAA CCT TTC        797
Val Pro Ser Ile Glu Lys Val Phe Pro Ser His Gln Pro Phe
                255                 260                 265

TTG GAA GAA TCA CCA TTG GCC AGA ATG AAA TCC GGA TCC TTT        839
Leu Glu Glu Ser Pro Leu Ala Arg Met Lys Ser Gly Ser Phe
                270                 275

AAC AAA GTA CCT TTA TTA GTT GGA TTT AAC AGT GCA GAA GGA        881
Asn Lys Val Pro Leu Leu Val Gly Phe Asn Ser Ala Glu Gly
280                 285                 290

CTT TTG TTC AAA TTC TTC ATG AAA GAA AAA CCA GAG ATG CTG        923
Leu Leu Phe Lys Phe Phe Met Lys Glu Lys Pro Glu Met Leu
        295                 300                 305

AAC CAA GCT GAA GCA GAT TTT GAA AGA CTC GTA CCA GCC GAA        965
Asn Gln Ala Glu Ala Asp Phe Glu Arg Leu Val Pro Ala Glu
                310                 315                 320
```

```
TTT GAA TTA GTC CAT GGA TCA GAG GAA TCG AAA AAA CTT GCA        1007
Phe Glu Leu Val His Gly Ser Glu Glu Ser Lys Lys Leu Ala
            325                 330                 335

GAA AAA ATC AGG AAG TTT TAC TTT GAC GAT AAA CCC GTT CCA        1049
Glu Lys Ile Arg Lys Phe Tyr Phe Asp Asp Lys Pro Val Pro
                340                 345

GAA AAT GAA CAG AAA TTT ATT GAC TTG ATA GGA GAT ATT TGG        1091
Glu Asn Glu Gln Lys Phe Ile Asp Leu Ile Gly Asp Ile Trp
350                 355                 360

TTT ACT AGA GGT GTT GAC AAG CAT GTC AAG TTG TCT GTG GAG        1133
Phe Thr Arg Gly Val Asp Lys His Val Lys Leu Ser Val Glu
        365                 370                 375

AAA CAA GAC GAA CCA GTT TAT TAT TAT GAA TAT TCC TTC TCG        1175
Lys Gln Asp Glu Pro Val Tyr Tyr Tyr Glu Tyr Ser Phe Ser
            380                 385                 390

GAA AGT CAT CCT GCA AAA GGA ACA TTT GGT GAT CAT AAT CTG        1217
Glu Ser His Pro Ala Lys Gly Thr Phe Gly Asp His Asn Leu
                395                 400                 405

ACT GGT GCA TGC CAT GGA GAA GAA CTT GTG AAT TTA TTC AAA        1259
Thr Gly Ala Cys His Gly Glu Glu Leu Val Asn Leu Phe Lys
                    410                 415

GTC GAG ATG ATG AAG CTG GAA AAA GAT AAA CCT AAT GTT CTA        1301
Val Glu Met Met Lys Leu Glu Lys Asp Lys Pro Asn Val Leu
420                 425                 430

TTA ACA AAA GAT AGA GTA CTT GCC ATG TGG ACT AAC TTC ATC        1343
Leu Thr Lys Asp Arg Val Leu Ala Met Trp Thr Asn Phe Ile
        435                 440                 445

AAA AAT GGA AAT CCT ACT CCT GAA GTA ACA GAA TTA TTG CCA        1385
Lys Asn Gly Asn Pro Thr Pro Glu Val Thr Glu Leu Leu Pro
            450                 455                 460

GTT AAA TGG GAA CCT GCC ACA AAA GAC AAG TTG AAT TAT TTG        1427
Val Lys Trp Glu Pro Ala Thr Lys Asp Lys Leu Asn Tyr Leu
                465                 470                 475

AAC ATT GAT GCC ACC TTA ACT TTG GGA ACA AAT CCT GAG GCA        1469
Asn Ile Asp Ala Thr Leu Thr Leu Gly Thr Asn Pro Glu Ala
                    480                 485

AAC CGA GTC AAA TTT TGG GAA GAC GCC ACA AAA TCT TTG CAC        1511
Asn Arg Val Lys Phe Trp Glu Asp Ala Thr Lys Ser Leu His
490                 495                 500

GGT CAA TAA TAATTTATGA AAATTGTTTT AAATACTTTA GGTAATATAT        1560
Gly Gln
    505

TAGGTAAATA AAAATTAAAA AATAACAATT TTTATGTTTT ATGTATTGGC        1610

TTATGTGTAT CAGTTCTAAT TTTATTTATT TATTCTTGTT TTGCTTGTTT        1660

TGAAATATCA TGGTTTTAAT TTTCAAAACA CAACGTCGTT TGTTTTTAGC        1710

AAAATTTCCA ATAGATATGT TATATTAAGT ACTCTGAAGT ATTTTTATAT        1760

ATACACTAAA ATCAGTAAAA ATACATTAAC TAAAAATATA AGATATTTTC        1810

AATAATTTTT TTTAAAGAAA ATACCAAAAA TAAAGTAAAA TTCCAAACGG        1860

AATTTTTGTT TAACTTAAAA ATAAAATTAA CTCTTCAATA ATTTTGATAA        1910

TTAGTATTTC TGATATCATT AGTGAAAATT ATATTTTGAT AATACGTATT        1960

TATATTTAAA ATAAAATTAT GT                                      1982
```

(2) INFORMATION FOR SEQ ID NO:14:

(i) SEQUENCE CHARACTERISTICS:
        (A) LENGTH: 505 amino acids (B) TYPE: amino acid
(D) TOPOLOGY: linear (ii) MOLECULE TYPE: protein (iii) SEQUENCE DESCRIPTION: SEQ ID NO:14:

```
Phe Ser Tyr Thr Gly Val Pro Tyr Ala Lys Pro Pro Val Gly
 1               5                  10
Glu Leu Arg Phe Lys Pro Pro Gln Lys Ala Glu Pro Trp Gln
 15              20                  25
Gly Val Phe Asn Ala Thr Leu Tyr Gly Asn Val Cys Lys Ser
     30              35                  40
Leu Asn Phe Phe Leu Lys Lys Ile Glu Gly Asp Glu Asp Cys
         45              50                  55
Leu Val Val Asn Val Tyr Ala Pro Lys Thr Thr Ser Asp Lys
             60              65                  70
Lys Leu Pro Val Phe Phe Trp Val His Gly Gly Phe Val
             75                  80
Thr Gly Ser Gly Asn Leu Glu Phe Gln Ser Pro Asp Tyr Leu
 85              90                  95
Val Asx Phe Asp Val Ile Phe Val Thr Phe Asn Tyr Arg Leu
         100             105                 110
Gly Pro Leu Gly Phe Leu Asn Leu Glu Leu Glu Gly Ala Pro
             115             120                 125
Gly Asn Val Gly Leu Leu Asp Gln Val Ala Ala Leu Lys Trp
             130                 135                 140
Thr Lys Glu Asn Ile Glu Lys Phe Gly Gly Asp Pro Glu Asn
                 145                 150
Ile Thr Ile Gly Gly Val Ser Ala Gly Gly Ala Ser Val His
 155                 160                 165
Tyr Leu Leu Ser His Thr Thr Gly Leu Tyr Lys Arg
     170                 175                 180
Ala Ile Ala Gln Ser Gly Ser Ala Phe Asn Pro Trp Ala Phe
         185                 190                 195
Gln Arg His Pro Val Lys Arg Ser Leu Gln Leu Ala Glu Ile
             200                 205                 210
Leu Gly His Pro Thr Asn Asn Thr Gln Asp Ala Leu Glu Phe
             215                 220
Leu Gln Lys Ala Pro Val Asp Ser Leu Leu Lys Lys Met Pro
 225                 230                 235
Ala Glu Thr Glu Gly Glu Ile Ile Glu Glu Phe Val Phe Val
 240                 245                 250
Pro Ser Ile Glu Lys Val Phe Pro Ser His Gln Pro Leu Leu
             255                 260                 265
Glu Glu Ser Pro Leu Ala Arg Met Lys Ser Gly Ser Phe Asn
             270                 275                 280
Lys Val Pro Leu Leu Val Gly Phe Asn Ser Ala Glu Gly Leu
             285                 290
Leu Phe Lys Phe Phe Met Lys Glu Lys Pro Glu Met Leu Asn
 295                 300                 305
Gln Ala Glu Ala Asp Phe Glu Arg Leu Val Pro Ala Glu Phe
             310                 315                 320
Glu Leu Val His Gly Ser Glu Glu Ser Lys Lys Leu Ala Glu
             325                 330                 335
```

```
Lys Ile Arg Lys Phe Tyr Phe Asp Asp Lys Pro Val Pro Glu
            340                 345                 350

Asn Glu Gln Lys Phe Ile Asp Leu Ile Gly Asp Ile Trp Phe
            355                 360

Thr Arg Gly Val Asp Lys His Val Lys Leu Ser Val Glu Lys
365                 370                 375

Gln Asp Glu Pro Val Tyr Tyr Tyr Glu Tyr Ser Phe Ser Glu
        380                 385                 390

Ser His Pro Ala Lys Gly Thr Phe Gly Asp His Asn Leu Thr
            395                 400                 405

Gly Ala Cys His Gly Glu Glu Leu Val Asn Leu Phe Lys Val
            410                 415                 420

Glu Met Met Lys Leu Glu Lys Asp Lys Pro Asn Val Leu Leu
                425                 430

Thr Lys Asp Arg Val Leu Ala Met Trp Thr Asn Phe Ile Lys
435                 440                 445

Asn Gly Asn Pro Thr Pro Glu Val Thr Glu Leu Leu Pro Val
            450                 455                 460

Lys Trp Glu Pro Ala Thr Lys Asp Lys Leu Asn Tyr Leu Asn
            465                 470                 475

Ile Asp Ala Thr Leu Thr Leu Gly Thr Asn Pro Glu Ala Asn
                480                 485                 490

Arg Val Lys Phe Trp Glu Asp Ala Thr Lys Ser Leu His Gly
            495                 500

Gln
505

(2) INFORMATION FOR SEQ ID NO:15:

(i) SEQUENCE CHARACTERISTICS:
        (A) LENGTH: 1982 nucleotides
        (B) TYPE: nucleic acid
        (C) STRANDEDNESS: single
        (D) TOPOLOGY: linear (ii) MOLECULE TYPE: cDNA (iii) SEQUENCE DESCRIPTION: SEQ ID NO:15:

ACATAATTTT ATTTTAAATA TAAATACGTA TTATCAAAAT ATAATTTTCA          50

CTAATGATAT CAGAAATACT AATTATCAAA ATTATTGAAG AGTTAATTTT         100

ATTTTTAAGT TAAACAAAAA TTCCGTTTGG AATTTTACTT TATTTTTGGT         150

ATTTTCTTTA AAAAAAATTA TTGAAAATAT CTTATATTTT TAGTTAATGT         200

ATTTTTACTG ATTTTAGTGT ATATATAAAA ATACTTCAGA GTACTTAATA         250

TAACATATCT ATTGGAAATT TTGCTAAAAA CAAACGACGT TGTGTTTTGA         300

AAATTAAAAC CATGATATTT CAAAACAAGC AAAACAAGAA TAAATAAATA         350

AAATTAGAAC TGATACACAT AAGCCAATAC ATAAAACATA AAAATTGTTA         400

TTTTTTAATT TTTATTTACC TAATATATTA CCTAAAGTAT TTAAAACAAT         450

TTTCATAAAT TATTATTGAC CGTGCAAAGA TTTTGTGGCG TCTTCCCAAA         500

ATTTGACTCG GTTTGCCTCA GGATTTGTTC CCAAAGTTAA GGTGGCATCA         550

ATGTTCAAAT AATTCAACTT GTCTTTTGTG GCAGGTTCCC ATTTAACTGG         600

CAATAATTCT GTTACTTCAG GAGTAGGATT TCCATTTTTG ATGAAGTTAG         650

TCCACATGGC AAGTACTCTA TCTTTTGTTA ATAGAACATT AGGTTTATCT         700
```

-continued

```
TTTTCCAGCT TCATCATCTC GACTTTGAAT AAATTCACAA GTTCTTCTCC           750

ATGGCATGCA CCAGTCAGAT TATGATCACC AAATGTTCCT TTTGCAGGAT           800

GACTTTCCGA GAAGGAATAT TCATAATAAT AAACTGGTTC GTCTTGTTTC           850

TCCACAGACA ACTTGACATG CTTGTCAACA CCTCTAGTAA ACCAAATATC           900

TCCTATCAAG TCAATAAATT TCTGTTCATT TTCTGGAACG GGTTTATCGT           950

CAAAGTAAAA CTTCCTGATT TTTTCTGCAA GTTTTTTCGA TTCCTCTGAT          1000

CCATGGACTA ATTCAAATTC GGCTGGTACG AGTCTTTCAA AATCTGCTTC          1050

AGCTTGGTTC AGCATCTCTG GTTTTTCTTT CATGAAGAAT TTGAACAAAA          1100

GTCCTTCTGC ACTGTTAAAT CCAACTAATA AAGGTACTTT GTTAAAGGAT          1150

CCGGATTTCA TTCTGGCCAA TGGTGATTCT TCCAAGAAAG GTTGGTGGGA          1200

TGGGAAAACT TTTTCAATTG ATGGTACGAA GACAAACTCT TCTATTATTT          1250

CACCTTCTGT TTCAGCTGGC ATTTTCTTCA GGAGACTGTC TACGGGGCT           1300

TTTTGTAAGA ATTCTAAAGC ATCTTGAGTA TTGTTTGTGG GATGACCCAA          1350

TATCTCAGCA AGTTGAAGAC TACGCTTTAC TGGATGTCTT TGGAAGGCCC          1400

ATGGATTAAA AGCACTTCCA CTTTGAGCAA TTGCCCTTTT GTAAAGTCCA          1450

GTGGTTGTAT GAGATAACAA AAGATAATGA ACACTTGCTC CACCAGCAGA          1500

AACACCACCA ATTGTAATAT TTTCTGGATC TCCACCAAAT TTCTCAATGT          1550

TTTCTTTGGT CCATTTCAGA GCTGCCACCT GATCCAATAA TCCTACATTT          1600

CCTGGAGCAC CCTCCAACTC CAAATTCAGA ATCCGAGAG GTCCCAATCG           1650

GTAATTGAAA GTTACGAAAA TAACATCAAA ATYTACTAAA TAATCTGGGC          1700

TTTGGAATTC TAAATTTCCG GATCCAGTCA CAAAACCACC ACCATGAACC          1750

CAGAAAAATA CTGGAAGTTT TTTATCAGAA GTTGTTTTTG GTGCGTACAC          1800

GTTTACTACC AAGCAGTCTT CGTCTCCTTC AATTTTCTTC AAGAAGAAAT          1850

TTAAAGATTT ACACACATTT CCGTATAATG TGGCGTTGAA AACACCTTGC          1900

CATGGCTCAG CTTTCTGTGG AGGCTTAAAT CTAAGTTCTC CAACAGGAGG          1950

TTTAGCATAA GGTACACCTG TGTAGCTAAA AT                             1982
```

(2) INFORMATION FOR SEQ ID NO:16:

(i) SEQUENCE CHARACTERISTICS:
        (A) LENGTH: 1515 nucleotides
        (B) TYPE: nucleic acid
        (C) STRANDEDNESS: single
        (D) TOPOLOGY: linear (ii) MOLECULE TYPE: cDNA (iii) FEATURE:
        (A) NAME/KEY: CDS
        (B) LOCATION: 1..1515

(iv) FEATURE:
        (A) NAME/KEY: Asx = Asn or Asp
        (B) LOCATION: 298

(xi) SEQUENCE DESCRIPTION: SEQ ID NO:16:

```
TTT AGC TAC ACA GGT GTA CCT TAT GCT AAA CCT CCT GTT              39
Phe Ser Tyr Thr Gly Val Pro Tyr Ala Lys Pro Pro Val
 1               5                  10

GGA GAA CTT AGA TTT AAG CCT CCA CAG AAA GCT GAG CCA TGG          81
```

```
Gly Glu Leu Arg Phe Lys Pro Pro Gln Lys Ala Glu Pro Trp
 15                  20                  25

CAA GGT GTT TTC AAC GCC ACA TTA TAC GGA AAT GTG TGT AAA         123
Gln Gly Val Phe Asn Ala Thr Leu Tyr Gly Asn Val Cys Lys
         30                  35                  40

TCT TTA AAT TTC TTC TTG AAG AAA ATT GAA GGA GAC GAA GAC         165
Ser Leu Asn Phe Phe Leu Lys Lys Ile Glu Gly Asp Glu Asp
             45                  50                  55

TGC TTG GTA GTA AAC GTG TAC GCA CCA AAA ACA ACT TCT GAT         207
Cys Leu Val Val Asn Val Tyr Ala Pro Lys Thr Thr Ser Asp
                 60                  65

AAA AAA CTT CCA GTA TTT TTC TGG GTT CAT GGT GGT GGT TTT         249
Lys Lys Leu Pro Val Phe Phe Trp Val His Gly Gly Gly Phe
 70                  75                  80

GTG ACT GGA TCC GGA AAT TTA GAA TTC CAA AGC CCA GAT TAT         291
Val Thr Gly Ser Gly Asn Leu Glu Phe Gln Ser Pro Asp Tyr
         85                  90                  95

TTA GTA RAT TTT GAT GTT ATT TTC GTA ACT TTC AAT TAC CGA         333
Leu Val Asx Phe Asp Val Ile Phe Val Thr Phe Asn Tyr Arg
             100                 105                 110

TTG GGA CCT CTC GGA TTT CTG AAT TTG GAG TTG GAG GGT GCT         375
Leu Gly Pro Leu Gly Phe Leu Asn Leu Glu Leu Glu Gly Ala
                 115                 120                 125

CCA GGA AAT GTA GGA TTA TTG GAT CAG GTG GCA GCT CTG AAA         417
Pro Gly Asn Val Gly Leu Leu Asp Gln Val Ala Ala Leu Lys
                     130                 135

TGG ACC AAA GAA AAC ATT GAG AAA TTT GGT GGA GAT CCA GAA         459
Trp Thr Lys Glu Asn Ile Glu Lys Phe Gly Gly Asp Pro Glu
 140                 145                 150

AAT ATT ACA ATT GGT GGT GTT TCT GCT GGT GGA GCA AGT GTT         501
Asn Ile Thr Ile Gly Gly Val Ser Ala Gly Gly Ala Ser Val
         155                 160                 165

CAT TAT CTT TTG TTA TCT CAT ACA ACC ACT GGA CTT TAC AAA         543
His Tyr Leu Leu Leu Ser His Thr Thr Thr Gly Leu Tyr Lys
             170                 175                 180

AGG GCA ATT GCT CAA AGT GGA AGT GCT TTT AAT CCA TGG GCC         585
Arg Ala Ile Ala Gln Ser Gly Ser Ala Phe Asn Pro Trp Ala
                 185                 190                 195

TTC CAA AGA CAT CCA GTA AAG CGT AGT CTT CAA CTT GCT GAG         627
Phe Gln Arg His Pro Val Lys Arg Ser Leu Gln Leu Ala Glu
                     200                 205

ATA TTG GGT CAT CCC ACA AAC AAT ACT CAA GAT GCT TTA GAA         669
Ile Leu Gly His Pro Thr Asn Asn Thr Gln Asp Ala Leu Glu
 210                 215                 220

TTC TTA CAA AAA GCC CCC GTA GAC AGT CTC CTG AAG AAA ATG         711
Phe Leu Gln Lys Ala Pro Val Asp Ser Leu Leu Lys Lys Met
 225                 230                 235

CCA GCT GAA ACA GAA GGT GAA ATA ATA GAA GAG TTT GTC TTC         753
Pro Ala Glu Thr Glu Gly Glu Ile Ile Glu Glu Phe Val Phe
         240                 245                 250

GTA CCA TCA ATT GAA AAA GTT TTC CCA TCC CAC CAA CCT TTC         795
Val Pro Ser Ile Glu Lys Val Phe Pro Ser His Gln Pro Leu
             255                 260                 265

TTG GAA GAA TCA CCA TTG GCC AGA ATG AAA TCC GGA TCC TTT         837
Leu Glu Glu Ser Pro Leu Ala Arg Met Lys Ser Gly Ser Phe
                 270                 275

AAC AAA GTA CCT TTA TTA GTT GGA TTT AAC AGT GCA GAA GGA         879
Asn Lys Val Pro Leu Leu Val Gly Phe Asn Ser Ala Glu Gly
 280                 285                 290
```

```
CTT TTG TTC AAA TTC TTC ATG AAA GAA AAA CCA GAG ATG CTG              921
Leu Leu Phe Lys Phe Phe Met Lys Glu Lys Pro Glu Met Leu
    295                 300                 305

AAC CAA GCT GAA GCA GAT TTT GAA AGA CTC GTA CCA GCC GAA              963
Asn Gln Ala Glu Ala Asp Phe Glu Arg Leu Val Pro Ala Glu
        310                 315                 320

TTT GAA TTA GTC CAT GGA TCA GAG GAA TCG AAA AAA CTT GCA             1005
Phe Glu Leu Val His Gly Ser Glu Glu Ser Lys Lys Leu Ala
                325                 330                 335

GAA AAA ATC AGG AAG TTT TAC TTT GAC GAT AAA CCC GTT CCA             1047
Glu Lys Ile Arg Lys Phe Tyr Phe Asp Asp Lys Pro Val Pro
                    340                 345

GAA AAT GAA CAG AAA TTT ATT GAC TTG ATA GGA GAT ATT TGG             1089
Glu Asn Glu Gln Lys Phe Ile Asp Leu Ile Gly Asp Ile Trp
350                 355                 360

TTT ACT AGA GGT GTT GAC AAG CAT GTC AAG TTG TCT GTG GAG             1131
Phe Thr Arg Gly Val Asp Lys His Val Lys Leu Ser Val Glu
    365                 370                 375

AAA CAA GAC GAA CCA GTT TAT TAT TAT GAA TAT TCC TTC TCG             1173
Lys Gln Asp Glu Pro Val Tyr Tyr Tyr Glu Tyr Ser Phe Ser
        380                 385                 390

GAA AGT CAT CCT GCA AAA GGA ACA TTT GGT GAT CAT AAT CTG             1215
Glu Ser His Pro Ala Lys Gly Thr Phe Gly Asp His Asn Leu
                395                 400                 405

ACT GGT GCA TGC CAT GGA GAA GAA CTT GTG AAT TTA TTC AAA             1257
Thr Gly Ala Cys His Gly Glu Glu Leu Val Asn Leu Phe Lys
                    410                 415

GTC GAG ATG ATG AAG CTG GAA AAA GAT AAA CCT AAT GTT CTA             1299
Val Glu Met Met Lys Leu Glu Lys Asp Lys Pro Asn Val Leu
420                 425                 430

TTA ACA AAA GAT AGA GTA CTT GCC ATG TGG ACT AAC TTC ATC             1341
Leu Thr Lys Asp Arg Val Leu Ala Met Trp Thr Asn Phe Ile
    435                 440                 445

AAA AAT GGA AAT CCT ACT CCT GAA GTA ACA GAA TTA TTG CCA             1383
Lys Asn Gly Asn Pro Thr Pro Glu Val Thr Glu Leu Leu Pro
        450                 455                 460

GTT AAA TGG GAA CCT GCC ACA AAA GAC AAG TTG AAT TAT TTG             1425
Val Lys Trp Glu Pro Ala Thr Lys Asp Lys Leu Asn Tyr Leu
                465                 470                 475

AAC ATT GAT GCC ACC TTA ACT TTG GGA ACA AAT CCT GAG GCA             1467
Asn Ile Asp Ala Thr Leu Thr Leu Gly Thr Asn Pro Glu Ala
                    480                 485

AAC CGA GTC AAA TTT TGG GAA GAC GCC ACA AAA TCT TTG CAC             1509
Asn Arg Val Lys Phe Trp Glu Asp Ala Thr Lys Ser Leu His
490                 495                 500

GGT CAA                                                             1515
Gly Gln
    505

(2) INFORMATION FOR SEQ ID NO:17:

(i) SEQUENCE CHARACTERISTICS:
        (A) LENGTH: 1515 nucleotides
        (B) TYPE: nucleic acid
        (C) STRANDEDNESS: single
        (D) TOPOLOGY: linear (ii) MOLECULE TYPE: cDNA (iii) SEQUENCE DESCRIPTION: SEQ ID NO:17:

TTGACCGTGC AAAGATTTTG TGGCGTCTTC CCAAAATTTG ACTCGGTTTG               50

CCTCAGGATT TGTTCCCAAA GTTAAGGTGG CATCAATGTT CAAATAATTC              100
```

```
AACTTGTCTT TTGTGGCAGG TTCCCATTTA ACTGGCAATA ATTCTGTTAC        150

TTCAGGAGTA GGATTTCCAT TTTTGATGAA GTTAGTCCAC ATGGCAAGTA        200

CTCTATCTTT TGTTAATAGA ACATTAGGTT TATCTTTTTC CAGCTTCATC        250

ATCTCGACTT TGAATAAATT CACAAGTTCT TCTCCATGGC ATGCACCAGT        300

CAGATTATGA TCACCAAATG TTCCTTTTGC AGGATGACTT TCCGAGAAGG        350

AATATTCATA ATAATAAACT GGTTCGTCTT GTTTCTCCAC AGACAACTTG        400

ACATGCTTGT CAACACCTCT AGTAAACCAA ATATCTCCTA TCAAGTCAAT        450

AAATTTCTGT TCATTTTCTG GAACGGGTTT ATCGTCAAAG TAAAACTTCC        500

TGATTTTTTC TGCAAGTTTT TTCGATTCCT CTGATCCATG GACTAATTCA        550

AATTCGGCTG GTACGAGTCT TTCAAAATCT GCTTCAGCTT GGTTCAGCAT        600

CTCTGGTTTT TCTTTCATGA AGAATTTGAA CAAAAGTCCT TCTGCACTGT        650

TAAATCCAAC TAATAAAGGT ACTTTGTTAA AGGATCCGGA TTTCATTCTG        700

GCCAATGGTG ATTCTTCCAA GAAAGGTTGG TGGGATGGGA AAACTTTTTC        750

AATTGATGGT ACGAAGACAA ACTCTTCTAT TATTTCACCT TCTGTTTCAG        800

CTGGCATTTT CTTCAGGAGA CTGTCTACGG GGGCTTTTTG TAAGAATTCT        850

AAAGCATCTT GAGTATTGTT TGTGGGATGA CCCAATATCT CAGCAAGTTG        900

AAGACTACGC TTTACTGGAT GTCTTTGGAA GGCCCATGGA TTAAAAGCAC        950

TTCCACTTTG AGCAATTGCC CTTTTGTAAA GTCCAGTGGT TGTATGAGAT        1000

AACAAAAGAT AATGAACACT TGCTCCACCA GCAGAAACAC CACCAATTGT        1050

AATATTTTCT GGATCTCCAC CAAATTTCTC AATGTTTTCT TTGGTCCATT        1100

TCAGAGCTGC CACCTGATCC AATAATCCTA CATTTCCTGG AGCACCCTCC        1150

AACTCCAAAT TCAGAAATCC GAGAGGTCCC AATCGGTAAT TGAAAGTTAC        1200

GAAAATAACA TCAAAATYTA CTAAATAATC TGGGCTTTGG AATTCTAAAT        1250

TTCCGGATCC AGTCACAAAA CCACCACCAT GAACCCAGAA AAATACTGGA        1300

AGTTTTTTAT CAGAAGTTGT TTTTGGTGCG TACACGTTTA CTACCAAGCA        1350

GTCTTCGTCT CCTTCAATTT TCTTCAAGAA GAAATTTAAA GATTTACACA        1400

CATTTCCGTA TAATGTGGCG TTGAAAACAC CTTGCCATGG CTCAGCTTTC        1450

TGTGGAGGCT TAAATCTAAG TTCTCCAACA GGAGGTTTAG CATAAGGTAC        1500

ACCTGTGTAG CTAAA        1515

(2) INFORMATION FOR SEQ ID NO:18:

(i) SEQUENCE CHARACTERISTICS:
        (A) LENGTH:  1792 nucleotides
        (B) TYPE:  nucleic acid
        (C) STRANDEDNESS:  single
        (D) TOPOLOGY:  linear (ii) MOLECULE TYPE:  cDNA (iii) FEATURE:
        (A) NAME/KEY:  CDS
        (B) LOCATION:  49..1701

(iv) SEQUENCE DESCRIPTION:  SEQ ID NO:18:

ACTGTGTGCT AATAATTCAG TACACACAGT CAATAGTCTA GATCCAAG           48

ATG TCT CGT GTT ATT TTT TTA AGT TGT ATT TTT TTG TTT AGT         90
```

```
Met Ser Arg Val Ile Phe Leu Ser Cys Ile Phe Leu Phe Ser
 1               5                  10
TTT AAT TTT ATA AAA TGT GAT CCC CCG ACT GTA ACT TTG CCC       132
Phe Asn Phe Ile Lys Cys Asp Pro Pro Thr Val Thr Leu Pro
 15              20                  25
CAG GGC GAA TTG GTT GGA AAA GCT TTG ACG AAC GAA AAT GGA       174
Gln Gly Glu Leu Val Gly Lys Ala Leu Thr Asn Glu Asn Gly
     30              35                  40
AAA GAG TAT TTT AGC TAC ACA GGT GTG CCT TAT GCT AAA CCT       216
Lys Glu Tyr Phe Ser Tyr Thr Gly Val Pro Tyr Ala Lys Pro
         45              50                  55
CCA GTT GGA GAA CTT AGA TTT AAG CCT CCA CAG AAA GCT GAG       258
Pro Val Gly Glu Leu Arg Phe Lys Pro Pro Gln Lys Ala Glu
             60              65                  70
CCA TGG AAT GGT GTT TTC AAC GCC ACA TCA CAT GGA AAT GTG       300
Pro Trp Asn Gly Val Phe Asn Ala Thr Ser His Gly Asn Val
                 75              80
TGC AAA GCT TTG AAT TTC TTC TTG AAA AAA ATT GAA GGA GAC       342
Cys Lys Ala Leu Asn Phe Phe Leu Lys Lys Ile Glu Gly Asp
 85              90                  95
GAA GAC TGC TTG TTG GTG AAT GTG TAC GCA CCA AAA ACA ACT       384
Glu Asp Cys Leu Leu Val Asn Val Tyr Ala Pro Lys Thr Thr
     100             105                 110
TCT GAC AAA AAA CTT CCA GTA TTT TTC TGG GTT CAT GGT GGC       426
Ser Asp Lys Lys Leu Pro Val Phe Phe Trp Val His Gly Gly
         115             120                 125
GGT TTT GTG ACT GGA TCC GGA AAT TTA GAA TTT CAA AGC CCA       468
Gly Phe Val Thr Gly Ser Gly Asn Leu Glu Phe Gln Ser Pro
             130             135                 140
GAT TAT TTA GTA AAT TAT GAT GTT ATT TTT GTA ACT TTC AAT       510
Asp Tyr Leu Val Asn Tyr Asp Val Ile Phe Val Thr Phe Asn
                 145             150
TAC CGA TTG GGA CCA CTC GGA TTT TTG AAT TTG GAG TTG GAA       552
Tyr Arg Leu Gly Pro Leu Gly Phe Leu Asn Leu Glu Leu Glu
 155             160                 165
GGT GCT CCT GGA AAT GTA GGA TTA TTG GAT CAG GTA GCA GCT       594
Gly Ala Pro Gly Asn Val Gly Leu Leu Asp Gln Val Ala Ala
     170             175                 180
TTG AAA TGG ACC AAA GAA AAT ATT GAG AAA TTT GGT GGA GAT       636
Leu Lys Trp Thr Lys Glu Asn Ile Glu Lys Phe Gly Gly Asp
         185             190                 195
CCA GAA AAT ATT ACA ATT GGT GGT GTT TCT GCT GGT GGA GCA       678
Pro Glu Asn Ile Thr Ile Gly Gly Val Ser Ala Gly Gly Ala
             200             205                 210
AGT GTT CAT TAT CTT TTA TTG TCA CAT ACA ACC ACT GGA CTT       720
Ser Val His Tyr Leu Leu Leu Ser His Thr Thr Thr Gly Leu
                 215             220
TAC AAA AGG GCA ATT GCT CAA AGT GGA AGT GCT TTA AAT CCA       762
Tyr Lys Arg Ala Ile Ala Gln Ser Gly Ser Ala Leu Asn Pro
 225             230                 235
TGG GCC TTC CAA AGA CAT CCA GTA AAG CGT AGT CTT CAA CTT       804
Trp Ala Phe Gln Arg His Pro Val Lys Arg Ser Leu Gln Leu
     240             245                 250
GCT GAG ATA TTA GGT CAT CCC ACA AAC AAC ACT CAA GAT GCT       846
Ala Glu Ile Leu Gly His Pro Thr Asn Asn Thr Gln Asp Ala
         255             260                 265
TTA GAA TTC TTA CAA AAA GCC CCA GTA GAC AGT CTC CTG AAA       888
Leu Glu Phe Leu Gln Lys Ala Pro Val Asp Ser Leu Leu Lys
             270             275                 280
```

```
AAA ATG CCA GCT GAA ACA GAA GGT GAA ATA ATA GAA GAG TTC                    930
Lys Met Pro Ala Glu Thr Glu Gly Glu Ile Ile Glu Glu Phe
                285                 290

GTC TTC GTA CCA TCA ATT GAA AAA GTT TTC CCA TCC CAC CAA                    972
Val Phe Val Pro Ser Ile Glu Lys Val Phe Pro Ser His Gln
295                 300                 305

CCT TTC TTG GAA GAA TCA CCA TTG GCC AGA ATG AAA TCT GGA                   1014
Pro Phe Leu Glu Glu Ser Pro Leu Ala Arg Met Lys Ser Gly
        310                 315                 320

TCC TTT AAC AAA GTA CCT TTA TTA GTT GGA TTC AAC AGC GCA                   1056
Ser Phe Asn Lys Val Pro Leu Leu Val Gly Phe Asn Ser Ala
            325                 330                 335

GAA GGA CTT TTG TAC AAA TTC TTT ATG AAA GAA AAA CCA GAG                   1098
Glu Gly Leu Leu Tyr Lys Phe Phe Met Lys Glu Lys Pro Glu
                340                 345                 350

ATG CTG AAC CAA GCT GAA GCA GAT TTC GAA AGA CTC GTA CCA                   1140
Met Leu Asn Gln Ala Glu Ala Asp Phe Glu Arg Leu Val Pro
                    355                 360

GCC GAA TTT GAA TTA GCC CAT GGA TCA GAA GAA TCG AAA AAA                   1182
Ala Glu Phe Glu Leu Ala His Gly Ser Glu Glu Ser Lys Lys
365                 370                 375

CTT GCA GAA AAA ATC AGG AAG TTT TAC TTT GAC GAT AAA CCC                   1224
Leu Ala Glu Lys Ile Arg Lys Phe Tyr Phe Asp Asp Lys Pro
        380                 385                 390

GTT CCT GAA AAT GAG CAG AAA TTT ATT GAC TTG ATA GGA GAT                   1266
Val Pro Glu Asn Glu Gln Lys Phe Ile Asp Leu Ile Gly Asp
            395                 400                 405

ATT TGG TTT ACT AGA GGC ATT GAC AAG CAT GTC AAG TTG TCT                   1308
Ile Trp Phe Thr Arg Gly Ile Asp Lys His Val Lys Leu Ser
                410                 415                 420

GTA GAA AAA CAA GAC GAG CCA GTA TAT TAT TAT GAA TAT TCT                   1350
Val Glu Lys Gln Asp Glu Pro Val Tyr Tyr Tyr Glu Tyr Ser
                    425                 430

TTC TCT GAA AGT CAT CCT GCA AAA GGA ACA TTT GGT GAC CAT                   1392
Phe Ser Glu Ser His Pro Ala Lys Gly Thr Phe Gly Asp His
435                 440                 445

AAC TTG ACT GGA GCA TGT CAT GGT GAA GAA CTT GTG AAT TTA                   1434
Asn Leu Thr Gly Ala Cys His Gly Glu Glu Leu Val Asn Leu
        450                 455                 460

TTC AAA GTC GAG ATG ATG AAG CTG GAA AAA GAT AAA CCG AAT                   1476
Phe Lys Val Glu Met Met Lys Leu Glu Lys Asp Lys Pro Asn
            465                 470                 475

GTT TTA TTA ACA AAA GAT AGG GTA CTT GCT ATG TGG ACG AAC                   1518
Val Leu Leu Thr Lys Asp Arg Val Leu Ala Met Trp Thr Asn
                480                 485                 490

TTC ATC AAA AAT GGA AAT CCT ACT CCT GAA GTA ACT GAA TTA                   1560
Phe Ile Lys Asn Gly Asn Pro Thr Pro Glu Val Thr Glu Leu
                    495                 500

TTG CCA GTT AAA TGG GAA CCT GCC ACA AAA GAC AAG TTG AAT                   1602
Leu Pro Val Lys Trp Glu Pro Ala Thr Lys Asp Lys Leu Asn
505                 510                 515

TAT TTG AAC ATT GAT GCC ACC TTA ACT TTG GGA ACA AAT CCA                   1644
Tyr Leu Asn Ile Asp Ala Thr Leu Thr Leu Gly Thr Asn Pro
        520                 525                 530

GAA GAA ACC CGA GTC AAA TTY TGG GAA GAT GCC ACA AAA ACT                   1686
Glu Glu Thr Arg Val Lys Phe Trp Glu Asp Ala Thr Lys Thr
            535                 540                 545

TTG CAC AGT CAA TAA AAATGTATGA AAATTGTTTT AATTATTTTA                      1731
Leu His Ser Gln
                550
```

GGTAATACAT TAGGTAAATA AAAATTNAAA AATAACNAAA AAAAAAAAAA    1781

AAAAAAAAAA A    1792

(2) INFORMATION FOR SEQ ID NO:19:

(i) SEQUENCE CHARACTERISTICS:
  (A) LENGTH: 550 amino acids
  (B) TYPE: amino acid
  (D) TOPOLOGY: linear (ii) MOLECULE TYPE: protein (iii) SEQUENCE DESCRIPTION: SEQ ID NO:19:

```
Met Ser Arg Val Ile Phe Leu Ser Cys Ile Phe Leu Phe Ser
  1               5                  10

Phe Asn Phe Ile Lys Cys Asp Pro Pro Thr Val Thr Leu Pro
 15                  20                  25

Gln Gly Glu Leu Val Gly Lys Ala Leu Thr Asn Glu Asn Gly
 30                  35                  40

Lys Glu Tyr Phe Ser Tyr Thr Gly Val Pro Tyr Ala Lys Pro
 45                  50                  55

Pro Val Gly Glu Leu Arg Phe Lys Pro Pro Gln Lys Ala Glu
     60                  65                  70

Pro Trp Asn Gly Val Phe Asn Ala Thr Ser His Gly Asn Val
             75                  80

Cys Lys Ala Leu Asn Phe Leu Lys Lys Ile Glu Gly Asp
 85                  90                  95

Glu Asp Cys Leu Leu Val Asn Val Tyr Ala Pro Lys Thr Thr
100                 105                 110

Ser Asp Lys Lys Leu Pro Val Phe Phe Trp Val His Gly Gly
            115                 120                 125

Gly Phe Val Thr Gly Ser Gly Asn Leu Glu Phe Gln Ser Pro
            130                 135                 140

Asp Tyr Leu Val Asn Tyr Asp Val Ile Phe Val Thr Phe Asn
                145                 150

Tyr Arg Leu Gly Pro Leu Gly Phe Leu Asn Leu Glu Leu Glu
155                 160                 165

Gly Ala Pro Gly Asn Val Gly Leu Leu Asp Gln Val Ala Ala
170                 175                 180

Leu Lys Trp Thr Lys Glu Asn Ile Glu Lys Phe Gly Gly Asp
            185                 190                 195

Pro Glu Asn Ile Thr Ile Gly Gly Val Ser Ala Gly Gly Ala
                200                 205                 210

Ser Val His Tyr Leu Leu Leu Ser His Thr Thr Thr Gly Leu
                215                 220

Tyr Lys Arg Ala Ile Ala Gln Ser Gly Ser Ala Leu Asn Pro
225                 230                 235

Trp Ala Phe Gln Arg His Pro Val Lys Arg Ser Leu Gln Leu
            240                 245                 250

Ala Glu Ile Leu Gly His Pro Thr Asn Asn Thr Gln Asp Ala
            255                 260                 265

Leu Glu Phe Leu Gln Lys Ala Pro Val Asp Ser Leu Leu Lys
            270                 275                 280

Lys Met Pro Ala Glu Thr Glu Gly Glu Ile Ile Glu Glu Phe
            285                 290
```

```
Val Phe Val Pro Ser Ile Glu Lys Val Phe Pro Ser His Gln
295                 300                 305

Pro Phe Leu Glu Glu Ser Pro Leu Ala Arg Met Lys Ser Gly
310                 315                 320

Ser Phe Asn Lys Val Pro Leu Leu Val Gly Phe Asn Ser Ala
        325                 330                 335

Glu Gly Leu Leu Tyr Lys Phe Phe Met Lys Glu Lys Pro Glu
                340                 345                 350

Met Leu Asn Gln Ala Glu Ala Asp Phe Glu Arg Leu Val Pro
                    355                 360

Ala Glu Phe Glu Leu Ala His Gly Ser Glu Glu Ser Lys Lys
365                 370                 375

Leu Ala Glu Lys Ile Arg Lys Phe Tyr Phe Asp Asp Lys Pro
380                 385                 390

Val Pro Glu Asn Glu Gln Lys Phe Ile Asp Leu Ile Gly Asp
                395                 400                 405

Ile Trp Phe Thr Arg Gly Ile Asp Lys His Val Lys Leu Ser
                410                 415                 420

Val Glu Lys Gln Asp Glu Pro Val Tyr Tyr Tyr Glu Tyr Ser
                425                 430

Phe Ser Glu Ser His Pro Ala Lys Gly Thr Phe Gly Asp His
435                 440                 445

Asn Leu Thr Gly Ala Cys His Gly Glu Glu Leu Val Asn Leu
        450                 455                 460

Phe Lys Val Glu Met Met Lys Leu Glu Lys Asp Lys Pro Asn
        465                 470                 475

Val Leu Leu Thr Lys Asp Arg Val Leu Ala Met Trp Thr Asn
                480                 485                 490

Phe Ile Lys Asn Gly Asn Pro Thr Pro Glu Val Thr Glu Leu
                495                 500

Leu Pro Val Lys Trp Glu Pro Ala Thr Lys Asp Lys Leu Asn
505                 510                 515

Tyr Leu Asn Ile Asp Ala Thr Leu Thr Leu Gly Thr Asn Pro
        520                 525                 530

Glu Glu Thr Arg Val Lys Phe Trp Glu Asp Ala Thr Lys Thr
        535                 540                 545

Leu His Ser Gln
        550

(2) INFORMATION FOR SEQ ID NO:20:

(i) SEQUENCE CHARACTERISTICS:
        (A) LENGTH: 1792 nucleotides
        (B) TYPE: nucleic acid
        (C) STRANDEDNESS: single
        (D) TOPOLOGY: linear (ii) MOLECULE TYPE: cDNA (iii) SEQUENCE DESCRIPTION: SEQ ID NO:20:

TTTTTTTTTT TTTTTTTTTT TTTTNGTTAT TTTTNAATTT TTATTTACCT          50

AATGTATTAC CTAAAATAAT TAAAACAATT TTCATACATT TTTATTGACT         100

GTGCAAAGTT TTTGTGGCAT CTTCCCARAA TTTGACTCGG GTTTCTTCTG         150

GATTTGTTCC CAAAGTTAAG GTGGCATCAA TGTTCAAATA ATTCAACTTG         200
```

-continued

```
TCTTTTGTGG CAGGTTCCCA TTTAACTGGC AATAATTCAG TTACTTCAGG          250

AGTAGGATTT CCATTTTTGA TGAAGTTCGT CCACATAGCA AGTACCCTAT          300

CTTTTGTTAA TAAAACATTC GGTTTATCTT TTTCCAGCTT CATCATCTCG          350

ACTTTGAATA AATTCACAAG TTCTTCACCA TGACATGCTC CAGTCAAGTT          400

ATGGTCACCA AATGTTCCTT TTGCAGGATG ACTTTCAGAG AAAGAATATT          450

CATAATAATA TACTGGCTCG TCTTGTTTTT CTACAGACAA CTTGACATGC          500

TTGTCAATGC CTCTAGTAAA CCAAATATCT CCTATCAAGT CAATAAATTT          550

CTGCTCATTT TCAGGAACGG GTTTATCGTC AAAGTAAAAC TTCCTGATTT          600

TTTCTGCAAG TTTTTTCGAT TCTTCTGATC CATGGGCTAA TTCAAATTCG          650

GCTGGTACGA GTCTTTCGAA ATCTGCTTCA GCTTGGTTCA GCATCTCTGG          700

TTTTTCTTTC ATAAAGAATT TGTACAAAAG TCCTTCTGCG CTGTTGAATC          750

CAACTAATAA AGGTACTTTG TTAAAGGATC CAGATTTCAT TCTGGCCAAT          800

GGTGATTCTT CCAAGAAAGG TTGGTGGGAT GGGAAAACTT TTTCAATTGA          850

TGGTACGAAG ACGAACTCTT CTATTATTTC ACCTTCTGTT TCAGCTGGCA          900

TTTTTTTCAG GAGACTGTCT ACTGGGGCTT TTTGTAAGAA TTCTAAAGCA          950

TCTTGAGTGT TGTTTGTGGG ATGACCTAAT ATCTCAGCAA GTTGAAGACT         1000

ACGCTTTACT GGATGTCTTT GGAAGGCCCA TGGATTTAAA GCACTTCCAC         1050

TTTGAGCAAT TGCCCTTTTG TAAAGTCCAG TGGTTGTATG TGACAATAAA         1100

AGATAATGAA CACTTGCTCC ACCAGCAGAA ACACCACCAA TTGTAATATT         1150

TTCTGGATCT CCACCAAATT TCTCAATATT TTCTTTGGTC CATTTCAAAG         1200

CTGCTACCTG ATCCAATAAT CCTACATTTC CAGGAGCACC TTCCAACTCC         1250

AAATTCAAAA ATCCGAGTGG TCCCAATCGG TAATTGAAAG TTACAAAAAT         1300

AACATCATAA TTTACTAAAT AATCTGGGCT TTGAAATTCT AAATTTCCGG         1350

ATCCAGTCAC AAAACCGCCA CCATGAACCC AGAAAAATAC TGGAAGTTTT         1400

TTGTCAGAAG TTGTTTTTGG TGCGTACACA TTCACCAACA AGCAGTCTTC         1450

GTCTCCTTCA ATTTTTTTCA AGAAGAAATT CAAAGCTTTG CACACATTTC         1500

CATGTGATGT GGCGTTGAAA ACACCATTCC ATGGCTCAGC TTTCTGTGGA         1550

GGCTTAAATC TAAGTTCTCC AACTGGAGGT TTAGCATAAG GCACACCTGT         1600

GTAGCTAAAA TACTCTTTTC CATTTTCGTT CGTCAAAGCT TTTCCAACCA         1650

ATTCGCCCTG GGGCAAAGTT ACAGTCGGGG GATCACATTT TATAAAATTA         1700

AAACTAAACA AAAAAATACA ACTTAAAAAA ATAACACGAG ACATCTTGGA         1750

TCTAGACTAT TGACTGTGTG TACTGAATTA TTAGCACACA GT                 1792
```

(2) INFORMATION FOR SEQ ID NO:21:

(i) SEQUENCE CHARACTERISTICS:
        (A) LENGTH: 1650 nucleotides
        (B) TYPE: nucleic acid
        (C) STRANDEDNESS: single
        (D) TOPOLOGY: linear (ii) MOLECULE TYPE: cDNA (iii) SEQUENCE DESCRIPTION: SEQ ID NO:21:

```
ATG TCT CGT GTT ATT TTT TTA AGT TGT ATT TTT TTG TTT AGT           42
Met Ser Arg Val Ile Phe Leu Ser Cys Ile Phe Leu Phe Ser
```

```
        1                 5                        10
TTT AAT TTT ATA AAA TGT GAT CCC CCG ACT GTA ACT TTG CCC           84
Phe Asn Phe Ile Lys Cys Asp Pro Pro Thr Val Thr Leu Pro
 15              20                  25

CAG GGC GAA TTG GTT GGA AAA GCT TTG ACG AAC GAA AAT GGA          126
Gln Gly Glu Leu Val Gly Lys Ala Leu Thr Asn Glu Asn Gly
     30              35                  40

AAA GAG TAT TTT AGC TAC ACA GGT GTG CCT TAT GCT AAA CCT          168
Lys Glu Tyr Phe Ser Tyr Thr Gly Val Pro Tyr Ala Lys Pro
         45              50                  55

CCA GTT GGA GAA CTT AGA TTT AAG CCT CCA CAG AAA GCT GAG          210
Pro Val Gly Glu Leu Arg Phe Lys Pro Pro Gln Lys Ala Glu
             60              65                  70

CCA TGG AAT GGT GTT TTC AAC GCC ACA TCA CAT GGA AAT GTG          252
Pro Trp Asn Gly Val Phe Asn Ala Thr Ser His Gly Asn Val
                 75              80

TGC AAA GCT TTG AAT TTC TTC TTG AAA AAA ATT GAA GGA GAC          294
Cys Lys Ala Leu Asn Phe Phe Leu Lys Lys Ile Glu Gly Asp
 85              90                  95

GAA GAC TGC TTG TTG GTG AAT GTG TAC GCA CCA AAA ACA ACT          336
Glu Asp Cys Leu Leu Val Asn Val Tyr Ala Pro Lys Thr Thr
    100             105                 110

TCT GAC AAA AAA CTT CCA GTA TTT TTC TGG GTT CAT GGT GGC          378
Ser Asp Lys Lys Leu Pro Val Phe Phe Trp Val His Gly Gly
        115             120                 125

GGT TTT GTG ACT GGA TCC GGA AAT TTA GAA TTT CAA AGC CCA          420
Gly Phe Val Thr Gly Ser Gly Asn Leu Glu Phe Gln Ser Pro
            130             135                 140

GAT TAT TTA GTA AAT TAT GAT GTT ATT TTT GTA ACT TTC AAT          462
Asp Tyr Leu Val Asn Tyr Asp Val Ile Phe Val Thr Phe Asn
                145             150

TAC CGA TTG GGA CCA CTC GGA TTT TTG AAT TTG GAG TTG GAA          504
Tyr Arg Leu Gly Pro Leu Gly Phe Leu Asn Leu Glu Leu Glu
155             160                 165

GGT GCT CCT GGA AAT GTA GGA TTA TTG GAT CAG GTA GCA GCT          546
Gly Ala Pro Gly Asn Val Gly Leu Leu Asp Gln Val Ala Ala
    170             175                 180

TTG AAA TGG ACC AAA GAA AAT ATT GAG AAA TTT GGT GGA GAT          588
Leu Lys Trp Thr Lys Glu Asn Ile Glu Lys Phe Gly Gly Asp
        185             190                 195

CCA GAA AAT ATT ACA ATT GGT GGT GTT TCT GCT GGT GGA GCA          630
Pro Glu Asn Ile Thr Ile Gly Gly Val Ser Ala Gly Gly Ala
            200             205                 210

AGT GTT CAT TAT CTT TTA TTG TCA CAT ACA ACC ACT GGA CTT          672
Ser Val His Tyr Leu Leu Leu Ser His Thr Thr Thr Gly Leu
                215             220

TAC AAA AGG GCA ATT GCT CAA AGT GGA AGT GCT TTA AAT CCA          714
Tyr Lys Arg Ala Ile Ala Gln Ser Gly Ser Ala Leu Asn Pro
225             230                 235

TGG GCC TTC CAA AGA CAT CCA GTA AAG CGT AGT CTT CAA CTT          756
Trp Ala Phe Gln Arg His Pro Val Lys Arg Ser Leu Gln Leu
    240             245                 250

GCT GAG ATA TTA GGT CAT CCC ACA AAC AAC ACT CAA GAT GCT          798
Ala Glu Ile Leu Gly His Pro Thr Asn Asn Thr Gln Asp Ala
        255             260                 265

TTA GAA TTC TTA CAA AAA GCC CCA GTA GAC AGT CTC CTG AAA          840
Leu Glu Phe Leu Gln Lys Ala Pro Val Asp Ser Leu Leu Lys
            270             275                 280

AAA ATG CCA GCT GAA ACA GAA GGT GAA ATA ATA GAA GAG TTC          882
```

```
          Lys Met Pro Ala Glu Thr Glu Gly Glu Ile Ile Glu Glu Phe
                          285                 290

GTC TTC GTA CCA TCA ATT GAA AAA GTT TTC CCA TCC CAC CAA            924
Val Phe Val Pro Ser Ile Glu Lys Val Phe Pro Ser His Gln
295                 300                 305

CCT TTC TTG GAA GAA TCA CCA TTG GCC AGA ATG AAA TCT GGA            966
Pro Phe Leu Glu Glu Ser Pro Leu Ala Arg Met Lys Ser Gly
310                 315                 320

TCC TTT AAC AAA GTA CCT TTA TTA GTT GGA TTC AAC AGC GCA           1008
Ser Phe Asn Lys Val Pro Leu Leu Val Gly Phe Asn Ser Ala
        325                 330                 335

GAA GGA CTT TTG TAC AAA TTC TTT ATG AAA GAA AAA CCA GAG           1050
Glu Gly Leu Leu Tyr Lys Phe Phe Met Lys Glu Lys Pro Glu
                340                 345                 350

ATG CTG AAC CAA GCT GAA GCA GAT TTC GAA AGA CTC GTA CCA           1092
Met Leu Asn Gln Ala Glu Ala Asp Phe Glu Arg Leu Val Pro
                    355                 360

GCC GAA TTT GAA TTA GCC CAT GGA TCA GAA GAA TCG AAA AAA           1134
Ala Glu Phe Glu Leu Ala His Gly Ser Glu Glu Ser Lys Lys
365                 370                 375

CTT GCA GAA AAA ATC AGG AAG TTT TAC TTT GAC GAT AAA CCC           1176
Leu Ala Glu Lys Ile Arg Lys Phe Tyr Phe Asp Asp Lys Pro
        380                 385                 390

GTT CCT GAA AAT GAG CAG AAA TTT ATT GAC TTG ATA GGA GAT           1218
Val Pro Glu Asn Glu Gln Lys Phe Ile Asp Leu Ile Gly Asp
                395                 400                 405

ATT TGG TTT ACT AGA GGC ATT GAC AAG CAT GTC AAG TTG TCT           1260
Ile Trp Phe Thr Arg Gly Ile Asp Lys His Val Lys Leu Ser
                    410                 415                 420

GTA GAA AAA CAA GAC GAG CCA GTA TAT TAT TAT GAA TAT TCT           1302
Val Glu Lys Gln Asp Glu Pro Val Tyr Tyr Tyr Glu Tyr Ser
                        425                 430

TTC TCT GAA AGT CAT CCT GCA AAA GGA ACA TTT GGT GAC CAT           1344
Phe Ser Glu Ser His Pro Ala Lys Gly Thr Phe Gly Asp His
435                 440                 445

AAC TTG ACT GGA GCA TGT CAT GGT GAA GAA CTT GTG AAT TTA           1386
Asn Leu Thr Gly Ala Cys His Gly Glu Glu Leu Val Asn Leu
        450                 455                 460

TTC AAA GTC GAG ATG ATG AAG CTG GAA AAA GAT AAA CCG AAT           1428
Phe Lys Val Glu Met Met Lys Leu Glu Lys Asp Lys Pro Asn
                465                 470                 475

GTT TTA TTA ACA AAA GAT AGG GTA CTT GCT ATG TGG ACG AAC           1470
Val Leu Leu Thr Lys Asp Arg Val Leu Ala Met Trp Thr Asn
                    480                 485                 490

TTC ATC AAA AAT GGA AAT CCT ACT CCT GAA GTA ACT GAA TTA           1512
Phe Ile Lys Asn Gly Asn Pro Thr Pro Glu Val Thr Glu Leu
                        495                 500

TTG CCA GTT AAA TGG GAA CCT GCC ACA AAA GAC AAG TTG AAT           1554
Leu Pro Val Lys Trp Glu Pro Ala Thr Lys Asp Lys Leu Asn
505                 510                 515

TAT TTG AAC ATT GAT GCC ACC TTA ACT TTG GGA ACA AAT CCA           1596
Tyr Leu Asn Ile Asp Ala Thr Leu Thr Leu Gly Thr Asn Pro
        520                 525                 530

GAA GAA ACC CGA GTC AAA TTY TGG GAA GAT GCC ACA AAA ACT           1638
Glu Glu Thr Arg Val Lys Phe Trp Glu Asp Ala Thr Lys Thr
                535                 540                 545

TTG CAC AGT CAA                                                    1650
Leu His Ser Gln
            550
```

(2) INFORMATION FOR SEQ ID NO:22:

(i) SEQUENCE CHARACTERISTICS:
        (A) LENGTH: 1650 nucleotides
        (B) TYPE: nucleic acid
        (C) STRANDEDNESS: single
        (D) TOPOLOGY: linear (ii) MOLECULE TYPE: cDNA (iii) SEQUENCE DESCRIPTION: SEQ ID NO:22:

```
TTGACTGTGC AAAGTTTTTG TGGCATCTTC CCARAATTTG ACTCGGGTTT         50
CTTCTGGATT TGTTCCCAAA GTTAAGGTGG CATCAATGTT CAAATAATTC        100
AACTTGTCTT TTGTGGCAGG TTCCCATTTA ACTGGCAATA ATTCAGTTAC        150
TTCAGGAGTA GGATTTCCAT TTTTGATGAA GTTCGTCCAC ATAGCAAGTA        200
CCCTATCTTT TGTTAATAAA ACATTCGGTT TATCTTTTTC CAGCTTCATC        250
ATCTCGACTT TGAATAAATT CACAAGTTCT TCACCATGAC ATGCTCCAGT        300
CAAGTTATGG TCACCAAATG TTCCTTTTGC AGGATGACTT TCAGAGAAAG        350
AATATTCATA ATAATATACT GGCTCGTCTT GTTTTTCTAC AGACAACTTG        400
ACATGCTTGT CAATGCCTCT AGTAAACCAA ATATCTCCTA TCAAGTCAAT        450
AAATTTCTGC TCATTTTCAG GAACGGGTTT ATCGTCAAAG TAAAACTTCC        500
TGATTTTTTC TGCAAGTTTT TTCGATTCTT CTGATCCATG GGCTAATTCA        550
AATTCGGCTG GTACGAGTCT TTCGAAATCT GCTTCAGCTT GGTTCAGCAT        600
CTCTGGTTTT TCTTTCATAA AGAATTTGTA CAAAAGTCCT TCTGCGCTGT        650
TGAATCCAAC TAATAAAGGT ACTTGTTAA AGGATCCAGA TTTCATTCTG         700
GCCAATGGTG ATTCTTCCAA GAAAGGTTGG TGGGATGGGA AAACTTTTTC        750
AATTGATGGT ACGAAGACGA ACTCTTCTAT TATTTCACCT TCTGTTTCAG        800
CTGGCATTTT TTTCAGGAGA CTGTCTACTG GGGCTTTTTG TAAGAATTCT        850
AAAGCATCTT GAGTGTTGTT TGTGGGATGA CCTAATATCT CAGCAAGTTG        900
AAGACTACGC TTTACTGGAT GTCTTTGGAA GGCCCATGGA TTTAAAGCAC        950
TTCCACTTTG AGCAATTGCC CTTTTGTAAA GTCCAGTGGT TGTATGTGAC       1000
AATAAAAGAT AATGAACACT TGCTCCACCA GCAGAAACAC CACCAATTGT       1050
AATATTTTCT GGATCTCCAC CAAATTTCTC AATATTTTCT TTGGTCCATT       1100
TCAAAGCTGC TACCTGATCC AATAATCCTA CATTTCCAGG AGCACCTTCC       1150
AACTCCAAAT TCAAAAATCC GAGTGGTCCC AATCGGTAAT TGAAAGTTAC       1200
AAAAATAACA TCATAATTTA CTAAATAATC TGGGCTTTGA AATTCTAAAT       1250
TTCCGGATCC AGTCACAAAA CCGCCACCAT GAACCCAGAA AAATACTGGA       1300
AGTTTTTTGT CAGAAGTTGT TTTTGGTGCG TACACATTCA CCAACAAGCA       1350
GTCTTCGTCT CCTTCAATTT TTTTCAAGAA GAAATTCAAA GCTTTGCACA       1400
CATTTCCATG TGATGTGGCG TTGAAAACAC CATTCCATGG CTCAGCTTTC       1450
TGTGGAGGCT TAAATCTAAG TTCTCCAACT GGAGGTTTAG CATAAGGCAC       1500
ACCTGTGTAG CTAAAATACT CTTTTCCATT TTCGTTCGTC AAAGCTTTTC       1550
CAACCAATTC GCCCTGGGGC AAAGTTACAG TCGGGGATC ACATTTTATA        1600
AAATTAAAAC TAAACAAAAA AATACAACTT AAAAAAATAA CACGAGACAT       1650
```

(2) INFORMATION FOR SEQ ID NO:23:

(i) SEQUENCE CHARACTERISTICS:
        (A) LENGTH: 1590 nucleotides
        (B) TYPE: nucleic acid
        (C) STRANDEDNESS: single
        (D) TOPOLOGY: linear (ii) MOLECULE TYPE: cDNA (iii) FEATURE:
        (A) NAME/KEY: CDS
        (B) LOCATION: 1..1590

(iv) SEQUENCE DESCRIPTION: SEQ ID NO:23:

```
GAT CCC CCG ACT GTA ACT TTG CCC CAG GGC GAA TTG GTT GGA              42
Asp Pro Pro Thr Val Thr Leu Pro Gln Gly Glu Leu Val Gly
 1               5                  10

AAA GCT TTG ACG AAC GAA AAT GGA AAA GAG TAT TTT AGC TAC              84
Lys Ala Leu Thr Asn Glu Asn Gly Lys Glu Tyr Phe Ser Tyr
15                  20                  25

ACA GGT GTG CCT TAT GCT AAA CCT CCA GTT GGA GAA CTT AGA             126
Thr Gly Val Pro Tyr Ala Lys Pro Pro Val Gly Glu Leu Arg
         30                  35                  40

TTT AAG CCT CCA CAG AAA GCT GAG CCA TGG AAT GGT GTT TTC             168
Phe Lys Pro Pro Gln Lys Ala Glu Pro Trp Asn Gly Val Phe
             45                  50                  55

AAC GCC ACA TCA CAT GGA AAT GTG TGC AAA GCT TTG AAT TTC             210
Asn Ala Thr Ser His Gly Asn Val Cys Lys Ala Leu Asn Phe
                 60                  65                  70

TTC TTG AAA AAA ATT GAA GGA GAC GAA GAC TGC TTG TTG GTG             252
Phe Leu Lys Lys Ile Glu Gly Asp Glu Asp Cys Leu Leu Val
                     75                  80

AAT GTG TAC GCA CCA AAA ACA ACT TCT GAC AAA AAA CTT CCA             294
Asn Val Tyr Ala Pro Lys Thr Thr Ser Asp Lys Lys Leu Pro
85                  90                  95

GTA TTT TTC TGG GTT CAT GGT GGC GGT TTT GTG ACT GGA TCC             336
Val Phe Phe Trp Val His Gly Gly Gly Phe Val Thr Gly Ser
        100                 105                 110

GGA AAT TTA GAA TTT CAA AGC CCA GAT TAT TTA GTA AAT TAT             378
Gly Asn Leu Glu Phe Gln Ser Pro Asp Tyr Leu Val Asn Tyr
            115                 120                 125

GAT GTT ATT TTT GTA ACT TTC AAT TAC CGA TTG GGA CCA CTC             420
Asp Val Ile Phe Val Thr Phe Asn Tyr Arg Leu Gly Pro Leu
                130                 135                 140

GGA TTT TTG AAT TTG GAG TTG GAA GGT GCT CCT GGA AAT GTA             462
Gly Phe Leu Asn Leu Glu Leu Glu Gly Ala Pro Gly Asn Val
                    145                 150

GGA TTA TTG GAT CAG GTA GCA GCT TTG AAA TGG ACC AAA GAA             504
Gly Leu Leu Asp Gln Val Ala Ala Leu Lys Trp Thr Lys Glu
155                 160                 165

AAT ATT GAG AAA TTT GGT GGA GAT CCA GAA AAT ATT ACA ATT             546
Asn Ile Glu Lys Phe Gly Gly Asp Pro Glu Asn Ile Thr Ile
        170                 175                 180

GGT GGT GTT TCT GCT GGT GGA GCA AGT GTT CAT TAT CTT TTA             588
Gly Gly Val Ser Ala Gly Gly Ala Ser Val His Tyr Leu Leu
            185                 190                 195

TTG TCA CAT ACA ACC ACT GGA CTT TAC AAA AGG GCA ATT GCT             630
Leu Ser His Thr Thr Thr Gly Leu Tyr Lys Arg Ala Ile Ala
                200                 205                 210

CAA AGT GGA AGT GCT TTA AAT CCA TGG GCC TTC CAA AGA CAT             672
Gln Ser Gly Ser Ala Leu Asn Pro Trp Ala Phe Gln Arg His
```

```
                        215                          220
CCA GTA AAG CGT AGT CTT CAA CTT GCT GAG ATA TTA GGT CAT          714
Pro Val Lys Arg Ser Leu Gln Leu Ala Glu Ile Leu Gly His
225                     230                 235

CCC ACA AAC AAC ACT CAA GAT GCT TTA GAA TTC TTA CAA AAA          756
Pro Thr Asn Asn Thr Gln Asp Ala Leu Glu Phe Leu Gln Lys
        240                 245                 250

GCC CCA GTA GAC AGT CTC CTG AAA AAA ATG CCA GCT GAA ACA          798
Ala Pro Val Asp Ser Leu Leu Lys Lys Met Pro Ala Glu Thr
            255                 260                 265

GAA GGT GAA ATA ATA GAA GAG TTC GTC TTC GTA CCA TCA ATT          840
Glu Gly Glu Ile Ile Glu Glu Phe Val Phe Val Pro Ser Ile
                270                 275                 280

GAA AAA GTT TTC CCA TCC CAC CAA CCT TTC TTG GAA GAA TCA          882
Glu Lys Val Phe Pro Ser His Gln Pro Phe Leu Glu Glu Ser
                    285                 290

CCA TTG GCC AGA ATG AAA TCT GGA TCC TTT AAC AAA GTA CCT          924
Pro Leu Ala Arg Met Lys Ser Gly Ser Phe Asn Lys Val Pro
295                 300                 305

TTA TTA GTT GGA TTC AAC AGC GCA GAA GGA CTT TTG TAC AAA          966
Leu Leu Val Gly Phe Asn Ser Ala Glu Gly Leu Leu Tyr Lys
    310                 315                 320

TTC TTT ATG AAA GAA AAA CCA GAG ATG CTG AAC CAA GCT GAA         1008
Phe Phe Met Lys Glu Lys Pro Glu Met Leu Asn Gln Ala Glu
        325                 330                 335

GCA GAT TTC GAA AGA CTC GTA CCA GCC GAA TTT GAA TTA GCC         1050
Ala Asp Phe Glu Arg Leu Val Pro Ala Glu Phe Glu Leu Ala
            340                 345                 350

CAT GGA TCA GAA GAA TCG AAA AAA CTT GCA GAA AAA ATC AGG         1092
His Gly Ser Glu Glu Ser Lys Lys Leu Ala Glu Lys Ile Arg
                355                 360

AAG TTT TAC TTT GAC GAT AAA CCC GTT CCT GAA AAT GAG CAG         1134
Lys Phe Tyr Phe Asp Asp Lys Pro Val Pro Glu Asn Glu Gln
365                 370                 375

AAA TTT ATT GAC TTG ATA GGA GAT ATT TGG TTT ACT AGA GGC         1176
Lys Phe Ile Asp Leu Ile Gly Asp Ile Trp Phe Thr Arg Gly
    380                 385                 390

ATT GAC AAG CAT GTC AAG TTG TCT GTA GAA AAA CAA GAC GAG         1218
Ile Asp Lys His Val Lys Leu Ser Val Glu Lys Gln Asp Glu
        395                 400                 405

CCA GTA TAT TAT TAT GAA TAT TCT TTC TCT GAA AGT CAT CCT         1260
Pro Val Tyr Tyr Tyr Glu Tyr Ser Phe Ser Glu Ser His Pro
            410                 415                 420

GCA AAA GGA ACA TTT GGT GAC CAT AAC TTG ACT GGA GCA TGT         1302
Ala Lys Gly Thr Phe Gly Asp His Asn Leu Thr Gly Ala Cys
                425                 430

CAT GGT GAA GAA CTT GTG AAT TTA TTC AAA GTC GAG ATG ATG         1344
His Gly Glu Glu Leu Val Asn Leu Phe Lys Val Glu Met Met
435                 440                 445

AAG CTG GAA AAA GAT AAA CCG AAT GTT TTA TTA ACA AAA GAT         1386
Lys Leu Glu Lys Asp Lys Pro Asn Val Leu Leu Thr Lys Asp
    450                 455                 460

AGG GTA CTT GCT ATG TGG ACG AAC TTC ATC AAA AAT GGA AAT         1428
Arg Val Leu Ala Met Trp Thr Asn Phe Ile Lys Asn Gly Asn
        465                 470                 475

CCT ACT CCT GAA GTA ACT GAA TTA TTG CCA GTT AAA TGG GAA         1470
Pro Thr Pro Glu Val Thr Glu Leu Leu Pro Val Lys Trp Glu
            480                 485                 490

CCT GCC ACA AAA GAC AAG TTG AAT TAT TTG AAC ATT GAT GCC         1512
```

```
         Pro Ala Thr Lys Asp Lys Leu Asn Tyr Leu Asn Ile Asp Ala
                     495                 500

ACC TTA ACT TTG GGA ACA AAT CCA GAA GAA ACC CGA GTC AAA              1554
Thr Leu Thr Leu Gly Thr Asn Pro Glu Glu Thr Arg Val Lys
505                 510                 515

TTY TGG GAA GAT GCC ACA AAA ACT TTG CAC AGT CAA                      1590
Phe Trp Glu Asp Ala Thr Lys Thr Leu His Ser Gln
520                 525                 530

(2) INFORMATION FOR SEQ ID NO:24:

(i) SEQUENCE CHARACTERISTICS:
        (A) LENGTH: 2836 nucleotides
        (B) TYPE: nucleic acid
        (C) STRANDEDNESS: single
        (D) TOPOLOGY: linear (ii) MOLECULE TYPE: cDNA (iii) FEATURE:
        (A) NAME/KEY: CDS
        (B) LOCATION: 99..1889

(iv) SEQUENCE DESCRIPTION: SEQ ID NO:24:

TAGACATGTC GTCTTCAAAA CGTCTATTTT ATCATAAACA AAACGAGATA                 50

AATAATAACA ATTAAGCAAC CAAAATGCAT TAAAAAACAC AATAAAAA                   98

ATG TTA CCT CAC AGT AGT GCA TTA GTT TTA TTT TTA TTT TTT               140
Met Leu Pro His Ser Ser Ala Leu Val Leu Phe Leu Phe Phe
 1               5                   10

TTA TTT TTC TTA TTT ACA CCT ATC TTG TGC ATA CTA TGG GAT               182
Leu Phe Phe Leu Phe Thr Pro Ile Leu Cys Ile Leu Trp Asp
15                  20                  25

AAC CTA GAT CAG CAT TTG TGC AGA GTT CAA TTT AAC GGG ATC               224
Asn Leu Asp Gln His Leu Cys Arg Val Gln Phe Asn Gly Ile
        30                  35                  40

ACG GAA GGA AAA CCG TTC CGA TAT AAA GAt CAT AGG AAT GAT               266
Thr Glu Gly Lys Pro Phe Arg Tyr Lys Asp His Arg Asn Asp
            45                  50                  55

GTA TAT TGT TCT TAT TTG GGA ATT CCT TAT GCC GAA CCG CCT               308
Val Tyr Cys Ser Tyr Leu Gly Ile Pro Tyr Ala Glu Pro Pro
                60                  65                  70

TTT GGA CCA TTA CGA TTT CAG TCT CCA AAA CCA ATA TCA AAT               350
Phe Gly Pro Leu Arg Phe Gln Ser Pro Lys Pro Ile Ser Asn
                    75                  80

CCA AAA ACA GGA TTC GTA CAG GCT CGA ACT TTG GGA GAC AAA               392
Pro Lys Thr Gly Phe Val Gln Ala Arg Thr Leu Gly Asp Lys
85                  90                  95

TGT TTC CAG GAA AGT CTA ATA TAT TCT TAT GCA GGA AGC GAA               434
Cys Phe Gln Glu Ser Leu Ile Tyr Ser Tyr Ala Gly Ser Glu
    100                 105                 110

GAT TGC TTA TAT CTG AAT ATA TTC ACG CCA GAG ACT GTT AAT               476
Asp Cys Leu Tyr Leu Asn Ile Phe Thr Pro Glu Thr Val Asn
        115                 120                 125

TCT GCG AAC AAT ACA AAA TAT CCT GTA ATG TTC TGG ATC CAT               518
Ser Ala Asn Asn Thr Lys Tyr Pro Val Met Phe Trp Ile His
            130                 135                 140

GGA GGC GCA TTC AAC CAA GGA TCA GGA TCT TAT AAT TTT TTT               560
Gly Gly Ala Phe Asn Gln Gly Ser Gly Ser Tyr Asn Phe Phe
                145                 150

GGA CCT GAT TAT TTG ATC AGG GAA GGA ATT ATT TTG GTC ACT               602
Gly Pro Asp Tyr Leu Ile Arg Glu Gly Ile Ile Leu Val Thr
155                 160                 165
```

```
ATC AAC TAT AGA TTA GGA GTT TTC GGT TTT CTA TCA GCG CCG                644
Ile Asn Tyr Arg Leu Gly Val Phe Gly Phe Leu Ser Ala Pro
        170                 175                 180

GAA TGG GAT ATC CAT GGA AAT ATG GGT CTA AAA GAC CAG AGA                686
Glu Trp Asp Ile His Gly Asn Met Gly Leu Lys Asp Gln Arg
            185                 190                 195

TTG GCA CTA AAA TGG GTT TAC GAC AAC ATC GAA AAG TTT GGT                728
Leu Ala Leu Lys Trp Val Tyr Asp Asn Ile Glu Lys Phe Gly
                200                 205                 210

GGA GAC AGA GAA AAA ATT ACA ATT GCT GGA GAA TCT GCT GGA                770
Gly Asp Arg Glu Lys Ile Thr Ile Ala Gly Glu Ser Ala Gly
                    215                 220

GCA GCA AGT GTC CAT TTT CTG ATG ATG GAC AAC TCG ACT AGA                812
Ala Ala Ser Val His Phe Leu Met Met Asp Asn Ser Thr Arg
225                 230                 235

AAA TAC TAC CAA AGG GCC ATT TTG CAG AGT GGG ACA TTA CTA                854
Lys Tyr Tyr Gln Arg Ala Ile Leu Gln Ser Gly Thr Leu Leu
        240                 245                 250

AAT CCG ACT GCT AAT CAA ATT CAA CTT CTG CAT AGA TTT GAA                896
Asn Pro Thr Ala Asn Gln Ile Gln Leu Leu His Arg Phe Glu
            255                 260                 265

AAA CTC AAA CAA GTG CTA AAC ATC ACG CAA AAA CAA GAA CTC                938
Lys Leu Lys Gln Val Leu Asn Ile Thr Gln Lys Gln Glu Leu
                270                 275                 280

CTA AAC CTG GAT AAA AAC CTA ATT TTA CGA GCA GCC TTA AAC                980
Leu Asn Leu Asp Lys Asn Leu Ile Leu Arg Ala Ala Leu Asn
                    285                 290

AGA GTT CCT GAT AGC AAC GAC CAT GAC CGA GAC ACA GTA CCA               1022
Arg Val Pro Asp Ser Asn Asp His Asp Arg Asp Thr Val Pro
295                 300                 305

GTA TTT AAT CCA GTC TTA GAA TCA CCA GAA TCT CCA GAT CCA               1064
Val Phe Asn Pro Val Leu Glu Ser Pro Glu Ser Pro Asp Pro
        310                 315                 320

ATA ACA TTT CCA TCT GCC TTG GAA AGA ATG AGA AAT GGT GAA               1106
Ile Thr Phe Pro Ser Ala Leu Glu Arg Met Arg Asn Gly Glu
            325                 330                 335

TTT CCT GAT GTC GAT GTC ATC ATT GGT TTC AAT AGT GCT GAA               1148
Phe Pro Asp Val Asp Val Ile Ile Gly Phe Asn Ser Ala Glu
                340                 345                 350

GGT TTA AGA TCT ATG GCA AGA GTA ACC AGA GGA AAC ATG GAA               1190
Gly Leu Arg Ser Met Ala Arg Val Thr Arg Gly Asn Met Glu
                    355                 360

GTT CAC AAG ACT TTG ACA AAT ATA GAA AGG GCT ATA CCT AGA               1232
Val His Lys Thr Leu Thr Asn Ile Glu Arg Ala Ile Pro Arg
365                 370                 375

GAT GCT AAT ATT TGG AAA AAT CCA AAT GGT ATT GAG GAG AAA               1274
Asp Ala Asn Ile Trp Lys Asn Pro Asn Gly Ile Glu Glu Lys
        380                 385                 390

AAA CTA ATA AAA ATG CTT ACA GAG TTT TAT GAC CAA GTG AAA               1316
Lys Leu Ile Lys Met Leu Thr Glu Phe Tyr Asp Gln Val Lys
            395                 400                 405

GAA CAA AAC GAT GAC ATT GAA GCC TAC GTC CAA CTA AAA GGC               1358
Glu Gln Asn Asp Asp Ile Glu Ala Tyr Val Gln Leu Lys Gly
                410                 415                 420

GAT GCT GGT TAC CTC CAA GGA ATC TAC CGT ACC TTG AAA GCC               1400
Asp Ala Gly Tyr Leu Gln Gly Ile Tyr Arg Thr Leu Lys Ala
                    425                 430

ATA TTT TTC AAT GAA TTC AGA AGG AAT TCC AAT TTG TAT TTG               1442
Ile Phe Phe Asn Glu Phe Arg Arg Asn Ser Asn Leu Tyr Leu
```

```
                  435                 440                 445
TAC AGG TTA TCA GAC GAT ACG TAT AGT GTA TAT AAA AGT TAT                  1484
Tyr Arg Leu Ser Asp Asp Thr Tyr Ser Val Tyr Lys Ser Tyr
        450                 455                 460

ATC TTG CCC TAT CGA TGG GGT TCC TTG CCA GGA GTT AGT CAT                  1526
Ile Leu Pro Tyr Arg Trp Gly Ser Leu Pro Gly Val Ser His
            465                 470                 475

GGT GAT GAT TTA GGA TAT CTT TTT GCA AAC TCG TTG GAT GTT                  1568
Gly Asp Asp Leu Gly Tyr Leu Phe Ala Asn Ser Leu Asp Val
                480                 485                 490

CCT ATT TTG GGA ACA ACG CAC ATT TCT ATA CCG CAA GAT GCT                  1610
Pro Ile Leu Gly Thr Thr His Ile Ser Ile Pro Gln Asp Ala
                    495                 500

ATG CAG ACT CTG GAA AGG ATG GTC AGG ATC TGG ACC AAT TTT                  1652
Met Gln Thr Leu Glu Arg Met Val Arg Ile Trp Thr Asn Phe
505                 510                 515

GTA AAG AAT GGA AAA CCT ACA TCA AAC ACT GAA GAT GCA TCA                  1694
Val Lys Asn Gly Lys Pro Thr Ser Asn Thr Glu Asp Ala Ser
        520                 525                 530

TGT GAT ACA AAA AGA CAT TTA AAC GAC ATT TTT TGG GAA CCA                  1736
Cys Asp Thr Lys Arg His Leu Asn Asp Ile Phe Trp Glu Pro
            535                 540                 545

TAC AAC GAC GAA GAA CCA AAA TAT TTG GAC ATG GGA AAA GAA                  1778
Tyr Asn Asp Glu Glu Pro Lys Tyr Leu Asp Met Gly Lys Glu
                550                 555                 560

AAT TTT GAA ATG AAA AAT ATT TTG GAA CTA AAA CGC ATG ATG                  1820
Asn Phe Glu Met Lys Asn Ile Leu Glu Leu Lys Arg Met Met
565                 570

CTT TGG GAT GAA GTT TAT AGA AAT GCG AAT TTG CGG TTT AGA                  1862
Leu Trp Asp Glu Val Tyr Arg Asn Ala Asn Leu Arg Phe Arg
    575                 580                 585

GTC TGT AAT GAA GAA AGT ATT AGA TGA GTTTTTTAA                            1899
Val Cys Asn Glu Glu Ser Ile Arg
        590                 595

TTTTACATAC AGCCGAGAGG AAACATGACT AAAATTGGAA AGAAAAATCA                   1949

GAAAAAGAAA AATCACATGG ACCATAGTAA CTTTATTACA TGATTTAGTT                   1999

TCAAGTGTAT CAAGAAAACT TATTGCATCA AAGAAAATAT TATTTTGCCA                   2049

AAATTCTTGG AAAAACACTT TTTATGACTG ACATGGCCCA TAATTGAAGC                   2099

TTTTTCTTCT TTTACCAAAT CGCCAAATTT TGTAGCGTCA GACACATTTA                   2149

TTTATGACAT GGCAATTAAT GTGTTAAACA TTCAACTCTA TATTAAAAAT                   2199

GGTAGTATTT TCTAATAAGA AGGTTATATA AAAAGACTTG AAAATAATAA                   2249

GATTTGCTCG GCTATATATA AAAACTTANC GTCTCGTTAT GCTAAACTTT                   2299

TTTGATGGTA AAAATATGTT GATTTTCCTA ATAATCTAAG ATATTATATT                   2349

TTAGATTAAA TTAAATATG ATATTTTCAA TTAATTAATT TTAGTTTTAA                    2399

ATGTACTATA TTTACCAGTA CTATGAAACT ATTTTAAATA TATTTTTTAT                   2449

TACAATATTT ATTTCTCAAA AATGTTTAGT GTAACAAGAC CATTAAATTA                   2499

GAGTTAATGT TGTAAATTAA ACTATTTTTT ATCTATCACA ACCGCTTAAT                   2549

TGGTGCAAAG AAAAATTTTA CTGTGATAAT ATTTGACATT TACACAATAT                   2599

TACGAATTGT AAACTCACAA TTATGTGAAT ATTGTTTTTT GTTAAAAAAA                   2649

CATACATGAC TTTTCTATAT CATTTTATAT TACGGTGATA TGGATTAATG                   2699

TCAACATGTA AAATACAAAT GCGGTTGTTA AAAATAATCT GTATTAAAAT                   2749
```

TGTTATATAA AATCTGAATA AATGTACTTT TAAGTAAAAA AAAAAAAAAA                2799

AAAAAAAAAA AAAAAAAAAA AAAAAAAAAA AAAAAA                              2836

(2) INFORMATION FOR SEQ ID NO:25:

(i) SEQUENCE CHARACTERISTICS:
        (A) LENGTH: 596 amino acids
        (B) TYPE: amino acid
        (D) TOPOLOGY: linear (ii) MOLECULE TYPE: protein (iii) SEQUENCE DESCRIPTION: SEQ ID NO:25:

```
Met Leu Pro His Ser Ser Ala Leu Val Leu Phe Leu Phe
 1               5                  10

Leu Phe Phe Leu Phe Thr Pro Ile Leu Cys Ile Leu Trp Asp
15                  20                  25

Asn Leu Asp Gln His Leu Cys Arg Val Gln Phe Asn Gly Ile
    30                  35                  40

Thr Glu Gly Lys Pro Phe Arg Tyr Lys Asp His Arg Asn Asp
        45                  50                  55

Val Tyr Cys Ser Tyr Leu Gly Ile Pro Tyr Ala Glu Pro Pro
            60                  65                  70

Phe Gly Pro Leu Arg Phe Gln Ser Pro Lys Pro Ile Ser Asn
                75                  80

Pro Lys Thr Gly Phe Val Gln Ala Arg Thr Leu Gly Asp Lys
85                  90                  95

Cys Phe Gln Glu Ser Leu Ile Tyr Ser Tyr Ala Gly Ser Glu
   100                 105                 110

Asp Cys Leu Tyr Leu Asn Ile Phe Thr Pro Glu Thr Val Asn
       115                 120                 125

Ser Ala Asn Asn Thr Lys Tyr Pro Val Met Phe Trp Ile His
           130                 135                 140

Gly Gly Ala Phe Asn Gln Gly Ser Gly Ser Tyr Asn Phe Phe
               145                 150

Gly Pro Asp Tyr Leu Ile Arg Glu Gly Ile Ile Leu Val Thr
155                 160                 165

Ile Asn Tyr Arg Leu Gly Val Phe Gly Phe Leu Ser Ala Pro
   170                 175                 180

Glu Trp Asp Ile His Gly Asn Met Gly Leu Lys Asp Gln Arg
       185                 190                 195

Leu Ala Leu Lys Trp Val Tyr Asp Asn Ile Glu Lys Phe Gly
           200                 205                 210

Gly Asp Arg Glu Lys Ile Thr Ile Ala Gly Glu Ser Ala Gly
               215                 220

Ala Ala Ser Val His Phe Leu Met Met Asp Asn Ser Thr Arg
225                 230                 235

Lys Tyr Tyr Gln Arg Ala Ile Leu Gln Ser Gly Thr Leu Leu
   240                 245                 250

Asn Pro Thr Ala Asn Gln Ile Gln Leu Leu His Arg Phe Glu
       255                 260                 265

Lys Leu Lys Gln Val Leu Asn Ile Thr Gln Lys Gln Glu Leu
           270                 275                 280

Leu Asn Leu Asp Lys Asn Leu Ile Leu Arg Ala Ala Leu Asn
               285                 290
```

```
Arg Val Pro Asp Ser Asn Asp His Asp Arg Asp Thr Val Pro
295                 300                 305

Val Phe Asn Pro Val Leu Glu Ser Pro Glu Ser Pro Asp Pro
    310                 315                 320

Ile Thr Phe Pro Ser Ala Leu Glu Arg Met Arg Asn Gly Glu
        325                 330                 335

Phe Pro Asp Val Asp Val Ile Ile Gly Phe Asn Ser Ala Glu
            340                 345                 350

Gly Leu Arg Ser Met Ala Arg Val Thr Arg Gly Asn Met Glu
                355                 360

Val His Lys Thr Leu Thr Asn Ile Glu Arg Ala Ile Pro Arg
365                 370                 375

Asp Ala Asn Ile Trp Lys Asn Pro Asn Gly Ile Glu Glu Lys
    380                 385                 390

Lys Leu Ile Lys Met Leu Thr Glu Phe Tyr Asp Gln Val Lys
        395                 400                 405

Glu Gln Asn Asp Asp Ile Glu Ala Tyr Val Gln Leu Lys Gly
            410                 415                 420

Asp Ala Gly Tyr Leu Gln Gly Ile Tyr Arg Thr Leu Lys Ala
                425                 430

Ile Phe Phe Asn Glu Phe Arg Arg Asn Ser Asn Leu Tyr Leu
435                 440                 445

Tyr Arg Leu Ser Asp Asp Thr Tyr Ser Val Tyr Lys Ser Tyr
    450                 455                 460

Ile Leu Pro Tyr Arg Trp Gly Ser Leu Pro Gly Val Ser His
        465                 470                 475

Gly Asp Asp Leu Gly Tyr Leu Phe Ala Asn Ser Leu Asp Val
            480                 485                 490

Pro Ile Leu Gly Thr Thr His Ile Ser Ile Pro Gln Asp Ala
                495                 500

Met Gln Thr Leu Glu Arg Met Val Arg Ile Trp Thr Asn Phe
505                 510                 515

Val Lys Asn Gly Lys Pro Thr Ser Asn Thr Glu Asp Ala Ser
    520                 525                 530

Cys Asp Thr Lys Arg His Leu Asn Asp Ile Phe Trp Glu Pro
        535                 540                 545

Tyr Asn Asp Glu Glu Pro Lys Tyr Leu Asp Met Gly Lys Glu
            550                 555                 560

Asn Phe Glu Met Lys Asn Ile Leu Glu Leu Lys Arg Met Met
                565                 570

Leu Trp Asp Glu Val Tyr Arg Asn Ala Asn Leu Arg Phe Arg
575                 580                 585

Val Cys Asn Glu Glu Ser Ile Arg
590                 595

(2) INFORMATION FOR SEQ ID NO:26:

(i) SEQUENCE CHARACTERISTICS:
        (A) LENGTH: 2836 nucleotides
        (B) TYPE: nucleic acid
        (C) STRANDEDNESS: single
        (D) TOPOLOGY: linear (ii) MOLECULE TYPE: cDNA (iii) SEQUENCE DESCRIPTION: SEQ ID NO:26:
```

-continued

```
TTTTTTTTTT TTTTTTTTTT TTTTTTTTTT TTTTTTTTTT TTTTTTTTTT          50

TTACTTAAAA GTACATTTAT TCAGATTTTA TATAACAATT TTAATACAGA         100

TTATTTTTAA CAACCGCATT TGTATTTTAC ATGTTGACAT TAATCCATAT         150

CACCGTAATA TAAATGATA TAGAAAAGTC ATGTATGTTT TTTTAACAAA          200

AAACAATATT CACATAATTG TGAGTTTACA ATTCGTAATA TTGTGTAAAT         250

GTCAAATATT ATCACAGTAA AATTTTTCTT TGCACCAATT AAGCGGTTGT         300

GATAGATAAA AAATAGTTTA ATTTACAACA TTAACTCTAA TTTAATGGTC         350

TTGTTACACT AAACATTTTT GAGAAATAAA TATTGTAATA AAAATATAT          400

TTAAAATAGT TTCATAGTAC TGGTAAATAT AGTACATTTA AAACTAAAAT         450

TAATTAATTG AAAATATCAT ATTTTAATTT AATCTAAAAT ATAATATCTT         500

AGATTATTAG GAAAATCAAC ATATTTTAC CATCAAAAAA GTTTAGCATA          550

ACGAGACGNT AAGTTTTTAT ATATAGCCGA GCAAATCTTA TTATTTTCAA         600

GTCTTTTTAT ATAACCTTCT TATTAGAAAA TACTACCATT TTTAATATAG         650

AGTTGAATGT TTAACACATT AATTGCCATG TCATAAATAA ATGTGTCTGA         700

CGCTACAAAA TTTGGCGATT TGGTAAAAGA AGAAAAAGCT TCAATTATGG         750

GCCATGTCAG TCATAAAAAG TGTTTTTCCA AGAATTTTGG CAAAATAATA         800

TTTTCTTTGA TGCAATAAGT TTTCTTGATA CACTTGAAAC TAAATCATGT         850

AATAAAGTTA CTATGGTCCA TGTGATTTTT CTTTTTCTGA TTTTTCTTTC         900

CAATTTTAGT CATGTTTCCT CTCGGCTGTA TGTAAAATTA AAAAAACTCA         950

TCTAATACTT TCTTCATTAC AGACTCTAAA CCGCAAATTC GCATTTCTAT        1000

AAACTTCATC CCAAAGCATC ATGCGTTTTA GTTCCAAAAT ATTTTTCATT        1050

TCAAAATTTT CTTTTCCCAT GTCCAAATAT TTTGGTTCTT CGTCGTTGTA        1100

TGGTTCCCAA AAAATGTCGT TTAAATGTCT TTTTGTATCA CATGATGCAT        1150

CTTCAGTGTT TGATGTAGGT TTTCCATTCT TTACAAAATT GGTCCAGATC        1200

CTGACCATCC TTTCCAGAGT CTGCATAGCA TCTTGCGGTA TAGAAATGTG        1250

CGTTGTTCCC AAAATAGGAA CATCCAACGA GTTTGCAAAA AGATATCCTA        1300

AATCATCACC ATGACTAACT CCTGGCAAGG AACCCCATCG ATAGGGCAAG        1350

ATATAACTTT TATATACACT ATACGTATCG TCTGATAACC TGTACAAATA        1400

CAAATTGGAA TTCCTTCTGA ATTCATTGAA AAATATGGCT TTCAAGGTAC        1450

GGTAGATTCC TTGGAGGTAA CCAGCATCGC CTTTTAGTTG GACGTAGGCT        1500

TCAATGTCAT CGTTTGTTC TTTCACTTGG TCATAAAACT CTGTAAGCAT         1550

TTTTATTAGT TTTTTCTCCT CAATACCATT TGGATTTTTC CAAATATTAG        1600

CATCTCTAGG TATAGCCCTT TCTATATTTG TCAAAGTCTT GTGAACTTCC        1650

ATGTTTCCTC TGGTTACTCT TGCCATAGAT CTTAAACCTT CAGCACTATT        1700

GAAACCAATG ATGACATCGA CATCAGGAAA TTCACCATTT CTCATTCTTT        1750

CCAAGGCAGA TGGAAATGTT ATTGGATCTG GAGATTCTGG TGATTCTAAG        1800

ACTGGATTAA ATACTGGTAC TGTGTCTCGG TCATGGTCGT TGCTATCAGG        1850

AACTCTGTTT AAGGCTGCTC GTAAAATTAG GTTTTTATCC AGGTTAGGA         1900

GTTCTTGTTT TTGCGTGATG TTTAGCACTT GTTTGAGTTT TCAAATCTA         1950
```

```
TGCAGAAGTT GAATTTGATT AGCAGTCGGA TTTAGTAATG TCCCACTCTG        2000

CAAAATGGCC CTTTGGTAGT ATTTTCTAGT CGAGTTGTCC ATCATCAGAA        2050

AATGGACACT TGCTGCTCCA GCAGATTCTC CAGCAATTGT AATTTTTTCT        2100

CTGTCTCCAC CAAACTTTTC GATGTTGTCG TAAACCCATT TTAGTGCCAA        2150

TCTCTGGTCT TTTAGACCCA TATTTCCATG GATATCCCAT TCCGGCGCTG        2200

ATAGAAAACC GAAAACTCCT AATCTATAGT TGATAGTGAC CAAAATAATT        2250

CCTTCCCTGA TCAAATAATC AGGTCCAAAA AAATTATAAG ATCCTGATCC        2300

TTGGTTGAAT GCGCCTCCAT GGATCCAGAA CATTACAGGA TATTTTGTAT        2350

TGTTCGCAGA ATTAACAGTC TCTGGCGTGA ATATATTCAG ATATAAGCAA        2400

TCTTCGCTTC CTGCATAAGA ATATATTAGA CTTTCCTGGA AACATTTGTC        2450

TCCCAAAGTT CGAGCCTGTA CGAATCCTGT TTTTGGATTT GATATTGGTT        2500

TTGGAGACTG AAATCGTAAT GGTCCAAAAG GCGGTTCGGC ATAAGGAATT        2550

CCCAAATAAG AACAATATAC ATCATTCCTA TGATCTTTAT ATCGGAACGG        2600

TTTTCCTTCC GTGATCCCGT TAAATTGAAC TCTGCACAAA TGCTGATCTA        2650

GGTTATCCCA TAGTATGCAC AAGATAGGTG TAAATAAGAA AAATAAAAAA        2700

AATAAAAATA AAACTAATGC ACTACTGTGA GGTAACATTT TTTATTGTGT        2750

TTTTTAATGC ATTTTGGTTG CTTAATTGTT ATTATTTATC TCGTTTTGTT        2800

TATGATAAAA TAGACGTTTT GAAGACGACA TGTCTA                      2836

(2) INFORMATION FOR SEQ ID NO:27:

(i) SEQUENCE CHARACTERISTICS:
        (A) LENGTH:  1710 nucleotides
        (B) TYPE:  nucleic acid
        (C) STRANDEDNESS:  single
        (D) TOPOLOGY:  linear (ii) MOLECULE TYPE:  cDNA (iii) FEATURE:
        (A) NAME/KEY:  CDS
        (B) LOCATION:  1..1710

(iv) SEQUENCE DESCRIPTION:  SEQ ID NO:27:

TGG GAT AAC CTA GAT CAG CAT TTG TGC AGA GTT CAA TTT AAC        42
Trp Asp Asn Leu Asp Gln His Leu Cys Arg Val Gln Phe Asn
 1               5                  10

GGG ATC ACG GAA GGA AAA CCG TTC CGA TAT AAA GAT CAT AGG        84
Gly Ile Thr Glu Gly Lys Pro Phe Arg Tyr Lys Asp His Arg
15              20                  25

AAT GAT GTA TAT TGT TCT TAT TTG GGA ATT CCT TAT GCC GAA       126
Asn Asp Val Tyr Cys Ser Tyr Leu Gly Ile Pro Tyr Ala Glu
        30                  35                  40

CCG CCT TTT GGA CCA TTA CGA TTT CAG TCT CCA AAA CCA ATA       168
Pro Pro Phe Gly Pro Leu Arg Phe Gln Ser Pro Lys Pro Ile
            45                  50                  55

TCA AAT CCA AAA ACA GGA TTC GTA CAG GCT CGA ACT TTG GGA       210
Ser Asn Pro Lys Thr Gly Phe Val Gln Ala Arg Thr Leu Gly
                60                  65                  70

GAC AAA TGT TTC CAG GAA AGT CTA ATA TAT TCT TAT GCA GGA       252
Asp Lys Cys Phe Gln Glu Ser Leu Ile Tyr Ser Tyr Ala Gly
                    75                  80

AGC GAA GAT TGC TTA TAT CTG AAT ATA TTC ACG CCA GAG ACT       294
Ser Glu Asp Cys Leu Tyr Leu Asn Ile Phe Thr Pro Glu Thr
```

```
                                   -continued
85                  90                  95

GTT AAT TCT GCG AAC AAT ACA AAA TAT CCT GTA ATG TTC TGG         336
Val Asn Ser Ala Asn Asn Thr Lys Tyr Pro Val Met Phe Trp
        100                 105                 110

ATC CAT GGA GGC GCA TTC AAC CAA GGA TCA GGA TCT TAT AAT         378
Ile His Gly Gly Ala Phe Asn Gln Gly Ser Gly Ser Tyr Asn
        115                 120                 125

TTT TTT GGA CCT GAT TAT TTG ATC AGG GAA GGA ATT ATT TTG         420
Phe Phe Gly Pro Asp Tyr Leu Ile Arg Glu Gly Ile Ile Leu
        130                 135                 140

GTC ACT ATC AAC TAT AGA TTA GGA GTT TTC GGT TTT CTA TCA         462
Val Thr Ile Asn Tyr Arg Leu Gly Val Phe Gly Phe Leu Ser
                145                 150

GCG CCG GAA TGG GAT ATC CAT GGA AAT ATG GGT CTA AAA GAC         504
Ala Pro Glu Trp Asp Ile His Gly Asn Met Gly Leu Lys Asp
155                 160                 165

CAG AGA TTG GCA CTA AAA TGG GTT TAC GAC AAC ATC GAA AAG         546
Gln Arg Leu Ala Leu Lys Trp Val Tyr Asp Asn Ile Glu Lys
        170                 175                 180

TTT GGT GGA GAC AGA GAA AAA ATT ACA ATT GCT GGA GAA TCT         588
Phe Gly Gly Asp Arg Glu Lys Ile Thr Ile Ala Gly Glu Ser
        185                 190                 195

GCT GGA GCA GCA AGT GTC CAT TTT CTG ATG ATG GAC AAC TCG         630
Ala Gly Ala Ala Ser Val His Phe Leu Met Met Asp Asn Ser
        200                 205                 210

ACT AGA AAA TAC TAC CAA AGG GCC ATT TTG CAG AGT GGG ACA         672
Thr Arg Lys Tyr Tyr Gln Arg Ala Ile Leu Gln Ser Gly Thr
        215                 220

TTA CTA AAT CCG ACT GCT AAT CAA ATT CAA CTT CTG CAT AGA         714
Leu Leu Asn Pro Thr Ala Asn Gln Ile Gln Leu Leu His Arg
225                 230                 235

TTT GAA AAA CTC AAA CAA GTG CTA AAC ATC ACG CAA AAA CAA         756
Phe Glu Lys Leu Lys Gln Val Leu Asn Ile Thr Gln Lys Gln
        240                 245                 250

GAA CTC CTA AAC CTG GAT AAA AAC CTA ATT TTA CGA GCA GCC         798
Glu Leu Leu Asn Leu Asp Lys Asn Leu Ile Leu Arg Ala Ala
        255                 260                 265

TTA AAC AGA GTT CCT GAT AGC AAC GAC CAT GAC CGA GAC ACA         840
Leu Asn Arg Val Pro Asp Ser Asn Asp His Asp Arg Asp Thr
        270                 275                 280

GTA CCA GTA TTT AAT CCA GTC TTA GAA TCA CCA GAA TCT CCA         882
Val Pro Val Phe Asn Pro Val Leu Glu Ser Pro Glu Ser Pro
        285                 290

GAT CCA ATA ACA TTT CCA TCT GCC TTG GAA AGA ATG AGA AAT         924
Asp Pro Ile Thr Phe Pro Ser Ala Leu Glu Arg Met Arg Asn
295                 300                 305

GGT GAA TTT CCT GAT GTC GAT GTC ATC ATT GGT TTC AAT AGT         966
Gly Glu Phe Pro Asp Val Asp Val Ile Ile Gly Phe Asn Ser
        310                 315                 320

GCT GAA GGT TTA AGA TCT ATG GCA AGA GTA ACC AGA GGA AAC         1008
Ala Glu Gly Leu Arg Ser Met Ala Arg Val Thr Arg Gly Asn
        325                 330                 335

ATG GAA GTT CAC AAG ACT TTG ACA AAT ATA GAA AGG GCT ATA         1050
Met Glu Val His Lys Thr Leu Thr Asn Ile Glu Arg Ala Ile
        340                 345                 350

CCT AGA GAT GCT AAT ATT TGG AAA AAT CCA AAT GGT ATT GAG         1092
Pro Arg Asp Ala Asn Ile Trp Lys Asn Pro Asn Gly Ile Glu
        355                 360

GAG AAA AAA CTA ATA AAA ATG CTT ACA GAG TTT TAT GAC CAA         1134
```

```
               Glu Lys Lys Leu Ile Lys Met Leu Thr Glu Phe Tyr Asp Gln
               365                 370                 375

GTG AAA GAA CAA AAC GAT GAC ATT GAA GCC TAC GTC CAA CTA              1176
Val Lys Glu Gln Asn Asp Asp Ile Glu Ala Tyr Val Gln Leu
    380                 385                 390

AAA GGC GAT GCT GGT TAC CTC CAA GGA ATC TAC CGT ACC TTG              1218
Lys Gly Asp Ala Gly Tyr Leu Gln Gly Ile Tyr Arg Thr Leu
        395                 400                 405

AAA GCC ATA TTT TTC AAT GAA TTC AGA AGG AAT TCC AAT TTG              1260
Lys Ala Ile Phe Phe Asn Glu Phe Arg Arg Asn Ser Asn Leu
            410                 415                 420

TAT TTG TAC AGG TTA TCA GAC GAT ACG TAT AGT GTA TAT AAA              1302
Tyr Leu Tyr Arg Leu Ser Asp Asp Thr Tyr Ser Val Tyr Lys
                425                 430

AGT TAT ATC TTG CCC TAT CGA TGG GGT TCC TTG CCA GGA GTT              1344
Ser Tyr Ile Leu Pro Tyr Arg Trp Gly Ser Leu Pro Gly Val
435                 440                 445

AGT CAT GGT GAT GAT TTA GGA TAT CTT TTT GCA AAC TCG TTG              1386
Ser His Gly Asp Asp Leu Gly Tyr Leu Phe Ala Asn Ser Leu
    450                 455                 460

GAT GTT CCT ATT TTG GGA ACA ACG CAC ATT TCT ATA CCG CAA              1428
Asp Val Pro Ile Leu Gly Thr Thr His Ile Ser Ile Pro Gln
        465                 470                 475

GAT GCT ATG CAG ACT CTG GAA AGG ATG GTC AGG ATC TGG ACC              1470
Asp Ala Met Gln Thr Leu Glu Arg Met Val Arg Ile Trp Thr
            480                 485                 490

AAT TTT GTA AAG AAT GGA AAA CCT ACA TCA AAC ACT GAA GAT              1512
Asn Phe Val Lys Asn Gly Lys Pro Thr Ser Asn Thr Glu Asp
                495                 500

GCA TCA TGT GAT ACA AAA AGA CAT TTA AAC GAC ATT TTT TGG              1554
Ala Ser Cys Asp Thr Lys Arg His Leu Asn Asp Ile Phe Trp
505                 510                 515

GAA CCA TAC AAC GAC GAA GAA CCA AAA TAT TTG GAC ATG GGA              1596
Glu Pro Tyr Asn Asp Glu Glu Pro Lys Tyr Leu Asp Met Gly
    520                 525                 530

AAA GAA AAT TTT GAA ATG AAA AAT ATT TTG GAA CTA AAA CGC              1638
Lys Glu Asn Phe Glu Met Lys Asn Ile Leu Glu Leu Lys Arg
        535                 540                 545

ATG ATG CTT TGG GAT GAA GTT TAT AGA AAT GCG AAT TTG CGG              1680
Met Met Leu Trp Asp Glu Val Tyr Arg Asn Ala Asn Leu Arg
            550                 555                 560

TTT AGA GTC TGT AAT GAA GAA AGT ATT AGA                              1710
Phe Arg Val Cys Asn Glu Glu Ser Ile Arg
                565                 570

(2) INFORMATION FOR SEQ ID NO:28:

(i) SEQUENCE CHARACTERISTICS:
        (A) LENGTH:  1788 nucleotides
        (B) TYPE:  nucleic acid
        (C) STRANDEDNESS:  single
        (D) TOPOLOGY:  linear (ii) MOLECULE TYPE:  cDNA (iii) FEATURE:
        (A) NAME/KEY:  CDS
        (B) LOCATION:  1..1788

(iv) SEQUENCE DESCRIPTION:  SEQ ID NO:28:

ATG TTA CCT CAC AGT AGT GCA TTA GTT TTA TTT TTA TTT TTT              42
Met Leu Pro His Ser Ser Ala Leu Val Leu Phe Leu Phe Phe
1               5                   10
```

```
TTA TTT TTC TTA TTT ACA CCT ATC TTG TGC ATA CTA TGG GAT             84
Leu Phe Phe Leu Phe Thr Pro Ile Leu Cys Ile Leu Trp Asp
 15              20                  25

AAC CTA GAT CAG CAT TTG TGC AGA GTT CAA TTT AAC GGG ATC            126
Asn Leu Asp Gln His Leu Cys Arg Val Gln Phe Asn Gly Ile
         30                  35                  40

ACG GAA GGA AAA CCG TTC CGA TAT AAA GAt CAT AGG AAT GAT            168
Thr Glu Gly Lys Pro Phe Arg Tyr Lys Asp His Arg Asn Asp
             45                  50                  55

GTA TAT TGT TCT TAT TTG GGA ATT CCT TAT GCC GAA CCG CCT            210
Val Tyr Cys Ser Tyr Leu Gly Ile Pro Tyr Ala Glu Pro Pro
                 60                  65                  70

TTT GGA CCA TTA CGA TTT CAG TCT CCA AAA CCA ATA TCA AAT            252
Phe Gly Pro Leu Arg Phe Gln Ser Pro Lys Pro Ile Ser Asn
                     75                  80

CCA AAA ACA GGA TTC GTA CAG GCT CGA ACT TTG GGA GAC AAA            294
Pro Lys Thr Gly Phe Val Gln Ala Arg Thr Leu Gly Asp Lys
 85              90                  95

TGT TTC CAG GAA AGT CTA ATA TAT TCT TAT GCA GGA AGC GAA            336
Cys Phe Gln Glu Ser Leu Ile Tyr Ser Tyr Ala Gly Ser Glu
        100                 105                 110

GAT TGC TTA TAT CTG AAT ATA TTC ACG CCA GAG ACT GTT AAT            378
Asp Cys Leu Tyr Leu Asn Ile Phe Thr Pro Glu Thr Val Asn
            115                 120                 125

TCT GCG AAC AAT ACA AAA TAT CCT GTA ATG TTC TGG ATC CAT            420
Ser Ala Asn Asn Thr Lys Tyr Pro Val Met Phe Trp Ile His
                130                 135                 140

GGA GGC GCA TTC AAC CAA GGA TCA GGA TCT TAT AAT TTT TTT            462
Gly Gly Ala Phe Asn Gln Gly Ser Gly Ser Tyr Asn Phe Phe
                    145                 150

GGA CCT GAT TAT TTG ATC AGG GAA GGA ATT ATT TTG GTC ACT            504
Gly Pro Asp Tyr Leu Ile Arg Glu Gly Ile Ile Leu Val Thr
155                 160                 165

ATC AAC TAT AGA TTA GGA GTT TTC GGT TTT CTA TCA GCG CCG            546
Ile Asn Tyr Arg Leu Gly Val Phe Gly Phe Leu Ser Ala Pro
        170                 175                 180

GAA TGG GAT ATC CAT GGA AAT ATG GGT CTA AAA GAC CAG AGA            588
Glu Trp Asp Ile His Gly Asn Met Gly Leu Lys Asp Gln Arg
            185                 190                 195

TTG GCA CTA AAA TGG GTT TAC GAC AAC ATC GAA AAG TTT GGT            630
Leu Ala Leu Lys Trp Val Tyr Asp Asn Ile Glu Lys Phe Gly
                200                 205                 210

GGA GAC AGA GAA AAA ATT ACA ATT GCT GGA GAA TCT GCT GGA            672
Gly Asp Arg Glu Lys Ile Thr Ile Ala Gly Glu Ser Ala Gly
                    215                 220

GCA GCA AGT GTC CAT TTT CTG ATG ATG GAC AAC TCG ACT AGA            714
Ala Ala Ser Val His Phe Leu Met Met Asp Asn Ser Thr Arg
225                 230                 235

AAA TAC TAC CAA AGG GCC ATT TTG CAG AGT GGG ACA TTA CTA            756
Lys Tyr Tyr Gln Arg Ala Ile Leu Gln Ser Gly Thr Leu Leu
        240                 245                 250

AAT CCG ACT GCT AAT CAA ATT CAA CTT CTG CAT AGA TTT GAA            798
Asn Pro Thr Ala Asn Gln Ile Gln Leu Leu His Arg Phe Glu
            255                 260                 265

AAA CTC AAA CAA GTG CTA AAC ATC ACG CAA AAA CAA GAA CTC            840
Lys Leu Lys Gln Val Leu Asn Ile Thr Gln Lys Gln Glu Leu
                270                 275                 280

CTA AAC CTG GAT AAA AAC CTA ATT TTA CGA GCA GCC TTA AAC            882
Leu Asn Leu Asp Lys Asn Leu Ile Leu Arg Ala Ala Leu Asn
```

-continued

```
                      285                           290
AGA GTT CCT GAT AGC AAC GAC CAT GAC CGA GAC ACA GTA CCA        924
Arg Val Pro Asp Ser Asn Asp His Asp Arg Asp Thr Val Pro
295                 300                 305

GTA TTT AAT CCA GTC TTA GAA TCA CCA GAA TCT CCA GAT CCA        966
Val Phe Asn Pro Val Leu Glu Ser Pro Glu Ser Pro Asp Pro
    310                 315                 320

ATA ACA TTT CCA TCT GCC TTG GAA AGA ATG AGA AAT GGT GAA       1008
Ile Thr Phe Pro Ser Ala Leu Glu Arg Met Arg Asn Gly Glu
        325                 330                 335

TTT CCT GAT GTC GAT GTC ATC ATT GGT TTC AAT AGT GCT GAA       1050
Phe Pro Asp Val Asp Val Ile Ile Gly Phe Asn Ser Ala Glu
            340                 345                 350

GGT TTA AGA TCT ATG GCA AGA GTA ACC AGA GGA AAC ATG GAA       1092
Gly Leu Arg Ser Met Ala Arg Val Thr Arg Gly Asn Met Glu
                355                 360

GTT CAC AAG ACT TTG ACA AAT ATA GAA AGG GCT ATA CCT AGA       1134
Val His Lys Thr Leu Thr Asn Ile Glu Arg Ala Ile Pro Arg
365                 370                 375

GAT GCT AAT ATT TGG AAA AAT CCA AAT GGT ATT GAG GAG AAA       1176
Asp Ala Asn Ile Trp Lys Asn Pro Asn Gly Ile Glu Glu Lys
    380                 385                 390

AAA CTA ATA AAA ATG CTT ACA GAG TTT TAT GAC CAA GTG AAA       1218
Lys Leu Ile Lys Met Leu Thr Glu Phe Tyr Asp Gln Val Lys
        395                 400                 405

GAA CAA AAC GAT GAC ATT GAA GCC TAC GTC CAA CTA AAA GGC       1260
Glu Gln Asn Asp Asp Ile Glu Ala Tyr Val Gln Leu Lys Gly
            410                 415                 420

GAT GCT GGT TAC CTC CAA GGA ATC TAC CGT ACC TTG AAA GCC       1302
Asp Ala Gly Tyr Leu Gln Gly Ile Tyr Arg Thr Leu Lys Ala
                425                 430

ATA TTT TTC AAT GAA TTC AGA AGG AAT TCC AAT TTG TAT TTG       1344
Ile Phe Phe Asn Glu Phe Arg Arg Asn Ser Asn Leu Tyr Leu
435                 440                 445

TAC AGG TTA TCA GAC GAT ACG TAT AGT GTA TAT AAA AGT TAT       1386
Tyr Arg Leu Ser Asp Asp Thr Tyr Ser Val Tyr Lys Ser Tyr
    450                 455                 460

ATC TTG CCC TAT CGA TGG GGT TCC TTG CCA GGA GTT AGT CAT       1428
Ile Leu Pro Tyr Arg Trp Gly Ser Leu Pro Gly Val Ser His
        465                 470                 475

GGT GAT GAT TTA GGA TAT CTT TTT GCA AAC TCG TTG GAT GTT       1470
Gly Asp Asp Leu Gly Tyr Leu Phe Ala Asn Ser Leu Asp Val
            480                 485                 490

CCT ATT TTG GGA ACA ACG CAC ATT TCT ATA CCG CAA GAT GCT       1512
Pro Ile Leu Gly Thr Thr His Ile Ser Ile Pro Gln Asp Ala
                495                 500

ATG CAG ACT CTG GAA AGG ATG GTC AGG ATC TGG ACC AAT TTT       1554
Met Gln Thr Leu Glu Arg Met Val Arg Ile Trp Thr Asn Phe
505                 510                 515

GTA AAG AAT GGA AAA CCT ACA TCA AAC ACT GAA GAT GCA TCA       1596
Val Lys Asn Gly Lys Pro Thr Ser Asn Thr Glu Asp Ala Ser
    520                 525                 530

TGT GAT ACA AAA AGA CAT TTA AAC GAC ATT TTT TGG GAA CCA       1638
Cys Asp Thr Lys Arg His Leu Asn Asp Ile Phe Trp Glu Pro
        535                 540                 545

TAC AAC GAC GAA GAA CCA AAA TAT TTG GAC ATG GGA AAA GAA       1680
Tyr Asn Asp Glu Glu Pro Lys Tyr Leu Asp Met Gly Lys Glu
            550                 555                 560

AAT TTT GAA ATG AAA AAT ATT TTG GAA CTA AAA CGC ATG ATG       1722
```

```
Asn Phe Glu Met Lys Asn Ile Leu Glu Leu Lys Arg Met Met
            565                 570

CTT TGG GAT GAA GTT TAT AGA AAT GCG AAT TTG CGG TTT AGA         1764
Leu Trp Asp Glu Val Tyr Arg Asn Ala Asn Leu Arg Phe Arg
575                 580                 585

GTC TGT AAT GAA GAA AGT ATT AGA                                 1788
Val Cys Asn Glu Glu Ser Ile Arg
    590                 595
```

(2) INFORMATION FOR SEQ ID NO:29:

(i) SEQUENCE CHARACTERISTICS:
        (A) LENGTH: 1788 nucleotides
        (B) TYPE: nucleic acid
        (C) STRANDEDNESS: single
        (D) TOPOLOGY: linear (ii) MOLECULE TYPE: cDNA (iii) SEQUENCE DESCRIPTION: SEQ ID NO:29:

```
TCTAATACTT TCTTCATTAC AGACTCTAAA CCGCAAATTC GCATTTCTAT            50

AAACTTCATC CCAAAGCATC ATGCGTTTTA GTTCCAAAAT ATTTTTCATT           100

TCAAAATTTT CTTTTCCCAT GTCCAAATAT TTTGGTTCTT CGTCGTTGTA           150

TGGTTCCCAA AAAATGTCGT TTAAATGTCT TTTTGTATCA CATGATGCAT           200

CTTCAGTGTT TGATGTAGGT TTTCCATTCT TTACAAAATT GGTCCAGATC           250

CTGACCATCC TTTCCAGAGT CTGCATAGCA TCTTGCGGTA TAGAAATGTG           300

CGTTGTTCCC AAAATAGGAA CATCCAACGA GTTTGCAAAA AGATATCCTA           350

AATCATCACC ATGACTAACT CCTGGCAAGG AACCCCATCG ATAGGGCAAG           400

ATATAACTTT TATATACACT ATACGTATCG TCTGATAACC TGTACAAATA           450

CAAATTGGAA TTCCTTCTGA ATTCATTGAA AAATATGGCT TCAAGGTAC            500

GGTAGATTCC TTGGAGGTAA CCAGCATCGC CTTTTAGTTG GACGTAGGCT           550

TCAATGTCAT CGTTTTGTTC TTTCACTTGG TCATAAAACT CTGTAAGCAT           600

TTTTATTAGT TTTTTCTCCT CAATACCATT TGGATTTTTC CAAATATTAG           650

CATCTCTAGG TATAGCCCTT TCTATATTTG TCAAAGTCTT GTGAACTTCC           700

ATGTTTCCTC TGGTTACTCT TGCCATAGAT CTTAAACCTT CAGCACTATT           750

GAAACCAATG ATGACATCGA CATCAGGAAA TTCACCATTT CTCATTCTTT           800

CCAAGGCAGA TGGAAATGTT ATTGGATCTG GAGATTCTGG TGATTCTAAG           850

ACTGGATTAA ATACTGGTAC TGTGTCTCGG TCATGGTCGT TGCTATCAGG           900

AACTCTGTTT AAGGCTGCTC GTAAAATTAG GTTTTTATCC AGGTTTAGGA           950

GTTCTTGTTT TTGCGTGATG TTTAGCACTT GTTTGAGTTT TTCAAATCTA          1000

TGCAGAAGTT GAATTTGATT AGCAGTCGGA TTTAGTAATG TCCCACTCTG          1050

CAAAATGGCC CTTTGGTAGT ATTTTCTAGT CGAGTTGTCC ATCATCAGAA          1100

AATGGACACT TGCTGCTCCA GCAGATTCTC CAGCAATTGT AATTTTTTCT          1150

CTGTCTCCAC CAAACTTTTC GATGTTGTCG TAAACCCATT TTAGTGCCAA          1200

TCTCTGGTCT TTTAGACCCA TATTTCCATG GATATCCCAT TCCGGCGCTG          1250

ATAGAAAACC GAAACTCCT AATCTATAGT TGATAGTGAC CAAAATAATT           1300

CCTTCCCTGA TCAAATAATC AGGTCCAAAA AAATTATAAG ATCCTGATCC          1350

TTGGTTGAAT GCGCCTCCAT GGATCCAGAA CATTACAGGA TATTTTGTAT          1400
```

```
TGTTCGCAGA ATTAACAGTC TCTGGCGTGA ATATATTCAG ATATAAGCAA         1450

TCTTCGCTTC CTGCATAAGA ATATATTAGA CTTTCCTGGA AACATTTGTC         1500

TCCCAAAGTT CGAGCCTGTA CGAATCCTGT TTTTGGATTT GATATTGGTT         1550

TTGGAGACTG AAATCGTAAT GGTCCAAAAG GCGGTTCGGC ATAAGGAATT         1600

CCCAAATAAG AACAATATAC ATCATTCCTA TGATCTTTAT ATCGGAACGG         1650

TTTTCCTTCC GTGATCCCGT TAAATTGAAC TCTGCACAAA TGCTGATCTA         1700

GGTTATCCCA TAGTATGCAC AAGATAGGTG TAAATAAGAA AAATAAAAAA         1750

AATAAAAATA AAACTAATGC ACTACTGTGA GGTAACAT                      1788
```

(2) INFORMATION FOR SEQ ID NO:30:

(i) SEQUENCE CHARACTERISTICS:
        (A) LENGTH: 2801 nucleotides
        (B) TYPE: nucleic acid
        (C) STRANDEDNESS: single
        (D) TOPOLOGY: linear (ii) MOLECULE TYPE: cDNA (iii) FEATURE:
        (A) NAME/KEY: CDS
        (B) LOCATION: 99..1886

(iv) SEQUENCE DESCRIPTION: SEQ ID NO:30:

```
GACATGTCGT CTTCAAAACG TCTATTTTAT CATAAACAAA ACGAGATAAA          50

TAATAACAAT TAAGCATCCA AAATGCATTA AAAAAAACAT CATAAAAA            98

ATG TTA CCT CAC AGT GCA TTA GTT TTA TTT TTA TTT TTT TTA        140
Met Leu Pro His Ser Ala Leu Val Leu Phe Leu Phe Phe Leu
  1               5                  10

TTT TTC TTA TTT ACA CCT GTC TTG TGC ATA CTA TGG GAT AAC        182
Phe Phe Leu Phe Thr Pro Val Leu Cys Ile Leu Trp Asp Asn
 15              20                  25

CTA GAT CAG CAT TTG TGC AGA GTT CAA TTT AAC GGG ATC ACG        224
Leu Asp Gln His Leu Cys Arg Val Gln Phe Asn Gly Ile Thr
     30                  35                  40

GAA GGA AAA CCG TTC CGA TAT AAA GAT CAT AAA AAT GAT GTA        266
Glu Gly Lys Pro Phe Arg Tyr Lys Asp His Lys Asn Asp Val
             45                  50                  55

TAT TGT TCC TAT TTG GGA ATT CCT TAT GCA GAA CCG CCT ATT        308
Tyr Cys Ser Tyr Leu Gly Ile Pro Tyr Ala Glu Pro Pro Ile
                 60                  65                  70

GGA CCA TTG CGA TTT CAG TCT CCA AAA CCA ATA TCA AAT CCA        350
Gly Pro Leu Arg Phe Gln Ser Pro Lys Pro Ile Ser Asn Pro
                     75                  80

AAA ACA GGA TTC GTT CAG GCT CGG TCT TTA GGA GAC AAA TGT        392
Lys Thr Gly Phe Val Gln Ala Arg Ser Leu Gly Asp Lys Cys
 85                  90                  95

TTC CAG GAA AGT CTA ATA TAT TCT TAT GCA GGA AGC GAA GAT        434
Phe Gln Glu Ser Leu Ile Tyr Ser Tyr Ala Gly Ser Glu Asp
            100                 105                 110

TGC TTA TAT CTG AAT ATA TTC ACG CCA GAG ACT GTT AAT TCT        476
Cys Leu Tyr Leu Asn Ile Phe Thr Pro Glu Thr Val Asn Ser
                115                 120                 125

GCG AAC AAT ACA AAA TAT CCT GTA ATG TTC TGG ATC CAT GGA        518
Ala Asn Asn Thr Lys Tyr Pro Val Met Phe Trp Ile His Gly
                    130                 135                 140

GGC GCA TTC AAC CAA GGA TCA GGA TCT TAT AAT TTT TTT GGA        560
```

```
                    -continued

Gly Ala Phe Asn Gln Gly Ser Gly Ser Tyr Asn Phe Phe Gly
                145                 150

CCT GAT TAT TTG ATC AGG GAA GGA ATT ATT TTG GTC ACT ATC         602
Pro Asp Tyr Leu Ile Arg Glu Gly Ile Ile Leu Val Thr Ile
155                 160                 165

AAC TAT AGA TTA GGA GTT TTC GGT TTT CTA TCA GCG CCG GAA         644
Asn Tyr Arg Leu Gly Val Phe Gly Phe Leu Ser Ala Pro Glu
    170                 175                 180

TGG GAT ATC CAT GGA AAT ATG GGT CTA AAA GAC CAG AGA TTG         686
Trp Asp Ile His Gly Asn Met Gly Leu Lys Asp Gln Arg Leu
                185                 190                 195

GCA CTA AAA TGG GTT TAT GAC AAC ATC GAA AAA TTT GGT GGA         728
Ala Leu Lys Trp Val Tyr Asp Asn Ile Glu Lys Phe Gly Gly
            200                 205                 210

GAC AGA GAT AAA ATC ACT ATA GCT GGA GAA TCT GCT GGA GCA         770
Asp Arg Asp Lys Ile Thr Ile Ala Gly Glu Ser Ala Gly Ala
                    215                 220

GCA AGT GTT CAT TTT CTG ATG ATG GAC AAT TCT ACT AGA AAA         812
Ala Ser Val His Phe Leu Met Met Asp Asn Ser Thr Arg Lys
225                 230                 235

TAC TAC CAA AGG GCA ATT TTG CAG AGT GGG ACA TTA CTC AAT         854
Tyr Tyr Gln Arg Ala Ile Leu Gln Ser Gly Thr Leu Leu Asn
    240                 245                 250

CCG ACT GCT AAT CAA ATT CAA CCT CTG CAT AGA TTT GAA AAA         896
Pro Thr Ala Asn Gln Ile Gln Pro Leu His Arg Phe Glu Lys
                255                 260                 265

CTA AAA CAA GTG CTG AAC ATC ACG CAA AAA CAA GAA CTC CTA         938
Leu Lys Gln Val Leu Asn Ile Thr Gln Lys Gln Glu Leu Leu
            270                 275                 280

AAT CTG GAC AAA AAT CAA ATT TTG CGA GCA GCC TTA AAC AGA         980
Asn Leu Asp Lys Asn Gln Ile Leu Arg Ala Ala Leu Asn Arg
                    285                 290

GTC CCA GAT AAC AAC GAC CAC GAA AGG GAC ACA GTA CCA GTA         1022
Val Pro Asp Asn Asn Asp His Glu Arg Asp Thr Val Pro Val
295                 300                 305

TTT AAT CCA GTC CTA GAA TCA CCA GAA TCT CCA GAC CCA ATA         1064
Phe Asn Pro Val Leu Glu Ser Pro Glu Ser Pro Asp Pro Ile
    310                 315                 320

ACA TTT CCA TCT GCT TTA GAA AGA ATG AGA AAT GGT GAA TTT         1106
Thr Phe Pro Ser Ala Leu Glu Arg Met Arg Asn Gly Glu Phe
                325                 330                 335

CCT GAC GTT GAT GTC ATC ATT GGA TTC AAT AGT GCT GAA GGT         1148
Pro Asp Val Asp Val Ile Ile Gly Phe Asn Ser Ala Glu Gly
            340                 345                 350

TTA AGA TCT ATG CCA AGA GTA ACC AGA GGA AAC ATG GAA GTT         1190
Leu Arg Ser Met Pro Arg Val Thr Arg Gly Asn Met Glu Val
                    355                 360

TAC AAG ACT TTG ACA AAT ATA GAG AGA GCT ATA CCT AGA GAT         1232
Tyr Lys Thr Leu Thr Asn Ile Glu Arg Ala Ile Pro Arg Asp
365                 370                 375

GCT AAT ATT TGG AAA AAT CCT AAT GGC ATT GAG GAG AAA AAA         1274
Ala Asn Ile Trp Lys Asn Pro Asn Gly Ile Glu Glu Lys Lys
    380                 385                 390

CTT ATA AAA ATG CTT ACA GAG TTT TAT GAC CAA GTT AAA GAA         1316
Leu Ile Lys Met Leu Thr Glu Phe Tyr Asp Gln Val Lys Glu
                395                 400                 405

CAA AAC GAT GAC ATC GAA GCC TAT GTC CAA CTA AAA GGC GAT         1358
Gln Asn Asp Asp Ile Glu Ala Tyr Val Gln Leu Lys Gly Asp
            410                 415                 420
```

```
GCT GGT TAT CTC CAA GGA ATT TAC CGT ACC TTG AAA GCC ATA                1400
Ala Gly Tyr Leu Gln Gly Ile Tyr Arg Thr Leu Lys Ala Ile
                425                 430

TTT TTC AAT GAA ATC AAA AGA AAT TCC AAC TTG TAT TTG TAT                1442
Phe Phe Asn Glu Ile Lys Arg Asn Ser Asn Leu Tyr Leu Tyr
435                 440                 445

AGG TTA TCA GAT GAT ACG TAT AGT GTA TAT AAA AGT TAT ATC                1484
Arg Leu Ser Asp Asp Thr Tyr Ser Val Tyr Lys Ser Tyr Ile
        450                 455                 460

TTG CCC TAT CGA TGG GGT TCC TTG CCA GGA GTT AGT CAT GGT                1526
Leu Pro Tyr Arg Trp Gly Ser Leu Pro Gly Val Ser His Gly
            465                 470                 475

GAT GAT TTA GGA TAT CTT TTT GCA AAC TCT TTG GAT GTT CCT                1568
Asp Asp Leu Gly Tyr Leu Phe Ala Asn Ser Leu Asp Val Pro
                480                 485                 490

ATT TTG GGA ACA ACG CAC ATT TCT ATA CCG CAA GAT GCT ATG                1610
Ile Leu Gly Thr Thr His Ile Ser Ile Pro Gln Asp Ala Met
                    495                 500

CAG ACT CTG GAA AGG ATG GTC AGG ATC TGG ACC AAT TTT GTA                1652
Gln Thr Leu Glu Arg Met Val Arg Ile Trp Thr Asn Phe Val
505                 510                 515

AAG AAT GGA AAA CCT ACA TCA AAC ACT GAA GAT GCA TCA TGT                1694
Lys Asn Gly Lys Pro Thr Ser Asn Thr Glu Asp Ala Ser Cys
        520                 525                 530

GAT ACA AAA AGA CAT TTA AAC GAC ATT TTT TGG GAA CCA TAC                1736
Asp Thr Lys Arg His Leu Asn Asp Ile Phe Trp Glu Pro Tyr
            535                 540                 545

AAC GAC GAA GAA CCA AAA TAT TTG GAC ATG GGA AAA GAA CAT                1778
Asn Asp Glu Glu Pro Lys Tyr Leu Asp Met Gly Lys Glu His
                550                 555                 560

TTT GAA ATG AAA AAT ATT TTG GAA CTA AAA CGC ATG ATG CTT                1820
Phe Glu Met Lys Asn Ile Leu Glu Leu Lys Arg Met Met Leu
                    565                 570

TGG GAT GAA GTT TAT AGA AAT GCG AAT TTG CGG TTT AGA GTC                1862
Trp Asp Glu Val Tyr Arg Asn Ala Asn Leu Arg Phe Arg Val
575                 580                 585

TGT AAT GAA GAA AGT ATT AGA TGA GTTTTTTTAA TTTTACATAC                  1906
Cys Asn Glu Glu Ser Ile Arg
        590                 595

AGCCGAGAGG AAACATGACT AAAATTGGAA AGAAAAATCA GAAAAAGAAA                 1956

AATCACATGG ACCATAGTAA CTTTATTACA TGATTTAGTT TCAAGTGTAT                 2006

CAAGAAAACT TATTGCATCA AAGAAAATAT TATTTTGCCA AAATTCTTGG                 2056

AAAAACACTT TTTATGACTG ACATGGCCCA TAATTGAAGC TTTTTCTTCT                 2106

TTTACCAAAT CGCCAAATTT TGTAGCGTCA GACACATTTA TTTATGACAT                 2156

GGCAATTAAT GTGTTAAACA TTCAACTCTA TATTAAAAAT GGTAGTATTT                 2206

TCTAATAAGA AGGTTATATA AAAAGACTTG AAAATAATAA GATTTGCTCG                 2256

GCTATATATA AAAACTTANC GTCTCGTTAT GCTAAACTTT TTTGATGGTA                 2306

AAAATATGTT GATTTTCCTA ATAATCTAAG ATATTATATT TTAGATTAAA                 2356

TTAAAATATG ATATTTTCAA TTAATTAATT TTAGTTTTAA ATGTACTATA                 2406

TTTACCAGTA CTATGAAACT ATTTTAAATA TATTTTTTAT TACAATATTT                 2456

ATTTCTCAAA AATGTTTAGT GTAACAAGAC CATTAAATTA GAGTTAATGT                 2506

TGTAAATTAA ACTATTTTTT ATCTATCACA ACCGCTTAAT TGGTGCAAAG                 2556

AAAAATTTTA CTGTGATAAT ATTTGACATT TACACAATAT TACGAATTGT                 2606
```

```
AAACTCACAA TTATGTGAAT ATTGTTTTTT GTTAAAAAAA CATACATGAC           2656

TTTTCTATAT CATTTTATAT TACGGTGATA TGGATTAATG TCAACATGTA           2706

AAATACAAAT GCGGTTGTTA AAAATAATCT GTATTAAAAT TGTTATATAA           2756

AATCTGAATA AATGTACTTT TAAGTAAAAA AAAAAAAAAA AAAAA                2801

(2) INFORMATION FOR SEQ ID NO:31:

(i) SEQUENCE CHARACTERISTICS:
        (A) LENGTH: 595 amino acids
        (B) TYPE: amino acid
        (D) TOPOLOGY: linear (ii) MOLECULE TYPE: protein (iii) SEQUENCE DESCRIPTION: SEQ ID NO:31:

Met Leu Pro His Ser Ala Leu Val Leu Phe Leu Phe Leu
 1               5                  10

Phe Phe Leu Phe Thr Pro Val Leu Cys Ile Leu Trp Asp Asn
15                  20                  25

Leu Asp Gln His Leu Cys Arg Val Gln Phe Asn Gly Ile Thr
    30                  35                  40

Glu Gly Lys Pro Phe Arg Tyr Lys Asp His Lys Asn Asp Val
        45                  50                  55

Tyr Cys Ser Tyr Leu Gly Ile Pro Tyr Ala Glu Pro Pro Ile
            60                  65                  70

Gly Pro Leu Arg Phe Gln Ser Pro Lys Pro Ile Ser Asn Pro
                75                  80

Lys Thr Gly Phe Val Gln Ala Arg Ser Leu Gly Asp Lys Cys
85                  90                  95

Phe Gln Glu Ser Leu Ile Tyr Ser Tyr Ala Gly Ser Glu Asp
    100                 105                 110

Cys Leu Tyr Leu Asn Ile Phe Thr Pro Glu Thr Val Asn Ser
        115                 120                 125

Ala Asn Asn Thr Lys Tyr Pro Val Met Phe Trp Ile His Gly
            130                 135                 140

Gly Ala Phe Asn Gln Gly Ser Gly Ser Tyr Asn Phe Phe Gly
                145                 150

Pro Asp Tyr Leu Ile Arg Glu Gly Ile Ile Leu Val Thr Ile
155                 160                 165

Asn Tyr Arg Leu Gly Val Phe Gly Phe Leu Ser Ala Pro Glu
    170                 175                 180

Trp Asp Ile His Gly Asn Met Gly Leu Lys Asp Gln Arg Leu
        185                 190                 195

Ala Leu Lys Trp Val Tyr Asp Asn Ile Glu Lys Phe Gly Gly
            200                 205                 210

Asp Arg Asp Lys Ile Thr Ile Ala Gly Glu Ser Ala Gly Ala
                215                 220

Ala Ser Val His Phe Leu Met Met Asp Asn Ser Thr Arg Lys
225                 230                 235

Tyr Tyr Gln Arg Ala Ile Leu Gln Ser Gly Thr Leu Leu Asn
    240                 245                 250

Pro Thr Ala Asn Gln Ile Gln Pro Leu His Arg Phe Glu Lys
        255                 260                 265

Leu Lys Gln Val Leu Asn Ile Thr Gln Lys Gln Glu Leu Leu
```

```
                       270                 275                 280
Asn Leu Asp Lys Asn Gln Ile Leu Arg Ala Ala Leu Asn Arg
                    285                 290

Val Pro Asp Asn Asn Asp His Glu Arg Asp Thr Val Pro Val
295                 300                 305

Phe Asn Pro Val Leu Glu Ser Pro Glu Ser Pro Asp Pro Ile
310                 315                 320

Thr Phe Pro Ser Ala Leu Glu Arg Met Arg Asn Gly Glu Phe
                325                 330                 335

Pro Asp Val Asp Val Ile Ile Gly Phe Asn Ser Ala Glu Gly
                    340                 345                 350

Leu Arg Ser Met Pro Arg Val Thr Arg Gly Asn Met Glu Val
                    355                 360

Tyr Lys Thr Leu Thr Asn Ile Glu Arg Ala Ile Pro Arg Asp
365                 370                 375

Ala Asn Ile Trp Lys Asn Pro Asn Gly Ile Glu Glu Lys Lys
            380                 385                 390

Leu Ile Lys Met Leu Thr Glu Phe Tyr Asp Gln Val Lys Glu
            395                 400                 405

Gln Asn Asp Asp Ile Glu Ala Tyr Val Gln Leu Lys Gly Asp
                410                 415                 420

Ala Gly Tyr Leu Gln Gly Ile Tyr Arg Thr Leu Lys Ala Ile
                    425                 430

Phe Phe Asn Glu Ile Lys Arg Asn Ser Asn Leu Tyr Leu Tyr
435                 440                 445

Arg Leu Ser Asp Thr Tyr Ser Val Tyr Lys Ser Tyr Ile
            450                 455                 460

Leu Pro Tyr Arg Trp Gly Ser Leu Pro Gly Val Ser His Gly
                465                 470                 475

Asp Asp Leu Gly Tyr Leu Phe Ala Asn Ser Leu Asp Val Pro
                480                 485                 490

Ile Leu Gly Thr Thr His Ile Ser Ile Pro Gln Asp Ala Met
                    495                 500

Gln Thr Leu Glu Arg Met Val Arg Ile Trp Thr Asn Phe Val
505                 510                 515

Lys Asn Gly Lys Pro Thr Ser Asn Thr Glu Asp Ala Ser Cys
    520                 525                 530

Asp Thr Lys Arg His Leu Asn Asp Ile Phe Trp Glu Pro Tyr
        535                 545                 545

Asn Asp Glu Glu Pro Lys Tyr Leu Asp Met Gly Lys Glu His
                550                 555                 560

Phe Glu Met Lys Asn Ile Leu Glu Leu Lys Arg Met Met Leu
                565                 570

Trp Asp Glu Val Tyr Arg Asn Ala Asn Leu Arg Phe Arg Val
575                 580                 585

Cys Asn Glu Glu Ser Ile Arg
    590                 595

(2) INFORMATION FOR SEQ ID NO:32:

(i) SEQUENCE CHARACTERISTICS:
        (A) LENGTH:  2801 nucleotides
        (B) TYPE:  nucleic acid
        (C) STRANDEDNESS:  single
        (D) TOPOLOGY:  linear
```

(ii) MOLECULE TYPE: cDNA (iii) SEQUENCE DESCRIPTION: SEQ ID NO:32:

| | | | | | |
|---|---|---|---|---|---|
| TTTTTTTTTT | TTTTTTTTTT | ACTTAAAAGT | ACATTTATTC | AGATTTTATA | 50 |
| TAACAATTTT | AATACAGATT | ATTTTTAACA | ACCGCATTTG | TATTTTACAT | 100 |
| GTTGACATTA | ATCCATATCA | CCGTAATATA | AAATGATATA | GAAAAGTCAT | 150 |
| GTATGTTTTT | TTAACAAAAA | ACAATATTCA | CATAATTGTG | AGTTTACAAT | 200 |
| TCGTAATATT | GTGTAAATGT | CAAATATTAT | CACAGTAAAA | TTTTTCTTTG | 250 |
| CACCAATTAA | GCGGTTGTGA | TAGATAAAAA | ATAGTTTAAT | TTACAACATT | 300 |
| AACTCTAATT | TAATGGTCTT | GTTACACTAA | ACATTTTTGA | GAAATAAATA | 350 |
| TTGTAATAAA | AAATATATTT | AAAATAGTTT | CATAGTACTG | GTAAATATAG | 400 |
| TACATTTAAA | ACTAAAATTA | ATTAATTGAA | AATATCATAT | TTTAATTTAA | 450 |
| TCTAAAATAT | AATATCTTAG | ATTATTAGGA | AAATCAACAT | ATTTTTACCA | 500 |
| TCAAAAAAGT | TTAGCATAAC | GAGACGNTAA | GTTTTTATAT | ATAGCCGAGC | 550 |
| AAATCTTATT | ATTTTCAAGT | CTTTTTATAT | AACCTTCTTA | TTAGAAAATA | 600 |
| CTACCATTTT | TAATATAGAG | TTGAATGTTT | AACACATTAA | TTGCCATGTC | 650 |
| ATAAATAAAT | GTGTCTGACG | CTACAAAATT | TGGCGATTTG | GTAAAAGAAG | 700 |
| AAAAAGCTTC | AATTATGGGC | CATGTCAGTC | ATAAAAAGTG | TTTTTCCAAG | 750 |
| AATTTTGGCA | AAATAATATT | TTCTTTGATG | CAATAAGTTT | TCTTGATACA | 800 |
| CTTGAAACTA | AATCATGTAA | TAAAGTTACT | ATGGTCCATG | TGATTTTTCT | 850 |
| TTTTCTGATT | TTTCTTTCCA | ATTTTAGTCA | TGTTTCCTCT | CGGCTGTATG | 900 |
| TAAAATTAAA | AAAACTCATC | TAATACTTTC | TTCATTACAG | ACTCTAAACC | 950 |
| GCAAATTCGC | ATTTCTATAA | ACTTCATCCC | AAAGCATCAT | GCGTTTTAGT | 1000 |
| TCCAAAATAT | TTTTCATTTC | AAAATGTTCT | TTTCCCATGT | CCAAATATTT | 1050 |
| TGGTTCTTCG | TCGTTGTATG | GTTCCCAAAA | AATGTCGTTT | AAATGTCTTT | 1100 |
| TTGTATCACA | TGATGCATCT | TCAGTGTTTG | ATGTAGGTTT | TCCATTCTTT | 1150 |
| ACAAAATTGG | TCCAGATCCT | GACCATCCTT | TCCAGAGTCT | GCATAGCATC | 1200 |
| TTGCGGTATA | GAAATGTGCG | TTGTTCCCAA | AATAGGAACA | TCCAAAGAGT | 1250 |
| TTGCAAAAAG | ATATCCTAAA | TCATCACCAT | GACTAACTCC | TGGCAAGGAA | 1300 |
| CCCCATCGAT | AGGGCAAGAT | ATAACTTTTA | TATACACTAT | ACGTATCATC | 1350 |
| TGATAACCTA | TACAAATACA | AGTTGGAATT | TCTTTTGATT | TCATTGAAAA | 1400 |
| ATATGGCTTT | CAAGGTACGG | TAAATTCCTT | GGAGATAACC | AGCATCGCCT | 1450 |
| TTTAGTTGGA | CATAGGCTTC | GATGTCATCG | TTTTGTTCTT | TAACTTGGTC | 1500 |
| ATAAAACTCT | GTAAGCATTT | TTATAAGTTT | TTTCTCCTCA | ATGCCATTAG | 1550 |
| GATTTTTCCA | AATATTAGCA | TCTCTAGGTA | TAGCTCTCTC | TATATTTGTC | 1600 |
| AAAGTCTTGT | AAACTTCCAT | GTTTCCTCTG | GTTACTCTTG | GCATAGATCT | 1650 |
| TAAACCTTCA | GCACTATTGA | ATCCAATGAT | GACATCAACG | TCAGGAAATT | 1700 |
| CACCATTTCT | CATTCTTTCT | AAAGCAGATG | GAAATGTTAT | TGGGTCTGGA | 1750 |
| GATTCTGGTG | ATTCTAGGAC | TGGATTAAAT | ACTGGTACTG | TGTCCCTTTC | 1800 |
| GTGGTCGTTG | TTATCTGGGA | CTCTGTTTAA | GGCTGCTCGC | AAAATTTGAT | 1850 |

-continued

```
TTTTGTCCAG ATTTAGGAGT TCTTGTTTTT GCGTGATGTT CAGCACTTGT        1900

TTTAGTTTTT CAAATCTATG CAGAGGTTGA ATTTGATTAG CAGTCGGATT        1950

GAGTAATGTC CCACTCTGCA AAATTGCCCT TTGGTAGTAT TTTCTAGTAG        2000

AATTGTCCAT CATCAGAAAA TGAACACTTG CTGCTCCAGC AGATTCTCCA        2050

GCTATAGTGA TTTTATCTCT GTCTCCACCA AATTTTTCGA TGTTGTCATA        2100

AACCCATTTT AGTGCCAATC TCTGGTCTTT TAGACCCATA TTTCCATGGA        2150

TATCCCATTC CGGCGCTGAT AGAAAACCGA AAACTCCTAA TCTATAGTTG        2200

ATAGTGACCA AAATAATTCC TTCCCTGATC AAATAATCAG GTCCAAAAAA        2250

ATTATAAGAT CCTGATCCTT GGTTGAATGC GCCTCCATGG ATCCAGAACA        2300

TTACAGGATA TTTTGTATTG TTCGCAGAAT TAACAGTCTC TGGCGTGAAT        2350

ATATTCAGAT ATAAGCAATC TTCGCTTCCT GCATAAGAAT ATATTAGACT        2400

TTCCTGGAAA CATTTGTCTC CTAAAGACCG AGCCTGAACG AATCCTGTTT        2450

TTGGATTTGA TATTGGTTTT GGAGACTGAA ATCGCAATGG TCCAATAGGC        2500

GGTTCTGCAT AAGGAATTCC CAAATAGGAA CAATATACAT CATTTTTATG        2550

ATCTTTATAT CGGAACGGTT TTCCTTCCGT GATCCCGTTA AATTGAACTC        2600

TGCACAAATG CTGATCTAGG TTATCCCATA GTATGCACAA GACAGGTGTA        2650

AATAAGAAAA ATAAAAAAAA TAAAAATAAA ACTAATGCAC TGTGAGGTAA        2700

CATTTTTTAT GATGTTTTTT TTAATGCATT TTGGATGCTT AATTGTTATT        2750

ATTTATCTCG TTTTGTTTAT GATAAAATAG ACGTTTTGAA GACGACATGT        2800

C                                                            2801
```

(2) INFORMATION FOR SEQ ID NO:33:

(i) SEQUENCE CHARACTERISTICS:
        (A) LENGTH: 1710 nucleotides
        (B) TYPE: nucleic acid
        (C) STRANDEDNESS: single
        (D) TOPOLOGY: linear (ii) MOLECULE TYPE: cDNA (iii) FEATURE:
        (A) NAME/KEY: CDS
        (B) LOCATION: 1..1710

(iv) SEQUENCE DESCRIPTION: SEQ ID NO:33:

```
TGG GAT AAC CTA GAT CAG CAT TTG TGC AGA GTT CAA TTT AAC           42
Trp Asp Asn Leu Asp Gln His Leu Cys Arg Val Gln Phe Asn
  1               5                  10

GGG ATC ACG GAA GGA AAA CCG TTC CGA TAT AAA GAT CAT AAA           84
Gly Ile Thr Glu Gly Lys Pro Phe Arg Tyr Lys Asp His Lys
 15              20                  25

AAT GAT GTA TAT TGT TCC TAT TTG GGA ATT CCT TAT GCA GAA          126
Asn Asp Val Tyr Cys Ser Tyr Leu Gly Ile Pro Tyr Ala Glu
     30                  35                  40

CCG CCT ATT GGA CCA TTG CGA TTT CAG TCT CCA AAA CCA ATA          168
Pro Pro Ile Gly Pro Leu Arg Phe Gln Ser Pro Lys Pro Ile
             45                  50                  55

TCA AAT CCA AAA ACA GGA TTC GTT CAG GCT CGG TCT TTA GGA          210
Ser Asn Pro Lys Thr Gly Phe Val Gln Ala Arg Ser Leu Gly
                 60                  65                  70

GAC AAA TGT TTC CAG GAA AGT CTA ATA TAT TCT TAT GCA GGA          252
Asp Lys Cys Phe Gln Glu Ser Leu Ile Tyr Ser Tyr Ala Gly
```

```
                    75                  80
AGC GAA GAT TGC TTA TAT CTG AAT ATA TTC ACG CCA GAG ACT          294
Ser Glu Asp Cys Leu Tyr Leu Asn Ile Phe Thr Pro Glu Thr
 85                  90                  95

GTT AAT TCT GCG AAC AAT ACA AAA TAT CCT GTA ATG TTC TGG          336
Val Asn Ser Ala Asn Asn Thr Lys Tyr Pro Val Met Phe Trp
         100                 105                 110

ATC CAT GGA GGC GCA TTC AAC CAA GGA TCA GGA TCT TAT AAT          378
Ile His Gly Gly Ala Phe Asn Gln Gly Ser Gly Ser Tyr Asn
             115                 120                 125

TTT TTT GGA CCT GAT TAT TTG ATC AGG GAA GGA ATT ATT TTG          420
Phe Phe Gly Pro Asp Tyr Leu Ile Arg Glu Gly Ile Ile Leu
                 130                 135                 140

GTC ACT ATC AAC TAT AGA TTA GGA GTT TTC GGT TTT CTA TCA          462
Val Thr Ile Asn Tyr Arg Leu Gly Val Phe Gly Phe Leu Ser
                     145                 150

GCG CCG GAA TGG GAT ATC CAT GGA AAT ATG GGT CTA AAA GAC          504
Ala Pro Glu Trp Asp Ile His Gly Asn Met Gly Leu Lys Asp
155                 160                 165

CAG AGA TTG GCA CTA AAA TGG GTT TAT GAC AAC ATC GAA AAA          546
Gln Arg Leu Ala Leu Lys Trp Val Tyr Asp Asn Ile Glu Lys
        170                 175                 180

TTT GGT GGA GAC AGA GAT AAA ATC ACT ATA GCT GGA GAA TCT          588
Phe Gly Gly Asp Arg Asp Lys Ile Thr Ile Ala Gly Glu Ser
            185                 190                 195

GCT GGA GCA GCA AGT GTT CAT TTT CTG ATG ATG GAC AAT TCT          630
Ala Gly Ala Ala Ser Val His Phe Leu Met Met Asp Asn Ser
                200                 205                 210

ACT AGA AAA TAC TAC CAA AGG GCA ATT TTG CAG AGT GGG ACA          672
Thr Arg Lys Tyr Tyr Gln Arg Ala Ile Leu Gln Ser Gly Thr
                    215                 220

TTA CTC AAT CCG ACT GCT AAT CAA ATT CAA CCT CTG CAT AGA          714
Leu Leu Asn Pro Thr Ala Asn Gln Ile Gln Pro Leu His Arg
225                 230                 235

TTT GAA AAA CTA AAA CAA GTG CTG AAC ATC ACG CAA AAA CAA          756
Phe Glu Lys Leu Lys Gln Val Leu Asn Ile Thr Gln Lys Gln
        240                 245                 250

GAA CTC CTA AAT CTG GAC AAA AAT CAA ATT TTG CGA GCA GCC          798
Glu Leu Leu Asn Leu Asp Lys Asn Gln Ile Leu Arg Ala Ala
            255                 260                 265

TTA AAC AGA GTC CCA GAT AAC AAC GAC CAC GAA AGG GAC ACA          840
Leu Asn Arg Val Pro Asp Asn Asn Asp His Glu Arg Asp Thr
                270                 275                 280

GTA CCA GTA TTT AAT CCA GTC CTA GAA TCA CCA GAA TCT CCA          882
Val Pro Val Phe Asn Pro Val Leu Glu Ser Pro Glu Ser Pro
                    285                 290

GAC CCA ATA ACA TTT CCA TCT GCT TTA GAA AGA ATG AGA AAT          924
Asp Pro Ile Thr Phe Pro Ser Ala Leu Glu Arg Met Arg Asn
295                 300                 305

GGT GAA TTT CCT GAC GTT GAT GTC ATC ATT GGA TTC AAT AGT          966
Gly Glu Phe Pro Asp Val Asp Val Ile Ile Gly Phe Asn Ser
        310                 315                 320

GCT GAA GGT TTA AGA TCT ATG CCA AGA GTA ACC AGA GGA AAC         1008
Ala Glu Gly Leu Arg Ser Met Pro Arg Val Thr Arg Gly Asn
            325                 330                 335

ATG GAA GTT TAC AAG ACT TTG ACA AAT ATA GAG AGA GCT ATA         1050
Met Glu Val Tyr Lys Thr Leu Thr Asn Ile Glu Arg Ala Ile
                340                 345                 350

CCT AGA GAT GCT AAT ATT TGG AAA AAT CCT AAT GGC ATT GAG         1092
```

```
Pro Arg Asp Ala Asn Ile Trp Lys Asn Pro Asn Gly Ile Glu
            355                 360

GAG AAA AAA CTT ATA AAA ATG CTT ACA GAG TTT TAT GAC CAA         1134
Glu Lys Lys Leu Ile Lys Met Leu Thr Glu Phe Tyr Asp Gln
365             370                 375

GTT AAA GAA CAA AAC GAT GAC ATC GAA GCC TAT GTC CAA CTA         1176
Val Lys Glu Gln Asn Asp Asp Ile Glu Ala Tyr Val Gln Leu
        380                 385                 390

AAA GGC GAT GCT GGT TAT CTC CAA GGA ATT TAC CGT ACC TTG         1218
Lys Gly Asp Ala Gly Tyr Leu Gln Gly Ile Tyr Arg Thr Leu
                395                 400                 405

AAA GCC ATA TTT TTC AAT GAA ATC AAA AGA AAT TCC AAC TTG         1260
Lys Ala Ile Phe Phe Asn Glu Ile Lys Arg Asn Ser Asn Leu
                    410                 415                 420

TAT TTG TAT AGG TTA TCA GAT GAT ACG TAT AGT GTA TAT AAA         1302
Tyr Leu Tyr Arg Leu Ser Asp Asp Thr Tyr Ser Val Tyr Lys
                        425                 430

AGT TAT ATC TTG CCC TAT CGA TGG GGT TCC TTG CCA GGA GTT         1344
Ser Tyr Ile Leu Pro Tyr Arg Trp Gly Ser Leu Pro Gly Val
435                 440                 445

AGT CAT GGT GAT GAT TTA GGA TAT CTT TTT GCA AAC TCT TTG         1386
Ser His Gly Asp Asp Leu Gly Tyr Leu Phe Ala Asn Ser Leu
        450                 455                 460

GAT GTT CCT ATT TTG GGA ACA ACG CAC ATT TCT ATA CCG CAA         1428
Asp Val Pro Ile Leu Gly Thr Thr His Ile Ser Ile Pro Gln
            465                 470                 475

GAT GCT ATG CAG ACT CTG GAA AGG ATG GTC AGG ATC TGG ACC         1470
Asp Ala Met Gln Thr Leu Glu Arg Met Val Arg Ile Trp Thr
                480                 485                 490

AAT TTT GTa AAG AAT GGA AAA CCT ACA TCA AAC ACT GAA GAT         1512
Asn Phe Val Lys Asn Gly Lys Pro Thr Ser Asn Thr Glu Asp
                    495                 500

GCA TCA TGT GAT ACA AAA AGA CAT TTA AAC GAC aTT TTT TGG         1554
Ala Ser Cys Asp Thr Lys Arg His Leu Asn Asp Ile Phe Trp
505                 510                 515

GAA CCA TAC AAC GAC GAA GAA CCA AAA TAT TTG GAC ATG GGA         1596
Glu Pro Tyr Asn Asp Glu Glu Pro Lys Tyr Leu Asp Met Gly
        520                 525                 530

AAA GAA CAT TTT GAA ATG AAA AAT ATT TTG GAA CTA AAA CGC         1638
Lys Glu His Phe Glu Met Lys Asn Ile Leu Glu Leu Lys Arg
            535                 540                 545

ATG ATG CTT TGG GAT GAA GTT TAT AGA AAT GCG AAT TTG CGG         1680
Met Met Leu Trp Asp Glu Val Tyr Arg Asn Ala Asn Leu Arg
                550                 555                 560

TTT AGA GTC TGT AAT GAA GAA AGT ATT AGA                         1710
Phe Arg Val Cys Asn Glu Glu Ser Ile Arg
                    565                 570
```

(2) INFORMATION FOR SEQ ID NO:34:

(i) SEQUENCE CHARACTERISTICS:
        (A) LENGTH: 1785 nucleotides
        (B) TYPE: nucleic acid
        (C) STRANDEDNESS: single
        (D) TOPOLOGY: linear (ii) MOLECULE TYPE: cDNA (iii) FEATURE:
        (A) NAME/KEY: CDS
        (B) LOCATION: 1..1785

(iv) SEQUENCE DESCRIPTION: SEQ ID NO:34:

```
ATG TTA CCT CAC AGT GCA TTA GTT TTA TTT TTA TTT TTT TTA          42
Met Leu Pro His Ser Ala Leu Val Leu Phe Leu Phe Phe Leu
 1               5                   10

TTT TTC TTA TTT ACA CCT GTC TTG TGC ATA CTA TGG GAT AAC          84
Phe Phe Leu Phe Thr Pro Val Leu Cys Ile Leu Trp Asp Asn
 15              20                  25

CTA GAT CAG CAT TTG TGC AGA GTT CAA TTT AAC GGG ATC ACG         126
Leu Asp Gln His Leu Cys Arg Val Gln Phe Asn Gly Ile Thr
 30              35                  40

GAA GGA AAA CCG TTC CGA TAT AAA GAT CAT AAA AAT GAT GTA         168
Glu Gly Lys Pro Phe Arg Tyr Lys Asp His Lys Asn Asp Val
         45              50                  55

TAT TGT TCC TAT TTG GGA ATT CCT TAT GCA GAA CCG CCT ATT         210
Tyr Cys Ser Tyr Leu Gly Ile Pro Tyr Ala Glu Pro Pro Ile
             60              65                  70

GGA CCA TTG CGA TTT CAG TCT CCA AAA CCA ATA TCA AAT CCA         252
Gly Pro Leu Arg Phe Gln Ser Pro Lys Pro Ile Ser Asn Pro
                 75              80

AAA ACA GGA TTC GTT CAG GCT CGG TCT TTA GGA GAC AAA TGT         294
Lys Thr Gly Phe Val Gln Ala Arg Ser Leu Gly Asp Lys Cys
 85              90                  95

TTC CAG GAA AGT CTA ATA TAT TCT TAT GCA GGA AGC GAA GAT         336
Phe Gln Glu Ser Leu Ile Tyr Ser Tyr Ala Gly Ser Glu Asp
         100             105                 110

TGC TTA TAT CTG AAT ATA TTC ACG CCA GAG ACT GTT AAT TCT         378
Cys Leu Tyr Leu Asn Ile Phe Thr Pro Glu Thr Val Asn Ser
             115             120                 125

GCG AAC AAT ACA AAA TAT CCT GTA ATG TTC TGG ATC CAT GGA         420
Ala Asn Asn Thr Lys Tyr Pro Val Met Phe Trp Ile His Gly
                 130             135                 140

GGC GCA TTC AAC CAA GGA TCA GGA TCT TAT AAT TTT TTT GGA         462
Gly Ala Phe Asn Gln Gly Ser Gly Ser Tyr Asn Phe Phe Gly
                     145             150

CCT GAT TAT TTG ATC AGG GAA GGA ATT ATT TTG GTC ACT ATC         504
Pro Asp Tyr Leu Ile Arg Glu Gly Ile Ile Leu Val Thr Ile
 155             160                 165

AAC TAT AGA TTA GGA GTT TTC GGT TTT CTA TCA GCG CCG GAA         546
Asn Tyr Arg Leu Gly Val Phe Gly Phe Leu Ser Ala Pro Glu
         170             175                 180

TGG GAT ATC CAT GGA AAT ATG GGT CTA AAA GAC CAG AGA TTG         588
Trp Asp Ile His Gly Asn Met Gly Leu Lys Asp Gln Arg Leu
             185             190                 195

GCA CTA AAA TGG GTT TAT GAC AAC ATC GAA AAA TTT GGT GGA         630
Ala Leu Lys Trp Val Tyr Asp Asn Ile Glu Lys Phe Gly Gly
                 200             205                 210

GAC AGA GAT AAA ATC ACT ATA GCT GGA GAA TCT GCT GGA GCA         672
Asp Arg Asp Lys Ile Thr Ile Ala Gly Glu Ser Ala Gly Ala
                     215             220

GCA AGT GTT CAT TTT CTG ATG ATG GAC AAT TCT ACT AGA AAA         714
Ala Ser Val His Phe Leu Met Met Asp Asn Ser Thr Arg Lys
 225             230                 235

TAC TAC CAA AGG GCA ATT TTG CAG AGT GGG ACA TTA CTC AAT         756
Tyr Tyr Gln Arg Ala Ile Leu Gln Ser Gly Thr Leu Leu Asn
         240             245                 250

CCG ACT GCT AAT CAA ATT CAA CCT CTG CAT AGA TTT GAA AAA         798
Pro Thr Ala Asn Gln Ile Gln Pro Leu His Arg Phe Glu Lys
             255             260                 265

CTA AAA CAA GTG CTG AAC ATC ACG CAA AAA CAA GAA CTC CTA         840
Leu Lys Gln Val Leu Asn Ile Thr Gln Lys Gln Glu Leu Leu
                 270             275                 280
```

```
AAT CTG GAC AAA AAT CAA ATT TTG CGA GCA GCC TTA AAC AGA              882
Asn Leu Asp Lys Asn Gln Ile Leu Arg Ala Ala Leu Asn Arg
            285                 290

GTC CCA GAT AAC AAC GAC CAC GAA AGG GAC ACA GTA CCA GTA              924
Val Pro Asp Asn Asn Asp His Glu Arg Asp Thr Val Pro Val
295                 300                 305

TTT AAT CCA GTC CTA GAA TCA CCA GAA TCT CCA GAC CCA ATA              966
Phe Asn Pro Val Leu Glu Ser Pro Glu Ser Pro Asp Pro Ile
        310                 315                 320

ACA TTT CCA TCT GCT TTA GAA AGA ATG AGA AAT GGT GAA TTT             1008
Thr Phe Pro Ser Ala Leu Glu Arg Met Arg Asn Gly Glu Phe
            325                 330                 335

CCT GAC GTT GAT GTC ATC ATT GGA TTC AAT AGT GCT GAA GGT             1050
Pro Asp Val Asp Val Ile Ile Gly Phe Asn Ser Ala Glu Gly
                340                 345                 350

TTA AGA TCT ATG CCA AGA GTA ACC AGA GGA AAC ATG GAA GTT             1092
Leu Arg Ser Met Pro Arg Val Thr Arg Gly Asn Met Glu Val
                    355                 360

TAC AAG ACT TTG ACA AAT ATA GAG AGA GCT ATA CCT AGA GAT             1134
Tyr Lys Thr Leu Thr Asn Ile Glu Arg Ala Ile Pro Arg Asp
365                 370                 375

GCT AAT ATT TGG AAA AAT CCT AAT GGC ATT GAG GAG AAA AAA             1176
Ala Asn Ile Trp Lys Asn Pro Asn Gly Ile Glu Glu Lys Lys
380                 385                 390

CTT ATA AAA ATG CTT ACA GAG TTT TAT GAC CAA GTT AAA GAA             1218
Leu Ile Lys Met Leu Thr Glu Phe Tyr Asp Gln Val Lys Glu
        395                 400                 405

CAA AAC GAT GAC ATC GAA GCC TAT GTC CAA CTA AAA GGC GAT             1260
Gln Asn Asp Asp Ile Glu Ala Tyr Val Gln Leu Lys Gly Asp
            410                 415                 420

GCT GGT TAT CTC CAA GGA ATT TAC CGT ACC TTG AAA GCC ATA             1302
Ala Gly Tyr Leu Gln Gly Ile Tyr Arg Thr Leu Lys Ala Ile
                425                 430

TTT TTC AAT GAA ATC AAA AGA AAT TCC AAC TTG TAT TTG TAT             1344
Phe Phe Asn Glu Ile Lys Arg Asn Ser Asn Leu Tyr Leu Tyr
435                 440                 445

AGG TTA TCA GAT GAT ACG TAT AGT GTA TAT AAA AGT TAT ATC             1386
Arg Leu Ser Asp Asp Thr Tyr Ser Val Tyr Lys Ser Tyr Ile
450                 455                 460

TTG CCC TAT CGA TGG GGT TCC TTG CCA GGA GTT AGT CAT GGT             1428
Leu Pro Tyr Arg Trp Gly Ser Leu Pro Gly Val Ser His Gly
        465                 470                 475

GAT GAT TTA GGA TAT CTT TTT GCA AAC TCT TTG GAT GTT CCT             1470
Asp Asp Leu Gly Tyr Leu Phe Ala Asn Ser Leu Asp Val Pro
            480                 485                 490

ATT TTG GGA ACA ACG CAC ATT TCT ATA CCG CAA GAT GCT ATG             1512
Ile Leu Gly Thr Thr His Ile Ser Ile Pro Gln Asp Ala Met
                495                 500

CAG ACT CTG GAA AGG ATG GTC AGG ATC TGG ACC AAT TTT GTA             1554
Gln Thr Leu Glu Arg Met Val Arg Ile Trp Thr Asn Phe Val
505                 510                 515

AAG AAT GGA AAA CCT ACA TCA AAC ACT GAA GAT GCA TCA TGT             1596
Lys Asn Gly Lys Pro Thr Ser Asn Thr Glu Asp Ala Ser Cys
        520                 525                 530

GAT ACA AAA AGA CAT TTA AAC GAC ATT TTT TGG GAA CCA TAC             1638
Asp Thr Lys Arg His Leu Asn Asp Ile Phe Trp Glu Pro Tyr
            535                 540                 545

AAC GAC GAA GAA CCA AAA TAT TTG GAC ATG GGA AAA GAA CAT             1680
Asn Asp Glu Glu Pro Lys Tyr Leu Asp Met Gly Lys Glu His
```

```
               550             555             560
TTT GAA ATG AAA AAT ATT TTG GAA CTA AAA CGC ATG ATG CTT            1722
Phe Glu Met Lys Asn Ile Leu Glu Leu Lys Arg Met Met Leu
                565             570

TGG GAT GAA GTT TAT AGA AAT GCG AAT TTG CGG TTT AGA GTC            1764
Trp Asp Glu Val Tyr Arg Asn Ala Asn Leu Arg Phe Arg Val
575             580             585

TGT AAT GAA GAA AGT ATT AGA                                        1785
Cys Asn Glu Glu Ser Ile Arg
    590             595
```

(2) INFORMATION FOR SEQ ID NO:35:

(i) SEQUENCE CHARACTERISTICS:
        (A) LENGTH: 1785 nucleotides
        (B) TYPE: nucleic acid
        (C) STRANDEDNESS: single
        (D) TOPOLOGY: linear (ii) MOLECULE TYPE: cDNA (iii) SEQUENCE DESCRIPTION: SEQ ID NO:35:

```
TCTAATACTT TCTTCATTAC AGACTCTAAA CCGCAAATTC GCATTTCTAT                50

AAACTTCATC CCAAAGCATC ATGCGTTTTA GTTCCAAAAT ATTTTTCATT               100

TCAAAATGTT CTTTTCCCAT GTCCAAATAT TTTGGTTCTT CGTCGTTGTA               150

TGGTTCCCAA AAAATGTCGT TTAAATGTCT TTTTGTATcA CATGATGCAT               200

CTTCAGTGTT TGATGTAGGT TTTCCATTCT TTACAAAATT GGTCCAGATC               250

CTGACCATCC TTTTCCAGAGT CTGCATAGCA TCTTGCGGTA TAGAAATGTG              300

CGTTGTTCCC AAAATAGGAA CATCCAAAGA GTTTGCAAAA AGATATCCTA               350

AATCATCACC ATGACTAACT CCTGGCAAGG AACCCCATCG ATAGGGCAAG               400

ATATAACTTT TATATACACT ATACGTATCA TCTGATAACC TATACAAATA               450

CAAGTTGGAA TTTCTTTTGA TTTCATTGAA AAATATGGCT TTCAAGGTAC               500

GGTAAATTCC TTGGAGATAA CCAGCATCGC CTTTTAGTTG GACATAGGCT               550

TCGATGTCAT CGTTTTGTTC TTTAACTTGG TCATAAAACT CTGTAAGCAT               600

TTTTATAAGT TTTTTCTCCT CAATGCCATT AGGATTTTTC CAAATATTAG               650

CATCTCTAGG TATAGCTCTC TCTATATTTG TCAAAGTCTT GTAAACTTCC               700

ATGTTTCCTC TGGTTACTCT TGGCATAGAT CTTAAACCTT CAGCACTATT               750

GAATCCAATG ATGACATCAA CGTCAGGAAA TTCACCATTT CTCATTCTTT               800

CTAAAGCAGA TGGAAATGTT ATTGGGTCTG GAGATTCTGG TGATTCTAGG               850

ACTGGATTAA ATACTGGTAC TGTGTCCCTT TCGTGGTCGT TGTTATCTGG               900

GACTCTGTTT AAGGCTGCTC GCAAAATTTG ATTTTTGTCC AGATTAGGA               950

GTTCTTGTTT TTGCGTGATG TTCAGCACTT GTTTTAGTTT TTCAAATCTA              1000

TGCAGAGGTT GAATTTGATT AGCAGTCGGA TTGAGTAATG TCCCACTCTG              1050

CAAAATTGCC CTTTGGTAGT ATTTTCTAGT AGAATTGTCC ATCATCAGAA              1100

AATGAACACT TGCTGCTCCA GCAGATTCTC CAGCTATAGT GATTTTATCT              1150

CTGTCTCCAC CAAATTTTTC GATGTTGTCA TAAACCCATT TTAGTGCCAA              1200

TCTCTGGTCT TTTAGACCCA TATTTCCATG GATATCCCAT TCCGGCGCTG              1250

ATAGAAAACC GAAAACTCCT AATCTATAGT TGATAGTGAC CAAAATAATT              1300
```

-continued

```
CCTTCCCTGA TCAAATAATC AGGTCCAAAA AAATTATAAG ATCCTGATCC         1350

TTGGTTGAAT GCGCCTCCAT GGATCCAGAA CATTACAGGA TATTTTGTAT         1400

TGTTCGCAGA ATTAACAGTC TCTGGCGTGA ATATATTCAG ATATAAGCAA         1450

TCTTCGCTTC CTGCATAAGA ATATATTAGA CTTTCCTGGA AACATTTGTC         1500

TCCTAAAGAC CGAGCCTGAA CGAATCCTGT TTTTGGATTT GATATTGGTT         1550

TTGGAGACTG AAATCGCAAT GGTCCAATAG GCGGTTCTGC ATAAGGAATT         1600

CCCAAATAGG AACAATATAC ATCATTTTTA TGATCTTTAT ATCGGAACGG         1650

TTTTCCTTCC GTGATCCCGT TAAATTGAAC TCTGCACAAA TGCTGATCTA         1700

GGTTATCCCA TAGTATGCAC AAGACAGGTG TAAATAAGAA AAATAAAAAA         1750

AATAAAAATA AAACTAATGC ACTGTGAGGT AACAT                         1785
```

(2) INFORMATION FOR SEQ ID NO:36:

(i) SEQUENCE CHARACTERISTICS:
        (A) LENGTH: 2007 nucleotides
        (B) TYPE: nucleic acid
        (C) STRANDEDNESS: single
        (D) TOPOLOGY: linear (ii) MOLECULE TYPE: cDNA (iii) FEATURE:
        (A) NAME/KEY: CDS
        (B) LOCATION: 11..1594

(iv) SEQUENCE DESCRIPTION: SEQ ID NO:36:

```
AGTTCCAACG ATG GCT GAT CTA CAA GTG ACT TTG CTT CAA GGT          43
           Met Ala Asp Leu Gln Val Thr Leu Leu Gln Gly
            1               5                  10

ACT TTA AAA GGA AAA GAG CAA ATT AGT GAA AAA GGA AAT GTG          85
Thr Leu Lys Gly Lys Glu Gln Ile Ser Glu Lys Gly Asn Val
         15                  20                  25

TTC CAT AGT TAT TCT GGA ATT CCA TAT GCC AAA CCT CCT GTA         127
Phe His Ser Tyr Ser Gly Ile Pro Tyr Ala Lys Pro Pro Val
                 30                  35

GGT GAT CTA AGA TTT AAG CCA CCT CAA CCT GCA GAA CCT TGG         169
Gly Asp Leu Arg Phe Lys Pro Pro Gln Pro Ala Glu Pro Trp
 40                  45                  50

TCA GGT GTT CTT GAT GCT AGT AAA GAA GGG AAT AGT TGT AGA         211
Ser Gly Val Leu Asp Ala Ser Lys Glu Gly Asn Ser Cys Arg
         55                  60                  65

TCA GTA CAT TTT ATT AAA AAA ATT AAA GTA GGG GCT GAA GAT         253
Ser Val His Phe Ile Lys Lys Ile Lys Val Gly Ala Glu Asp
             70                  75                  80

TGT TTA TAC CTC AAT GTC TAT GTA CCA AAA ACA TCA GAG AAA         295
Cys Leu Tyr Leu Asn Val Tyr Val Pro Lys Thr Ser Glu Lys
                 85                  90                  95

TCA CTT CTT CCA GTA ATG GTA TGG ATA CAT GGA GGA GGC TTC         337
Ser Leu Leu Pro Val Met Val Trp Ile His Gly Gly Gly Phe
                    100                 105

TTC ATG GGA TCT GGA AAT AGT GAT ATG TAT GGT CCT GAA TAT         379
Phe Met Gly Ser Gly Asn Ser Asp Met Tyr Gly Pro Glu Tyr
110                 115                 120

TTG ATG GAT TAT GGA ATT GTT CTG GTT ACT TTC AAT TAT CGA         421
Leu Met Asp Tyr Gly Ile Val Leu Val Thr Phe Asn Tyr Arg
        125                 130                 135

TTA GGT GTT TTG GGA TTT TTG AAC CTG GGA ATA GAA GAA GCG         463
Leu Gly Val Leu Gly Phe Leu Asn Leu Gly Ile Glu Glu Ala
```

-continued

```
              140                 145                 150
CCT GGC AAT GTT GGT TTG ATG GAC CAG GTT GAA GCT CTA AAA              505
Pro Gly Asn Val Gly Leu Met Asp Gln Val Glu Ala Leu Lys
            155                 160                 165

TGG GTA AAA AAC AAT ATT GCA TCC TTT GGT GGT GAC CCC AAC              547
Trp Val Lys Asn Asn Ile Ala Ser Phe Gly Gly Asp Pro Asn
                170                 175

AAT GTG ACT ATT TTT GGA GAA TCA GCA GGT GGT GCA AGT GTT              589
Asn Val Thr Ile Phe Gly Glu Ser Ala Gly Gly Ala Ser Val
180                 185                 190

CAT TAT TTG ATG TTA TCA GAT CTT TCC AAA GGA CTT TTT CAT              631
His Tyr Leu Met Leu Ser Asp Leu Ser Lys Gly Leu Phe His
    195                 200                 205

AAA GCG ATC TCA CAA AGT GGA AGT GCT TTT AAT CCT TGG GCA              673
Lys Ala Ile Ser Gln Ser Gly Ser Ala Phe Asn Pro Trp Ala
        210                 215                 220

CTT CAA CAT GAT AAT AAT AAA GAA AAT GCA TTC CGC CTC TGC              715
Leu Gln His Asp Asn Asn Lys Glu Asn Ala Phe Arg Leu Cys
            225                 230                 235

AAA CTT CTG GGT CAT CCT GTC GAT AAC GAG ACA GAA GCT CTA              757
Lys Leu Leu Gly His Pro Val Asp Asn Glu Thr Glu Ala Leu
                240                 245

AAA ATC CTT CGT CAA GCC CCC ATA GAT GAT CTT ATA GAC AAC              799
Lys Ile Leu Arg Gln Ala Pro Ile Asp Asp Leu Ile Asp Asn
250                 255                 260

AGA ATA AAA CCA AAA GAC AAA GGC CAA CTT ATT ATA GAC TAT              841
Arg Ile Lys Pro Lys Asp Lys Gly Gln Leu Ile Ile Asp Tyr
    265                 270                 275

CCT TTT CTA CCA ACA ATA GAA AAA CGT TAT CAA AAT TTT GAA              883
Pro Phe Leu Pro Thr Ile Glu Lys Arg Tyr Gln Asn Phe Glu
        280                 285                 290

CCA TTC TTG GAC CAG TCT CCA TTA TCA AAA ATG CAA TCA GGC              925
Pro Phe Leu Asp Gln Ser Pro Leu Ser Lys Met Gln Ser Gly
            295                 300                 305

AAT TTC ACA AAA GTC CCA TTT ATA TGT GGA TAC AAC AGT GCT              967
Asn Phe Thr Lys Val Pro Phe Ile Cys Gly Tyr Asn Ser Ala
                310                 315

GAA GGA ATT TTA GGT TTA ATG GAC TTC AAG GAT GAC CCA AAT             1009
Glu Gly Ile Leu Gly Leu Met Asp Phe Lys Asp Asp Pro Asn
320                 325                 330

ATA TTT GAG AAG TTT GAA GCT GAT TTT GAA AGA TTT GTA CCA             1051
Ile Phe Glu Lys Phe Glu Ala Asp Phe Glu Arg Phe Val Pro
    335                 340                 345

GTA GAT TTG AAT CTA ACT TTA AGG TCT AAG GAA TCT AAA AAA             1093
Val Asp Leu Asn Leu Thr Leu Arg Ser Lys Glu Ser Lys Lys
        350                 355                 360

TTG GCT GAA GAA ATG AGA AAG TTT TAT TAC CAA GAC GAA CCT             1135
Leu Ala Glu Glu Met Arg Lys Phe Tyr Tyr Gln Asp Glu Pro
            365                 370                 375

GTT TCT TCA GAC AAC AAA GAA AAA TTT GTC AGT GTT ATT AGT             1177
Val Ser Ser Asp Asn Lys Glu Lys Phe Val Ser Val Ile Ser
                380                 385

GAT ACT TGG TTT TTG AGA GGG ATT AAA AAT ACT GCA AGA TAT             1219
Asp Thr Trp Phe Leu Arg Gly Ile Lys Asn Thr Ala Arg Tyr
390                 395                 400

ATA ATT GAA CAT TCC TCA GAA CCG TTA TAT TTA TAT GTT TAT             1261
Ile Ile Glu His Ser Ser Glu Pro Leu Tyr Leu Tyr Val Tyr
    405                 410                 415

AGT TTT GAT GAT TTT GGT TTT TTG AAG AAA CTT GTA TTA GAT             1303
```

```
Ser Phe Asp Asp Phe Gly Phe Leu Lys Lys Leu Val Leu Asp
        420                 425                 430

CCT AAT ATT GAA GGA GCA GCT CAT GGA GAT GAG CTG GGA TAT          1345
Pro Asn Ile Glu Gly Ala Ala His Gly Asp Glu Leu Gly Tyr
            435                 440                 445

CTT TTC AAG ATG AGT TTT ACA GAA TTT CCA AAA GAT TTA CCA          1387
Leu Phe Lys Met Ser Phe Thr Glu Phe Pro Lys Asp Leu Pro
                450                 455

AGT GCA GTG GTG AAT AGG GAA CGA TTG TTG CAA CTT TGG ACA          1429
Ser Ala Val Val Asn Arg Glu Arg Leu Leu Gln Leu Trp Thr
460                 465                 470

AAT TTT GCA AAA ACA GGA AAT CCC ACT CCT GAA ATC AAT GAT          1471
Asn Phe Ala Lys Thr Gly Asn Pro Thr Pro Glu Ile Asn Asp
        475                 480                 485

GTT ATA ACA ACA AAA TGG GAT AAA GCT ACT GAG GAA AAA TCA          1513
Val Ile Thr Thr Lys Trp Asp Lys Ala Thr Glu Glu Lys Ser
            490                 495                 500

GAT CAT ATG GAT ATC GAT AAT ACT TTG AGA ATG ATT CCA GAT          1555
Asp His Met Asp Ile Asp Asn Thr Leu Arg Met Ile Pro Asp
                505                 510                 515

CCT GAT GCA AAA CGA CTT AGA TTT TGG AAT AAA TTT TTA TGA          1597
Pro Asp Ala Lys Arg Leu Arg Phe Trp Asn Lys Phe Leu
520                 525

TAAATATACC AATTATCGAT TTTATTATAG AGTTTCTGTA TTAGTATAAT            1647

TATCACGTTT AGATGTACGA GATTCAATTG GCTCTAATTG AAGTATATTT            1697

CGATTTCAAA TTTACTCTGA TTATTGGAAA AAAAGCTTTT ACAGTTGTAA            1747

TAATCAAGAA GTAGGTGGTA AATTTAGAAC AAATTCTGTT TTAGTGATTT            1797

GCGCATTCAA CAGATGGTGT ACTGTGCCTA AATTTGTCGC TCTTCTTGAA            1847

GAACTGAACT AAAAATGTGA TTAATGGACG CCACATTATT TATATTTGAT            1897

ATTATTACCA TCTTTGTATC ATATTTGCTT TTATTTTTTC ATTTTTTTTT            1947

TATTTCAAAT ATATTGTTTT TTTATAAAAA AAAAAAAAAA AAAAAAAAAA            1997

AAAAAAAAAA                                                        2007

(2) INFORMATION FOR SEQ ID NO:37:

(i) SEQUENCE CHARACTERISTICS:
        (A) LENGTH:   528 amino acids
        (B) TYPE:     amino acid
        (D) TOPOLOGY: linear (ii) MOLECULE TYPE:  protein (iii) SEQUENCE DESCRIPTION:  SEQ ID NO:37:

Met Ala Asp Leu Gln Val Thr Leu Leu Gln Gly Thr Leu Lys
  1               5                  10

Gly Lys Glu Gln Ile Ser Glu Lys Gly Asn Val Phe His Ser
 15                 20                  25

Tyr Ser Gly Ile Pro Tyr Ala Lys Pro Pro Val Gly Asp Leu
         30                  35                  40

Arg Phe Lys Pro Pro Gln Pro Ala Glu Pro Trp Ser Gly Val
             45                  50                  55

Leu Asp Ala Ser Lys Glu Gly Asn Ser Cys Arg Ser Val His
                 60                  65                  70

Phe Ile Lys Lys Ile Lys Val Gly Ala Glu Asp Cys Leu Tyr
                     75                  80
```

-continued

```
Leu Asn Val Tyr Val Pro Lys Thr Ser Glu Lys Ser Leu Leu
 85                  90                  95

Pro Val Met Val Trp Ile His Gly Gly Phe Phe Met Gly
            100                 105                 110

Ser Gly Asn Ser Asp Met Tyr Gly Pro Glu Tyr Leu Met Asp
                115                 120                 125

Tyr Gly Ile Val Leu Val Thr Phe Asn Tyr Arg Leu Gly Val
            130                 135                 140

Leu Gly Phe Leu Asn Leu Gly Ile Glu Glu Ala Pro Gly Asn
                145                 150

Val Gly Leu Met Asp Gln Val Glu Ala Leu Lys Trp Val Lys
155                 160                 165

Asn Asn Ile Ala Ser Phe Gly Asp Pro Asn Asn Val Thr
    170                 175                 180

Ile Phe Gly Glu Ser Ala Gly Gly Ala Ser Val His Tyr Leu
            185                 190                 195

Met Leu Ser Asp Leu Ser Lys Gly Leu Phe His Lys Ala Ile
                200                 205                 210

Ser Gln Ser Gly Ser Ala Phe Asn Pro Trp Ala Leu Gln His
                215                 220

Asp Asn Asn Lys Glu Asn Ala Phe Arg Leu Cys Lys Leu Leu
225                 230                 235

Gly His Pro Val Asp Asn Glu Thr Glu Ala Leu Lys Ile Leu
    240                 245                 250

Arg Gln Ala Pro Ile Asp Asp Leu Ile Asp Asn Arg Ile Lys
                255                 260                 265

Pro Lys Asp Lys Gly Gln Leu Ile Ile Asp Tyr Pro Phe Leu
                270                 275                 280

Pro Thr Ile Glu Lys Arg Tyr Gln Asn Phe Glu Pro Phe Leu
                285                 290

Asp Gln Ser Pro Leu Ser Lys Met Gln Ser Gly Asn Phe Thr
295                 300                 305

Lys Val Pro Phe Ile Cys Gly Tyr Asn Ser Ala Glu Gly Ile
    310                 315                 320

Leu Gly Leu Met Asp Phe Lys Asp Pro Asn Ile Phe Glu
    325                 330                 335

Lys Phe Glu Ala Asp Phe Glu Arg Phe Val Pro Val Asp Leu
            340                 345                 350

Asn Leu Thr Leu Arg Ser Lys Glu Ser Lys Lys Leu Ala Glu
                355                 360

Glu Met Arg Lys Phe Tyr Tyr Gln Asp Glu Pro Val Ser Ser
365                 370                 375

Asp Asn Lys Glu Lys Phe Val Ser Val Ile Ser Asp Thr Trp
    380                 385                 390

Phe Leu Arg Gly Ile Lys Asn Thr Ala Arg Tyr Ile Ile Glu
            395                 400                 405

His Ser Ser Glu Pro Leu Tyr Leu Tyr Val Tyr Ser Phe Asp
                410                 415                 420

Asp Phe Gly Phe Leu Lys Lys Leu Val Leu Asp Pro Asn Ile
                425                 430

Glu Gly Ala Ala His Gly Asp Glu Leu Gly Tyr Leu Phe Lys
435                 440                 445

Met Ser Phe Thr Glu Phe Pro Lys Asp Leu Pro Ser Ala Val
```

```
                450                 455                 460
Val Asn Arg Glu Arg Leu Leu Gln Leu Trp Thr Asn Phe Ala
            465                 470                 475

Lys Thr Gly Asn Pro Thr Pro Glu Ile Asn Asp Val Ile Thr
            480                 485                 490

Thr Lys Trp Asp Lys Ala Thr Glu Glu Lys Ser Asp His Met
            495                 500

Asp Ile Asp Asn Thr Leu Arg Met Ile Pro Asp Pro Asp Ala
505                 510                 515

Lys Arg Leu Arg Phe Trp Asn Lys Phe Leu
            520                 525

(2) INFORMATION FOR SEQ ID NO:38:

(i) SEQUENCE CHARACTERISTICS:
        (A) LENGTH: 2007 nucleotides
        (B) TYPE: nucleic acid
        (C) STRANDEDNESS: single
        (D) TOPOLOGY: linear (ii) MOLECULE TYPE: cDNA (iii) SEQUENCE DESCRIPTION: SEQ ID NO:38:
```

| | | |
|---|---|---|
| TTTTTTTTTT TTTTTTTTTT TTTTTTTTTT TTTTTATAAA AAAACAATAT | 50 | |
| ATTTGAAATA AAAAAAAAAT GAAAAAATAA AAGCAAATAT GATACAAAGA | 100 | |
| TGGTAATAAT ATCAAATATA AATAATGTGG CGTCCATTAA TCACATTTTT | 150 | |
| AGTTCAGTTC TTCAAGAAGA GCGACAAATT TAGGCACAGT ACACCATCTG | 200 | |
| TTGAATGCGC AAATCACTAA AACAGAATTT GTTCTAAATT TACCACCTAC | 250 | |
| TTCTTGATTA TTACAACTGT AAAAGCTTTT TTTCCAATAA TCAGAGTAAA | 300 | |
| TTTGAAATCG AAATATACTT CAATTAGAGC CAATTGAATC TCGTACATCT | 350 | |
| AAACGTGATA ATTATACTAA TACAGAAACT CTATAATAAA ATCGATAATT | 400 | |
| GGTATATTTA TCATAAAAAT TTATTCCAAA ATCTAAGTCG TTTTGCATCA | 450 | |
| GGATCTGGAA TCATTCTCAA AGTATTATCG ATATCCATAT GATCTGATTT | 500 | |
| TTCCTCAGTA GCTTTATCCC ATTTTGTTGT TATAACATCA TTGATTTCAG | 550 | |
| GAGTGGGATT TCCTGTTTTT GCAAAATTTG TCCAAAGTTG CAACAATCGT | 600 | |
| TCCCTATTCA CCACTGCACT TGGTAAATCT TTTGGAAATT CTGTAAAACT | 650 | |
| CATCTTGAAA AGATATCCCA GCTCATCTCC ATGAGCTGCT CCTTCAATAT | 700 | |
| TAGGATCTAA TACAAGTTTC TTCAAAAAAC CAAAATCATC AAAACTATAA | 750 | |
| ACATATAAAT ATAACGGTTC TGAGGAATGT TCAATTATAT ATCTTGCAGT | 800 | |
| ATTTTTAATC CCTCTCAAAA ACCAAGTATC ACTAATAACA CTGACAAATT | 850 | |
| TTTCTTTGTT GTCTGAAGAA ACAGGTTCGT CTTGGTAATA AAACTTTCTC | 900 | |
| ATTTCTTCAG CCAATTTTTT AGATTCCTTA GACCTTAAAG TTAGATTCAA | 950 | |
| ATCTACTGGT ACAAATCTTT CAAAATCAGC TTCAAACTTC TCAAATATAT | 1000 | |
| TTGGGTCATC CTTGAAGTCC ATTAAACCTA AAATTCCTTC AGCACTGTTG | 1050 | |
| TATCCACATA TAAATGGGAC TTTTGTGAAA TTGCCTGATT GCATTTTTGA | 1100 | |
| TAATGGAGAC TGGTCCAAGA ATGGTTCAAA ATTTTGATAA CGTTTTTCTA | 1150 | |
| TTGTTGGTAG AAAAGGATAG TCTATAATAA GTTGGCCTTT GTCTTTTGGT | 1200 | |
| TTTATTCTGT TGTCTATAAG ATCATCTATG GGGGCTTGAC GAAGGATTTT | 1250 | |

```
TAGAGCTTCT GTCTCGTTAT CGACAGGATG ACCCAGAAGT TTGCAGAGGC         1300

GGAATGCATT TTCTTTATTA TTATCATGTT GAAGTGCCCA AGGATTAAAA         1350

GCACTTCCAC TTTGTGAGAT CGCTTTATGA AAAAGTCCTT TGGAAAGATC         1400

TGATAACATC AAATAATGAA CACTTGCACC ACCTGCTGAT TCTCCAAAAA         1450

TAGTCACATT GTTGGGGTCA CCACCAAAGG ATGCAATATT GTTTTTTACC         1500

CATTTTAGAG CTTCAACCTG GTCCATCAAA CCAACATTGC CAGGCGCTTC         1550

TTCTATTCCC AGGTTCAAAA ATCCCAAAAC ACCTAATCGA TAATTGAAAG         1600

TAACCAGAAC AATTCCATAA TCCATCAAAT ATTCAGGACC ATACATATCA         1650

CTATTTCCAG ATCCCATGAA GAAGCCTCCT CCATGTATCC ATACCATTAC         1700

TGGAAGAAGT GATTTCTCTG ATGTTTTTGG TACATAGACA TTGAGGTATA         1750

AACAATCTTC AGCCCCTACT TTAATTTTTT TAATAAAATG TACTGATCTA         1800

CAACTATTCC CTTCTTTACT AGCATCAAGA ACACCTGACC AAGGTTCTGC         1850

AGGTTGAGGT GGCTTAAATC TTAGATCACC TACAGGAGGT TTGGCATATG         1900

GAATTCCAGA ATAACTATGG AACACATTTC CTTTTTCACT AATTTGCTCT         1950

TTTCCTTTTA AAGTACCTTG AAGCAAAGTC ACTTGTAGAT CAGCCATCGT         2000

TGGAACT                                                       2007

(2) INFORMATION FOR SEQ ID NO:39:

(i) SEQUENCE CHARACTERISTICS:
        (A) LENGTH: 12 amino acids
        (B) TYPE: amino acid
        (C) TOPOLOGY: linear (ii) MOLECULE TYPE: peptide (iii) SEQUENCE DESCRIPTION: SEQ ID NO:39:

Asp Pro Pro Thr Val Thr Leu Pro Gln Gly Glu Leu
1               5                   10

(2) INFORMATION FOR SEQ ID NO:40:

(i) SEQUENCE CHARACTERISTICS:
        (A) LENGTH: 22 amino acids
        (B) TYPE: amino acid
        (C) TOPOLOGY: linear (ii) MOLECULE TYPE: peptide (iii) FEATURE:
        (A) NAME/KEY: Xaa = any amino acid
        (B) LOCATION: 21

(iv) SEQUENCE DESCRIPTION: SEQ ID NO:40:

Asp Pro Pro Thr Val Thr Leu Pro Gln Gly Glu Leu Val Gly
1               5                   10

Lys Ala Thr Asn Glu Asn Xaa Lys
15                  20

(2) INFORMATION FOR SEQ ID NO:41:

(i) SEQUENCE CHARACTERISTICS:
        (A) LENGTH: 12 amino acids
        (B) TYPE: amino acid
        (C) TOPOLOGY: linear (ii) MOLECULE TYPE: peptide
```

(iii) SEQUENCE DESCRIPTION: SEQ ID NO:41:

Asp Pro Pro Thr Val Thr Leu Pro Gln Gly Glu Leu
1               5                  10

(2) INFORMATION FOR SEQ ID NO:42:

(i) SEQUENCE CHARACTERISTICS:
          (A) LENGTH: 21 amino acids
          (B) TYPE: amino acid
          (C) TOPOLOGY: linear (ii) MOLECULE TYPE: peptide (iii) SEQUENCE DESCRIPTION: SEQ ID NO:42:

Asp Pro Pro Thr Val Thr Leu Pro Gln Gly Glu Leu Val Gly
1               5                  10

Lys Ala Leu Ser Asn Glu Asn
15                  20

(2) INFORMATION FOR SEQ ID NO:43:

(i) SEQUENCE CHARACTERISTICS:
          (A) LENGTH: 8 amino acids
          (B) TYPE: amino acid
          (C) TOPOLOGY: linear (ii) MOLECULE TYPE: peptide (iii) SEQUENCE DESCRIPTION: SEQ ID NO:43:

Asp Pro Pro Thr Val Thr Leu Pro
1               5

(2) INFORMATION FOR SEQ ID NO:44:

(i) SEQUENCE CHARACTERISTICS:
          (A) LENGTH: 23 amino acids
          (B) TYPE: amino acid
          (C) TOPOLOGY: linear (ii) MOLECULE TYPE: peptide (iii) SEQUENCE DESCRIPTION: SEQ ID NO:44:

Asp Pro Pro Thr Val Thr Leu Pro Gln Gly Glu Leu Val Gly
1               5                  10

Lys Ala Leu Thr Asn Glu Asn Gly Lys
15                  20

(2) INFORMATION FOR SEQ ID NO:45:

(i) SEQUENCE CHARACTERISTICS:
          (A) LENGTH: 20 bases
          (B) TYPE: nucleic acid
          (C) STRANDEDNESS: single
          (D) TOPOLOGY: linear (ii) MOLECULE TYPE: primer (xi) SEQUENCE DESCRIPTION: SEQ ID NO:45:

AATTAACCCT CACTAAAGGG                                                     20

(2) INFORMATION FOR SEQ ID NO:46:

(i) SEQUENCE CHARACTERISTICS:
          (A) LENGTH: 17 bases
          (B) TYPE: nucleic acid
          (C) STRANDEDNESS: single (D) TOPOLOGY:  linear (ii) MOLECULE TYPE:  primer (iii) FEATURE:
        (A) NAME/KEY:  R = A or G
        (B) LOCATION:  2, 12, 14

(iv) FEATURE:
        (A) NAME/KEY:  D = A, G or T
        (B) LOCATION:  3, 6, 9, 15

(v) SEQUENCE DESCRIPTION:  SEQ ID NO:46:

ARDCCDCCDC CRTRDAT                                                          17

(2) INFORMATION FOR SEQ ID NO:47:

(i) SEQUENCE CHARACTERISTICS:
        (A) LENGTH:  38 bases
        (B) TYPE:  nucleic acid
        (C) STRANDEDNESS:  single
        (D) TOPOLOGY:  linear (ii) MOLECULE TYPE:  primer (iii) SEQUENCE DESCRIPTION:  SEQ ID NO:47:

TGTGCTCGAG ATGGGATAAC CTAGATCAGC ATTTGTGC                                   38

(2) INFORMATION FOR SEQ ID NO:48:

(i) SEQUENCE CHARACTERISTICS:
        (A) LENGTH:  35 bases
        (B) TYPE:  nucleic acid
        (C) STRANDEDNESS:  single
        (D) TOPOLOGY:  linear (ii) MOLECULE TYPE:  primer (iii) SEQUENCE DESCRIPTION:  SEQ ID NO:48:

TTAAGGTACC TCATCTAATA CTTCCTTCAT TACAG                                      35

(2) INFORMATION FOR SEQ ID NO:49:

(i) SEQUENCE CHARACTERISTICS:
        (A) LENGTH:  36 bases
        (B) TYPE:  nucleic acid
        (C) STRANDEDNESS:  single
        (D) TOPOLOGY:  linear (ii) MOLECULE TYPE:  primer (iii) SEQUENCE DESCRIPTION:  SEQ ID NO:49:

AAAACTGCAG TATAAATATG TTACCTCACA GTAGTG                                     36

(2) INFORMATION FOR SEQ ID NO:50:

(i) SEQUENCE CHARACTERISTICS:
        (A) LENGTH:  34 bases
        (B) TYPE:  nucleic acid
        (C) STRANDEDNESS:  single
        (D) TOPOLOGY:  linear (ii) MOLECULE TYPE:  primer (iii) SEQUENCE DESCRIPTION:  SEQ ID NO:50:

TGCTCTAGAT TATCTAATAC TTCCTTCATT ACAG                                       34

(2) INFORMATION FOR SEQ ID NO:51:

```
    (i) SEQUENCE CHARACTERISTICS:
        (A) LENGTH:  1584 nucleotides
        (B) TYPE:  nucleic acid
        (C) STRANDEDNESS:  single
        (D) TOPOLOGY:  linear (ii) MOLECULE TYPE:  cDNA (iii) FEATURE:
        (A) NAME/KEY:  CDS
        (B) LOCATION:  1..1584

(iv) SEQUENCE DESCRIPTION:  SEQ ID NO:51:

ATG GCT GAT CTA CAA GTG ACT TTG CTT CAA GGT ACT TTA AAA           42
Met Ala Asp Leu Gln Val Thr Leu Leu Gln Gly Thr Leu Lys
  1               5                  10

GGA AAA GAG CAA ATT AGT GAA AAA GGA AAT GTG TTC CAT AGT           84
Gly Lys Glu Gln Ile Ser Glu Lys Gly Asn Val Phe His Ser
 15                  20                  25

TAT TCT GGA ATT CCA TAT GCC AAA CCT CCT GTA GGT GAT CTA          126
Tyr Ser Gly Ile Pro Tyr Ala Lys Pro Pro Val Gly Asp Leu
     30                  35                  40

AGA TTT AAG CCA CCT CAA CCT GCA GAA CCT TGG TCA GGT GTT          168
Arg Phe Lys Pro Pro Gln Pro Ala Glu Pro Trp Ser Gly Val
             45                  50                  55

CTT GAT GCT AGT AAA GAA GGG AAT AGT TGT AGA TCA GTA CAT          210
Leu Asp Ala Ser Lys Glu Gly Asn Ser Cys Arg Ser Val His
                 60                  65                  70

TTT ATT AAA AAA ATT AAA GTA GGG GCT GAA GAT TGT TTA TAC          252
Phe Ile Lys Lys Ile Lys Val Gly Ala Glu Asp Cys Leu Tyr
                     75                  80

CTC AAT GTC TAT GTA CCA AAA ACA TCA GAG AAA TCA CTT CTT          294
Leu Asn Val Tyr Val Pro Lys Thr Ser Glu Lys Ser Leu Leu
 85                  90                  95

CCA GTA ATG GTA TGG ATA CAT GGA GGA GGC TTC TTC ATG GGA          336
Pro Val Met Val Trp Ile His Gly Gly Gly Phe Phe Met Gly
    100                 105                 110

TCT GGA AAT AGT GAT ATG TAT GGT CCT GAA TAT TTG ATG GAT          378
Ser Gly Asn Ser Asp Met Tyr Gly Pro Glu Tyr Leu Met Asp
            115                 120                 125

TAT GGA ATT GTT CTG GTT ACT TTC AAT TAT CGA TTA GGT GTT          420
Tyr Gly Ile Val Leu Val Thr Phe Asn Tyr Arg Leu Gly Val
                130                 135                 140

TTG GGA TTT TTG AAC CTG GGA ATA GAA GAA GCG CCT GGC AAT          462
Leu Gly Phe Leu Asn Leu Gly Ile Glu Glu Ala Pro Gly Asn
                    145                 150

GTT GGT TTG ATG GAC CAG GTT GAA GCT CTA AAA TGG GTA AAA          504
Val Gly Leu Met Asp Gln Val Glu Ala Leu Lys Trp Val Lys
155                 160                 165

AAC AAT ATT GCA TCC TTT GGT GGT GAC CCC AAC AAT GTG ACT          546
Asn Asn Ile Ala Ser Phe Gly Gly Asp Pro Asn Asn Val Thr
    170                 175                 180

ATT TTT GGA GAA TCA GCA GGT GGT GCA AGT GTT CAT TAT TTG          588
Ile Phe Gly Glu Ser Ala Gly Gly Ala Ser Val His Tyr Leu
            185                 190                 195

ATG TTA TCA GAT CTT TCC AAA GGA CTT TTT CAT AAA GCG ATC          630
Met Leu Ser Asp Leu Ser Lys Gly Leu Phe His Lys Ala Ile
                200                 205                 210

TCA CAA AGT GGA AGT GCT TTT AAT CCT TGG GCA CTT CAA CAT          672
Ser Gln Ser Gly Ser Ala Phe Asn Pro Trp Ala Leu Gln His
                    215                 220

GAT AAT AAT AAA GAA AAT GCA TTC CGC CTC TGC AAA CTT CTG          714
```

-continued

```
            Asp Asn Asn Lys Glu Asn Ala Phe Arg Leu Cys Lys Leu Leu
            225                 230                 235

GGT CAT CCT GTC GAT AAC GAG ACA GAA GCT CTA AAA ATC CTT         756
Gly His Pro Val Asp Asn Glu Thr Glu Ala Leu Lys Ile Leu
    240                 245                 250

CGT CAA GCC CCC ATA GAT GAT CTT ATA GAC AAC AGA ATA AAA         798
Arg Gln Ala Pro Ile Asp Asp Leu Ile Asp Asn Arg Ile Lys
        255                 260                 265

CCA AAA GAC AAA GGC CAA CTT ATT ATA GAC TAT CCT TTT CTA         840
Pro Lys Asp Lys Gly Gln Leu Ile Ile Asp Tyr Pro Phe Leu
            270                 275                 280

CCA ACA ATA GAA AAA CGT TAT CAA AAT TTT GAA CCA TTC TTG         882
Pro Thr Ile Glu Lys Arg Tyr Gln Asn Phe Glu Pro Phe Leu
                285                 290

GAC CAG TCT CCA TTA TCA AAA ATG CAA TCA GGC AAT TTC ACA         924
Asp Gln Ser Pro Leu Ser Lys Met Gln Ser Gly Asn Phe Thr
295                 300                 305

AAA GTC CCA TTT ATA TGT GGA TAC AAC AGT GCT GAA GGA ATT         966
Lys Val Pro Phe Ile Cys Gly Tyr Asn Ser Ala Glu Gly Ile
    310                 315                 320

TTA GGT TTA ATG GAC TTC AAG GAT GAC CCA AAT ATA TTT GAG        1008
Leu Gly Leu Met Asp Phe Lys Asp Asp Pro Asn Ile Phe Glu
        325                 330                 335

AAG TTT GAA GCT GAT TTT GAA AGA TTT GTA CCA GTA GAT TTG        1050
Lys Phe Glu Ala Asp Phe Glu Arg Phe Val Pro Val Asp Leu
            340                 345                 350

AAT CTA ACT TTA AGG TCT AAG GAA TCT AAA AAA TTG GCT GAA        1092
Asn Leu Thr Leu Arg Ser Lys Glu Ser Lys Lys Leu Ala Glu
                355                 360

GAA ATG AGA AAG TTT TAT TAC CAA GAC GAA CCT GTT TCT TCA        1134
Glu Met Arg Lys Phe Tyr Tyr Gln Asp Glu Pro Val Ser Ser
365                 370                 375

GAC AAC AAA GAA AAA TTT GTC AGT GTT ATT AGT GAT ACT TGG        1176
Asp Asn Lys Glu Lys Phe Val Ser Val Ile Ser Asp Thr Trp
    380                 385                 390

TTT TTG AGA GGG ATT AAA AAT ACT GCA AGA TAT ATA ATT GAA        1218
Phe Leu Arg Gly Ile Lys Asn Thr Ala Arg Tyr Ile Ile Glu
        395                 400                 405

CAT TCC TCA GAA CCG TTA TAT TTA TAT GTT TAT AGT TTT GAT        1260
His Ser Ser Glu Pro Leu Tyr Leu Tyr Val Tyr Ser Phe Asp
            410                 415                 420

GAT TTT GGT TTT TTG AAG AAA CTT GTA TTA GAT CCT AAT ATT        1302
Asp Phe Gly Phe Leu Lys Lys Leu Val Leu Asp Pro Asn Ile
                425                 430

GAA GGA GCA GCT CAT GGA GAT GAG CTG GGA TAT CTT TTC AAG        1344
Glu Gly Ala Ala His Gly Asp Glu Leu Gly Tyr Leu Phe Lys
435                 440                 445

ATG AGT TTT ACA GAA TTT CCA AAA GAT TTA CCA AGT GCA GTG        1386
Met Ser Phe Thr Glu Phe Pro Lys Asp Leu Pro Ser Ala Val
    450                 455                 460

GTG AAT AGG GAA CGA TTG TTG CAA CTT TGG ACA AAT TTT GCA        1428
Val Asn Arg Glu Arg Leu Leu Gln Leu Trp Thr Asn Phe Ala
        465                 470                 475

AAA ACA GGA AAT CCC ACT CCT GAA ATC AAT GAT GTT ATA ACA        1470
Lys Thr Gly Asn Pro Thr Pro Glu Ile Asn Asp Val Ile Thr
            480                 485                 490

ACA AAA TGG GAT AAA GCT ACT GAG GAA AAA TCA GAT CAT ATG        1512
Thr Lys Trp Asp Lys Ala Thr Glu Glu Lys Ser Asp His Met
                495                 500
```

```
GAT ATC GAT AAT ACT TTG AGA ATG ATT CCA GAT CCT GAT GCA         1554
Asp Ile Asp Asn Thr Leu Arg Met Ile Pro Asp Pro Asp Ala
505                 510                 515

AAA CGA CTT AGA TTT TGG AAT AAA TTT TTA                         1584
Lys Arg Leu Arg Phe Trp Asn Lys Phe Leu
    520                 525
```

(2) INFORMATION FOR SEQ ID NO:52:

(i) SEQUENCE CHARACTERISTICS:
        (A) LENGTH: 1584 nucleotides
        (B) TYPE: nucleic acid
        (C) STRANDEDNESS: single
        (D) TOPOLOGY: linear (ii) MOLECULE TYPE: cDNA (iii) SEQUENCE DESCRIPTION: SEQ ID NO:52:

```
TAAAAATTTA TTCCAAAATC TAAGTCGTTT TGCATCAGGA TCTGGAATCA             50

TTCTCAAAGT ATTATCGATA TCCATATGAT CTGATTTTTC CTCAGTAGCT            100

TTATCCCATT TTGTTGTTAT AACATCATTG ATTTCAGGAG TGGGATTTCC            150

TGTTTTTGCA AAATTTGTCC AAAGTTGCAA CAATCGTTCC CTATTCACCA            200

CTGCACTTGG TAAATCTTTT GGAAATTCTG TAAAACTCAT CTTGAAAAGA            250

TATCCCAGCT CATCTCCATG AGCTGCTCCT TCAATATTAG GATCTAATAC            300

AAGTTTCTTC AAAAAACCAA AATCATCAAA ACTATAAACA TATAAATATA            350

ACGGTTCTGA GGAATGTTCA ATTATATATC TTGCAGTATT TTTAATCCCT            400

CTCAAAAACC AAGTATCACT AATAACACTG ACAAATTTTT CTTTGTTGTC            450

TGAAGAAACA GGTTCGTCTT GGTAATAAAA CTTTCTCATT TCTTCAGCCA            500

ATTTTTAGA TTCCTTAGAC CTTAAAGTTA GATTCAAATC TACTGGTACA             550

AATCTTTCAA AATCAGCTTC AAACTTCTCA ATATATTTG GGTCATCCTT             600

GAAGTCCATT AAACCTAAAA TTCCTTCAGC ACTGTTGTAT CCACATATAA            650

ATGGGACTTT TGTGAAATTG CCTGATTGCA TTTTTGATAA TGGAGACTGG            700

TCCAAGAATG GTTCAAAATT TTGATAACGT TTTTCTATTG TTGGTAGAAA            750

AGGATAGTCT ATAATAAGTT GGCCTTTGTC TTTTGGTTTT ATTCTGTTGT            800

CTATAAGATC ATCTATGGGG GCTTGACGAA GGATTTTTAG AGCTTCTGTC            850

TCGTTATCGA CAGGATGACC CAGAAGTTTG CAGAGGCGGA ATGCATTTTC            900

TTTATTATTA TCATGTTGAA GTGCCCAAGG ATTAAAAGCA CTTCCACTTT            950

GTGAGATCGC TTTATGAAAA AGTCCTTTGG AAAGATCTGA TAACATCAAA           1000

TAATGAACAC TTGCACCACC TGCTGATTCT CCAAAAATAG TCACATTGTT           1050

GGGGTCACCA CCAAAGGATG CAATATTGTT TTTTACCCAT TTTAGAGCTT           1100

CAACCTGGTC CATCAAACCA ACATTGCCAG GCGCTTCTTC TATTCCCAGG           1150

TTCAAAAATC CCAAAACACC TAATCGATAA TTGAAAGTAA CCAGAACAAT           1200

TCCATAATCC ATCAAATATT CAGGACCATA CATATCACTA TTTCCAGATC           1250

CCATGAAGAA GCCTCCTCCA TGTATCCATA CCATTACTGG AAGAAGTGAT           1300

TTCTCTGATG TTTTTGGTAC ATAGACATTG AGGTATAAAC AATCTTCAGC           1350

CCCTACTTTA ATTTTTTTAA TAAAATGTAC TGATCTACAA CTATTCCCTT           1400

CTTTACTAGC ATCAAGAACA CCTGACCAAG GTTCTGCAGG TTGAGGTGGC           1450
```

```
TTAAATCTTA GATCACCTAC AGGAGGTTTG GCATATGGAA TTCCAGAATA         1500

ACTATGGAAC ACATTTCCTT TTTCACTAAT TTGCTCTTTT CCTTTTAAAG         1550

TACCTTGAAG CAAAGTCACT TGTAGATCAG CCAT                          1584

(2) INFORMATION FOR SEQ ID NO:53:

(i) SEQUENCE CHARACTERISTICS:
        (A) LENGTH: 530 amino acids
        (B) TYPE:   amino acid
        (D) TOPOLOGY: linear (ii) MOLECULE TYPE: protein (iii) SEQUENCE DESCRIPTION: SEQ ID NO:53:

Asp Pro Pro Thr Val Thr Leu Pro Gln Gly Glu Leu Val Gly
  1               5                  10

Lys Ala Leu Thr Asn Glu Asn Gly Lys Glu Tyr Phe Ser Tyr
 15                  20                  25

Thr Gly Val Pro Tyr Ala Lys Pro Pro Val Gly Glu Leu Arg
     30                  35                  40

Phe Lys Pro Pro Gln Lys Ala Glu Pro Trp Asn Gly Val Phe
         45                  50                  55

Asn Ala Thr Ser His Gly Asn Val Cys Lys Ala Leu Asn Phe
             60                  65                  70

Phe Leu Lys Lys Ile Glu Gly Asp Glu Asp Cys Leu Leu Val
                 75                  80

Asn Val Tyr Ala Pro Lys Thr Thr Ser Asp Lys Lys Leu Pro
 85                  90                  95

Val Phe Phe Trp Val His Gly Gly Phe Val Thr Gly Ser
100                 105                 110

Gly Asn Leu Glu Phe Gln Ser Pro Asp Tyr Leu Val Asn Tyr
            115                 120                 125

Asp Val Ile Phe Val Thr Phe Asn Tyr Arg Leu Gly Pro Leu
                130                 135                 140

Gly Phe Leu Asn Leu Glu Leu Glu Gly Ala Pro Gly Asn Val
                145                 150

Gly Leu Leu Asp Gln Val Ala Ala Leu Lys Trp Thr Lys Glu
155                 160                 165

Asn Ile Glu Lys Phe Gly Gly Asp Pro Glu Asn Ile Thr Ile
    170                 175                 180

Gly Gly Val Ser Ala Gly Gly Ala Ser Val His Tyr Leu Leu
        185                 190                 195

Leu Ser His Thr Thr Gly Leu Tyr Lys Arg Ala Ile Ala
            200                 205                 210

Gln Ser Gly Ser Ala Leu Asn Pro Trp Ala Phe Gln Arg His
                215                 220

Pro Val Lys Arg Ser Leu Gln Leu Ala Glu Ile Leu Gly His
225                 230                 235

Pro Thr Asn Asn Thr Gln Asp Ala Leu Glu Phe Leu Gln Lys
    240                 245                 250

Ala Pro Val Asp Ser Leu Leu Lys Lys Met Pro Ala Glu Thr
        255                 260                 265

Glu Gly Glu Ile Ile Glu Glu Phe Val Phe Val Pro Ser Ile
            270                 275                 280

Glu Lys Val Phe Pro Ser His Gln Pro Phe Leu Glu Glu Ser
```

```
                285                 290
Pro Leu Ala Arg Met Lys Ser Gly Ser Phe Asn Lys Val Pro
295                 300                 305

Leu Leu Val Gly Phe Asn Ser Ala Glu Gly Leu Leu Tyr Lys
        310                 315                 320

Phe Phe Met Lys Glu Lys Pro Glu Met Leu Asn Gln Ala Glu
            325                 330                 335

Ala Asp Phe Glu Arg Leu Val Pro Ala Glu Phe Glu Leu Ala
                340                 345                 350

His Gly Ser Glu Glu Ser Lys Lys Leu Ala Glu Lys Ile Arg
                    355                 360

Lys Phe Tyr Phe Asp Asp Lys Pro Val Pro Glu Asn Glu Gln
365                 370                 375

Lys Phe Ile Asp Leu Ile Gly Asp Ile Trp Phe Thr Arg Gly
        380                 385                 390

Ile Asp Lys His Val Lys Leu Ser Val Glu Lys Gln Asp Glu
            395                 400                 405

Pro Val Tyr Tyr Tyr Glu Tyr Ser Phe Ser Glu Ser His Pro
                410                 415                 420

Ala Lys Gly Thr Phe Gly Asp His Asn Leu Thr Gly Ala Cys
                    425                 430

His Gly Glu Glu Leu Val Asn Leu Phe Lys Val Glu Met Met
435                 440                 445

Lys Leu Glu Lys Asp Lys Pro Asn Val Leu Leu Thr Lys Asp
        450                 455                 460

Arg Val Leu Ala Met Trp Thr Asn Phe Ile Lys Asn Gly Asn
            465                 470                 475

Pro Thr Pro Glu Val Thr Glu Leu Leu Pro Val Lys Trp Glu
                480                 485                 490

Pro Ala Thr Lys Asp Lys Leu Asn Tyr Leu Asn Ile Asp Ala
                    495                 500

Thr Leu Thr Leu Gly Thr Asn Pro Glu Glu Thr Arg Val Lys
505                 510                 515

Phe Trp Glu Asp Ala Thr Lys Thr Leu His Ser Gln
        520                 525                 530

(2) INFORMATION FOR SEQ ID NO:54:

(i) SEQUENCE CHARACTERISTICS:
        (A) LENGTH:  570 amino acids
        (B) TYPE:  amino acid
        (D) TOPOLOGY:  linear (ii) MOLECULE TYPE:  protein (iii) SEQUENCE DESCRIPTION:  SEQ ID NO:54:

Trp Asp Asn Leu Asp Gln His Leu Cys Arg Val Gln Phe Asn
1               5                   10

Gly Ile Thr Glu Gly Lys Pro Phe Arg Tyr Lys Asp His Arg
15                  20                  25

Asn Asp Val Tyr Cys Ser Tyr Leu Gly Ile Pro Tyr Ala Glu
            30                  35                  40

Pro Pro Phe Gly Pro Leu Arg Phe Gln Ser Pro Lys Pro Ile
                45                  50                  55

Ser Asn Pro Lys Thr Gly Phe Val Gln Ala Arg Thr Leu Gly
                    60                  65                  70
```

-continued

```
Asp Lys Cys Phe Gln Glu Ser Leu Ile Tyr Ser Tyr Ala Gly
                75                      80
Ser Glu Asp Cys Leu Tyr Leu Asn Ile Phe Thr Pro Glu Thr
85                  90                      95
Val Asn Ser Ala Asn Asn Thr Lys Tyr Pro Val Met Phe Trp
            100                 105                 110
Ile His Gly Gly Ala Phe Asn Gln Gly Ser Gly Ser Tyr Asn
        115                 120                 125
Phe Phe Gly Pro Asp Tyr Leu Ile Arg Glu Gly Ile Ile Leu
            130                 135                 140
Val Thr Ile Asn Tyr Arg Leu Gly Val Phe Gly Phe Leu Ser
                145                 150
Ala Pro Glu Trp Asp Ile His Gly Asn Met Gly Leu Lys Asp
155                 160                 165
Gln Arg Leu Ala Leu Lys Trp Val Tyr Asp Asn Ile Glu Lys
        170                 175                 180
Phe Gly Gly Asp Arg Glu Lys Ile Thr Ile Ala Gly Glu Ser
            185                 190                 195
Ala Gly Ala Ala Ser Val His Phe Leu Met Met Asp Asn Ser
            200                 205                 210
Thr Arg Lys Tyr Tyr Gln Arg Ala Ile Leu Gln Ser Gly Thr
                215                 220
Leu Leu Asn Pro Thr Ala Asn Gln Ile Gln Leu Leu His Arg
225                 230                 235
Phe Glu Lys Leu Lys Gln Val Leu Asn Ile Thr Gln Lys Gln
        240                 245                 250
Glu Leu Leu Asn Leu Asp Lys Asn Leu Ile Leu Arg Ala Ala
            255                 260                 265
Leu Asn Arg Val Pro Asp Ser Asn Asp His Asp Arg Asp Thr
                270                 275                 280
Val Pro Val Phe Asn Pro Val Leu Glu Ser Pro Glu Ser Pro
                285                 290
Asp Pro Ile Thr Phe Pro Ser Ala Leu Glu Arg Met Arg Asn
295                 300                 305
Gly Glu Phe Pro Asp Val Asp Val Ile Ile Gly Phe Asn Ser
        310                 315                 320
Ala Glu Gly Leu Arg Ser Met Ala Arg Val Thr Arg Gly Asn
            325                 330                 335
Met Glu Val His Lys Thr Leu Thr Asn Ile Glu Arg Ala Ile
                340                 345                 350
Pro Arg Asp Ala Asn Ile Trp Lys Asn Pro Asn Gly Ile Glu
                355                 360
Glu Lys Lys Leu Ile Lys Met Leu Thr Glu Phe Tyr Asp Gln
365                 370                 375
Val Lys Glu Gln Asn Asp Asp Ile Glu Ala Tyr Val Gln Leu
        380                 385                 390
Lys Gly Asp Ala Gly Tyr Leu Gln Gly Ile Tyr Arg Thr Leu
            395                 400                 405
Lys Ala Ile Phe Phe Asn Glu Phe Arg Arg Asn Ser Asn Leu
                410                 415                 420
Tyr Leu Tyr Arg Leu Ser Asp Asp Thr Tyr Ser Val Tyr Lys
                425                 430
```

```
Ser Tyr Ile Leu Pro Tyr Arg Trp Gly Ser Leu Pro Gly Val
435                 440                 450

Ser His Gly Asp Asp Leu Gly Tyr Leu Phe Ala Asn Ser Leu
    450                 455                 460

Asp Val Pro Ile Leu Gly Thr Thr His Ile Ser Ile Pro Gln
        465                 470                 475

Asp Ala Met Gln Thr Leu Glu Arg Met Val Arg Ile Trp Thr
            480                 485                 490

Asn Phe Val Lys Asn Gly Lys Pro Thr Ser Asn Thr Glu Asp
                495                 500

Ala Ser Cys Asp Thr Lys Arg His Leu Asn Asp Ile Phe Trp
505                 510                 515

Glu Pro Tyr Asn Asp Glu Glu Pro Lys Tyr Leu Asp Met Gly
    520                 525                 530

Lys Glu Asn Phe Glu Met Lys Asn Ile Leu Glu Leu Lys Arg
        535                 540                 545

Met Met Leu Trp Asp Glu Val Tyr Arg Asn Ala Asn Leu Arg
            550                 555                 560

Phe Arg Val Cys Asn Glu Gly Ser Ile Arg
                565                 570

(2) INFORMATION FOR SEQ ID NO:55:

(i) SEQUENCE CHARACTERISTICS:
        (A) LENGTH:  570 amino acids
        (B) TYPE:  amino acid
        (D) TOPOLOGY:  linear (ii) MOLECULE TYPE:  protein (iii) SEQUENCE DESCRIPTION:  SEQ ID NO:55:

Trp Asp Asn Leu Asp Gln His Leu Cys Arg Val Gln Phe Asn
1                   5                   10

Gly Ile Thr Glu Gly Lys Pro Phe Arg Tyr Lys Asp His Lys
15                  20                  25

Asn Asp Val Tyr Cys Ser Tyr Leu Gly Ile Pro Tyr Ala Glu
        30                  35                  40

Pro Pro Ile Gly Pro Leu Arg Phe Gln Ser Pro Lys Pro Ile
            45                  50                  55

Ser Asn Pro Lys Thr Gly Phe Val Gln Ala Arg Ser Leu Gly
                60                  65                  70

Asp Lys Cys Phe Gln Glu Ser Leu Ile Tyr Ser Tyr Ala Gly
                    75                  80

Ser Glu Asp Cys Leu Tyr Leu Asn Ile Phe Thr Pro Glu Thr
85                  90                  95

Val Asn Ser Ala Asn Asn Thr Lys Tyr Pro Val Met Phe Trp
    100                 105                 110

Ile His Gly Gly Ala Phe Asn Gln Gly Ser Gly Ser Tyr Asn
        115                 120                 125

Phe Phe Gly Pro Asp Tyr Leu Ile Arg Glu Gly Ile Ile Leu
            130                 135                 140

Val Thr Ile Asn Tyr Arg Leu Gly Val Phe Gly Phe Leu Ser
                145                 150

Ala Pro Glu Trp Asp Ile His Gly Asn Met Gly Leu Lys Asp
155                 160                 165

Gln Arg Leu Ala Leu Lys Trp Val Tyr Asp Asn Ile Glu Lys
```

-continued

```
            170                 175                 180
Phe Gly Gly Asp Arg Asp Lys Ile Thr Ile Ala Gly Glu Ser
            185                 190                 195
Ala Gly Ala Ala Ser Val His Phe Leu Met Met Asp Asn Ser
            200                 205                 210
Thr Arg Lys Tyr Tyr Gln Arg Ala Ile Leu Gln Ser Gly Thr
            215                 220
Leu Leu Asn Pro Thr Ala Asn Gln Ile Gln Pro Leu His Arg
225             230                 235
Phe Glu Lys Leu Lys Gln Val Leu Asn Ile Thr Gln Lys Gln
    240                 245                 250
Glu Leu Leu Asn Leu Asp Lys Asn Gln Ile Leu Arg Ala Ala
        255                 260                 265
Leu Asn Arg Val Pro Asp Asn Asn Asp His Glu Arg Asp Thr
            270                 275                 280
Val Pro Val Phe Asn Pro Val Leu Glu Ser Pro Glu Ser Pro
                285                 290
Asp Pro Ile Thr Phe Pro Ser Ala Leu Glu Arg Met Arg Asn
295                 300                 305
Gly Glu Phe Pro Asp Val Asp Val Ile Ile Gly Phe Asn Ser
    310                 315                 320
Ala Glu Gly Leu Arg Ser Met Pro Arg Val Thr Arg Gly Asn
            325                 330                 335
Met Glu Val Tyr Lys Thr Leu Thr Asn Ile Glu Arg Ala Ile
                340                 345                 350
Pro Arg Asp Ala Asn Ile Trp Lys Asn Pro Asn Gly Ile Glu
                355                 360
Glu Lys Lys Leu Ile Lys Met Leu Thr Glu Phe Tyr Asp Gln
365                 370                 375
Val Lys Glu Gln Asn Asp Asp Ile Glu Ala Tyr Val Gln Leu
    380                 385                 390
Lys Gly Asp Ala Gly Tyr Leu Gln Gly Ile Tyr Arg Thr Leu
        395                 400                 405
Lys Ala Ile Phe Phe Asn Glu Ile Lys Arg Asn Ser Asn Leu
            410                 415                 420
Tyr Leu Tyr Arg Leu Ser Asp Asp Thr Tyr Ser Val Tyr Lys
                425                 430
Ser Tyr Ile Leu Pro Tyr Arg Trp Gly Ser Leu Pro Gly Val
435                 440                 445
Ser His Gly Asp Asp Leu Gly Tyr Leu Phe Ala Asn Ser Leu
    450                 455                 460
Asp Val Pro Ile Leu Gly Thr Thr His Ile Ser Ile Pro Gln
        465                 470                 475
Asp Ala Met Gln Thr Leu Glu Arg Met Val Arg Ile Trp Thr
            480                 485                 490
Asn Phe Val Lys Asn Gly Lys Pro Thr Ser Asn Thr Glu Asp
                495                 500
Ala Ser Cys Asp Thr Lys Arg His Leu Asn Asp Ile Phe Trp
505                 510                 515
Glu Pro Tyr Asn Asp Glu Pro Lys Tyr Leu Asp Met Gly
    520                 525                 530
Lys Glu His Phe Glu Met Lys Asn Ile Leu Glu Leu Lys Arg
        535                 540                 545
```

```
Met Met Leu Trp Asp Glu Val Tyr Arg Asn Ala Asn Leu Arg
        550                 555                 560

Phe Arg Val Cys Asn Glu Gly Ser Ile Arg
            565                 570

(2) INFORMATION FOR SEQ ID NO:56:

(i) SEQUENCE CHARACTERISTICS:
        (A) LENGTH:  20 bases
        (B) TYPE:  nucleic acid
        (C) STRANDEDNESS:  single
        (D) TOPOLOGY:  linear (ii) MOLECULE TYPE:  primer (iii) SEQUENCE DESCRIPTION:  SEQ ID NO:56:

GTGCGTACAC GTTTACTACC                                              20

(2) INFORMATION FOR SEQ ID NO:57:

(i) SEQUENCE CHARACTERISTICS:
        (A) LENGTH:  2144 nucleotides
        (B) TYPE:  nucleic acid
        (C) STRANDEDNESS:  single
        (D) TOPOLOGY:  linear (ii) MOLECULE TYPE:  cDNA (iii) FEATURE:
        (A) NAME/KEY:  CDS
        (B) LOCATION:  30..1682

(iv) FEATURE:
        (A) NAME/KEY:  Asx = Asn or Asp
        (B) LOCATION:  462

(v) SEQUENCE DESCRIPTION:  SEQ ID NO:57:

GTACACATAG TCAATAGTCT AGATCCAAG ATG TCT CGT GTT ATT TTT             47
                               Met Ser Arg Val Ile Phe
                                 1               5

TTA AGT TGT ATT TTT TTG TTT AGT TTT AAT TTT ATA AAA TGT             89
Leu Ser Cys Ile Phe Leu Phe Ser Phe Asn Phe Ile Lys Cys
            10                  15                  20

GAT TCC CCG ACT GTA ACT TTG CCC CAA GGC GAA TTG GTT GGA            131
Asp Ser Pro Thr Val Thr Leu Pro Gln Gly Glu Leu Val Gly
                25                  30

AAA GCT TTG ACG AAC GAA AAT GGA AAA GAG TAT TTT AGC TAC            173
Lys Ala Leu Thr Asn Glu Asn Gly Lys Glu Tyr Phe Ser Tyr
 35             40                  45

ACA GGT GTA CCT TAT GCT AAA CCT CCT GTT GGA GAA CTT AGA            215
Thr Gly Val Pro Tyr Ala Lys Pro Pro Val Gly Glu Leu Arg
     50                 55                  60

TTT AAG CCT CCA CAG AAA GCT GAG CCA TGG CAA GGT GTT TTC            257
Phe Lys Pro Pro Gln Lys Ala Glu Pro Trp Gln Gly Val Phe
         65                 70                  75

AAC GCC ACA TTA TAC GGA AAT GTG TGT AAA TCT TTA AAT TTC            299
Asn Ala Thr Leu Tyr Gly Asn Val Cys Lys Ser Leu Asn Phe
             80                 85                  90

TTC TTG AAG AAA ATT GAA GGA GAC GAA GAC TGC TTG GTA GTA            341
Phe Leu Lys Lys Ile Glu Gly Asp Glu Asp Cys Leu Val Val
                 95                 100

AAC GTG TAC GCA CCA AAA ACA ACT TCT GAT AAA AAA CTT CCA            383
Asn Val Tyr Ala Pro Lys Thr Thr Ser Asp Lys Lys Leu Pro
105                 110                 115
```

```
GTA TTT TTC TGG GTT CAT GGT GGT GGT TTT GTG ACT GGA TCC                    425
Val Phe Phe Trp Val His Gly Gly Gly Phe Val Thr Gly Ser
    120                 125                 130

GGA AAT TTA GAA TTC CAA AGC CCA GAT TAT TTA GTA RAT TTT                    467
Gly Asn Leu Glu Phe Gln Ser Pro Asp Tyr Leu Val Asx Phe
        135                 140                 145

GAT GTT ATT TTC GTA ACT TTC AAT TAC CGA TTG GGA CCT CTC                    509
Asp Val Ile Phe Val Thr Phe Asn Tyr Arg Leu Gly Pro Leu
            150                 155                 160

GGA TTT CTG AAT TTG GAG TTG GAG GGT GCT CCA GGA AAT GTA                    551
Gly Phe Leu Asn Leu Glu Leu Glu Gly Ala Pro Gly Asn Val
                165                 170

GGA TTA TTG GAT CAG GTG GCA GCT CTG AAA TGG ACC AAA GAA                    593
Gly Leu Leu Asp Gln Val Ala Ala Leu Lys Trp Thr Lys Glu
175                 180                 185

AAC ATT GAG AAA TTT GGT GGA GAT CCA GAA AAT ATT ACA ATT                    635
Asn Ile Glu Lys Phe Gly Gly Asp Pro Glu Asn Ile Thr Ile
        190                 195                 200

GGT GGT GTT TCT GCT GGT GGA GCA AGT GTT CAT TAT CTT TTG                    677
Gly Gly Val Ser Ala Gly Gly Ala Ser Val His Tyr Leu Leu
            205                 210                 215

TTA TCT CAT ACA ACC ACT GGA CTT TAC AAA AGG GCA ATT GCT                    719
Leu Ser His Thr Thr Thr Gly Leu Tyr Lys Arg Ala Ile Ala
                220                 225                 230

CAA AGT GGA AGT GCT TTT AAT CCA TGG GCC TTC CAA AGA CAT                    761
Gln Ser Gly Ser Ala Phe Asn Pro Trp Ala Phe Gln Arg His
                    235                 240

CCA GTA AAG CGT AGT CTT CAA CTT GCT GAG ATA TTG GGT CAT                    803
Pro Val Lys Arg Ser Leu Gln Leu Ala Glu Ile Leu Gly His
245                 250                 255

CCC ACA AAC AAT ACT CAA GAT GCT TTA GAA TTC TTA CAA AAA                    845
Pro Thr Asn Asn Thr Gln Asp Ala Leu Glu Phe Leu Gln Lys
        260                 265                 270

GCC CCC GTA GAC AGT CTC CTG AAG AAA ATG CCA GCT GAA ACA                    887
Ala Pro Val Asp Ser Leu Leu Lys Lys Met Pro Ala Glu Thr
            275                 280                 285

GAA GGT GAA ATA ATA GAA GAG TTT GTC TTC GTA CCA TCA ATT                    929
Glu Gly Glu Ile Ile Glu Glu Phe Val Phe Val Pro Ser Ile
                290                 295                 300

GAA AAA GTT TTC CCA TCC CAC CAA CCT TTC TTG GAA GAA TCA                    971
Glu Lys Val Phe Pro Ser His Gln Pro Phe Leu Glu Glu Ser
                    305                 310

CCA TTG GCC AGA ATG AAA TCC GGA TCC TTT AAC AAA GTA CCT                   1013
Pro Leu Ala Arg Met Lys Ser Gly Ser Phe Asn Lys Val Pro
315                 320                 325

TTA TTA GTT GGA TTT AAC AGT GCA GAA GGA CTT TTG TTC AAA                   1055
Leu Leu Val Gly Phe Asn Ser Ala Glu Gly Leu Leu Phe Lys
        330                 335                 340

TTC TTC ATG AAA GAA AAA CCA GAG ATG CTG AAC CAA GCT GAA                   1097
Phe Phe Met Lys Glu Lys Pro Glu Met Leu Asn Gln Ala Glu
            345                 350                 355

GCA GAT TTT GAA AGA CTC GTA CCA GCC GAA TTT GAA TTA GTC                   1139
Ala Asp Phe Glu Arg Leu Val Pro Ala Glu Phe Glu Leu Val
                360                 365                 370

CAT GGA TCA GAG GAA TCG AAA AAA CTT GCA GAA AAA ATC AGG                   1181
His Gly Ser Glu Glu Ser Lys Lys Leu Ala Glu Lys Ile Arg
                    375                 380

AAG TTT TAC TTT GAC GAT AAA CCC GTT CCA GAA AAT GAA CAG                   1223
Lys Phe Tyr Phe Asp Asp Lys Pro Val Pro Glu Asn Glu Gln
385                 390                 395
```

```
AAA TTT ATT GAC TTG ATA GGA GAT ATT TGG TTT ACT AGA GGT         1265
Lys Phe Ile Asp Leu Ile Gly Asp Ile Trp Phe Thr Arg Gly
        400                 405                 410

GTT GAC AAG CAT GTC AAG TTG TCT GTG GAG AAA CAA GAC GAA         1307
Val Asp Lys His Val Lys Leu Ser Val Glu Lys Gln Asp Glu
            415                 420                 425

CCA GTT TAT TAT TAT GAA TAT TCC TTC TCG GAA AGT CAT CCT         1349
Pro Val Tyr Tyr Tyr Glu Tyr Ser Phe Ser Glu Ser His Pro
                430                 435                 440

GCA AAA GGA ACA TTT GGT GAT CAT AAT CTG ACT GGT GCA TGC         1391
Ala Lys Gly Thr Phe Gly Asp His Asn Leu Thr Gly Ala Cys
                    445                 450

CAT GGA GAA GAA CTT GTG AAT TTA TTC AAA GTC GAG ATG ATG         1433
His Gly Glu Glu Leu Val Asn Leu Phe Lys Val Glu Met Met
455                 460                 465

AAG CTG GAA AAA GAT AAA CCT AAT GTT CTA TTA ACA AAA GAT         1475
Lys Leu Glu Lys Asp Lys Pro Asn Val Leu Leu Thr Lys Asp
        470                 475                 480

AGA GTA CTT GCC ATG TGG ACT AAC TTC ATC AAA AAT GGA AAT         1517
Arg Val Leu Ala Met Trp Thr Asn Phe Ile Lys Asn Gly Asn
            485                 490                 495

CCT ACT CCT GAA GTA ACA GAA TTA TTG CCA GTT AAA TGG GAA         1559
Pro Thr Pro Glu Val Thr Glu Leu Leu Pro Val Lys Trp Glu
                500                 505                 510

CCT GCC ACA AAA GAC AAG TTG AAT TAT TTG AAC ATT GAT GCC         1601
Pro Ala Thr Lys Asp Lys Leu Asn Tyr Leu Asn Ile Asp Ala
                    515                 520

ACC TTA ACT TTG GGA ACA AAT CCT GAG GCA AAC CGA GTC AAA         1643
Thr Leu Thr Leu Gly Thr Asn Pro Glu Ala Asn Arg Val Lys
525                 530                 535

TTT TGG GAA GAC GCC ACA AAA TCT TTG CAC GGT CAA TAA             1682
Phe Trp Glu Asp Ala Thr Lys Ser Leu His Gly Gln
        540                 545                 550

TAATTTATGA AAATTGTTTT AAATACTTTA GGTAATATAT TAGGTAAATA          1732

AAAATTAAAA AATAACAATT TTTATGTTTT ATGTATTGGC TTATGTGTAT          1782

CAGTTCTAAT TTTATTTATT TATTCTTGTT TTGCTTGTTT TGAAATATCA          1832

TGGTTTTAAT TTTCAAAACA CAACGTCGTT TGTTTTTAGC AAAATTTCCA          1882

ATAGATATGT TATATTAAGT ACTCTGAAGT ATTTTTATAT ATACACTAAA          1932

ATCAGTAAAA ATACATTAAC TAAAAATATA AGATATTTTC AATAATTTTT         1982

TTTAAAGAAA ATACCAAAAA TAAAGTAAAA TTCCAAACGG AATTTTTGTT         2032

TAACTTAAAA ATAAAATTAA CTCTTCAATA ATTTTGATAA TTAGTATTTC         2082

TGATATCATT AGTGAAAATT ATATTTTGAT AATACGTATT TATATTTAAA         2132

ATAAAATTAT GT                                                   2144
```

(2) INFORMATION FOR SEQ ID NO:58:

(i) SEQUENCE CHARACTERISTICS:
        (A) LENGTH: 550 amino acids
        (B) TYPE: amino acid
        (D) TOPOLOGY: linear (ii) MOLECULE TYPE: protein (iii) SEQUENCE DESCRIPTION: SEQ ID NO:58:

Met Ser Arg Val Ile Phe Leu Ser Cys Ile Phe Leu Phe Ser

```
  1               5                   10
Phe Asn Phe Ile Lys Cys Asp Ser Pro Thr Val Thr Leu Pro
 15                  20                  25
Gln Gly Glu Leu Val Gly Lys Ala Leu Thr Asn Glu Asn Gly
         30                  35                  40
Lys Glu Tyr Phe Ser Tyr Thr Gly Val Pro Tyr Ala Lys Pro
                 45                  50                  55
Pro Val Gly Glu Leu Arg Phe Lys Pro Pro Gln Lys Ala Glu
             60                  65                  70
Pro Trp Gln Gly Val Phe Asn Ala Thr Leu Tyr Gly Asn Val
                 75                  80
Cys Lys Ser Leu Asn Phe Phe Leu Lys Lys Ile Glu Gly Asp
 85                  90                  95
Glu Asp Cys Leu Val Val Asn Val Tyr Ala Pro Lys Thr Thr
        100                 105                 110
Ser Asp Lys Lys Leu Pro Val Phe Phe Trp Val His Gly Gly
            115                 120                 125
Gly Phe Val Thr Gly Ser Gly Asn Leu Glu Phe Gln Ser Pro
                130                 135                 140
Asp Tyr Leu Val Asx Phe Asp Val Ile Phe Val Thr Phe Asn
                145                 150
Tyr Arg Leu Gly Pro Leu Gly Phe Leu Asn Leu Glu Leu Glu
155                 160                 165
Gly Ala Pro Gly Asn Val Gly Leu Leu Asp Gln Val Ala Ala
        170                 175                 180
Leu Lys Trp Thr Lys Glu Asn Ile Glu Lys Phe Gly Gly Asp
            185                 190                 195
Pro Glu Asn Ile Thr Ile Gly Gly Val Ser Ala Gly Gly Ala
                200                 205                 210
Ser Val His Tyr Leu Leu Leu Ser His Thr Thr Thr Gly Leu
                215                 220
Tyr Lys Arg Ala Ile Ala Gln Ser Gly Ser Ala Phe Asn Pro
225                 230                 235
Trp Ala Phe Gln Arg His Pro Val Lys Arg Ser Leu Gln Leu
        240                 245                 250
Ala Glu Ile Leu Gly His Pro Thr Asn Asn Thr Gln Asp Ala
        255                 260                 265
Leu Glu Phe Leu Gln Lys Ala Pro Val Asp Ser Leu Leu Lys
            270                 275                 280
Lys Met Pro Ala Glu Thr Glu Gly Glu Ile Ile Glu Glu Phe
                285                 290
Val Phe Val Pro Ser Ile Glu Lys Val Phe Pro Ser His Gln
295                 300                 305
Pro Phe Leu Glu Glu Ser Pro Leu Ala Arg Met Lys Ser Gly
        310                 315                 320
Ser Phe Asn Lys Val Pro Leu Leu Val Gly Phe Asn Ser Ala
            325                 330                 335
Glu Gly Leu Leu Phe Lys Phe Met Lys Glu Lys Pro Glu
                340                 345                 350
Met Leu Asn Gln Ala Glu Ala Asp Phe Glu Arg Leu Val Pro
                355                 360
Ala Glu Phe Glu Leu Val His Gly Ser Glu Glu Ser Lys Lys
365                 370                 375
```

```
Leu Ala Glu Lys Ile Arg Lys Phe Tyr Phe Asp Asp Lys Pro
    380                 385                 390

Val Pro Glu Asn Glu Gln Lys Phe Ile Asp Leu Ile Gly Asp
        395                 400                 405

Ile Trp Phe Thr Arg Gly Val Asp Lys His Val Lys Leu Ser
            410                 415                 420

Val Glu Lys Gln Asp Glu Pro Val Tyr Tyr Glu Tyr Ser
                425                 430

Phe Ser Glu Ser His Pro Ala Lys Gly Thr Phe Gly Asp His
435                 440                 445

Asn Leu Thr Gly Ala Cys His Gly Glu Glu Leu Val Asn Leu
    450                 455                 460

Phe Lys Val Glu Met Met Lys Leu Glu Lys Asp Lys Pro Asn
        465                 470                 475

Val Leu Leu Thr Lys Asp Arg Val Leu Ala Met Trp Thr Asn
            480                 485                 490

Phe Ile Lys Asn Gly Asn Pro Thr Pro Glu Val Thr Glu Leu
                495                 500

Leu Pro Val Lys Trp Glu Pro Ala Thr Lys Asp Lys Leu Asn
505                 510                 515

Tyr Leu Asn Ile Asp Ala Thr Leu Thr Leu Gly Thr Asn Pro
    520                 525                 530

Glu Ala Asn Arg Val Lys Phe Trp Glu Asp Ala Thr Lys Ser
        535                 540                 545

Leu His Gly Gln
            550

(2) INFORMATION FOR SEQ ID NO:59:

(i) SEQUENCE CHARACTERISTICS:
        (A) LENGTH: 2144 nucleotides
        (B) TYPE: nucleic acid
        (C) STRANDEDNESS: single
        (D) TOPOLOGY: linear (ii) MOLECULE TYPE: cDNA (iii) SEQUENCE DESCRIPTION: SEQ ID NO:59:

ACATAATTTT ATTTTAAATA TAAATACGTA TTATCAAAAT ATAATTTTCA         50

CTAATGATAT CAGAAATACT AATTATCAAA ATTATTGAAG AGTTAATTTT        100

ATTTTTAAGT TAAACAAAAA TTCCGTTTGG AATTTTACTT TATTTTTGGT        150

ATTTTCTTTA AAAAAAATTA TTGAAAATAT CTTATATTTT TAGTTAATGT        200

ATTTTTACTG ATTTTAGTGT ATATATAAAA ATACTTCAGA GTACTTAATA        250

TAACATATCT ATTGGAAATT TTGCTAAAAA CAAACGACGT TGTGTTTTGA        300

AAATTAAAAC CATGATATTT CAAAACAAGC AAAACAAGAA TAAATAAATA        350

AAATTAGAAC TGATACACAT AAGCCAATAC ATAAAACATA AAAATTGTTA        400

TTTTTTAATT TTTATTTACC TAATATATTA CCTAAAGTAT TTAAAACAAT        450

TTTCATAAAT TATTATTGAC CGTGCAAAGA TTTTGTGGCG TCTTCCCAAA        500

ATTTGACTCG GTTTGCCTCA GGATTTGTTC CCAAAGTTAA GGTGGCATCA        550

ATGTTCAAAT AATTCAACTT GTCTTTTGTG GCAGGTTCCC ATTTAACTGG        600

CAATAATTCT GTTACTTCAG GAGTAGGATT TCCATTTTTG ATGAAGTTAG        650
```

```
TCCACATGGC AAGTACTCTA TCTTTTGTTA ATAGAACATT AGGTTTATCT          700

TTTTCCAGCT TCATCATCTC GACTTTGAAT AAATTCACAA GTTCTTCTCC          750

ATGGCATGCA CCAGTCAGAT TATGATCACC AAATGTTCCT TTTGCAGGAT          800

GACTTTCCGA GAAGGAATAT TCATAATAAT AAACTGGTTC GTCTTGTTTC          850

TCCACAGACA ACTTGACATG CTTGTCAACA CCTCTAGTAA ACCAAATATC          900

TCCTATCAAG TCAATAAATT TCTGTTCATT TTCTGGAACG GGTTTATCGT          950

CAAAGTAAAA CTTCCTGATT TTTTCTGCAA GTTTTTTCGA TTCCTCTGAT         1000

CCATGGACTA ATTCAAATTC GGCTGGTACG AGTCTTTCAA AATCTGCTTC         1050

AGCTTGGTTC AGCATCTCTG GTTTTTCTTT CATGAAGAAT TTGAACAAAA         1100

GTCCTTCTGC ACTGTTAAAT CCAACTAATA AAGGTACTTT GTTAAAGGAT         1150

CCGGATTTCA TTCTGGCCAA TGGTGATTCT TCCAAGAAAG GTTGGTGGGA         1200

TGGGAAAACT TTTTCAATTG ATGGTACGAA GACAAACTCT TCTATTATTT         1250

CACCTTCTGT TTCAGCTGGC ATTTTCTTCA GGAGACTGTC TACGGGGCT          1300

TTTTGTAAGA ATTCTAAAGC ATCTTGAGTA TTGTTTGTGG GATGACCCAA         1350

TATCTCAGCA AGTTGAAGAC TACGCTTTAC TGGATGTCTT TGGAAGGCCC         1400

ATGGATTAAA AGCACTTCCA CTTTGAGCAA TTGCCCTTTT GTAAAGTCCA         1450

GTGGTTGTAT GAGATAACAA AAGATAATGA ACACTTGCTC CACCAGCAGA         1500

AACACCACCA ATTGTAATAT TTTCTGGATC TCCACCAAAT TTCTCAATGT         1550

TTTCTTTGGT CCATTTCAGA GCTGCCACCT GATCCAATAA TCCTACATTT         1600

CCTGGAGCAC CCTCCAACTC CAAATTCAGA AATCCGAGAG GTCCCAATCG         1650

GTAATTGAAA GTTACGAAAA TAACATCAAA ATYTACTAAA TAATCTGGGC         1700

TTTGGAATTC TAAATTTCCG GATCCAGTCA CAAAACCACC ACCATGAACC         1750

CAGAAAAATA CTGGAAGTTT TTTATCAGAA GTTGTTTTTG GTGCGTACAC         1800

GTTTACTACC AAGCAGTCTT CGTCTCCTTC AATTTTCTTC AAGAAGAAAT         1850

TTAAAGATTT ACACACATTT CCGTATAATG TGGCGTTGAA AACACCTTGC         1900

CATGGCTCAG CTTTCTGTGG AGGCTTAAAT CTAAGTTCTC CAACAGGAGG         1950

TTTAGCATAA GGTACACCTG TGTAGCTAAA ATACTCTTTT CCATTTTCGT         2000

TCGTCAAAGC TTTTCCAACC AATTCGCCTT GGGGCAAAGT TACAGTCGGG         2050

GAATCACATT TTATAAAATT AAAACTAAAC AAAAAAATAC AACTTAAAAA         2100

AATAACACGA GACATCTTGG ATCTAGACTA TTGACTATGT GTAC              2144
```

(2) INFORMATION FOR SEQ ID NO:60:

(i) SEQUENCE CHARACTERISTICS:
  (A) LENGTH: 1650 nucleotides
  (B) TYPE: nucleic acid
  (C) STRANDEDNESS: single
  (D) TOPOLOGY: linear (ii) MOLECULE TYPE: cDNA (iii) FEATURE:
  (A) NAME/KEY: CDS
  (B) LOCATION: 1..1650

(iv) FEATURE:
  (A) NAME/KEY: Asx = Asn or Asp
  (B) LOCATION: 433

(v) SEQUENCE DESCRIPTION: SEQ ID NO:60:

| | | | | | | | | | | | | | |
|---|---|---|---|---|---|---|---|---|---|---|---|---|---|
| ATG | TCT | CGT | GTT | ATT | TTT | TTA | AGT | TGT | ATT | TTT | TTG | TTT | AGT | 42 |
| Met | Ser | Arg | Val | Ile | Phe | Leu | Ser | Cys | Ile | Phe | Leu | Phe | Ser | |
| 1 | | | | 5 | | | | | 10 | | | | | |

| TTT | AAT | TTT | ATA | AAA | TGT | GAT | TCC | CCG | ACT | GTA | ACT | TTG | CCC | 84 |
| Phe | Asn | Phe | Ile | Lys | Cys | Asp | Ser | Pro | Thr | Val | Thr | Leu | Pro | |
| 15 | | | | | 20 | | | | | 25 | | | | |

| CAA | GGC | GAA | TTG | GTT | GGA | AAA | GCT | TTG | ACG | AAC | GAA | AAT | GGA | 126 |
| Gln | Gly | Glu | Leu | Val | Gly | Lys | Ala | Leu | Thr | Asn | Glu | Asn | Gly | |
| | 30 | | | | | 35 | | | | | 40 | | | |

| AAA | GAG | TAT | TTT | AGC | TAC | ACA | GGT | GTA | CCT | TAT | GCT | AAA | CCT | 168 |
| Lys | Glu | Tyr | Phe | Ser | Tyr | Thr | Gly | Val | Pro | Tyr | Ala | Lys | Pro | |
| | | 45 | | | | | 50 | | | | | 55 | | |

| CCT | GTT | GGA | GAA | CTT | AGA | TTT | AAG | CCT | CCA | CAG | AAA | GCT | GAG | 210 |
| Pro | Val | Gly | Glu | Leu | Arg | Phe | Lys | Pro | Pro | Gln | Lys | Ala | Glu | |
| | | | 60 | | | | | 65 | | | | | 70 | |

| CCA | TGG | CAA | GGT | GTT | TTC | AAC | GCC | ACA | TTA | TAC | GGA | AAT | GTG | 252 |
| Pro | Trp | Gln | Gly | Val | Phe | Asn | Ala | Thr | Leu | Tyr | Gly | Asn | Val | |
| | | | | 75 | | | | | 80 | | | | | |

| TGT | AAA | TCT | TTA | AAT | TTC | TTC | TTG | AAG | AAA | ATT | GAA | GGA | GAC | 294 |
| Cys | Lys | Ser | Leu | Asn | Phe | Phe | Leu | Lys | Lys | Ile | Glu | Gly | Asp | |
| 85 | | | | | 90 | | | | | 95 | | | | |

| GAA | GAC | TGC | TTG | GTA | GTA | AAC | GTG | TAC | GCA | CCA | AAA | ACA | ACT | 336 |
| Glu | Asp | Cys | Leu | Val | Val | Asn | Val | Tyr | Ala | Pro | Lys | Thr | Thr | |
| | 100 | | | | | 105 | | | | | 110 | | | |

| TCT | GAT | AAA | AAA | CTT | CCA | GTA | TTT | TTC | TGG | GTT | CAT | GGT | GGT | 378 |
| Ser | Asp | Lys | Lys | Leu | Pro | Val | Phe | Phe | Trp | Val | His | Gly | Gly | |
| | | 115 | | | | | 120 | | | | | 125 | | |

| GGT | TTT | GTG | ACT | GGA | TCC | GGA | AAT | TTA | GAA | TTC | CAA | AGC | CCA | 420 |
| Gly | Phe | Val | Thr | Gly | Ser | Gly | Asn | Leu | Glu | Phe | Gln | Ser | Pro | |
| | | | | 130 | | | | | 135 | | | | | 140 |

| GAT | TAT | TTA | GTA | RAT | TTT | GAT | GTT | ATT | TTC | GTA | ACT | TTC | AAT | 462 |
| Asp | Tyr | Leu | Val | Asx | Phe | Asp | Val | Ile | Phe | Val | Thr | Phe | Asn | |
| | | | | 145 | | | | | 150 | | | | | |

| TAC | CGA | TTG | GGA | CCT | CTC | GGA | TTT | CTG | AAT | TTG | GAG | TTG | GAG | 504 |
| Tyr | Arg | Leu | Gly | Pro | Leu | Gly | Phe | Leu | Asn | Leu | Glu | Leu | Glu | |
| 155 | | | | | 160 | | | | | 165 | | | | |

| GGT | GCT | CCA | GGA | AAT | GTA | GGA | TTA | TTG | GAT | CAG | GTG | GCA | GCT | 546 |
| Gly | Ala | Pro | Gly | Asn | Val | Gly | Leu | Leu | Asp | Gln | Val | Ala | Ala | |
| | 170 | | | | | 175 | | | | | 180 | | | |

| CTG | AAA | TGG | ACC | AAA | GAA | AAC | ATT | GAG | AAA | TTT | GGT | GGA | GAT | 588 |
| Leu | Lys | Trp | Thr | Lys | Glu | Asn | Ile | Glu | Lys | Phe | Gly | Gly | Asp | |
| | | 185 | | | | | 190 | | | | | 195 | | |

| CCA | GAA | AAT | ATT | ACA | ATT | GGT | GGT | GTT | TCT | GCT | GGT | GGA | GCA | 630 |
| Pro | Glu | Asn | Ile | Thr | Ile | Gly | Gly | Val | Ser | Ala | Gly | Gly | Ala | |
| | | | 200 | | | | | 205 | | | | | 210 | |

| AGT | GTT | CAT | TAT | CTT | TTG | TTA | TCT | CAT | ACA | ACC | ACT | GGA | CTT | 672 |
| Ser | Val | His | Tyr | Leu | Leu | Leu | Ser | His | Thr | Thr | Thr | Gly | Leu | |
| | | | | 215 | | | | | 220 | | | | | |

| TAC | AAA | AGG | GCA | ATT | GCT | CAA | AGT | GGA | AGT | GCT | TTT | AAT | CCA | 714 |
| Tyr | Lys | Arg | Ala | Ile | Ala | Gln | Ser | Gly | Ser | Ala | Phe | Asn | Pro | |
| 225 | | | | | 230 | | | | | 235 | | | | |

| TGG | GCC | TTC | CAA | AGA | CAT | CCA | GTA | AAG | CGT | AGT | CTT | CAA | CTT | 756 |
| Trp | Ala | Phe | Gln | Arg | His | Pro | Val | Lys | Arg | Ser | Leu | Gln | Leu | |
| | 240 | | | | | 245 | | | | | 250 | | | |

| GCT | GAG | ATA | TTG | GGT | CAT | CCC | ACA | AAC | AAT | ACT | CAA | GAT | GCT | 798 |
| Ala | Glu | Ile | Leu | Gly | His | Pro | Thr | Asn | Asn | Thr | Gln | Asp | Ala | |
| | | 255 | | | | | 260 | | | | | 265 | | |

| TTA | GAA | TTC | TTA | CAA | AAA | GCC | CCC | GTA | GAC | AGT | CTC | CTG | AAG | 840 |

```
Leu Glu Phe Leu Gln Lys Ala Pro Val Asp Ser Leu Leu Lys
        270                 275                 280

AAA ATG CCA GCT GAA ACA GAA GGT GAA ATA ATA GAA GAG TTT           882
Lys Met Pro Ala Glu Thr Glu Gly Glu Ile Ile Glu Glu Phe
            285                 290

GTC TTC GTA CCA TCA ATT GAA AAA GTT TTC CCA TCC CAC CAA           924
Val Phe Val Pro Ser Ile Glu Lys Val Phe Pro Ser His Gln
295                 300                 305

CCT TTC TTG GAA GAA TCA CCA TTG GCC AGA ATG AAA TCC GGA           966
Pro Phe Leu Glu Glu Ser Pro Leu Ala Arg Met Lys Ser Gly
        310                 315                 320

TCC TTT AAC AAA GTA CCT TTA TTA GTT GGA TTT AAC AGT GCA           1008
Ser Phe Asn Lys Val Pro Leu Leu Val Gly Phe Asn Ser Ala
            325                 330                 335

GAA GGA CTT TTG TTC AAA TTC TTC ATG AAA GAA AAA CCA GAG           1050
Glu Gly Leu Leu Phe Lys Phe Phe Met Lys Glu Lys Pro Glu
                340                 345                 350

ATG CTG AAC CAA GCT GAA GCA GAT TTT GAA AGA CTC GTA CCA           1092
Met Leu Asn Gln Ala Glu Ala Asp Phe Glu Arg Leu Val Pro
        355                 360

GCC GAA TTT GAA TTA GTC CAT GGA TCA GAG GAA TCG AAA AAA           1134
Ala Glu Phe Glu Leu Val His Gly Ser Glu Glu Ser Lys Lys
365                 370                 375

CTT GCA GAA AAA ATC AGG AAG TTT TAC TTT GAC GAT AAA CCC           1176
Leu Ala Glu Lys Ile Arg Lys Phe Tyr Phe Asp Asp Lys Pro
        380                 385                 390

GTT CCA GAA AAT GAA CAG AAA TTT ATT GAC TTG ATA GGA GAT           1218
Val Pro Glu Asn Glu Gln Lys Phe Ile Asp Leu Ile Gly Asp
            395                 400                 405

ATT TGG TTT ACT AGA GGT GTT GAC AAG CAT GTC AAG TTG TCT           1260
Ile Trp Phe Thr Arg Gly Val Asp Lys His Val Lys Leu Ser
                410                 415                 420

GTG GAG AAA CAA GAC GAA CCA GTT TAT TAT TAT GAA TAT TCC           1302
Val Glu Lys Gln Asp Glu Pro Val Tyr Tyr Tyr Glu Tyr Ser
                    425                 430

TTC TCG GAA AGT CAT CCT GCA AAA GGA ACA TTT GGT GAT CAT           1344
Phe Ser Glu Ser His Pro Ala Lys Gly Thr Phe Gly Asp His
435                 440                 445

AAT CTG ACT GGT GCA TGC CAT GGA GAA GAA CTT GTG AAT TTA           1386
Asn Leu Thr Gly Ala Cys His Gly Glu Glu Leu Val Asn Leu
        450                 455                 460

TTC AAA GTC GAG ATG ATG AAG CTG GAA AAA GAT AAA CCT AAT           1428
Phe Lys Val Glu Met Met Lys Leu Glu Lys Asp Lys Pro Asn
            465                 470                 475

GTT CTA TTA ACA AAA GAT AGA GTA CTT GCC ATG TGG ACT AAC           1470
Val Leu Leu Thr Lys Asp Arg Val Leu Ala Met Trp Thr Asn
                480                 485                 490

TTC ATC AAA AAT GGA AAT CCT ACT CCT GAA GTA ACA GAA TTA           1512
Phe Ile Lys Asn Gly Asn Pro Thr Pro Glu Val Thr Glu Leu
                    495                 500

TTG CCA GTT AAA TGG GAA CCT GCC ACA AAA GAC AAG TTG AAT           1554
Leu Pro Val Lys Trp Glu Pro Ala Thr Lys Asp Lys Leu Asn
505                 510                 515

TAT TTG AAC ATT GAT GCC ACC TTA ACT TTG GGA ACA AAT CCT           1596
Tyr Leu Asn Ile Asp Ala Thr Leu Thr Leu Gly Thr Asn Pro
        520                 525                 530

GAG GCA AAC CGA GTC AAA TTT TGG GAA GAC GCC ACA AAA TCT           1638
Glu Ala Asn Arg Val Lys Phe Trp Glu Asp Ala Thr Lys Ser
            535                 540                 545
```

```
TTG CAC GGT CAA                                                      1650
Leu His Gly Gln
        550

(2) INFORMATION FOR SEQ ID NO:61:

(i) SEQUENCE CHARACTERISTICS:
        (A) LENGTH:  1650 nucleotides
        (B) TYPE:  nucleic acid
        (C) STRANDEDNESS:  single
        (D) TOPOLOGY:  linear (ii) MOLECULE TYPE:  cDNA (iii) SEQUENCE DESCRIPTION:  SEQ ID NO:61:

TTGACCGTGC AAAGATTTTG TGGCGTCTTC CCAAAATTTG ACTCGGTTTG                  50

CCTCAGGATT TGTTCCCAAA GTTAAGGTGG CATCAATGTT CAAATAATTC                 100

AACTTGTCTT TTGTGGCAGG TTCCCATTTA ACTGGCAATA ATTCTGTTAC                 150

TTCAGGAGTA GGATTTCCAT TTTTGATGAA GTTAGTCCAC ATGGCAAGTA                 200

CTCTATCTTT TGTTAATAGA ACATTAGGTT TATCTTTTC CAGCTTCATC                  250

ATCTCGACTT TGAATAAATT CACAAGTTCT TCTCCATGGC ATGCACCAGT                 300

CAGATTATGA TCACCAAATG TTCCTTTTGC AGGATGACTT TCCGAGAAGG                 350

AATATTCATA ATAATAAACT GGTTCGTCTT GTTTCTCCAC AGACAACTTG                 400

ACATGCTTGT CAACACCTCT AGTAAACCAA ATATCTCCTA TCAAGTCAAT                 450

AAATTTCTGT TCATTTTCTG GAACGGGTTT ATCGTCAAAG TAAAACTTCC                 500

TGATTTTTTC TGCAAGTTTT TTCGATTCCT CTGATCCATG GACTAATTCA                 550

AATTCGGCTG GTACGAGTCT TTCAAAATCT GCTTCAGCTT GGTTCAGCAT                 600

CTCTGGTTTT TCTTTCATGA AGAATTTGAA CAAAAGTCCT TCTGCACTGT                 650

TAAATCCAAC TAATAAAGGT ACTTTGTTAA AGGATCCGGA TTTCATTCTG                 700

GCCAATGGTG ATTCTTCCAA GAAAGGTTGG TGGGATGGGA AAACTTTTTC                 750

AATTGATGGT ACGAAGACAA ACTCTTCTAT TATTTCACCT TCTGTTTCAG                 800

CTGGCATTTT CTTCAGGAGA CTGTCTACGG GGGCTTTTTG TAAGAATTCT                 850

AAAGCATCTT GAGTATTGTT TGTGGGATGA CCCAATATCT CAGCAAGTTG                 900

AAGACTACGC TTTACTGGAT GTCTTTGGAA GGCCCATGGA TTAAAAGCAC                 950

TTCCACTTTG AGCAATTGCC CTTTTGTAAA GTCCAGTGGT TGTATGAGAT                1000

AACAAAAGAT AATGAACACT TGCTCCACCA GCAGAAACAC CACCAATTGT                1050

AATATTTTCT GGATCTCCAC CAAATTTCTC AATGTTTTCT TTGGTCCATT                1100

TCAGAGCTGC CACCTGATCC AATAATCCTA CATTTCCTGG AGCACCCTCC                1150

AACTCCAAAT TCAGAAATCC GAGAGGTCCC AATCGGTAAT TGAAAGTTAC                1200

GAAAATAACA TCAAAATYTA CTAAATAATC TGGGCTTTGG AATTCTAAAT                1250

TTCCGGATCC AGTCACAAAA CCACCACCAT GAACCCAGAA AAATACTGGA                1300

AGTTTTTTAT CAGAAGTTGT TTTTGGTGCG TACACGTTTA CTACCAAGCA                1350

GTCTTCGTCT CCTTCAATTT TCTTCAAGAA GAAATTTAAA GATTTACACA                1400

CATTTCCGTA TAATGTGGCG TTGAAAACAC CTTGCCATGG CTCAGCTTTC                1450

TGTGGAGGCT TAAATCTAAG TTCTCCAACA GGAGGTTTAG CATAAGGTAC                1500

ACCTGTGTAG CTAAAATACT CTTTTCCATT TTCGTTCGTC AAAGCTTTTC                1550
```

```
CAACCAATTC GCCTTGGGGC AAAGTTACAG TCGGGGAATC ACATTTTATA          1600

AAATTAAAAC TAAACAAAAA AATACAACTT AAAAAAATAA CACGAGACAT          1650
```

(2) INFORMATION FOR SEQ ID NO:62:

(i) SEQUENCE CHARACTERISTICS:
        (A) LENGTH: 29 bases
        (B) TYPE: nucleic acid
        (C) STRANDEDNESS: single
        (D) TOPOLOGY: linear (ii) MOLECULE TYPE: primer (iii) SEQUENCE DESCRIPTION: SEQ ID NO:62:

```
AAACTCGAGT CCCCCGACTG TAACTTTGC                                29
```

(2) INFORMATION FOR SEQ ID NO:63:

(i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:63:

```
TCATCTGCAG TTATTGACTG TGCAAAGTTT TTGTGG                        36
```

(2) INFORMATION FOR SEQ ID NO:64:

(i) SEQUENCE CHARACTERISTICS:
        (A) LENGTH: 32 bases
        (B) TYPE: nucleic acid
        (C) STRANDEDNESS: single
        (D) TOPOLOGY: linear (ii) MOLECULE TYPE: primer (iii) SEQUENCE DESCRIPTION: SEQ ID NO:64:

```
TTCCGGATCC GGCTGATCTA CAAGTGACTT TG                            32
```

(2) INFORMATION FOR SEQ ID NO:65:

(i) SEQUENCE CHARACTERISTICS:
        (A) LENGTH: 34 bases
        (B) TYPE: nucleic acid
        (C) STRANDEDNESS: single
        (D) TOPOLOGY: linear (ii) MOLECULE TYPE: primer (iii) SEQUENCE DESCRIPTION: SEQ ID NO:65:

```
TGGTACTCGA GTCATAAAAA TTTATTCCAA AATC                          34
```

(2) INFORMATION FOR SEQ ID NO:66:

(i) SEQUENCE CHARACTERISTICS:
        (A) LENGTH: 39 bases
        (B) TYPE: nucleic acid
        (C) STRANDEDNESS: single
        (D) TOPOLOGY: linear (ii) MOLECULE TYPE: primer (iii) SEQUENCE DESCRIPTION: SEQ ID NO:66:

```
AAAACTGCAG TATAAATATG TTACCTCACA GTGCATTAG                     39
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated protein or truncated protein of at least about 5 contiguous amino acids encoded by a nucleic acid molecule that hybridizes only with a nucleic acid molecule having a nucleic acid sequence selected from the group consisting of:
   a nucleic acid molecule comprising a nucleic acid sequence selected from the group consisting of SEQ ID NO:3, SEQ ID NO:6, SEQ ID NO:9, SEQ ID NO:12, SEQ ID NO:15, SEQ ID NO:17, SEQ ID NO:20, SEQ ID NO:22, SEQ ID NO:26, SEQ ID NO:29, SEQ ID NO:32, SEQ ID NO:35, SEQ ID NO:38, SEQ ID NO:52, SEQ ID NO:59 and SEQ ID NO:61;
   or an isolated protein comprising an amino acid sequence selected from the group consisting of: SEQ ID NO:39, SEQ ID NO:40, SEQ ID NO:41, SEQ ID NO:42, SEQ ID NO:43, SEQ ID NO:44, SEQ ID NO:53, SEQ ID NO:54 and SEQ ID NO:55 or a truncated protein thereof having at least about 5 contiguous amino acids,
   wherein the protein or truncated protein is capable of eliciting a specific immune response against arthropod esterase proteins.

2. The protein of claim 1, wherein said protein, when administered to an animal, elicits an immune response against a carboxylesterase protein.

3. The protein of claim 1, wherein said protein is encoded by a nucleic acid molecule that hybridizes only with nucleic acid molecule $nfE6_{1792}$.

4. The protein of claim 1, wherein said protein is selected from the group consisting of: a protein comprising an amino acid sequence selected from the group consisting of SEQ ID NO:2, SEQ ID NO:5, SEQ ID NO:8, SEQ ID NO:11, SEQ ID NO:14, SEQ ID NO:19, SEQ ID NO:25, SEQ ID NO:31, SEQ ID NO:37, SEQ ID NO:39, SEQ ID NO:40, SEQ ID NO:41, SEQ ID NO:42, SEQ ID NO:43, SEQ ID NO:44, SEQ ID NO:53, SEQ ID NO:54, SEQ ID NO:55 and SEQ ID NO:58; and a protein encoded by an allelic variant of a nucleic acid molecule encoding a protein selected from the group consisting of SEQ ID NO:2, SEQ ID NO:5, SEQ ID NO:8, SEQ ID NO:11, SEQ ID NO:14, SEQ ID NO:19, SEQ ID NO:25, SEQ ID NO:31, SEQ ID NO:37, SEQ ID NO:39, SEQ ID NO:40, SEQ ID NO:41, SEQ ID NO:42, SEQ ID NO:43, SEQ ID NO:44, SEQ ID NO:53, SEQ ID NO:54, SEQ ID NO:55 and SEQ ID NO:58.

5. An isolated antibody that selectively binds to a protein as set forth in claim 1.

6. An isolated flea protein selected from the group consisting of: a protein comprising an amino acid sequence selected from the group consisting of SEQ ID NO:2, SEQ ID NO:5, SEQ ID NO:8, SEQ ID NO:11, SEQ ID NO:14, SEQ ID NO:19, SEQ ID NO:25, SEQ ID NO:31, SEQ ID NO:37, SEQ ID NO:39, SEQ ID NO:40, SEQ ID NO:41, SEQ ID NO:42, SEQ ID NO:43, SEQ ID NO:44, SEQ ID NO:53, SEQ ID NO:54, SEQ ID NO:55 and SEQ ID NO:58; and a protein encoded by an allelic variant of a nucleic acid molecule encoding a protein comprising any of said amino acid sequences.

7. An isolated flea protein that hydrolyzes $\alpha$-naphthyl acetate to produce $\alpha$-naphthyl acetate contained in about 20 mM Tris at about pH 8.0 for about 15 minutes at about 37° C. wherein said protein comprises an amino acid sequence selected from the group consisting of SEQ ID NO:5, SEQ ID NO:19, SEQ ID NO:39, SEQ ID NO:40, SEQ ID NO:41, SEQ ID NO:42, SEQ ID NO:43, SEQ ID NO:44 and SEQ ID NO:53.

* * * * *